US012637422B2

(12) United States Patent
Payne et al.

(10) Patent No.: US 12,637,422 B2
(45) **Date of Patent: *May 26, 2026**

(54) IONIZABLE CATIONIC LIPID FOR RNA DELIVERY

(71) Applicant: Arcturus Therapeutics, Inc., San Diego, CA (US)

(72) Inventors: Joseph E. Payne, San Diego, CA (US); Padmanabh Chivukula, San Diego, CA (US); Priya Karmali, San Diego, CA (US); Steven P. Tanis, Carlsbad, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 1162 days.

This patent is subject to a terminal disclaimer.

(21) Appl. No.: 17/216,357

(22) Filed: Mar. 29, 2021

(65) Prior Publication Data

US 2021/0323914 A1 Oct. 21, 2021

Related U.S. Application Data

(63) Continuation of application No. 16/709,800, filed on Dec. 10, 2019, now Pat. No. 10,961,188, which is a (Continued)

(51) Int. Cl.

| | |
|---|---|
| ***C07C 333/04*** | (2006.01) |
| ***C07C 271/22*** | (2006.01) |

(52) U.S. Cl.

CPC .......... *C07C 333/04* (2013.01); *C07C 271/22* (2013.01)

(58) Field of Classification Search

CPC ............................ C07C 333/04; C07C 271/22

See application file for complete search history.

(56) References Cited

U.S. PATENT DOCUMENTS

| | | | |
|---|---|---|---|
| 4,511,069 | A | 4/1985 | Kalat |
| 4,778,810 | A | 10/1988 | Wenig et al. |

(Continued)

FOREIGN PATENT DOCUMENTS

| | | | |
|---|---|---|---|
| CN | 102215820 | A | 10/2011 |
| CN | 102884041 | A | 1/2013 |

(Continued)

OTHER PUBLICATIONS

European Search Report issued in European Application No. 23196560.9, mailed on Mar. 27, 2024, 7 pages.

(Continued)

*Primary Examiner* — Andrew D Kosar
*Assistant Examiner* — John D Mcanany
(74) *Attorney, Agent, or Firm* — Greenberg Traurig, LLP

(57) ABSTRACT

Disclosed herein is a compound of Formula I, wherein $R_1$ is a branched chain alkyl consisting of 10 to 31 carbons; $R_2$ is a linear alkyl, alkenyl, or alkynyl consisting of 2 to 20 carbons, or a branched chain alkyl consisting of 10 to 31 carbons; $L_1$ and $L_2$ are the same or different, each a linear alkane of 1 to 20 carbons or a linear alkene of 2 to 20 carbons; $X_1$ is S or O; $R_3$ is a linear or branched alkylene consisting of 1 to 6 carbons; and $R_4$ and $R_5$ are the same or different, each a hydrogen or a linear or branched alkyl consisting of 1 to 6 carbons; or a pharmaceutically acceptable salt or solvate thereof.

(Continued)

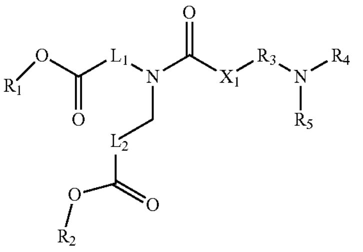

I

20 Claims, 19 Drawing Sheets

Related U.S. Application Data continuation of application No. 15/849,573, filed on Dec. 20, 2017, now Pat. No. 10,526,284.

(56) References Cited

U.S. PATENT DOCUMENTS

| | | | | |
|---|---|---|---|---|
| 5,849,902 | A | 12/1998 | Arrow et al. | |
| 7,982,027 | B2 * | 7/2011 | MacLachlan | A61P 3/06 435/458 |
| 8,158,601 | B2 | 4/2012 | Chen et al. | |
| 9,011,903 | B2 | 4/2015 | Niitsu et al. | |
| 9,365,610 | B2 | 6/2016 | Payne et al. | |
| 9,567,296 | B2 | 2/2017 | Payne et al. | |
| 9,593,077 | B2 | 3/2017 | Payne et al. | |
| 9,670,152 | B2 | 6/2017 | Payne et al. | |
| 9,834,510 | B2 | 12/2017 | Payne et al. | |
| 9,850,202 | B2 | 12/2017 | Payne et al. | |
| 9,896,413 | B2 | 2/2018 | Payne et al. | |
| 9,951,002 | B2 | 4/2018 | Payne et al. | |
| 10,526,284 | B2 * | 1/2020 | Payne | C07C 271/22 |
| 11,744,887 | B2 * | 9/2023 | Sullivan | A61K 9/5123 424/450 |
| 2010/0160168 | A1 | 6/2010 | Lindner | |
| 2012/0027803 | A1 | 2/2012 | Manoharan et al. | |
| 2012/0165275 | A1 * | 6/2012 | Holmes | A61P 7/06 548/542 |
| 2013/0022665 | A1 | 1/2013 | Niitsu et al. | |
| 2013/0115274 | A1 | 5/2013 | Knopov et al. | |
| 2013/0129811 | A1 | 5/2013 | Kuboyama et al. | |
| 2013/0274504 | A1 | 10/2013 | Colletti et al. | |
| 2015/0306039 | A1 | 10/2015 | Akinc et al. | |
| 2017/0114010 | A1 | 4/2017 | Payne et al. | |
| 2017/0190661 | A1 | 7/2017 | Payne et al. | |
| 2018/0169268 | A1 | 6/2018 | Payne et al. | |
| 2018/0170865 | A1 | 6/2018 | Payne et al. | |
| 2018/0170866 | A1 | 6/2018 | Payne et al. | |
| 2018/0208555 | A1 | 7/2018 | Payne et al. | |
| 2020/0297634 | A1 | 9/2020 | Karmali et al. | |
| 2023/0295081 | A1 | 9/2023 | Rajappan et al. | |
| 2024/0391870 | A1 | 11/2024 | Rajappan et al. | |

FOREIGN PATENT DOCUMENTS

| | | | | |
|---|---|---|---|---|
| CN | 104066712 | A | 9/2014 | |
| CN | 104640841 | A | 5/2015 | |
| CN | 105873902 | A | 8/2016 | |
| CN | 107207428 | A | 9/2017 | |
| EP | 1502576 | A2 | 2/2005 | |
| EP | 3496243 | A1 | 6/2019 | |
| EP | 4122920 | A1 | 1/2023 | |
| FR | 1481016 | A | 5/1967 | |
| JP | 61089286 | | 5/1986 | |
| JP | 61136584 | | 6/1986 | |
| JP | 2013095755 | A | 5/2013 | |
| JP | 2015523990 | A | 8/2015 | |
| JP | 2016538343 | A | 12/2016 | |
| JP | 2017535610 | A | 11/2017 | |
| JP | 2019533410 | A | 11/2019 | |
| JP | 2020504728 | A | 2/2020 | |
| JP | 2020504730 | A | 2/2020 | |
| JP | 2021073263 | A | 5/2021 | |
| JP | 6905062 | B2 | 6/2021 | |
| JP | 2021088588 | A | 6/2021 | |
| JP | 2021195408 | A | 12/2021 | |
| KR | 20190122653 | A | 10/2019 | |
| KR | 20190134593 | A | 12/2019 | |
| WO | 9207065 | A1 | 4/1992 | |
| WO | 9315187 | A1 | 8/1993 | |
| WO | 2010057160 | A1 | 5/2010 | |
| WO | 2010061880 | A1 | 6/2010 | |
| WO | 2011136368 | A1 | 11/2011 | |
| WO | 2011153493 | A2 | 12/2011 | |
| WO | WO-2012044638 | A1 * | 4/2012 | A61K 9/14 |
| WO | 2012170952 | A2 | 12/2012 | |
| WO | 2012170952 | A9 | 2/2013 | |
| WO | 2013065825 | A1 | 5/2013 | |
| WO | 2013086373 | A1 | 6/2013 | |
| WO | 2013185116 | A1 | 12/2013 | |
| WO | 2015074085 | A1 | 5/2015 | |
| WO | 2016081029 | A1 | 5/2016 | |
| WO | 2018118102 | A1 | 6/2018 | |
| WO | 2022235935 | A2 | 11/2022 | |
| WO | 2023086514 | A1 | 5/2023 | |

OTHER PUBLICATIONS

International Preliminary Report on Patentability Patent Application No. PCT/US2017/015886, mailed on May 23, 2019, 48 pages.

International Search Report and Written Opinion received for PCT Application No. PCT/US2017/067756, mailed on Mar. 26, 2018, 7 pages.

International Search Report and Written Opinion received on Patent Application No. PCT/US2014/066242, mailed on Feb. 10, 2015, 9 pages.

International Search Report and Written Opinion received on Patent Application No. PCT/US2015/030218, mailed on Aug. 25, 2015, 9 pages.

International Search Report and Written Opinion received on Patent Application No. PCT/US2017/015886, mailed on Aug. 29, 2017, 8 pages.

Dorwald, F. Zaragoza (2005) "Side Reactions in Organic Synthesis: A Guide to Successful Synthesis Design", Wiley-VCH, 390 pages.

Healy et al. (2017) "Pharmaceutical Solvates, Hydrates and Amorphous Forms: A Special Emphasis on Cocrystals", Advanced Drug Delivery Reviews, 22 pages.

Merriam-Webster. "Definition of alkylene", In Merriam-Webster.com dictionary, retrieved Jan. 16, 2017, from https://www.merriam-webster.com/dictionary/alkylene.

Reeck et al. (Aug. 28, 1987) ""Homology" in proteins and nucleic acids: a terminology muddle and a way out of it", Cell, 50(5):667.

Reusch (1999) "Heterocyclic Chemistry—Heterocyclic Compounds", Virtual Textbook of Organic Chemistry, 14 pages.

Reusch (1999) "Virtual Textbook of Organic Chemistry", https://www2.chemistry.msu.edu/faculty/reusch/VirtTxtJml/intro1.htm, accessed Jul. 13, 2016, 4 pages.

Wan et al. (2013) "Lipid Nanoparticle Delivery Systems for siRNA-Based Therapeutics", Drug Delivery and Translational Research, 10 pages.

Extended European Search Report for EP Application No. 22893632.4, mailed on Oct. 22, 2025, 12 pages.

International Search Report and Written Opinion for International Application No. PCT/US2022/049607, mailed on Mar. 16, 2023, 10 pages.

International Search Report and Written Opinion for International Application No. PCT/US2024/028521, mailed on Jul. 31, 2024, 15 pages.

(56) References Cited

OTHER PUBLICATIONS

Database Pubchem (Dec. 19, 2020) "SCHEMBL22457018", Pubchem SID 439158409, 7 pages.

* cited by examiner

ATX-0082

ATX-0134

IONIZABLE CATIONIC LIPID FOR RNA DELIVERY

CROSS REFERENCE TO RELATED APPLICATIONS

This application is a continuation of U.S. application Ser. No. 16/709,800, filed Dec. 10, 2019, now U.S. Pat. No. 10,961,188, which in turn is a continuation of U.S. application Ser. No. 15/849,573, filed Dec. 20, 2017, now U.S. Pat. No. 10,526,284, each of which is incorporated herein by reference in their entirety.

BACKGROUND

A number of different types of nucleic acids are currently being developed as therapeutics for the treatment of a number of diseases. As these molecules are being developed, there has been developed a need to produce them in a form that is stable and has a long shelf-life and that can be easily incorporated into an anhydrous organic or anhydrous polar aprotic solvent to enable encapsulations of the nucleic acids without the side-reactions that can occur in a polar aqueous solution or nonpolar solvents.

The description herein relates to novel lipid compositions that facilitate the intracellular delivery of biologically active and therapeutic molecules. The description relates also to pharmaceutical compositions that comprise such lipid compositions, and that are useful to deliver therapeutically effective amounts of biologically active molecules into the cells of patients.

The delivery of a therapeutic compound to a subject is important for its therapeutic effects and usually it can be impeded by limited ability of the compound to reach targeted cells and tissues. Improvement of such compounds to enter the targeted cells of tissues by a variety of means of delivery is crucial. The description herein relates the novel lipids, in compositions and methods for preparation that facilitate the targeted intracellular delivery of biological active molecules.

Examples of biologically active molecules for which effective targeting to a patient's tissues is often not achieved include: numerous proteins including immunoglobulin proteins, polynucleotides such as genomic DNA, cDNA, or mRNA antisense polynucleotides; and many low molecular weight compounds, whether synthetic or naturally occurring, such as the peptide hormones and antibiotics.

One of the fundamental challenges now facing medical practitioners is that a number of different types of nucleic acids are currently being developed as therapeutics for the treatment of a number of diseases. These nucleic acids include mRNA for gene expression, DNA in gene therapy, plasmids, small interfering nucleic acids (siNA), siRNA, and microRNA (miRNA) for use in RNA interference (RNAi), antisense molecules, ribozymes, antagomirs, and aptamers. As these nucleic acids are being developed, there is a need to produce lipid Formulations that are easy to make and can be readily delivered to a target tissue.

SUMMARY

In one aspect, disclosed herein a compound of Formula I

I

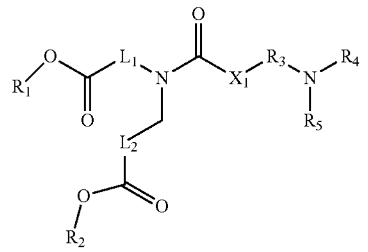

wherein $R_1$ is

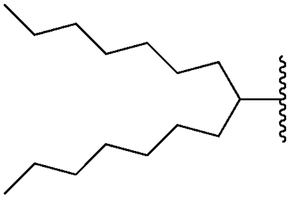,

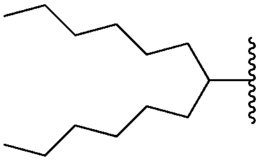,

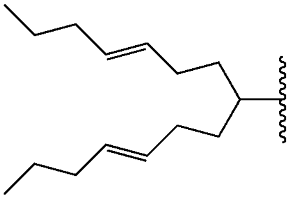,

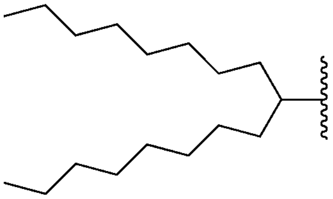,

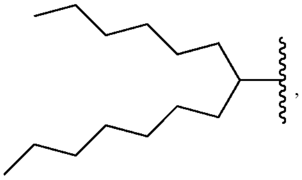, 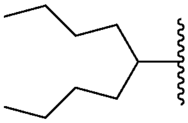 or

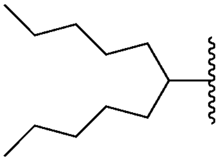;

$R_2$ is

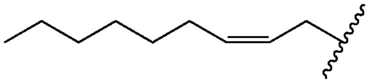

,

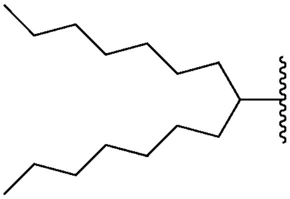

or

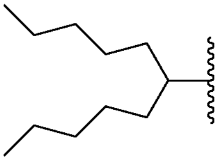

;

$L_1$ and $L_2$ are each independently a linear $C_1$-$C_{15}$ alkyl; X is O or S; $R_3$ is a linear $C_1$-$C_6$ alkyl; and $R_4$ and $R_5$ are each independently a linear $C_1$-$C_6$ alkyl; or a pharmaceutically acceptable salt or solvate thereof.

In another aspect, disclosed herein is a compound of Formula I

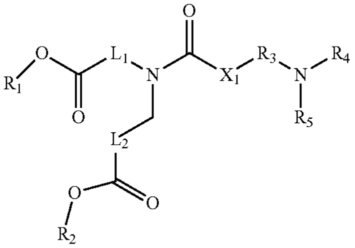

I wherein $R_1$ is

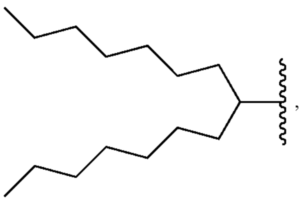 [SMILES: *C(CCCCCCC)CCCCCCC]

,

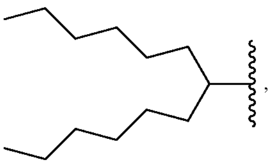

,

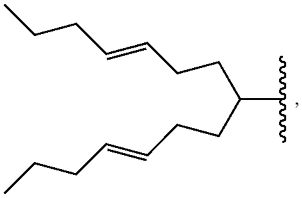 [SMILES: *C(CC/C=C/CCC)CC/C=C/CCC]

,

-continued

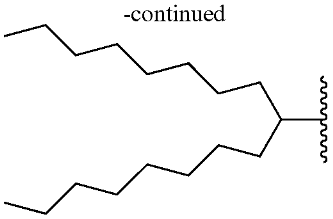

,

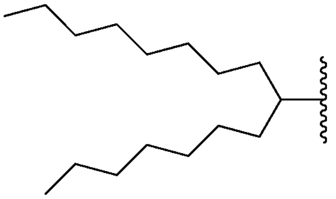

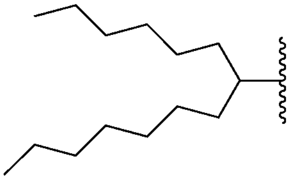

,

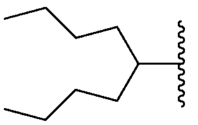

or

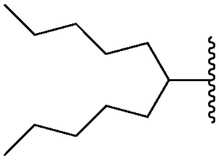

;

$R_2$ is

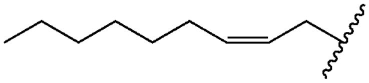

,

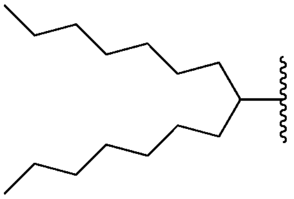

or

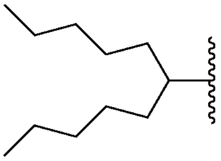

;

$L_1$ and $L_2$ are each independently a linear $C_1$-$C_3$ alkyl; X is O or S; $R_3$ is linear $C_1$-$C_3$ alkyl; $R_4$ and $R_5$ are each independently a linear $C_1$-$C_2$ alkyl; or a pharmaceutically acceptable salt or solvate thereof.

In another embodiment, cationic lipids described herein are in a pharmaceutical composition. The pharmaceutical composition preferably comprises a lipid nanoparticle comprising a nucleic acid, preferably a RNA polynucleotide. The lipid nanoparticle preferably increases the lifetime of RNA in the circulation. In another embodiment, upon administration of the pharmaceutical composition, the lipid nanoparticle therein delivers the nucleic acid to cells in the body. Preferably, the nucleic acid has an activity of suppressing the expression of a target gene. Alternatively, the nucleic acid has an activity of increasing production of a protein it encodes upon expression in cells of the body.

What is also described herein is a method for introducing a nucleic acid into a cell of a mammal by using any of the compositions, above. The cell may be in a liver, lung, kidney, brain, blood, spleen, or bone. The composition preferably is administered intravenously, subcutaneously, intraperitoneally, or intrathecally. Preferably, the compositions described herein are used in a method for treating cancer or inflammatory disease. The disease may be one selected from the group consisting of immune disorder, cancer, renal disease, fibrotic disease, genetic abnormality, inflammation, and cardiovascular disorder.

DETAILED DESCRIPTION

Figure 1:
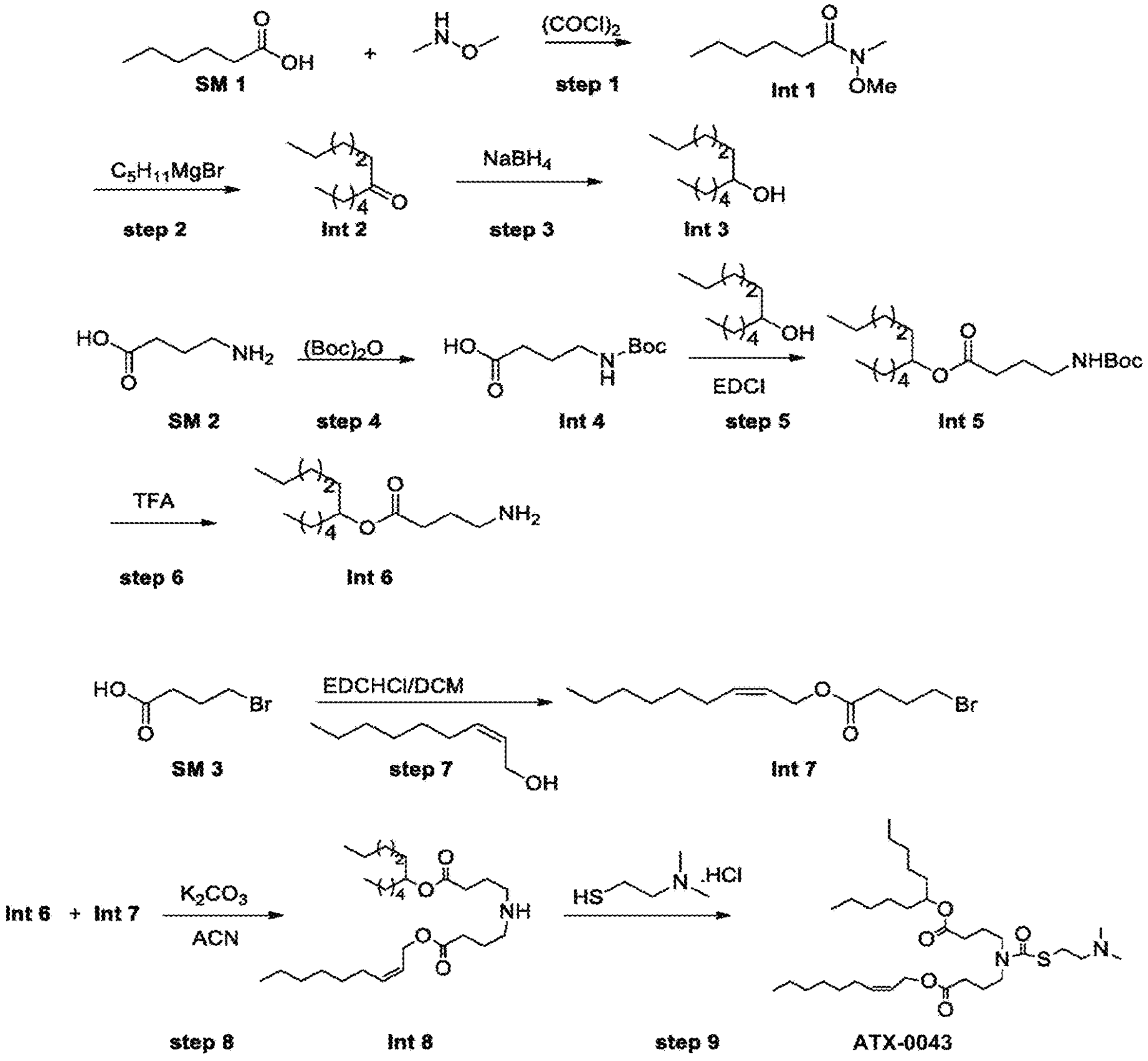
FIG. 1 shows the synthetic pathway of ATX-0043 from hexanoate (SM 1), 4-aminobutanoic acid (SM 2), and 4-bromobutyric acid (SM 3). Intermediates (Ints) 1-8 and reactions are described in Example 2.

In one aspect, disclosed herein is a compound of Formula I

I

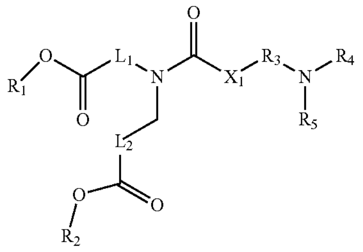

wherein $R_1$ is a branched chain alkyl consisting of 10 to 31 carbons; $R_2$ is a linear alkyl, alkenyl, or alkynyl consisting of 2 to 20 carbons, or a branched chain alkyl consisting of 10 to 31 carbons; $L_1$ and $L_2$ are the same or different, each a linear alkane of 1 to 20 carbons or a linear alkene of 2 to 20 carbons; $X_1$ is S or O; $R_3$ is a linear or branched alkylene consisting of 1 to 6 carbons; and $R_4$ and $R_5$ are the same or different, each a hydrogen or a linear or branched alkyl consisting of 1 to 6 carbons; or a pharmaceutically acceptable salt thereof.

Another aspect of what is described is a compound of Formula I

I

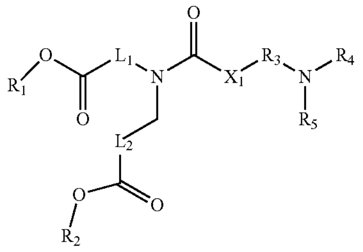

wherein $R_1$ is a branched, noncyclic alkyl or alkenyl of 8, 9, 10, 11, 12, 13, 14, 16, 17, 18, 19, 20, 21, or 22 carbons; $L_1$ is linear alkane of 1 to 15 carbons; $R_2$ is a linear alkyl or alkenyl of 5, 6, 7, 8, 9, 10, 11, 12, 13, 14 or 15 carbons or a branched, noncyclic alkyl or alkenyl of 8, 9, 10, 11, 12, 13, 14, 16, 17, 18, 19, 20, 21, or 22 carbons; $L_2$ is a linear alkane of 4, 5, 6, 7, 8, 9, 10, 11, 12, 13, 14 or 15 carbons; X is O or S; $R_3$ is a linear alkane of 1, 2, 3, 4, 5, or 6 carbons; and $R_4$ and $R_5$ are the same or different, each a linear or branched, noncyclic alkyl of 1, 2, 3, 4, 5, or 6 carbons; or a pharmaceutically acceptable salt or solvate thereof.

In some embodiments, $R_1$ has 8, 9, 10, 11, 12, 13, 14, 16, or 17 carbons.

In some embodiments, $R_1$ comprises two identical alkyl or alkenyl groups.
In some embodiments, $R_1$ comprises an alkenyl group.
In some embodiments, $R_2$ is an alkenyl.
In some embodiments, $R_2$ is a branched, noncyclic alkyl.
In some embodiments, $L_2$ has 4, 5, 6, or 7 carbons.
In some embodiments, the compound is selected from the group consisting of
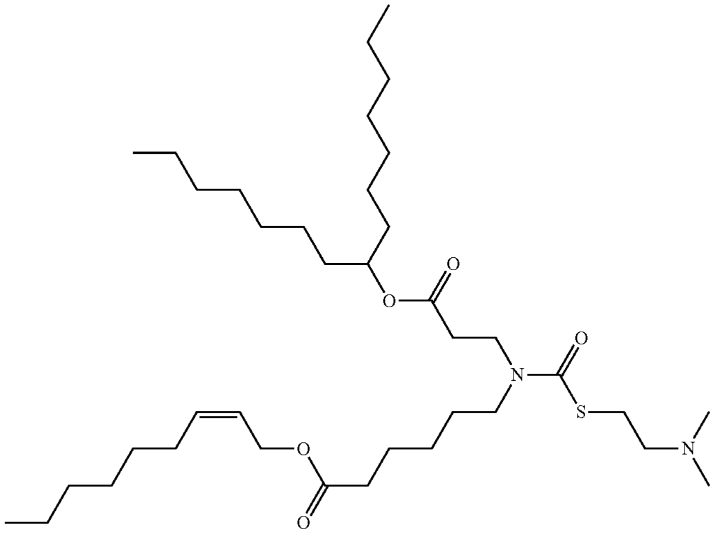
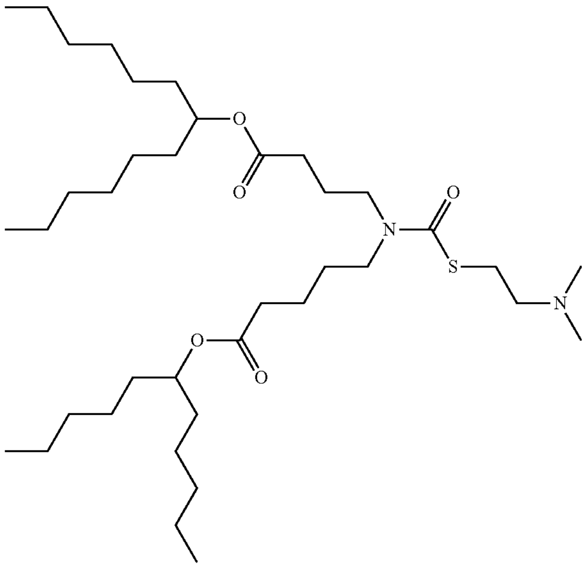
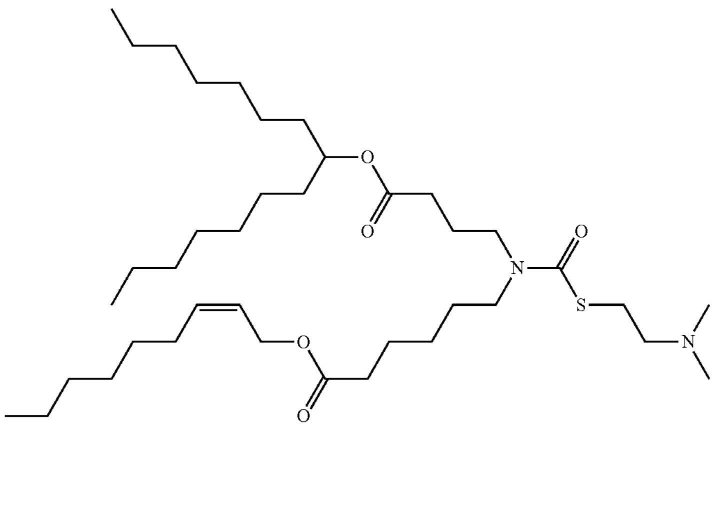

-continued
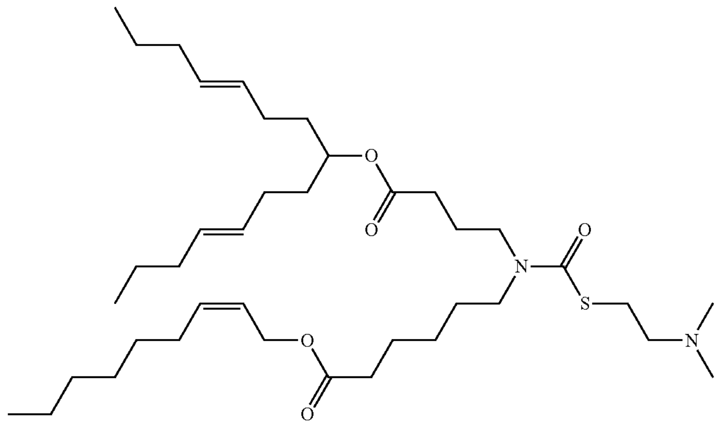
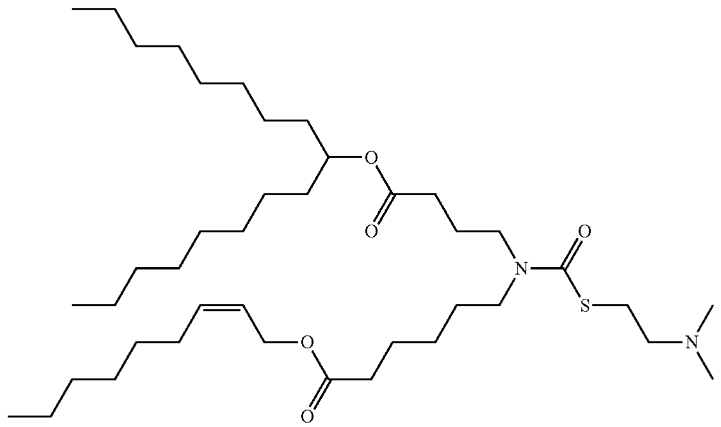
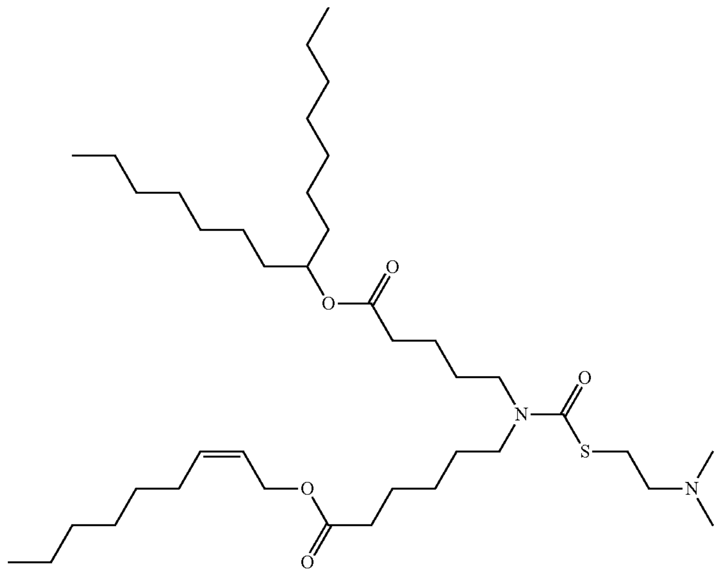

-continued
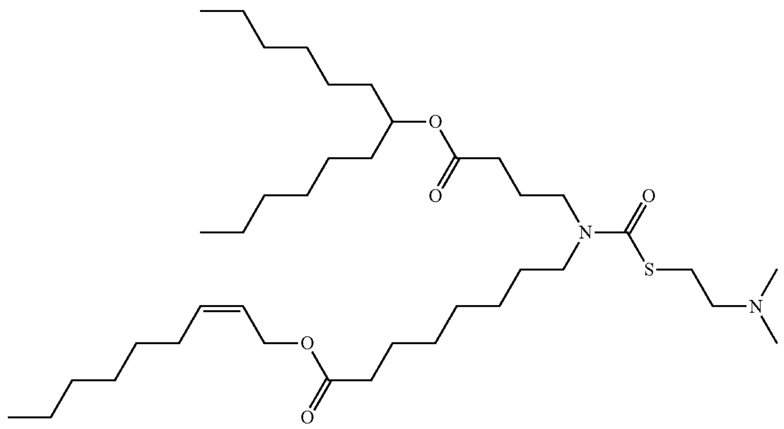
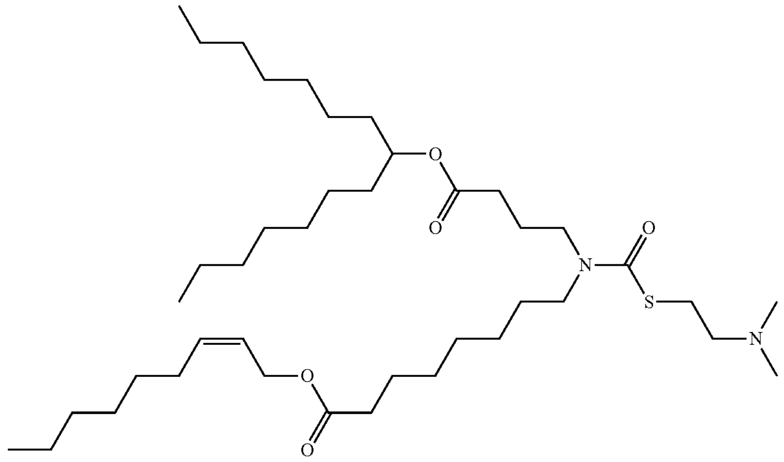
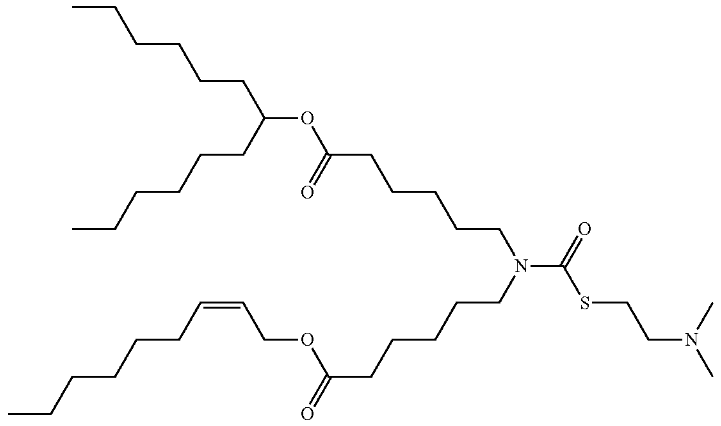

-continued
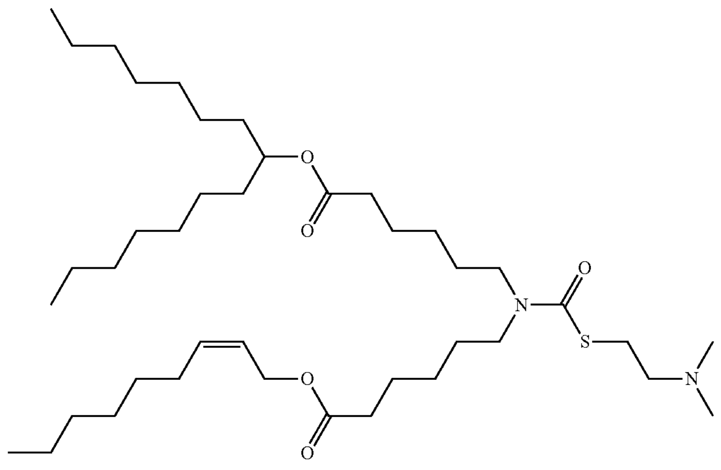
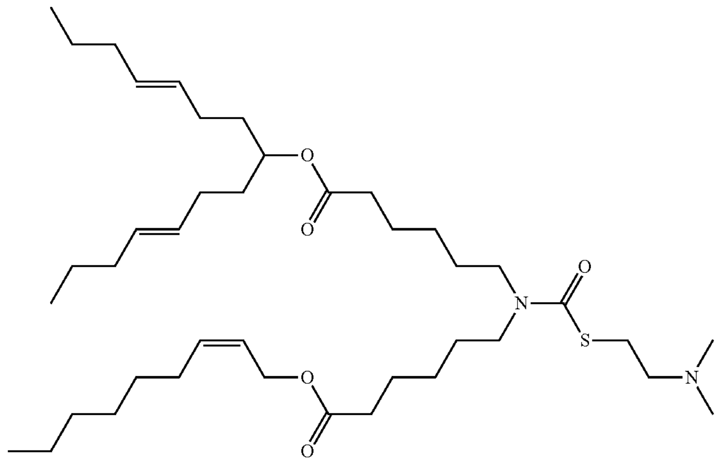
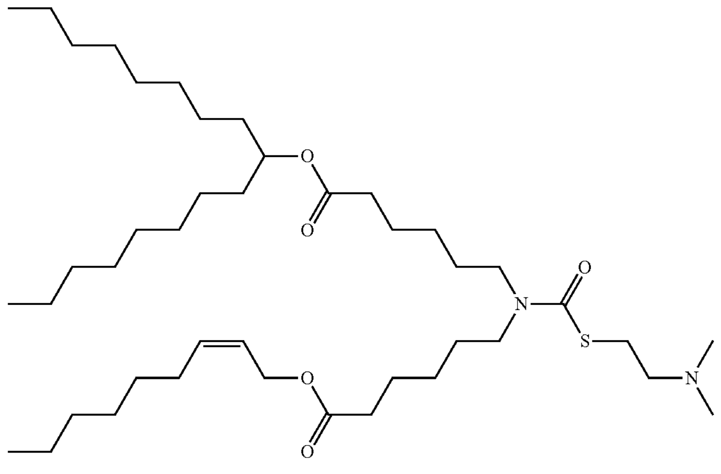

-continued
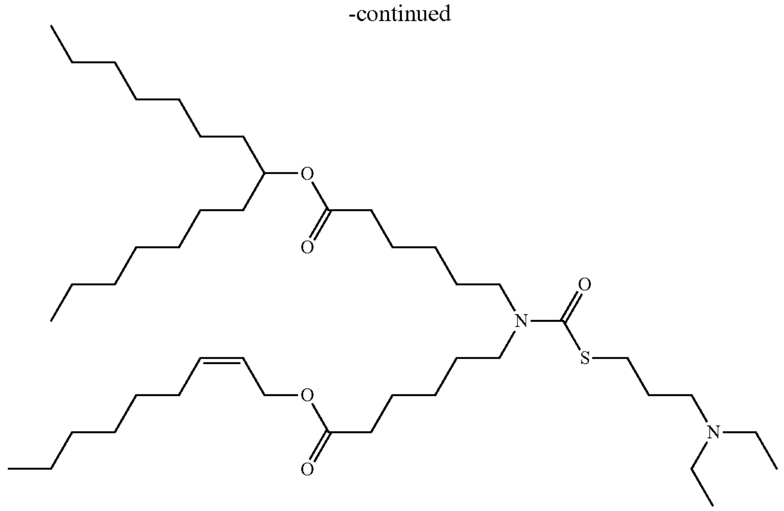
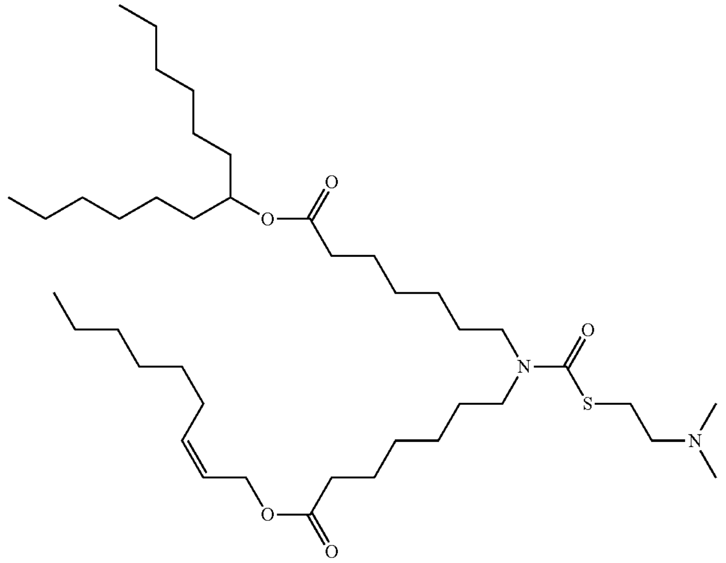
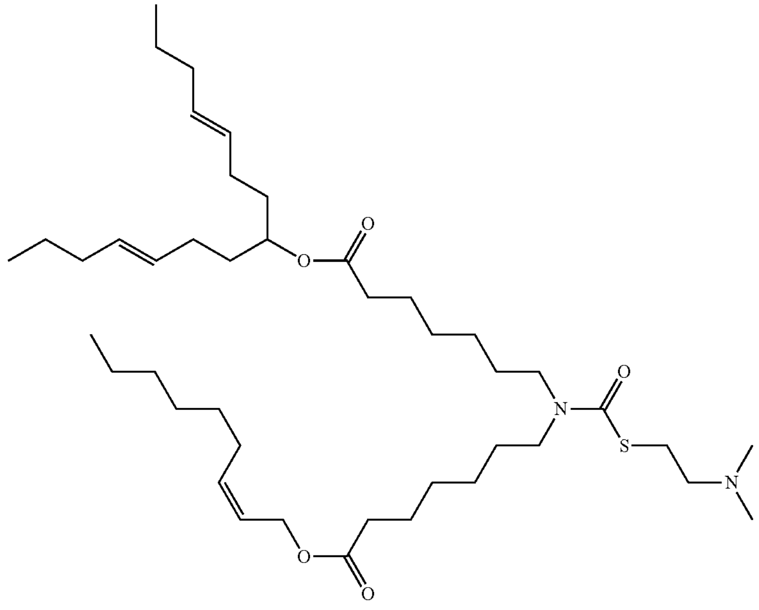

-continued
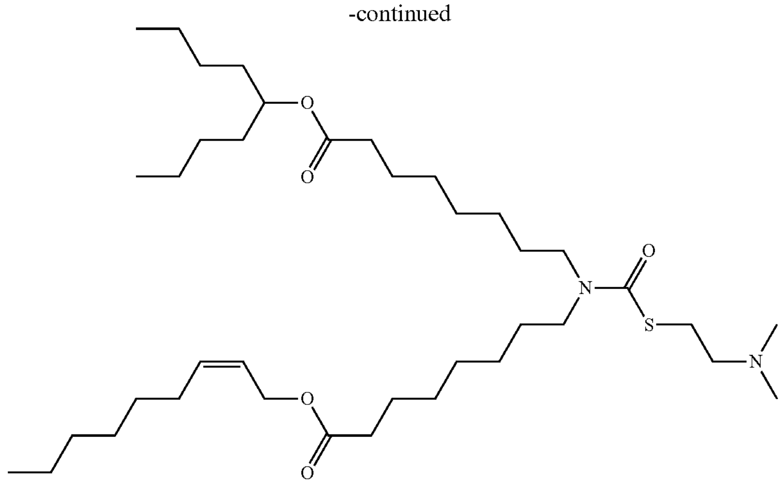
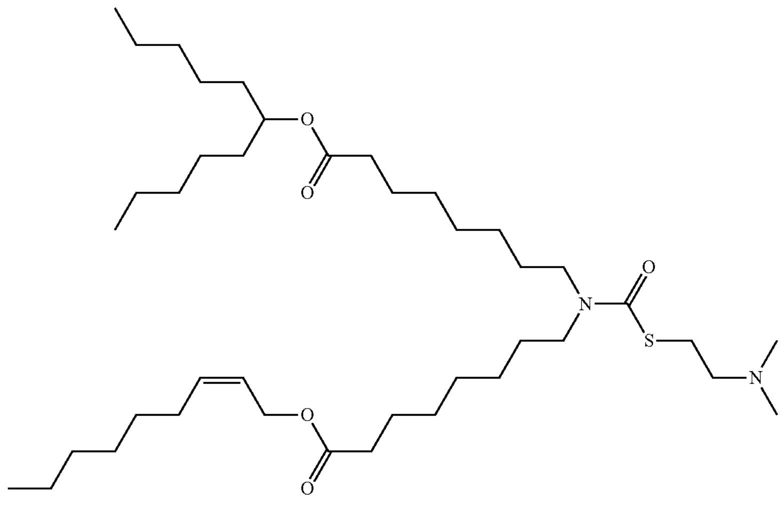
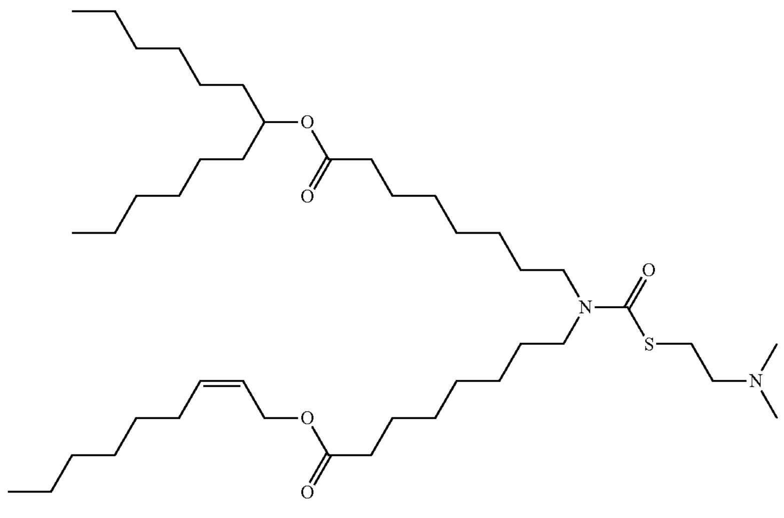

-continued

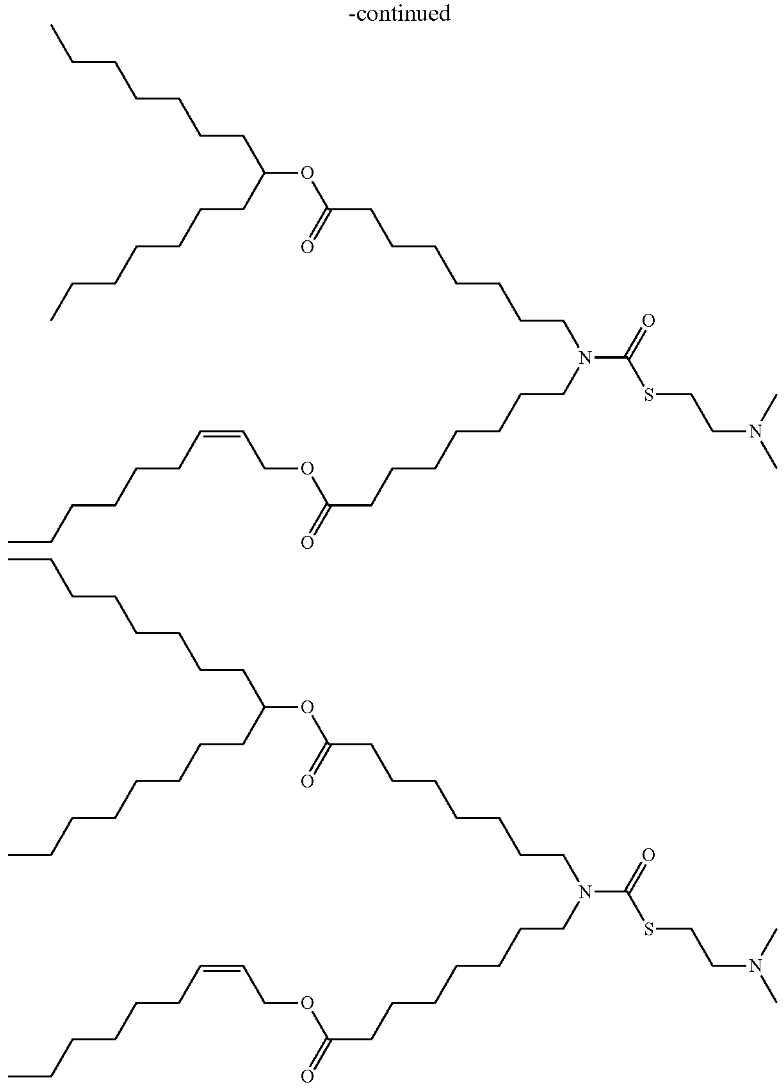

Another aspect of what is described is a compound of Formula I

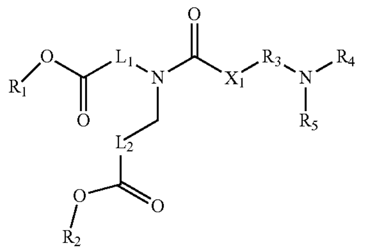

I wherein $R_1$ is a branched, noncyclic alkyl or alkenyl of 12, 13, 14, 16, 17, 18, 19, 20, 21, or 22 carbons; $L_1$ is a linear alkane of 1, 2, 3, 4, 5, 6, 7, 8, 9, 10, 11, 12, 13, 14, or 15 carbons; $R_2$ is linear alkyl or alkenyl of 5, 6, 7, 8, 9, 10, 11, 12, 13, 14 or 15 carbons or a branched, noncyclic alkyl of 10, 11, 12, 13, 14, 16, 17, 18, 19, 20, 21, or 22 carbons; $L_2$ is a linear alkane of 1, 2, 3, 4, 5, 6, 7, 8, 9, 10, 11, 12, 13, 14 or 15 carbons; X is O or S; $R_3$ is linear alkane of 1, 2, 3, 4, 5, or 6 carbons; $R_4$ and $R_5$ are the same or different, each a linear or branched, noncyclic alkyl of 1, 2, 3, 4, 5, or 6 carbons; a 1 mM solution of the compound has a pKa of 5.6 to 7.0 as measured by fluorescence of 6-(p-toluidino)-2-naphthalenesulfonic; and the compound has a c-Log D value is between 10 and 14; or a pharmaceutically acceptable salt or solvate thereof.

In some embodiments, $R_1$ has 12, 13, 14, 16, or 17 carbons.

In some embodiments, $R_1$ comprises two identical alkyl or alkenyl groups.

In some embodiments, $R_1$ comprises an alkyl group.

In some embodiments, $R_2$ is an alkenyl.

In some embodiments, $R_2$ is a branched, noncyclic alkyl.

In some embodiments, $L_1$ and $L_2$ independently have 1, 2, or 3 carbons.

In some embodiments, $L_1$ and $L_2$ both have 3 carbons.

In some embodiments, $R_3$ is propylene or butylene.

In some embodiments, the compound's c-Log D value is at least 11 and its measured pKa more basic than 6.

In some embodiments, the compound is selected from the group consisting of
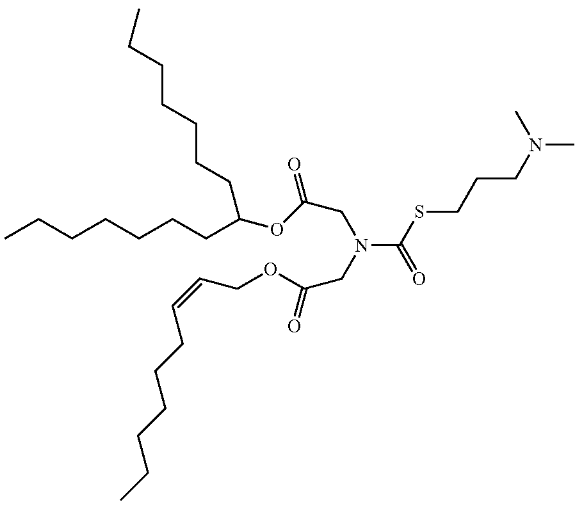
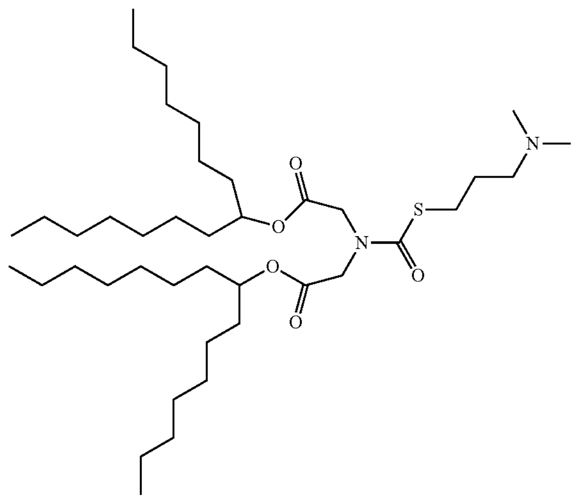
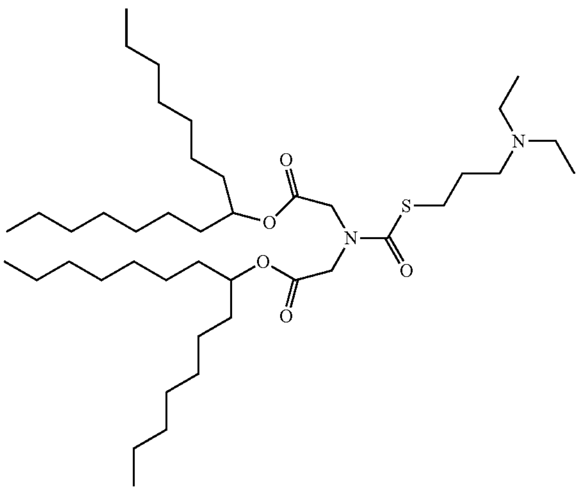
-continued
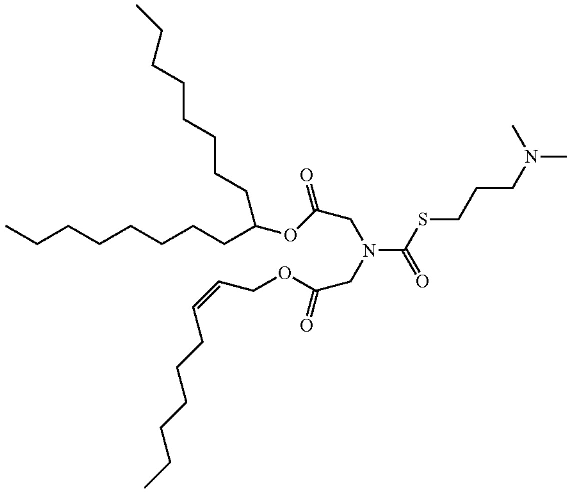
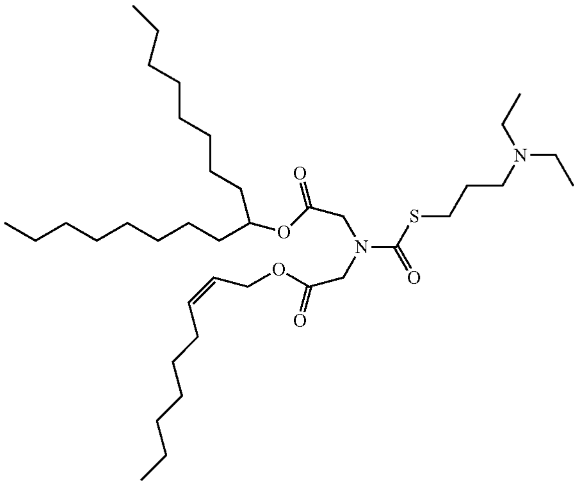
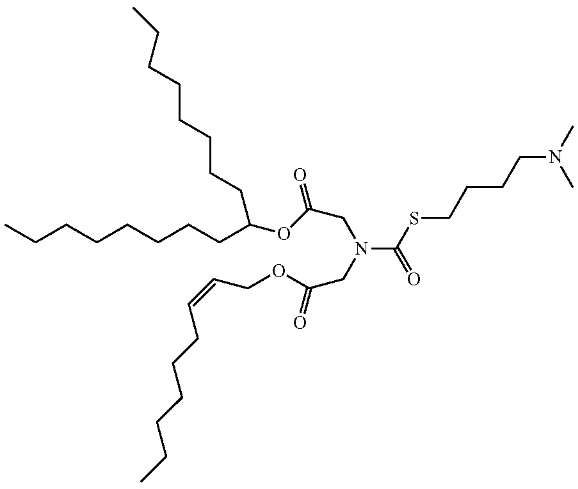

-continued
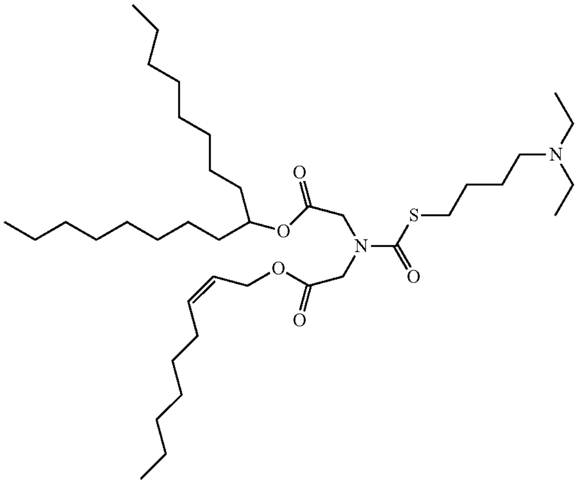
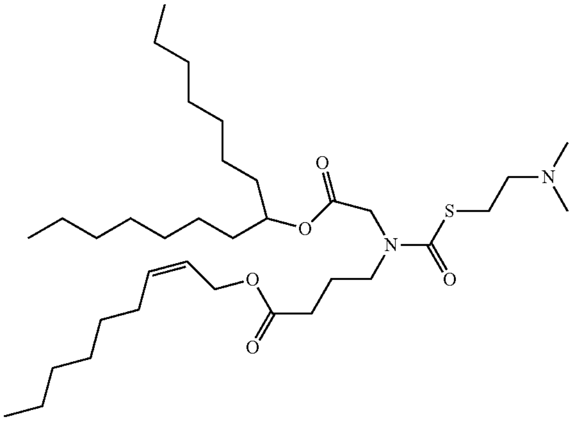
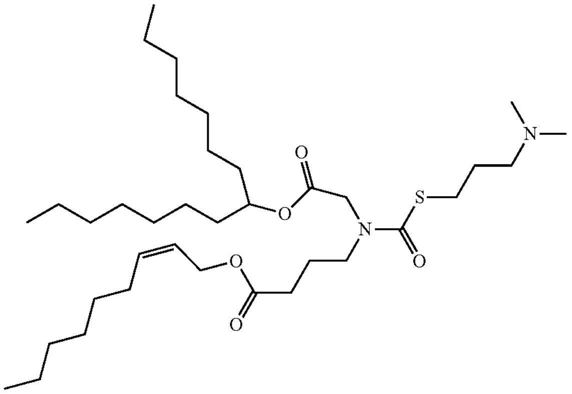
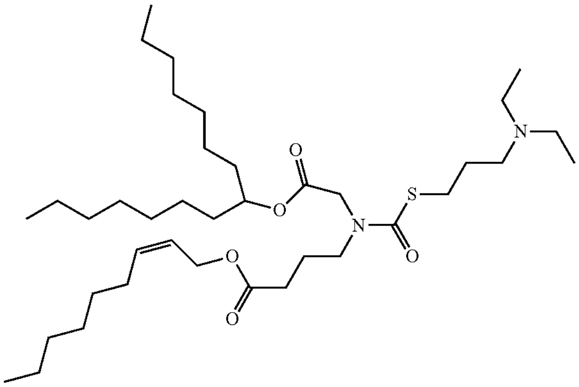
-continued
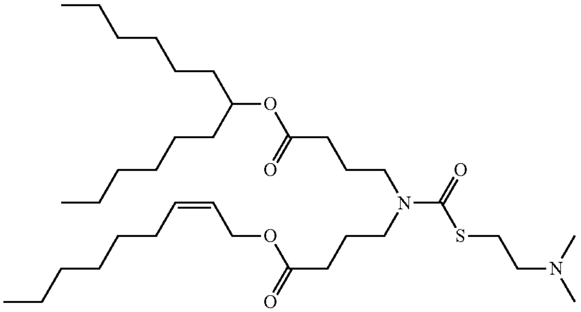
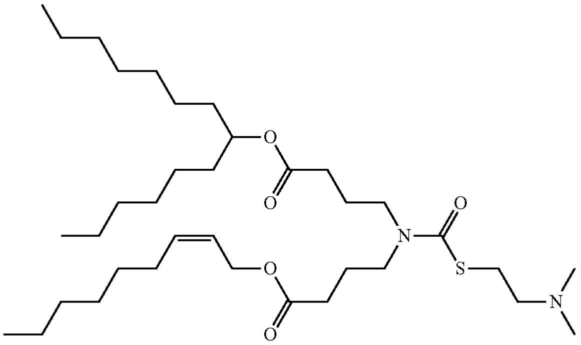
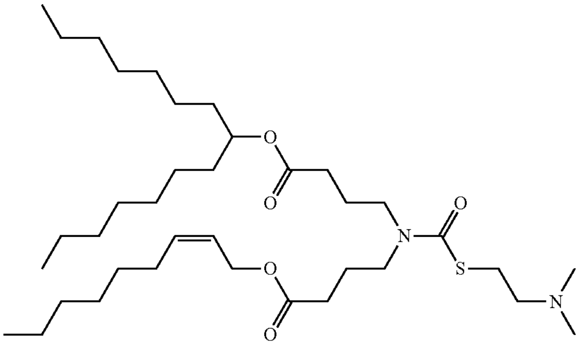
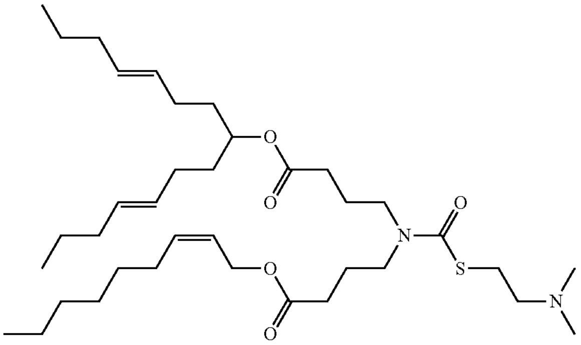
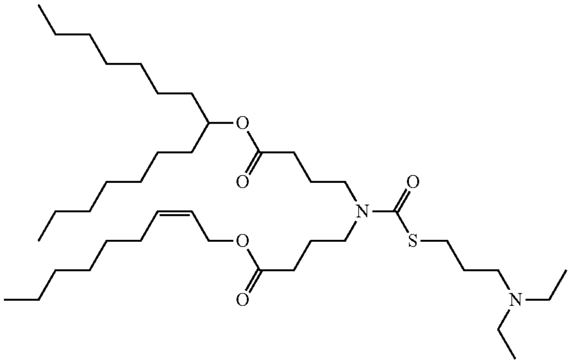

-continued
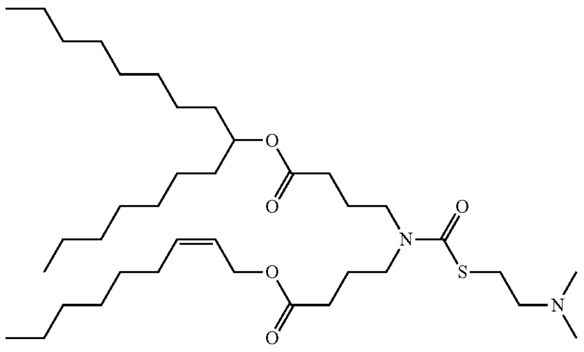
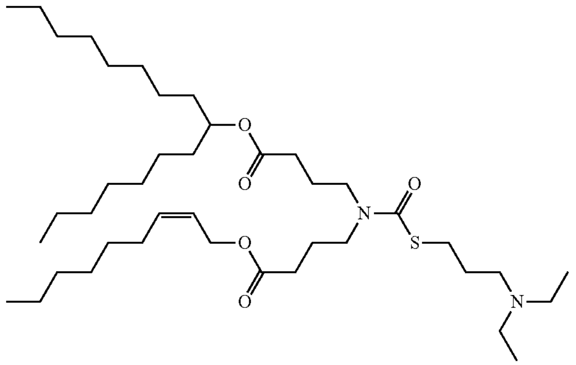
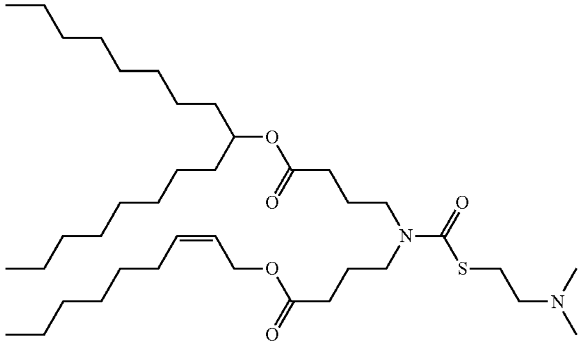
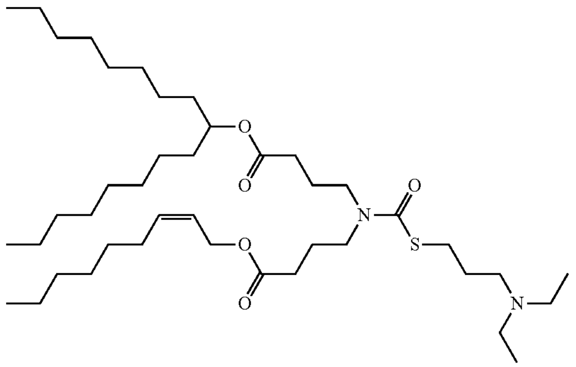
-continued
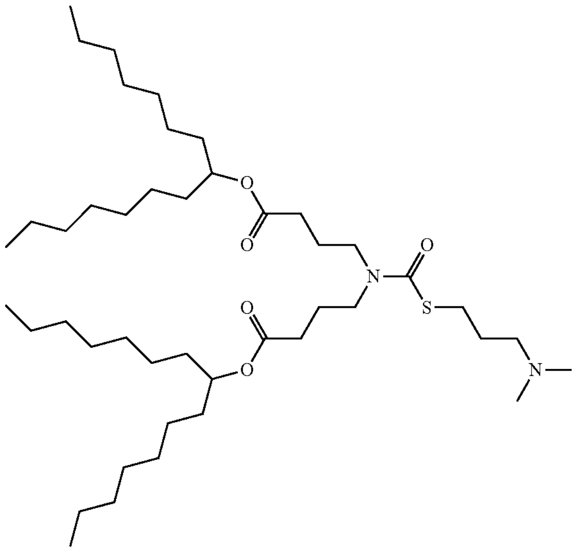
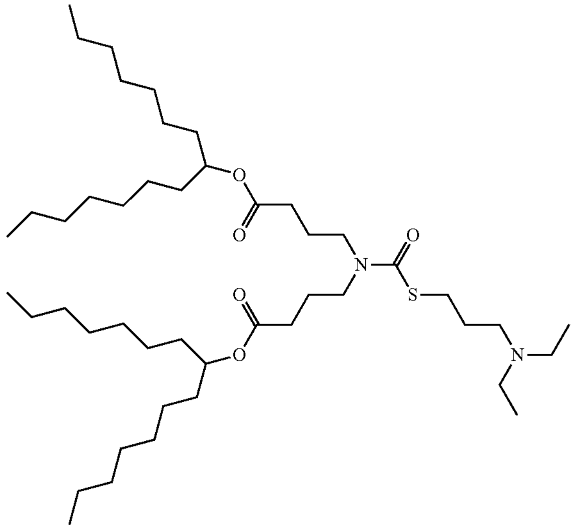
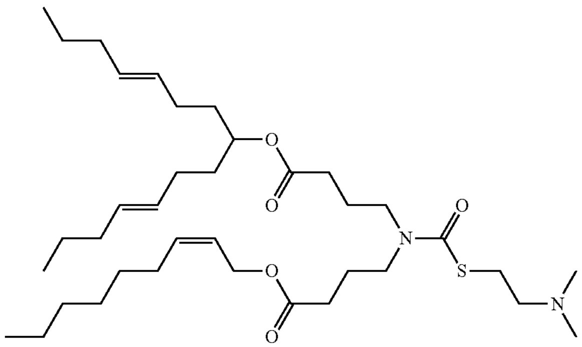

Another aspect of what is describe is a compound of Formula I

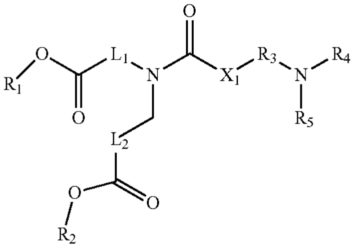

I wherein $R_1$ is a branched, noncyclic alkyl of 12, 13, 14, 16, 17, 18, 19, 20, 21, or 22 carbons; $L_1$ is a linear alkane of 1, 2, or 3 carbons; $R_2$ is linear alkenyl of 8, 9, 10, 11, or 12 carbons or a branched, noncyclic alkyl of 12, 13, 14, 16, or 17 carbons; $L_2$ is a linear alkane of 1, 2, or 3 carbons; X is O or S; $R_3$ is linear alkane of 2 or 3 carbons; $R_4$ and $R_5$ are the same or different, each a linear or branched, noncyclic alkyl of 1 or 2 carbons; or a pharmaceutically acceptable salt or solvate thereof.

In another aspect, disclosed herein is a compound of Formula I

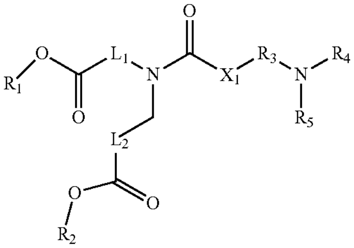

I wherein $R_1$ is

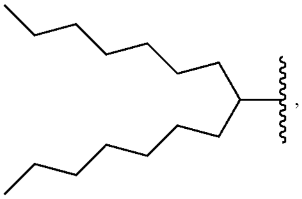

,

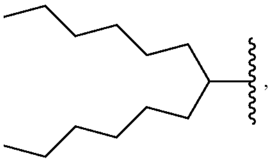

,

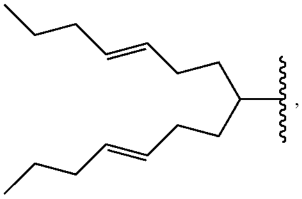

,

-continued

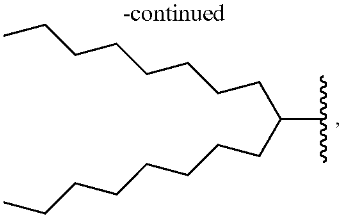

,

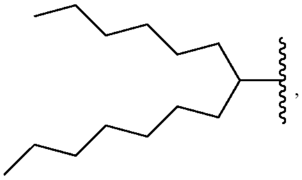

,

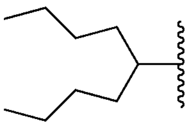

or

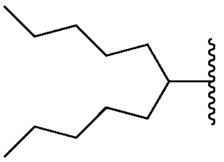

;

$R_2$ is

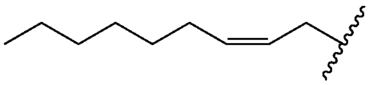

,

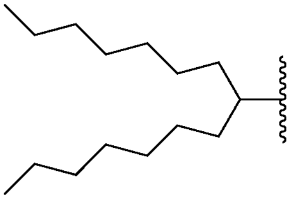

or

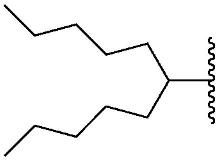

;

$L_1$ and $L_2$ are each independently a linear $C_1$-$C_{15}$ alkyl; X is O or S; $R_3$ is a linear $C_1$-$C_6$ alkyl; and $R_4$ and $R_5$ are each independently a linear $C_1$-$C_6$ alkyl; or a pharmaceutically acceptable salt or solvate thereof.

In some embodiments, $L_2$ is $C_5$-$C_7$ alkyl.

In some embodiments, $L_1$ is $C_3$-$C_7$ alkyl.

In some embodiments, $R_3$ is ethyl, propyl or butyl.

In some embodiments, $R_4$ and $R_5$ are each independently methyl or ethyl.

In some embodiments, $R_1$ is

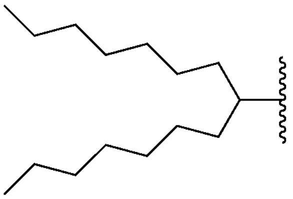

;

$R_2$ is

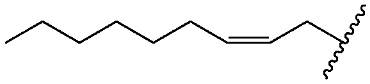
;

$L_1$ and $L_2$ are each $C_3$-$C_6$ alkyl; X is S or O; $R_3$ is ethyl; and $R_4$ and $R_5$ are each methyl.

In some embodiments, $R_1$ is

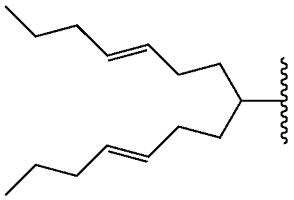
;

$R_2$ is

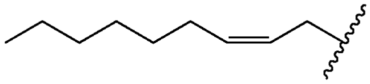
;

$L_1$ and $L_2$ are each $C_3$-$C_6$ alkyl; X is S or O; $R_3$ is ethyl; and $R_4$ and $R_5$ are each methyl.

In yet another aspect, disclosed herein is a compound of Formula I

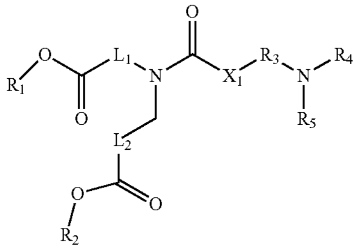
I wherein $R_1$ is

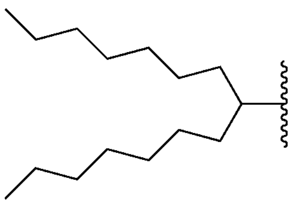
,

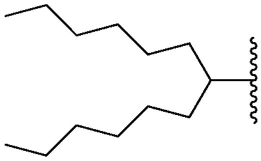
,

-continued

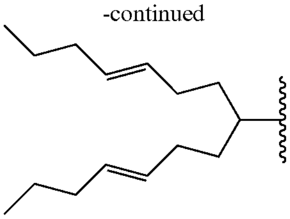
,

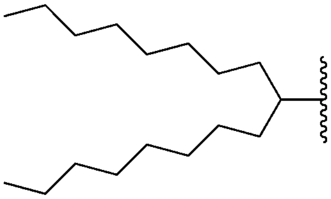
,

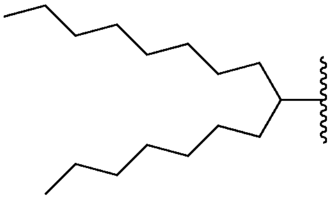

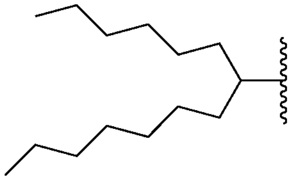
,

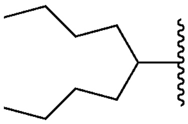
or

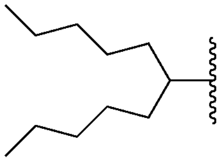
;

$R_2$ is

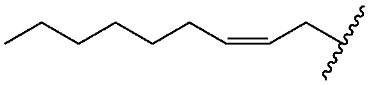
,

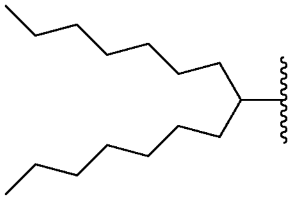
or

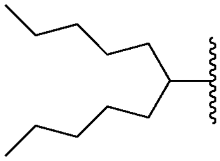
;

$L_1$ and $L_2$ are each independently a linear $C_1$-$C_3$ alkyl; X is O or S; $R_3$ is linear $C_1$-$C_3$ alkyl; $R_4$ and $R_5$ are each independently a $C_1$-$C_2$ alkyl; or a pharmaceutically acceptable salt or solvate thereof.

In some embodiments, $L_1$ and $L_2$ are each independently $C_1$-$C_3$ alkyl.

In some embodiments, $R_3$ is ethyl, propyl or butyl.

In some embodiments, $R_4$ and $R_5$ are each independently methyl or ethyl.

In some embodiments, $R_1$ is

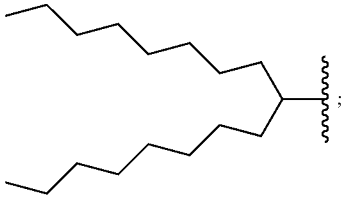 [SMILES: *C(CCCCCCCC)CCCCCCCC]

$R_2$ is

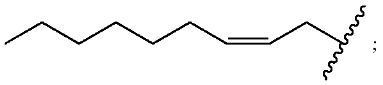 [SMILES: *C/C=C\CCCCCC]

$L_1$ and $L_2$ are each $C_1$-$C_3$ alkyl; X is S or O; $R_3$ is a linear $C_4$ alkyl; and $R_4$ and $R_5$ are each ethyl.

In some embodiments, $R_1$ is

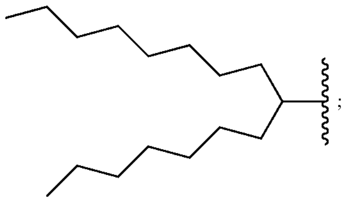 [SMILES: *C(CCCCCCC)CCCCCCCC]

$R_2$ is

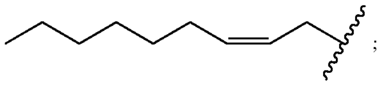 [SMILES: *C/C=C\CCCCCC]

$L_1$ and $L_2$ are each $C_1$-$C_3$ alkyl; X is S or O; $R_3$ is a linear $C_3$ alkyl; and $R_4$ and $R_5$ are each ethyl.

In some embodiments, $R_1$ is

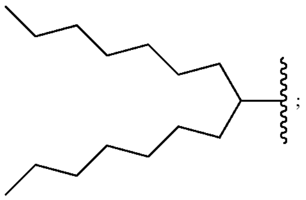 [SMILES: *C(CCCCCCC)CCCCCCC]

$R_2$ is

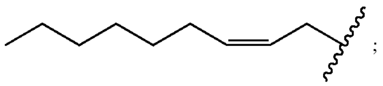 [SMILES: *C/C=C\CCCCCC]

$L_1$ and $L_2$ are each $C_1$-$C_3$ alkyl; X is S or O; $R_3$ is ethyl; and $R_4$ and $R_5$ are each methyl.

In some embodiments, $R_1$ is

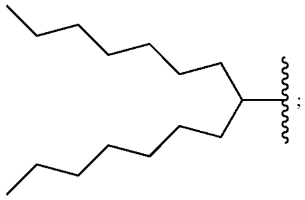

$R_2$ is

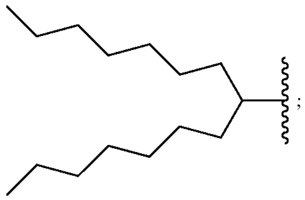 [SMILES: *C(CCCCCCC)CCCCCCC]

$L_1$ and $L_2$ are each $C_1$-$C_3$ alkyl; X is S or O; $R_3$ is a $C_3$ alkyl; and $R_4$ and $R_5$ are each methyl.

In another aspect, disclosed herein is a pharmaceutical composition comprising compound of Formula I

I

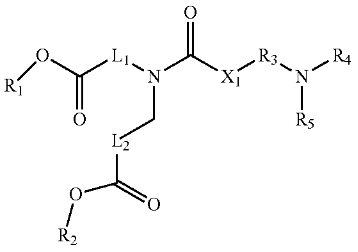

wherein $R_1$ is

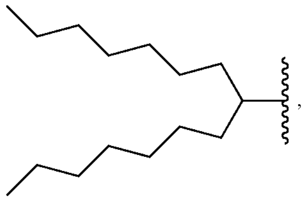 [SMILES: *C(CCCCCCC)CCCCCCC]

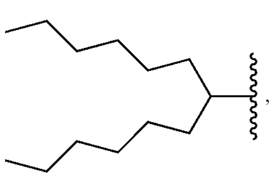

-continued
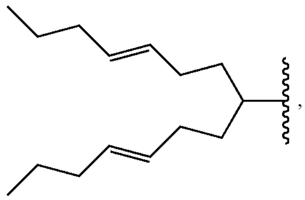,
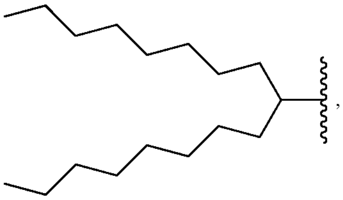,
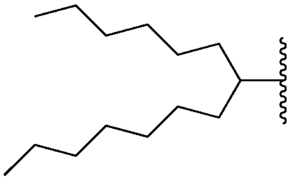, 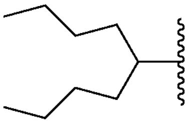 or
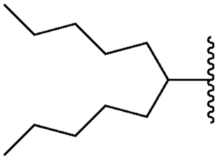;
$R_2$ is
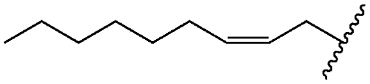,
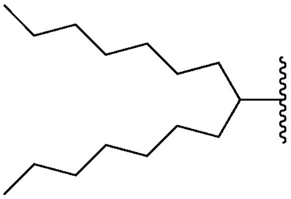 or
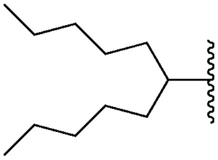;
$L_1$ and $L_2$ are each independently a linear $C_1$-$C_{15}$ alkyl; X is O or S; $R_3$ is a linear $C_1$-$C_6$ alkyl; and $R_4$ and $R_5$ are each independently a linear $C_1$-$C_6$ alkyl; or a pharmaceutically acceptable salt or solvate thereof.
In another aspect, disclosed herein is a pharmaceutical composition comprising compound of Formula I
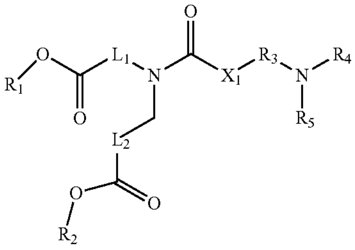
I
wherein
$R_1$ is
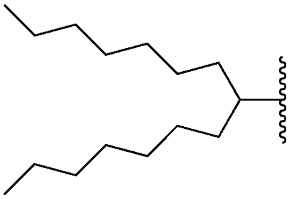,
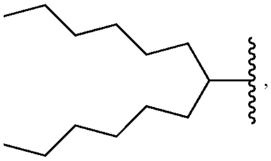,
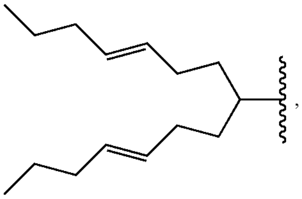,
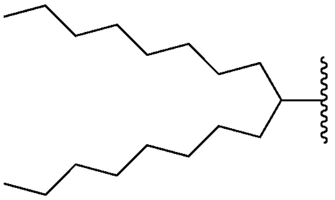,
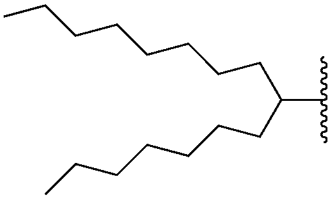
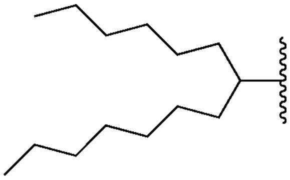, 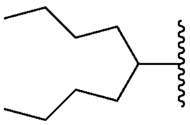 or -continued

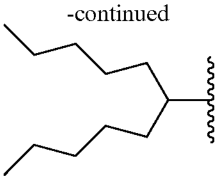

;

$R_2$ is

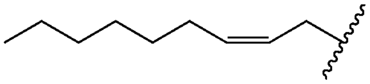

,

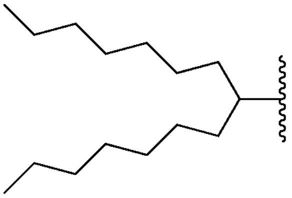

or

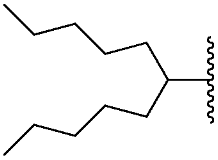

;

$L_1$ and $L_2$ are each independently a linear $C_1$-$C_3$ alkyl; X is O or S; $R_3$ is linear $C_1$-$C_3$ alkyl; $R_4$ and $R_5$ are each independently a $C_1$-$C_2$ alkyl; or a pharmaceutically acceptable salt or solvate thereof.

In some embodiments, the pharmaceutical composition further comprises the compound of Formula I in a lipid nanoparticle, wherein the lipid nanoparticle encapsulates a mRNA.

In some embodiments, the lipid nanoparticle further comprises a neutral lipid and/or a conjugated lipid.

In some embodiments, the pharmaceutical composition further comprises a mRNA encoding a biologically active protein.

In some embodiments, the pharmaceutical composition further comprises an RNA comprising a nucleotide sequence homologous to a mRNA in a target cell.

Definitions

"At least one" means one or more (e.g., 1-3, 1-2, or 1).

"Composition" means a product comprising the specified ingredients in the specified amounts, as well as any product that results, directly or indirectly, from combination of the specified ingredients in the specified amounts.

"In combination with" means the administration of a compound of Formula I with other medicaments in the methods of treatment of this invention, meaning that the compounds of Formula I and the other medicaments are administered sequentially or concurrently in separate dosage forms, or are administered concurrently in the same dosage form.

"Mammal" means a human or other mammal or means a human being.

"Patient" means both human and other mammals, preferably human.

"Alkyl" means a saturated or unsaturated, straight or branched, hydrocarbon chain. In various embodiments, the alkyl group has 1-18 carbons, i.e. is a $C_1$-$C_{18}$ group, or is a $C_1$-$C_{12}$ group, a $C_1$-$C_6$ group, or a $C_1$-$C_4$ group. Independently, in various embodiments, the alkyl group has zero branches (i.e., is a straight chain), one branch, two branches, or more than two branches. "Alkenyl" is an unsaturated alkyl that may have one double bond, two double bonds, or more than two double bonds. "Alkynyl" is an unsaturated alkyl that may have one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having one to six carbons in the chain which chain may be straight or branched. Non-limiting examples of suitable alkyl groups include methyl, ethyl, n-propyl, isopropyl, n-butyl, t-butyl, n-pentyl, and hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Carboxyalkyl" means an HOOC-alkyl-group, wherein alkyl is as defined above, bound to the parent moiety through the alkyl group.

"Commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif., 1972; T. L. Glichrist, "Heterocyclic Chemistry," 2nd Ed. John Wiley and Sons, New York, 1992; J. March, "Advanced Organic Chemistry: reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" means a saturated or unsaturated, straight or branched, chain containing carbon and at least one heteroatom. The heteroalkyl group may, in various embodiments, have one heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have, e.g., 1-2 substituents, or 1-3 substituents, or 1-4 substituents. Exemplary heteroalkyl substituents include esters (—C(O)—O—R) and carbonyls (—C(O)—).

"Hydroxyalkyl" refers to an HO-alkyl group, wherein alkyl is previously defined herein. Preferred hydroxyalkyls contain lower alkyl. Non-limiting examples of suitable hydroxyalkyl groups include hydroxymethyl and 2-hydroxyethyl.

"Hydrate" means a solvate wherein the solvent molecule is $H_2O$.

"Lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids, glycolipids, cationic lipids, non-cationic lipids, neutral lipids, and anionic lipids, all described in more detail herein; and (3) "derived lipids" such as steroids.

"Lipid particle" means a lipid Formulation that can be used to deliver a therapeutic nucleic acid (e.g., mRNA) to a target site of interest (e.g., cell, tissue, organ, and the like). In preferred embodiments, the lipid particle is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

Lipid particles typically have a mean diameter of from 30 nm to 150 nm, from 40 nm to 150 nm, from 50 nm to 150 nm, from 60 nm to 130 nm, from 70 nm to 110 nm, from 70 nm to 100 nm, from 80 nm to 100 nm, from 90 nm to 100 nm, from 70 to 90 nm, from 80 nm to 90 nm, from 70 nm to 80 nm, or 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease.

"Lipid encapsulated" means a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

"Lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

"Amphipathic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

"Neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

"Non-cationic lipid" means an amphipathic lipid or a neutral lipid or anionic lipid, and is described in more detail below.

"Anionic lipid" means a lipid that is negatively charged at physiological pH. These lipids include, but are not limited to phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

"Hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

"Cationic lipid" and "amino lipid" are used interchangeably mean those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, γ-DLen-C2K-DMA, DLin-M-C2-DMA (also known as MC2), DLin-M-C3-DMA (also known as MC3) and (DLin-MP-DMA)(also known as 1-Bl 1).

"Substituted" means substitution with specified groups other than hydrogen, or with one or more groups, moieties, or radicals which can be the same or different, with each, for example, being independently selected.

"Antisense nucleic acid", means a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof "Antisense RNA" is an RNA strand having a sequence complementary to a target gene mRNA, that can induce RNAi by binding to the target gene mRNA. "Antisense RNA" is an RNA strand having a sequence complementary to a target gene mRNA and thought to induce RNAi by binding to the target gene mRNA. "Sense RNA" has a sequence complementary to the antisense RNA and annealed to its complementary antisense RNA to form iNA. These antisense and sense RNAs have been conventionally synthesized with an RNA synthesizer.

"Nucleic acid" means deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

"RNA" means a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

"Nucleotides" means natural bases (standard) and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

"Complementary nucleotide bases" means a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (i.e. join by hydrogen bonding) with each other. By "complementary" it is meant that a nucleic acid can form hydrogen bond(s) with another nucleic acid sequence either by traditional Watson-Crick or by other non-traditional modes of binding.

"MicroRNAs" (miRNA) means single-stranded RNA molecules of 21-23 nucleotides in length, which regulate gene expression miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression "Small interfering RNA (siRNA)" and "short interfering RNA" and "silencing RNA" mean a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

"RNAi" means an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

Compound of Formula I

Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when compound of Formula I contain both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of a compound of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compound are discussed, for example, by S. Berge et al, *J. Pharmaceutical Sciences* (1977) 66(1)1-19; P. Gould, International *J. Pharmaceutics* (1986) 33 201-217; Anderson et al., The Practice of Medicinal Chemistry (1996), Academic Press, New York; and in The Orange Book (Food & Drug Administration, Washington, D.C. on their website). These disclosures are incorporated by reference herein.

Exemplary basic salts include ammonium salts, alkali metal salts such as sodium, lithium, and potassium salts, alkaline earth metal salts such as calcium and magnesium salts, salts with organic bases (for example, organic amines)

such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine or lysine. Basic nitrogen-containing groups may be quarternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compound of Formula I for purposes of the disclosure.

Compound of Formula I can exist in unsolvated and solvated forms, including hydrated forms. In general, the solvated forms, with pharmaceutically acceptable solvents such as water, ethanol, and the like, are equivalent to the unsolvated forms for the purposes of this disclosure.

Compound of Formula I and salts, solvates thereof, may exist in their tautomeric form (for example, as an amide or imino ether). All such tautomeric forms are contemplated herein as part of the present disclosure.

Also, within the scope of the present disclosure are polymorphs of the compound of this disclosure (i.e., polymorphs of the compound of Formula I are within the scope of this disclosure).

All stereoisomers (for example, geometric isomers, optical isomers, and the like) of the present compound (including those of the salts, solvates, and prodrugs of the compound as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compound of this disclosure may, for example, be substantially free of other isomers, or may be admixed, for example, as racemates or with all other, or other selected, stereoisomers. The chiral centers of the compound herein can have the S or R configuration as defined by the IUPAC 1974 Recommendations. The use of the terms "salt", "solvate", and the like, is intended to equally apply to the salt and solvate of enantiomers, stereoisomers, rotamers, tautomers, racemates, or prodrugs of the disclosed compound.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Lipid Particles

A compound of Formula I includes a pharmaceutically acceptable salt thereof, in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid preferably has an activity of suppressing the expression of the target gene by utilizing RNA interference (RNAi). The lipid composition preferably further comprises a nucleic acid and a neutral lipid or a polymer. The lipid composition preferably encapsulates the nucleic acid.

The description provides lipid particles comprising one or more therapeutic mRNA molecules encapsulated within the lipid particles.

In some embodiments, the mRNA is fully encapsulated within the lipid portion of the lipid particle such that the mRNA in the lipid particle is resistant in aqueous solution to nuclease degradation. In other embodiments, the lipid particles described herein are substantially non-toxic to mammals such as humans. The lipid particles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid particles of the invention also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1. In one embodiment, the lipid particles have a lipid:RNA ratio (mass/mass ratio) of 12:1. In another embodiment, the lipid particles have a lipid:mRNA ratio (mass/mass ratio) of 13:1.

In preferred embodiments, the lipid particles comprise an mRNA, a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may comprise at least 1, 2, 3, 4, 5, 6, 7, 8, 9, 10, or more mRNA that express one or more polypeptides.

In the nucleic acid-lipid particles, the mRNA may be fully encapsulated within the lipid portion of the particle, thereby protecting the nucleic acid from nuclease degradation. In preferred embodiments, a lipid particle comprising an mRNA is fully encapsulated within the lipid portion of the particle, thereby protecting the nucleic acid from nuclease degradation. In certain instances, the mRNA in the lipid particle is not substantially degraded after exposure of the particle to a nuclease at 37° C. for at least 20, 30, 45, or 60 minutes. In certain other instances, the mRNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the particle. One of the benefits of the Formulations of the present invention is that the nucleic acid-lipid particle compositions are substantially non-toxic to mammals such as humans.

"Fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal Formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-1)/I_0$, where/and $I_0$ refers to the fluorescence intensities before and after the addition of detergent.

In other embodiments, the present invention provides a nucleic acid-lipid particle composition comprising a plurality of nucleic acid-lipid particles.

The lipid particle comprises mRNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the mRNA encapsulated therein.

Depending on the intended use of the lipid particles, the proportions of the components can be varied and the delivery efficiency of a particular Formulation can be measured using assays know in the art.

Cationic Lipids

The description includes synthesis of certain cationic lipid compounds. The compounds are particularly suitable for delivering polynucleotides to cells and tissues as demonstrated in subsequent sections. The lipomacrocycle compound described herein may be used for other purposes as well as, for example, recipients and additives.

The synthetic methods for the cationic lipid compounds can be synthesized with the skills in the art. Those skilled in the art will recognize other methods to produce these compounds, and also to produce the other compounds of the description.

The cationic lipid compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The lipomacrocycle compounds may be combined with other cationic lipid compounds, polymers (synthetic or natural), surfactants, cholesterol, carbohydrates, proteins, or lipids, to form the particles. These particles may then optionally be combined with a pharmaceutical excipient to form a pharmaceutical composition.

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, or drugs, to a patient, tissue, organ, or cell. These novel compounds may also be used as materials for coating, additives, excipients, materials, or bioengineering.

The cationic lipid compounds of the present description provide for several different uses in the drug delivery art. The amine-containing portion of the cationic lipid compounds may be used to complex polynucleotides, thereby enhancing the delivery of polynucleotide and preventing their degradation. The cationic lipid compounds may also be used in the formation of picoparticles, nanoparticles, microparticles, liposomes, and micelles containing the agent to be delivered. Preferably, the cationic lipid compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have a measured pKa (in the Formulation milieu) in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

Neutral Helper Lipids

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the non-cationic lipid present in lipid particles comprises or consists of a mixture of one or more phospholipids and cholesterol or a derivative thereof.

In other embodiments, the non-cationic lipid present in the lipid particles comprises or consists of one or more phospholipids, e.g., a cholesterol-free lipid particle Formulation. In yet other embodiments, the non-cationic lipid present in the lipid particles comprises or consists of cholesterol or a derivative thereof, e.g., a phospholipid-free lipid particle Formulation.

Other examples of non-cationic lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the non-cationic lipid comprises from 10 mol % to 60 mol %, from 20 mol % to 55 mol %, from 20 mol % to 45 mol %, 20 mol % to 40 mol %, from 25 mol % to 50 mol %, from 25 mol % to 45 mol %, from 30 mol % to 50 mol %, from 30 mol % to 45 mol %, from 30 mol % to 40 mol %, from 35 mol % to 45 mol %, from 37 mol % to 42 mol %, or 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, the phospholipid component in the mixture may comprise from 2 mol % to 20 mol %, from 2 mol % to 15 mol %, from 2 mol % to 12 mol %, from 4 mol % to 15 mol %, or from 4 mol % to 10 mol % (or any fraction thereof or range therein) of the total lipid present in the particle. In certain preferred embodiments, the phospholipid component in the mixture comprises from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

In other embodiments, the cholesterol component in the mixture may comprise from 25 mol % to 45 mol %, from 25 mol % to 40 mol %, from 30 mol % to 45 mol %, from 30 mol % to 40 mol %, from 27 mol % to 37 mol %, from 25 mol % to 30 mol %, or from 35 mol % to 40 mol % (or any fraction thereof or range therein) of the total lipid present in the particle. In certain preferred embodiments, the cholesterol component in the mixture comprises from 25 mol % to 35 mol %, from 27 mol % to 35 mol %, from 29 mol % to 35 mol %, from 30 mol % to 35 mol %, from 30 mol % to 34 mol %, from 31 mol % to 33 mol %, or 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle Formulation may comprise from 25 mol % to 45 mol %, from 25 mol % to 40 mol %, from 30 mol % to 45 mol %, from 30 mol % to 40 mol %, from 31 mol % to 39 mol %, from 32 mol % to 38 mol %, from 33 mol % to 37 mol %, from 35 mol % to 45 mol %, from 30 mol % to 35 mol %, from 35 mol % to 40 mol %, or 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle.

In other embodiments, the non-cationic lipid comprises from 5 mol % to 90 mol %, from 10 mol % to 85 mol %, from 20 mol % to 80 mol %, 10 mol % (e.g., phospholipid only), or 60 mol % (e.g., phospholipid and cholesterol or derivative thereof) (or any fraction thereof or range therein) of the total lipid present in the particle.

The percentage of non-cationic lipid present in the lipid particles is a target amount, and that the actual amount of non-cationic lipid present in the Formulation may vary, for example, by ±5 mol %.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5-10% phospholipid, and 1-10% PEG. The composition may contain 60-70% cationic lipid compound, 25-35% cholesterol, and 5-10% PEG. The composition may contain up to 90% cationic lipid compound and 2-15% helper lipid.

The Formulation may be a lipid particle Formulation, for example containing 8-30% compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

In addition to cationic, the lipid particles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

In a preferred embodiment, the lipid conjugate is a PEG-lipid. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-$NH_2$).

The PEG moiety of the PEG-lipid conjugates described herein may comprise an average molecular weight ranging from 550 daltons to 10,000 daltons. In certain instances, the PEG moiety has an average molecular weight of from 750 daltons to 5,000 daltons (e.g., from 1,000 daltons to 5,000 daltons, from 1,500 daltons to 3,000 daltons, from 750 daltons to 3,000 daltons, from 750 daltons to 2,000 daltons). In preferred embodiments, the PEG moiety has an average molecular weight of 2,000 daltons or 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)$CCH_2CH_2C(O)$—), succinamidyl (—NHC(O)$CH_2CH_2C$(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{15}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl).

The term "dialkyloxypropyl" or "DAA" includes a compound having 2 alkyl chains, $R_1$ and $R_2$, both of which have independently between 2 and 30 carbons. The alkyl groups can be saturated or have varying degrees of unsaturation.

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{15}$) conjugate. In these embodiments, the PEG preferably has an average molecular weight of 750 or 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from 0.1 mol % to 2 mol %, from 0.5 mol % to 2 mol %, from 1 mol % to 2 mol %, from 0.6 mol % to 1.9 mol %, from 0.7 mol % to 1.8 mol %, from 0.8 mol % to 1.7 mol %, from 0.9 mol % to 1.6 mol %, from 0.9 mol % to 1.8 mol %, from 1 mol % to 1.8 mol %, from 1 mol % to 1.7 mol %, from 1.2 mol % to 1.8 mol %, from 1.2 mol % to 1.7 mol %, from 1.3 mol % to 1.6 mol %, or from 1.4 mol % to 1.5 mol % (or any fraction thereof or range therein) of the total lipid present in the particle. In other embodiments, the lipid conjugate (e.g., PEG-lipid) comprises from 0 mol % to 20 mol %, from 0.5 mol % to 20 mol %, from 2 mol % to 20 mol %, from 1.5 mol % to 18 mol %, from 2 mol % to 15 mol %, from 4 mol % to 15 mol %, from 2 mol % to 12 mol %, from 5 mol % to 12 mol %, or 2 mol % (or any fraction thereof or range therein) of the total lipid present in the particle.

In further embodiments, the lipid conjugate (e.g., PEG-lipid) comprises from 4 mol % to 10 mol %, from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

The percentage of lipid conjugate (e.g., PEG-lipid) present in the lipid particles of the invention is a target amount, and the actual amount of lipid conjugate present in the Formulation may vary, for example, by ±2 mol %. One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. In addition, other variables including, e.g., pH, temperature, or ionic strength, can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Compositions and Formulations for Administration

The nucleic acid-lipid compositions of this disclosure may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic, a cationic lipid, an amphiphile, a phospholipid, cholesterol, and a PEG-linked cholesterol may be administered to a subject having a disease or disorder associated with expression or overexpression of a gene that can be reduced, decreased, downregulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in either a liquid or a solid form. Preferred systems for dispensing liquids as a nasal spray are disclosed in U.S. Pat. No. 4,511,069. Such Formulations may be conveniently prepared by dissolving compositions according to the present disclosure in water to produce an aqueous solution, and rendering said solution sterile. The Formulations may be presented in multi-dose containers, for example in the sealed dispensing system disclosed in U.S. Pat. No. 4,511,069. Other suitable nasal spray delivery systems have been described in TRANSDERMAL SYSTEMIC MEDICATION, Y. W. Chien ed., Elsevier Publishers, New York, 1985; and in U.S. Pat. No. 4,778,810. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally Formulated with a surface active agent, such as a nonionic surfactant (e.g., polysorbate-80), and one or more buffers. In some embodiments of the present disclosure, the nasal spray solution further comprises a propellant. The pH of the nasal spray solution may be from pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

To Formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the Formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer, and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3,000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time-release Formulation, for example in a composition which includes a slow release polymer. The active agent can be prepared with carriers that will protect against rapid release, for example a controlled release vehicle such as a polymer, microencapsulated delivery system, or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

EXAMPLES

Example 1: Exemplary Lipids

Exemplary compounds of Formula I are provided in Table 1. The structure of the Compound is shown in the first column. The designation of the compound is given according to Formula I

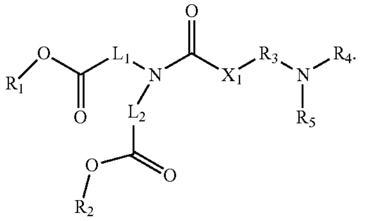

I

The first pair of numbers denotes the number of carbons in the ester, including the carbonyl, for $L_1$ and $L_2$; the pair of numbers in the parenthesis denotes the number of carbons in each branch of the branched alkyl, $R_1$ or if $R_2$ is also branched, $R_1/R_2$ (an asterisk denotes a double bond); the number of carbons in $R_3$ is given; and the last line denotes the substitution for $R_4$ and $R_5$. The ATX number is given for reference herein. Calculated Log D values (c-Log D) and calculated pKa (c-pKa) values are given, as well as measured pKa in parenthesis (measured in the Formulation milieu). The c-Log D and c-pKa values are generated by ACD Labs Structure Designer v12.0. Bioactivity is percentage in vivo Factor VII knockdown at a dose of 0.03 mg/kg, unless otherwise designated.

TABLE 1

| Compound | Designation | c-LogD | c-pKa (pKa) | Bio-activity |
|---|---|---|---|---|
| 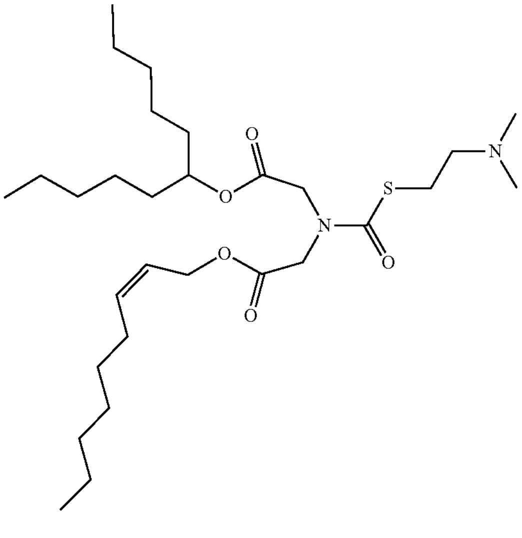 [SMILES: CCCCCC/C=C\COC(=O)CN(CC(=O)OC(CCCCC)CCCCC)C(=O)SCCN(C)C] | 2,2 (5,5) 2-C $CH_3$ | 8.29 | 8.56 (5.39) | 0 |

TABLE 1-continued
| Compound | Designa-tion | c-LogD | c-pKa (pKa) | Bio-activity |
|---|---|---|---|---|
| 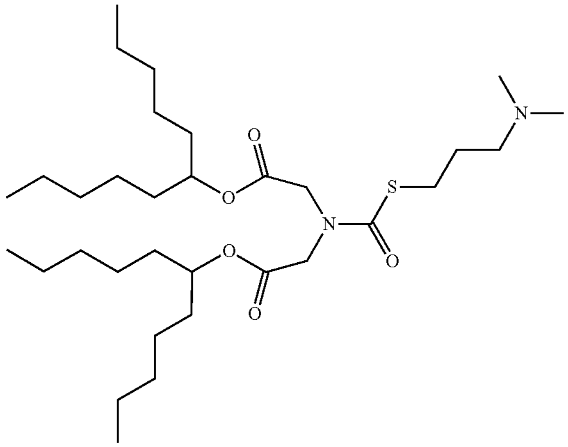 [SMILES: CCCCCC(CCCCC)OC(=O)CN(CC(=O)OC(CCCCC)CCCCC)C(=O)SCCCN(C)C] | 2,2 (5,5/5,5) 3-C $CH_3$ | 8.96 | 9.30 (6.28) (6.17) | 0 |
| 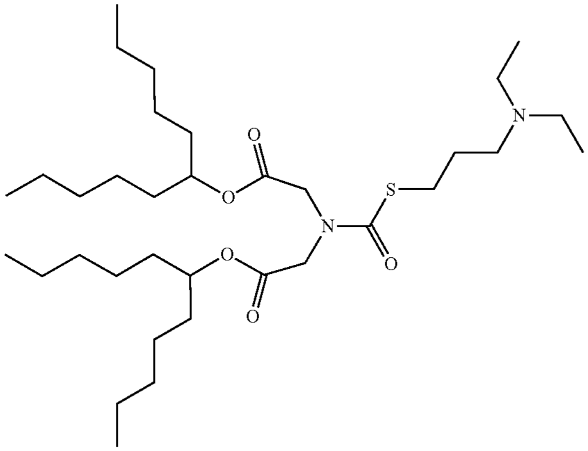 [SMILES: CCCCCC(CCCCC)OC(=O)CN(CC(=O)OC(CCCCC)CCCCC)C(=O)SCCCN(CC)CC] | 2,2 (5,5/5,5) 3-C $CH_2CH_3$ | 9.26 | 10.16 (6.21) | |
| 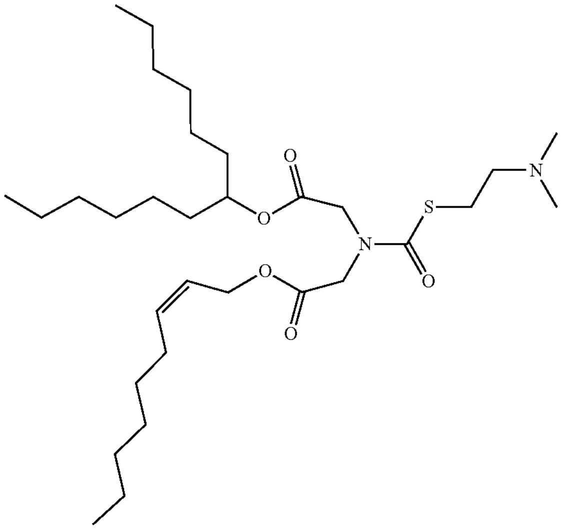 [SMILES: CCCCCC/C=C\COC(=O)CN(CC(=O)OC(CCCCCC)CCCCCC)C(=O)SCCN(C)C] | 2,2 (6,6) 2-C $CH_3$ | 9.81 | 8.56 | |

TABLE 1-continued
| Compound | Designa-tion | c-LogD | c-pKa (pKa) | Bio-activity |
|---|---|---|---|---|
| 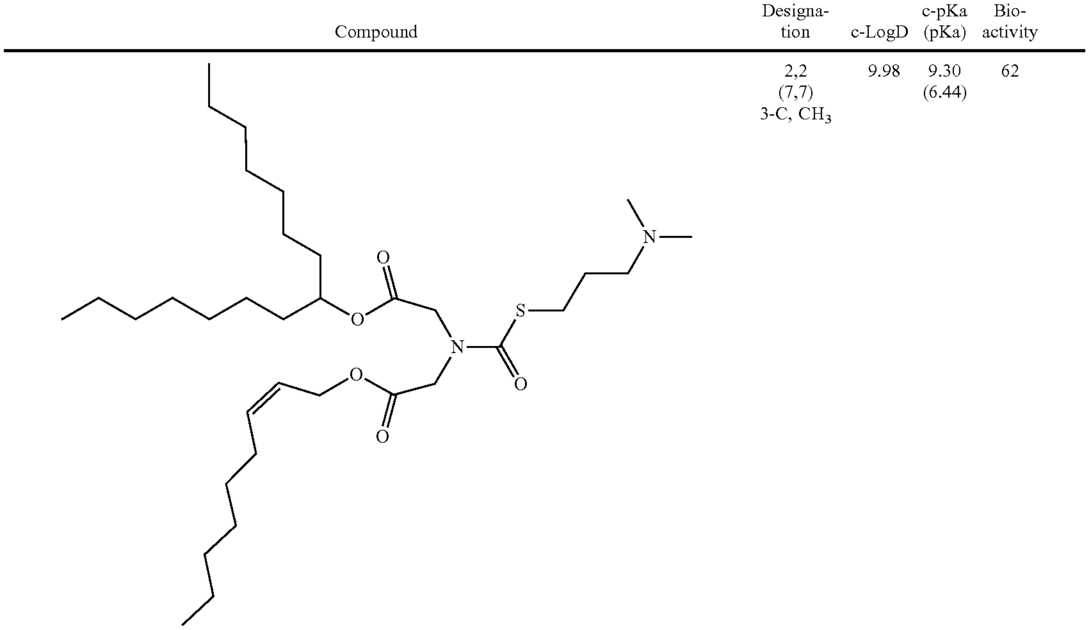 | 2,2 (7,7) 3-C, $CH_3$ | 9.98 | 9.30 (6.44) | 62 |
| 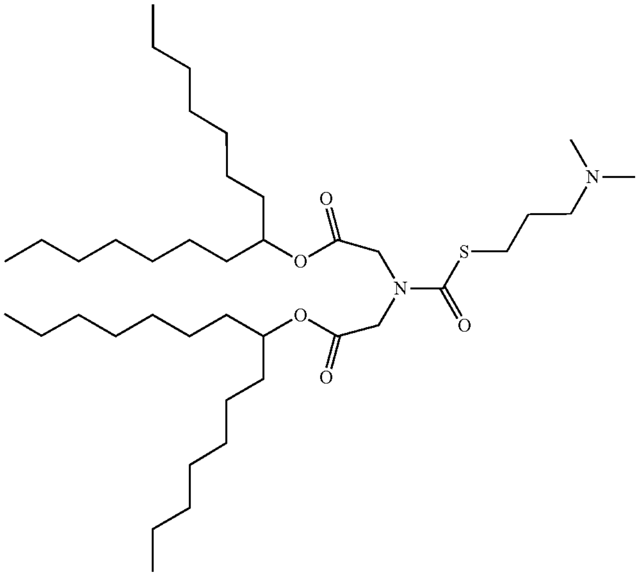 [SMILES: CCCCCCCC(CCCCCCC)OC(=O)CN(CC(=O)OC(CCCCCCC)CCCCCCC)C(=O)SCCCN(C)C] | 2,2 (7,7/7,7) 3-C $CH_3$ | 13.04 | 9.3 (5.68) | 25 |

TABLE 1-continued
| Compound | Designation | c-LogD | c-pKa (pKa) | Bio-activity |
|---|---|---|---|---|
| 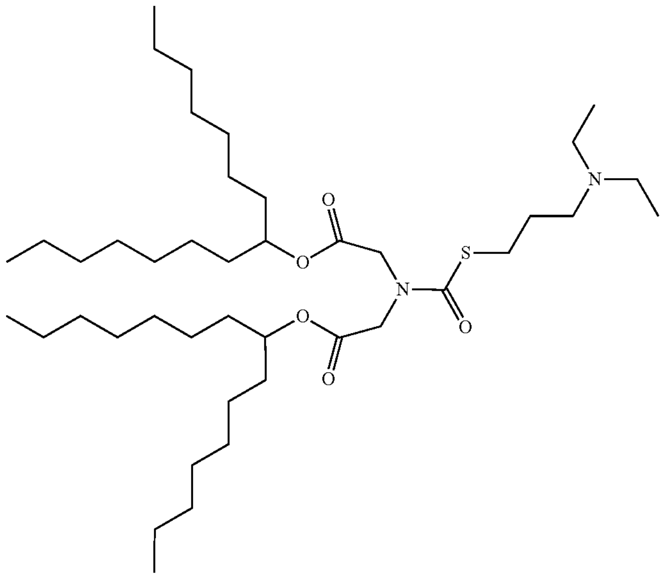 [SMILES: CCCCCCCC(CCCCCCC)OC(=O)CN(CC(=O)OC(CCCCCCC)CCCCCCC)C(=O)SCCCN(CC)CC] | 2,2 (7,7/7,7) 3-C $CH_2CH_3$ | 13.34 | 10.16 (5.62) | 25 |
| 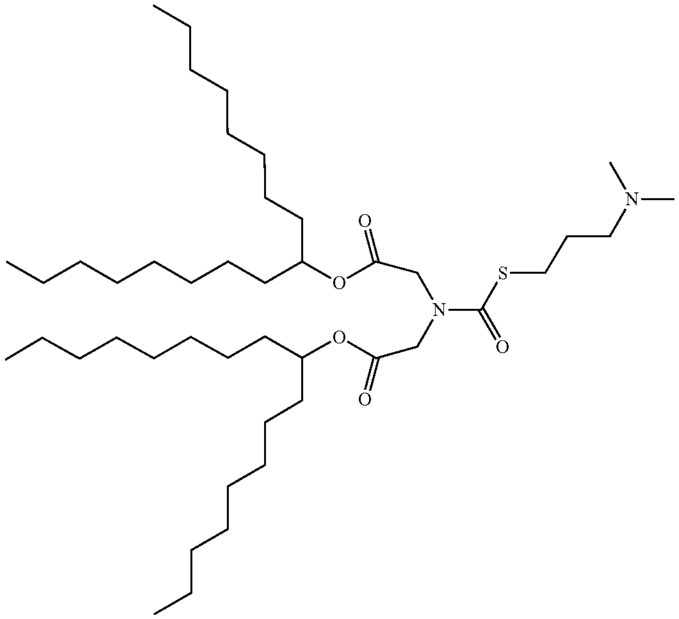 [SMILES: CCCCCCCCC(CCCCCCCC)OC(=O)CN(CC(=O)OC(CCCCCCCC)CCCCCCCC)C(=O)SCCCN(C)C] | 2,2 (8,8/8,8) 3-C $CH_3$ | 15.74 | 9.34 | |

TABLE 1-continued
| Compound | Designa-tion | c-LogD | c-pKa (pKa) | Bio-activity |
|---|---|---|---|---|
| 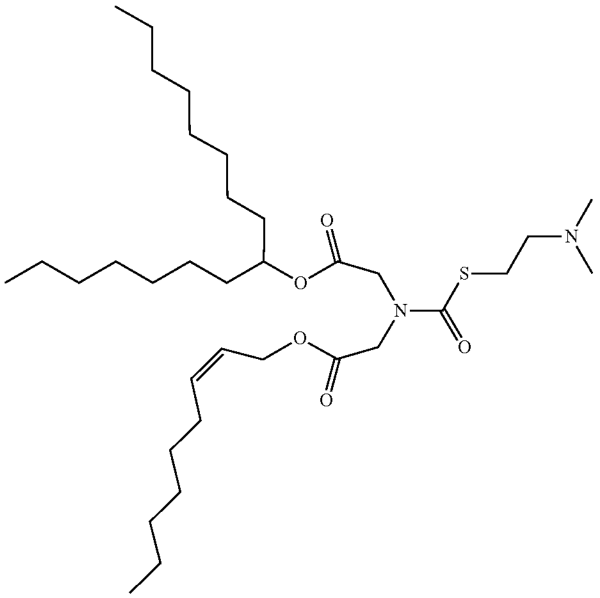 [SMILES: CCCCCC/C=C\COC(=O)CN(CC(=O)OC(CCCCCCC)CCCCCCCC)C(=O)SCCN(C)C] | 2,2 (8,7) 2-C | 10.83 | 8.56 (5.14) | 0 |
| 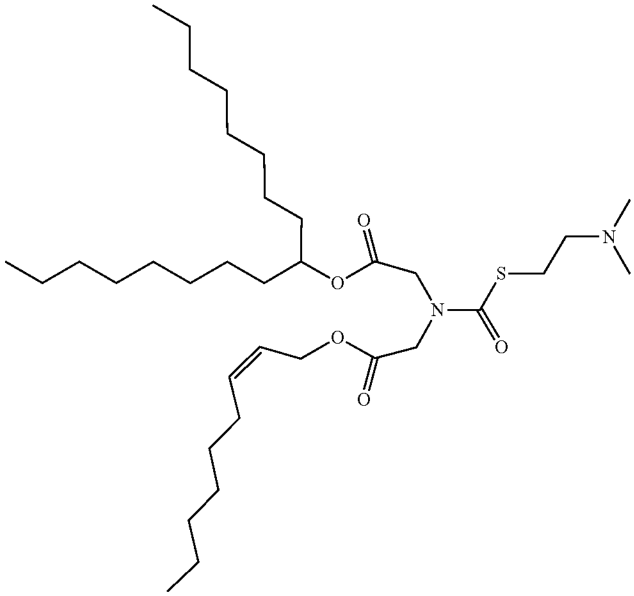 [SMILES: CCCCCC/C=C\COC(=O)CN(CC(=O)OC(CCCCCCCC)CCCCCCCC)C(=O)SCCN(C)C] | 2,2 (8,8) 2-C $CH_3$ | 11.34 | 8.56 (5.13) | 0 |

TABLE 1-continued
| Compound | Designation | c-LogD | c-pKa (pKa) | Bioactivity |
|---|---|---|---|---|
| 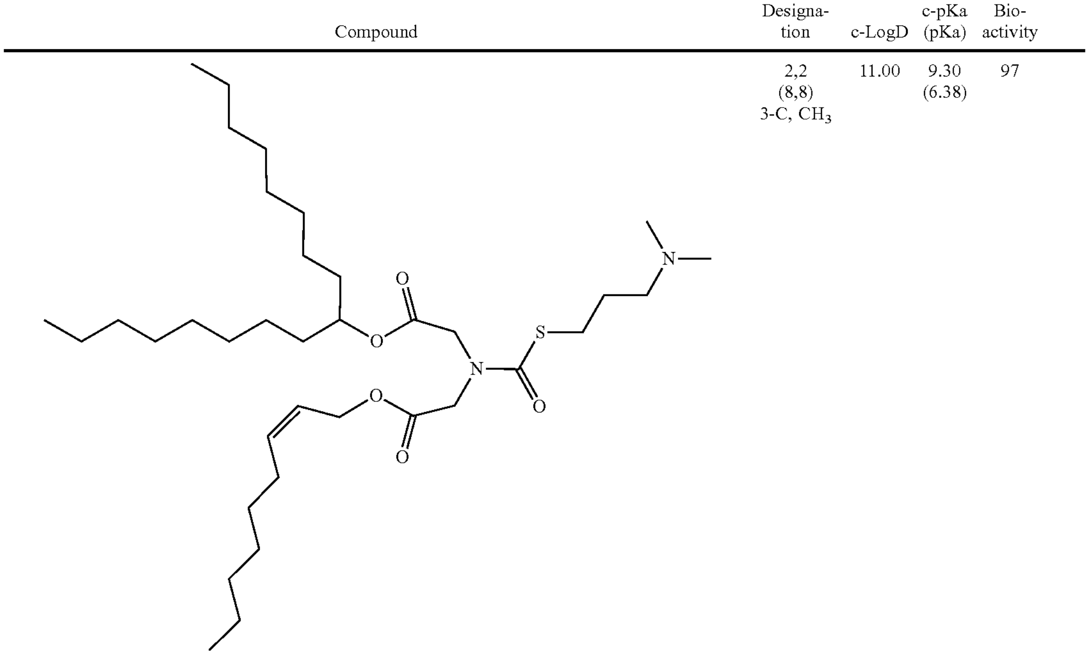 | 2,2 (8,8) 3-C, $CH_3$ | 11.00 | 9.30 (6.38) | 97 |
| 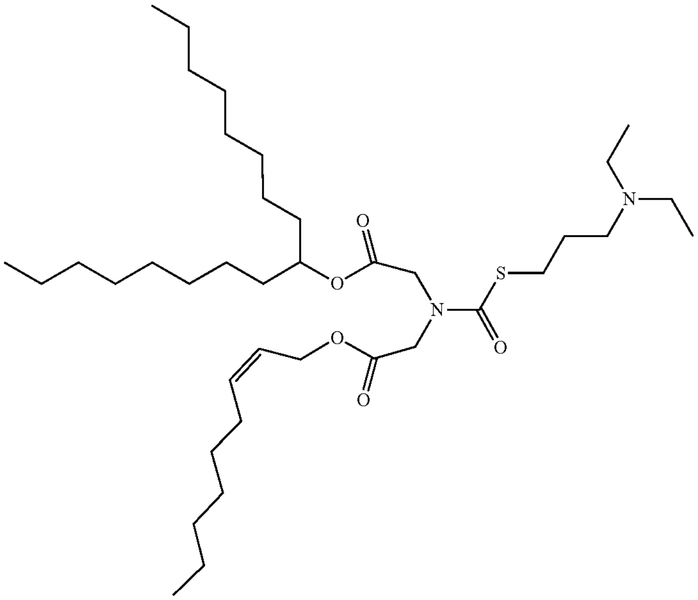 [SMILES: CCCCCC/C=C\COC(=O)CN(CC(=O)OC(CCCCCCCC)CCCCCCCC)C(=O)SCCCN(CC)CC] | 2,2 (8,8) 3-C, $CH_2CH_3$ | 11.30 | 10.16 (6.20) | 82 |

TABLE 1-continued
| Compound | Designation | c-LogD | c-pKa (pKa) | Bioactivity |
|---|---|---|---|---|
| 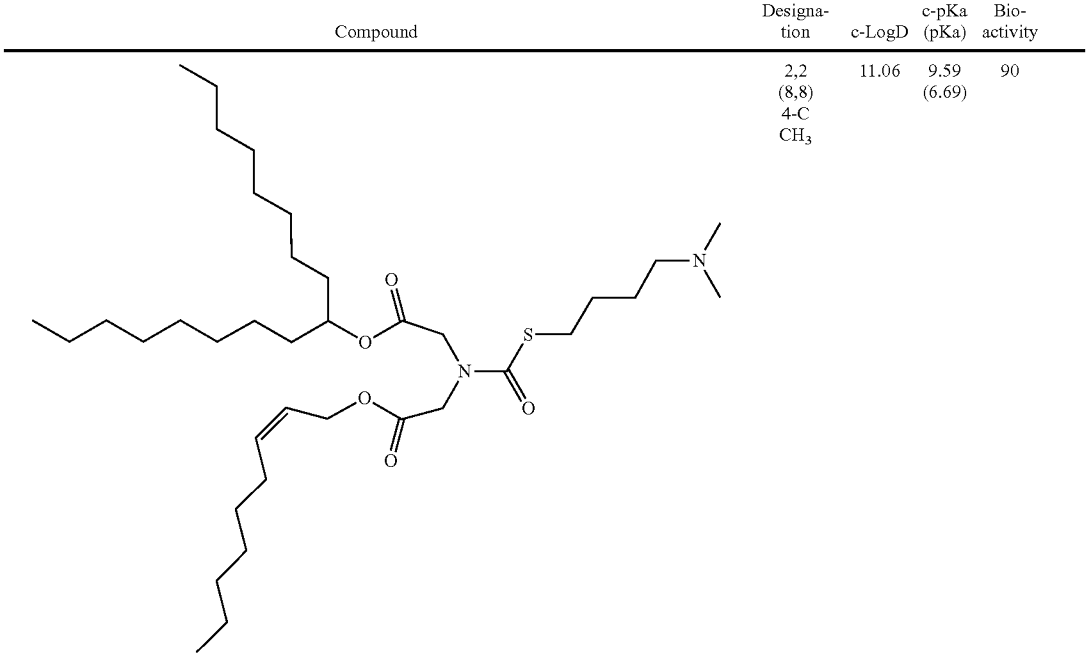 | 2,2 (8,8) 4-C $CH_3$ | 11.06 | 9.59 (6.69) | 90 |
| 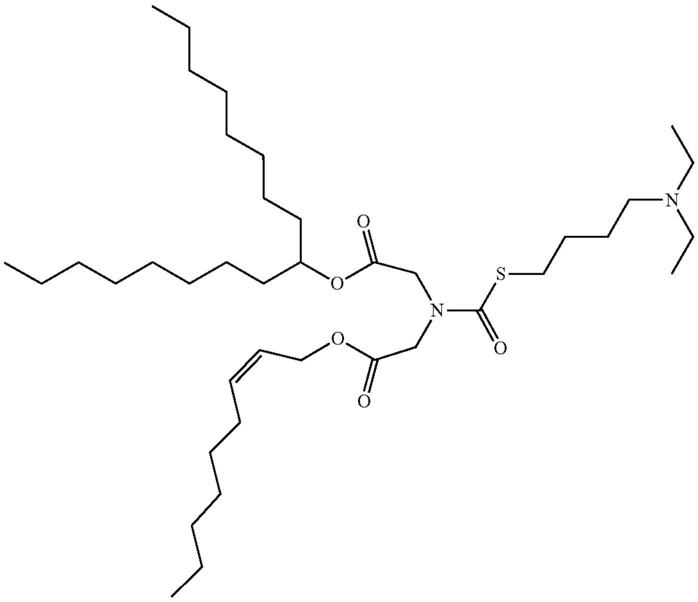 [SMILES: CCCCCC/C=C\COC(=O)CN(CC(=O)OC(CCCCCCCC)CCCCCCCC)C(=O)SCCCCN(CC)CC] | 2,2 (8,8) 4-C $CH_2CH_3$ | 11.56 | 10.41 (6.90) | 97 |

TABLE 1-continued
| Compound | Designation | c-LogD | c-pKa (pKa) | Bio-activity |
|---|---|---|---|---|
| 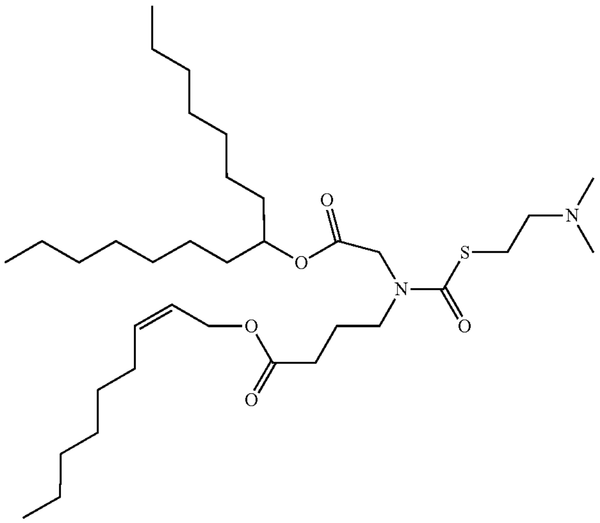 [SMILES: CCCCCC/C=C\COC(=O)CCCN(CC(=O)OC(CCCCCCC)CCCCCCC)C(=O)SCCN(C)C] | 2,4 (7,7) 2-C $CH_3$ | 10.53 | 8.5 (5.83) | 40 |
| 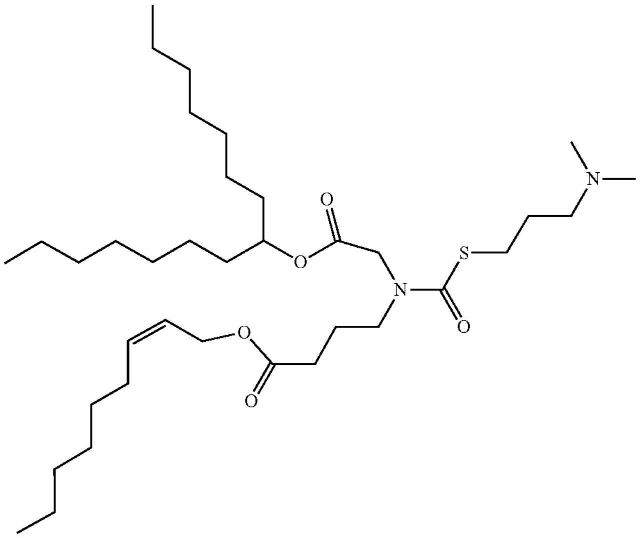 [SMILES: CCCCCC/C=C\COC(=O)CCCN(CC(=O)OC(CCCCCCC)CCCCCCC)C(=O)SCCCN(C)C] | 2,4 (7,7) 3-C, $CH_3$ | 10.17 | 9.31 (6.85) | 53 |
| 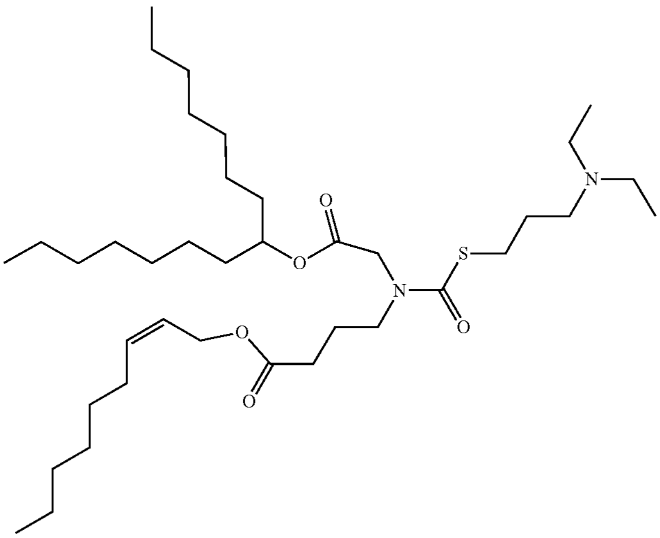 [SMILES: CCCCCC/C=C\COC(=O)CCCN(CC(=O)OC(CCCCCCC)CCCCCCC)C(=O)SCCCN(CC)CC] | 2,4 (7,7) 3-C, $CH_2CH_3$ | 10.49 | 10.16 (6.53) | 70 |

TABLE 1-continued
| Compound | Designation | c-LogD | c-pKa (pKa) | Bio-activity |
|---|---|---|---|---|
| 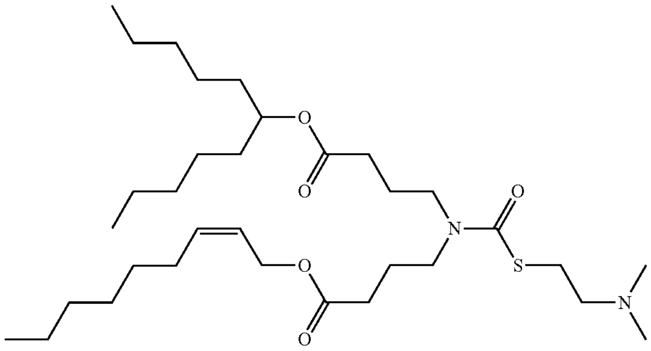 [SMILES: CCCCCC/C=C\COC(=O)CCCN(CCCC(=O)OC(CCCCC)CCCCC)C(=O)SCCN(C)C] | 4,4 (5,5) 2-C $CH_3$ | 8.87 | 8.68 | |
| 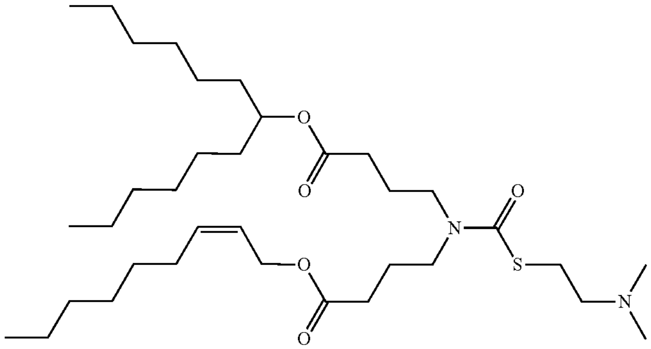 [SMILES: CCCCCC/C=C\COC(=O)CCCN(CCCC(=O)OC(CCCCCC)CCCCCC)C(=O)SCCN(C)C] | 4,4 (6,6) 2-C $CH_3$ | 9.89 | 8.68 (6.05) | 13 |
| 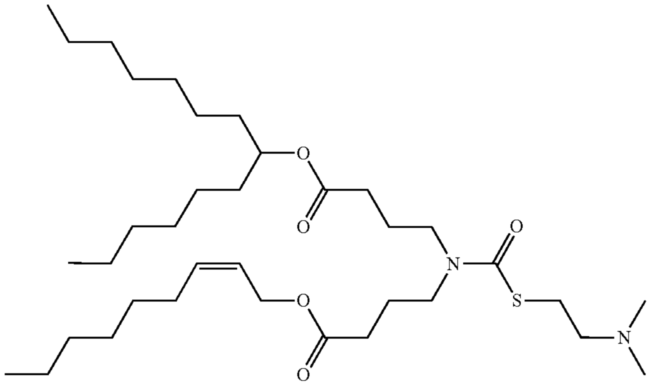 [SMILES: CCCCCC/C=C\COC(=O)CCCN(CCCC(=O)OC(CCCCCC)CCCCCCC)C(=O)SCCN(C)C] | 4,4 (7,6) 2-C $CH_3$ | 10.40 | 8.68 (5.95) | 86 |
| 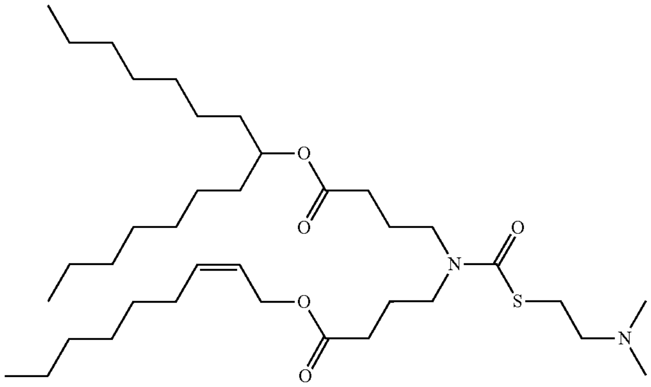 | 4,4 (7,7) 2-C $CH_3$ | 10.91 | 8.68 (6.04) | 93 |

TABLE 1-continued
| Compound | Designa-tion | c-LogD | c-pKa (pKa) | Bio-activity |
|---|---|---|---|---|
| 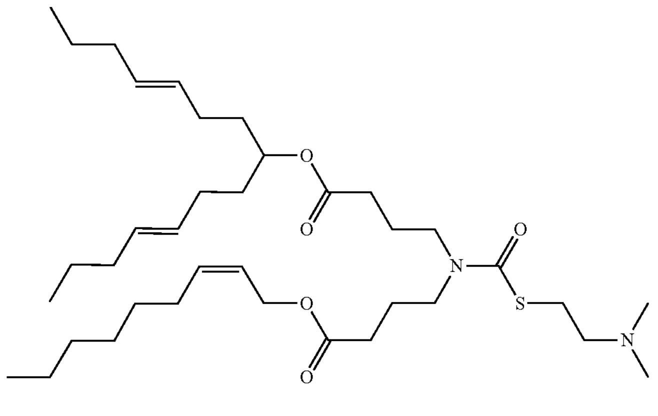 [SMILES: CCC/C=C/CCC(CC/C=C/CCC)OC(=O)CCCN(CCCC(=O)OC/C=C\CCCCCC)C(=O)SCCN(C)C] | 4,4 (7*,7*) 2-C $CH_3$ | 10.06 | 8.68 (6.00) | 72 |
| 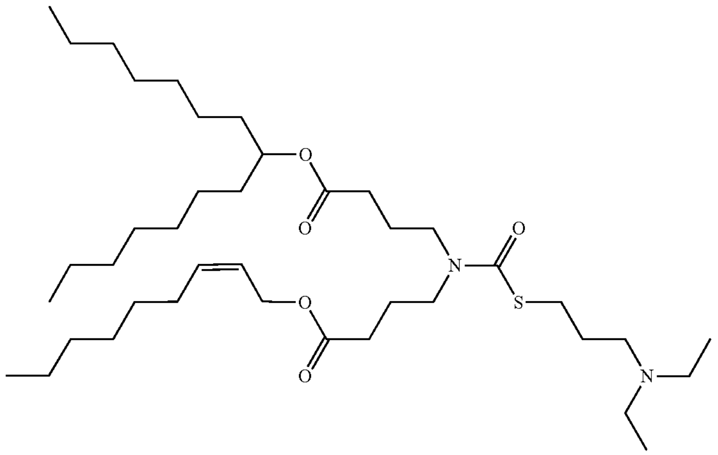 [SMILES: CCCCCC/C=C\COC(=O)CCCN(CCCC(=O)OC(CCCCCCC)CCCCCCC)C(=O)SCCCN(CC)CC] | 4,4 (7,7) 3-C, $CH_2CH_3$ | 10.92 | 10.20 (6.66) | 96 |
| 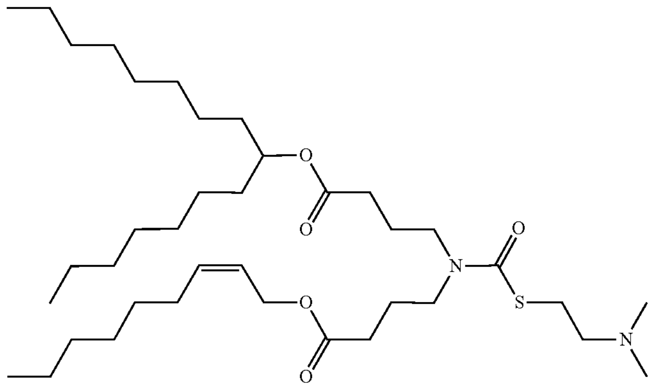 [SMILES: CCCCCC/C=C\COC(=O)CCCN(CCCC(=O)OC(CCCCCCC)CCCCCCCC)C(=O)SCCN(C)C] | 4,4 (8,7) 2-C $CH_3$ | 11.42 | 8.68 (5.70) | 86 |

TABLE 1-continued
| Compound | Designation | c-LogD | c-pKa (pKa) | Bio-activity |
|---|---|---|---|---|
| 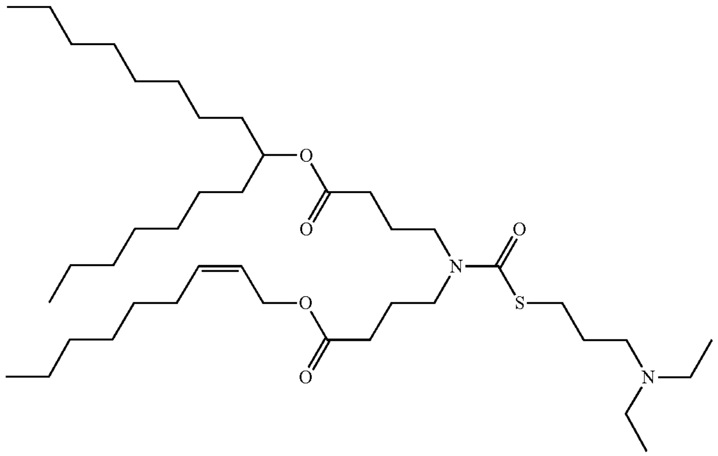 [SMILES: CCCCCC/C=C\COC(=O)CCCN(CCCC(=O)OC(CCCCCCC)CCCCCCCC)C(=O)SCCCN(CC)CC] | 4,4 (8,7) 3-C-$CH_2CH_3$ | 11.43 | 10.20 (6.65) | 93 |
| 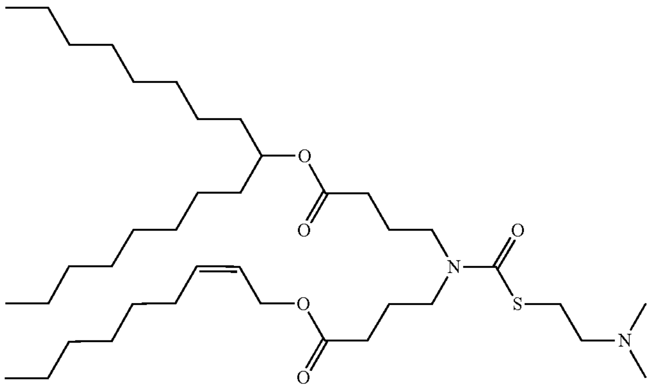 [SMILES: CCCCCC/C=C\COC(=O)CCCN(CCCC(=O)OC(CCCCCCCC)CCCCCCCC)C(=O)SCCN(C)C] | 4,4 (8,8) 2-C CH | 11.93 | 8.68 (6.06) | 80 |
| 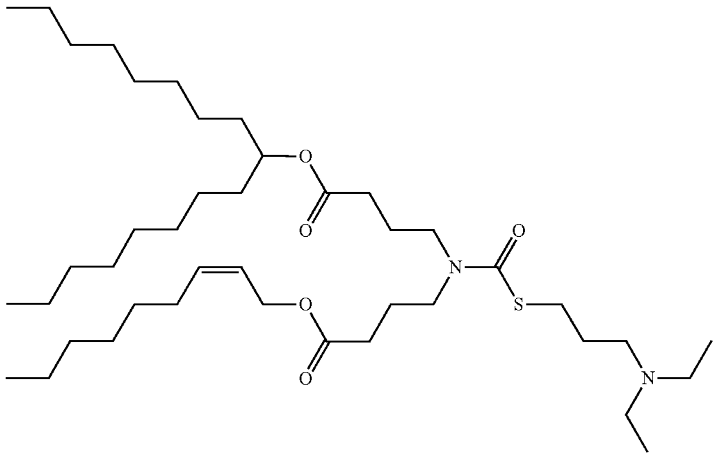 [SMILES: CCCCCC/C=C\COC(=O)CCCN(CCCC(=O)OC(CCCCCCCC)CCCCCCCC)C(=O)SCCCN(CC)CC] | 4,4 (8,8) 3-C, $CH_2CH_3$ | 11.93 | 10.20 (6.58) | 75 |

TABLE 1-continued
| Compound | Designation | c-LogD | c-pKa (pKa) | Bio-activity |
|---|---|---|---|---|
| 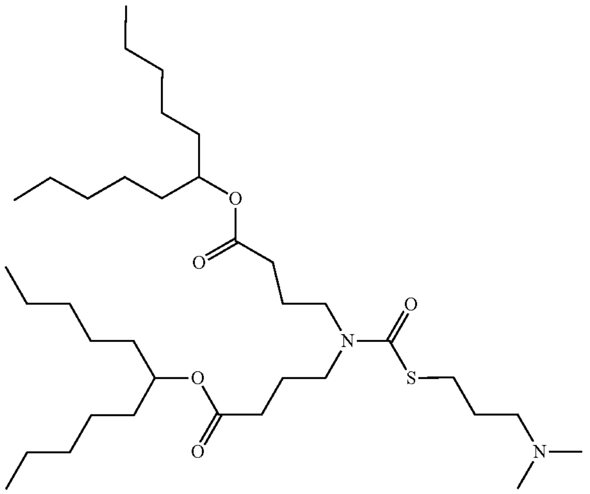 [SMILES: CCCCCC(CCCCC)OC(=O)CCCN(CCCC(=O)OC(CCCCC)CCCCC)C(=O)SCCCN(C)C] | 4,4 (5,5/5,5) 3-C $CH_3$ | 9.63 | 9.34 (6.80) | 14 (0.1 mg/kg) |
| 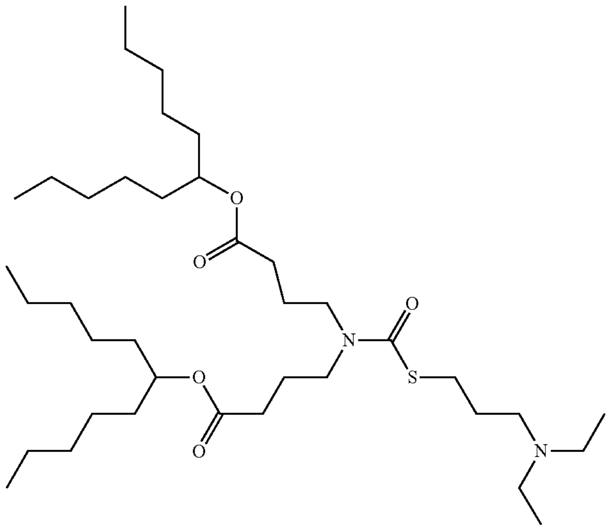 [SMILES: CCCCCC(CCCCC)OC(=O)CCCN(CCCC(=O)OC(CCCCC)CCCCC)C(=O)SCCCN(CC)CC] | 4,4 (5,5/5,5) 3-C $CH_2CH_3$ | 9.95 | 10.20 (5.56) | 27 (0.1 mg/kg) |

TABLE 1-continued
| Compound | Designa-tion | c-LogD | c-pKa (pKa) | Bio-activity |
|---|---|---|---|---|
| 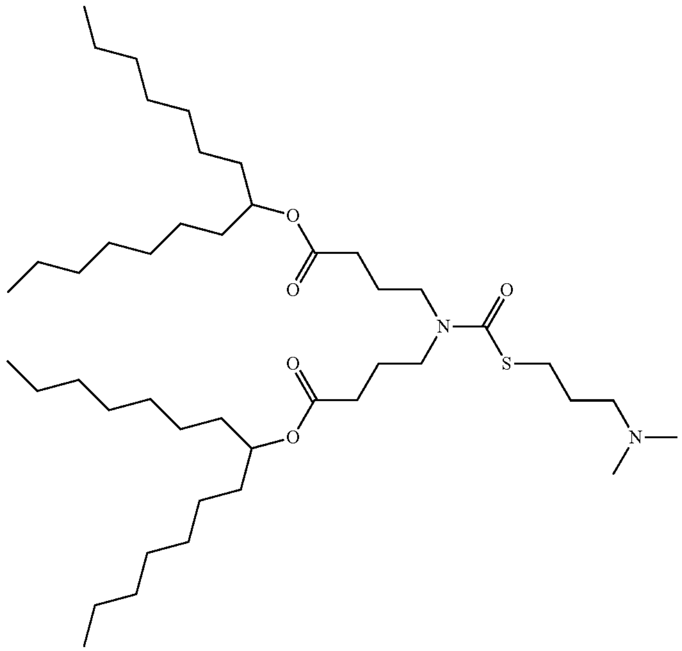 [SMILES: CCCCCCCC(CCCCCCC)OC(=O)CCCN(CCCC(=O)OC(CCCCCCC)CCCCCCC)C(=O)SCCCN(C)C] | 4,4 (7,7/7,7) 3-C $CH_3$ | 13.70 | 9.34 (6.38) | 99 |
| 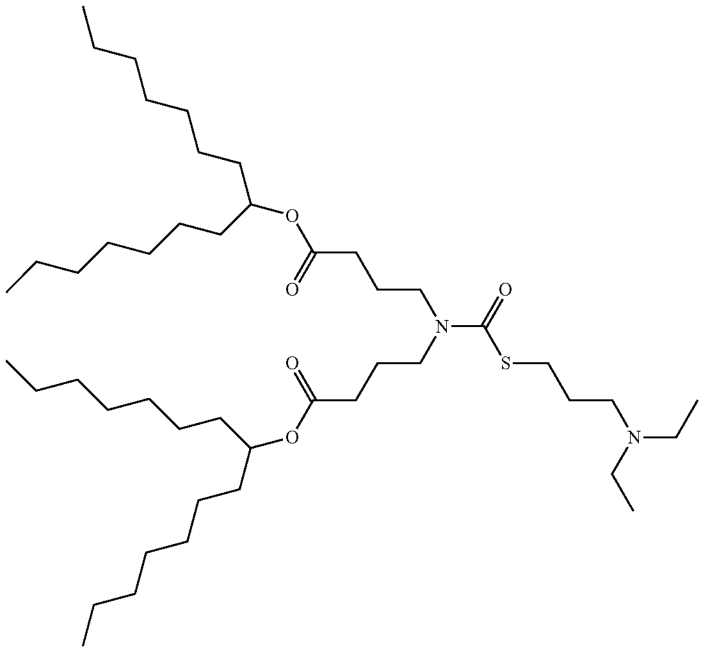 [SMILES: CCCCCCCC(CCCCCCC)OC(=O)CCCN(CCCC(=O)OC(CCCCCCC)CCCCCCC)C(=O)SCCCN(CC)CC] | 4,4 (7,7/7,7) 3-C $CH_2CH_3$ | 14.03 | 10.20 (6.31) | 97 |

TABLE 1-continued
| Compound | Designa-tion | c-LogD | c-pKa (pKa) | Bio-activity |
|---|---|---|---|---|
| 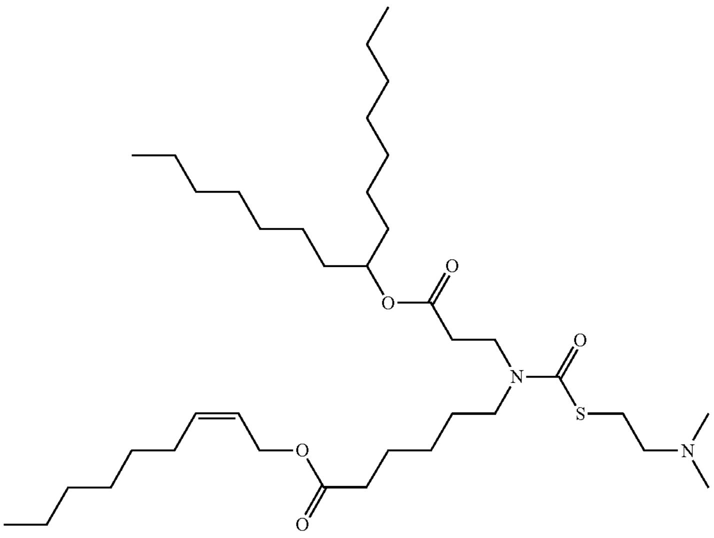 [SMILES: CCCCCC/C=C\COC(=O)CCCCCN(CCC(=O)OC(CCCCCCC)CCCCCCC)C(=O)SCCN(C)C] | 3,6 (7,7) 2-C $CH_3$ | 11.35 | 8.67 (5.77) | 43 |
| 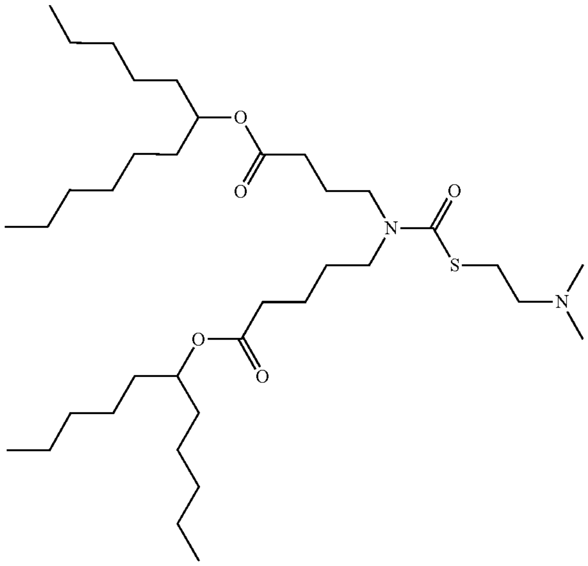 [SMILES: CCCCCCC(CCCCC)OC(=O)CCCN(CCCCC(=O)OC(CCCCC)CCCCC)C(=O)SCCN(C)C] | 4,5 (6,6/5,5) 2-C $CH_3$ | 11.34 | 8.68 | 56 |
| 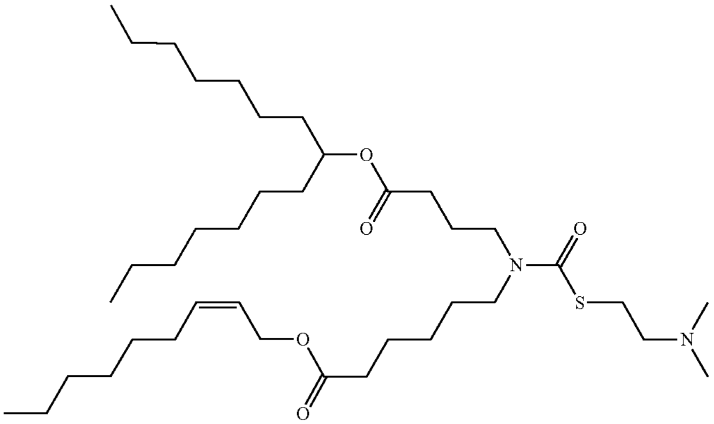 [SMILES: CCCCCC/C=C\COC(=O)CCCCCN(CCCC(=O)OC(CCCCCCC)CCCCCCC)C(=O)SCCN(C)C] | 4,6 (7,7) 2-C $CH_3$ | 11.65 | 8.68 (5.98) | 65 |

TABLE 1-continued
| Compound | Designation | c-LogD | c-pKa (pKa) | Bio-activity |
|---|---|---|---|---|
| 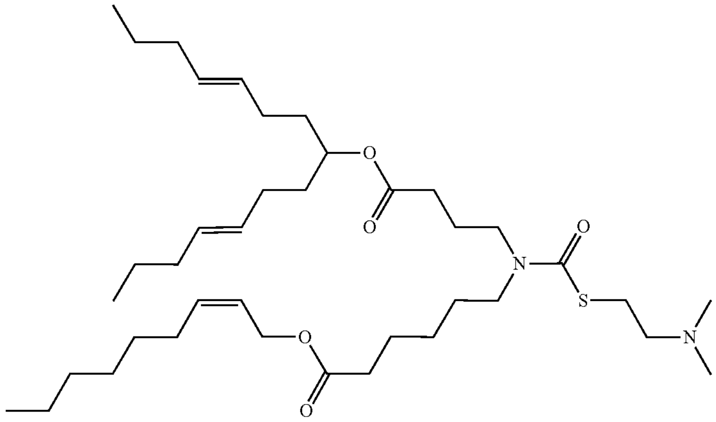 [SMILES: CCC/C=C/CCC(CC/C=C/CCC)OC(=O)CCCN(CCCCCC(=O)OC/C=C\CCCCCC)C(=O)SCCN(C)C] | 4,6 (7*,7*) 2-C $CH_3$ | 10.80 | 8.68 (5.93) | 75 |
| 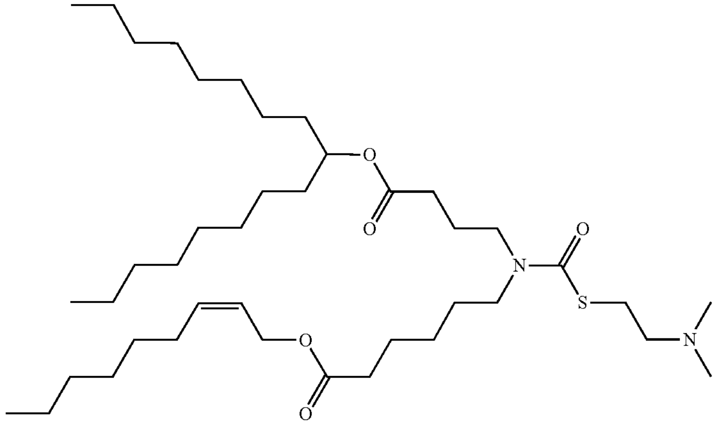 [SMILES: CCCCCC/C=C\COC(=O)CCCCCN(CCCC(=O)OC(CCCCCCCC)CCCCCCCC)C(=O)SCCN(C)C] | 4,6 (8,8) 2-C $CH_3$ | 12.67 | 8.68 (5.38) | 81 |
| 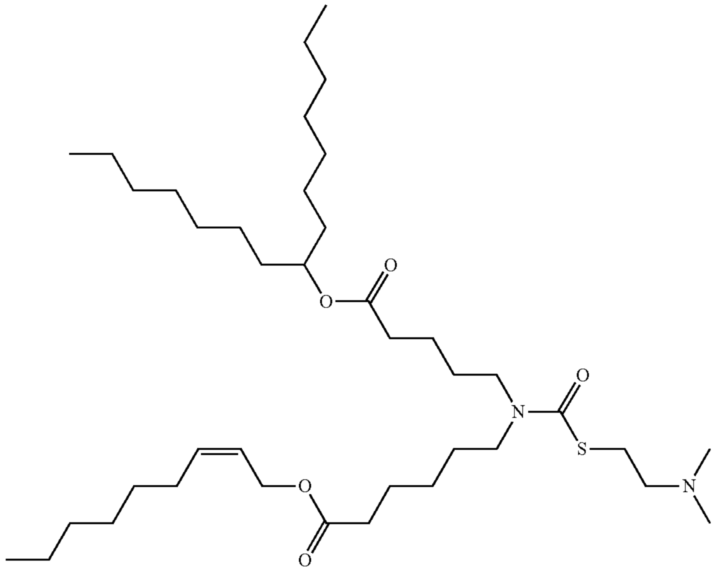 [SMILES: CCCCCC/C=C\COC(=O)CCCCCN(CCCCC(=O)OC(CCCCCCC)CCCCCCC)C(=O)SCCN(C)C] | 5,6 (7,7) 2-C $CH_3$ | 12.03 | 8.68 (5.90) | 90 |

TABLE 1-continued
| Compound | Designation | c-LogD | c-pKa (pKa) | Bio-activity |
|---|---|---|---|---|
| 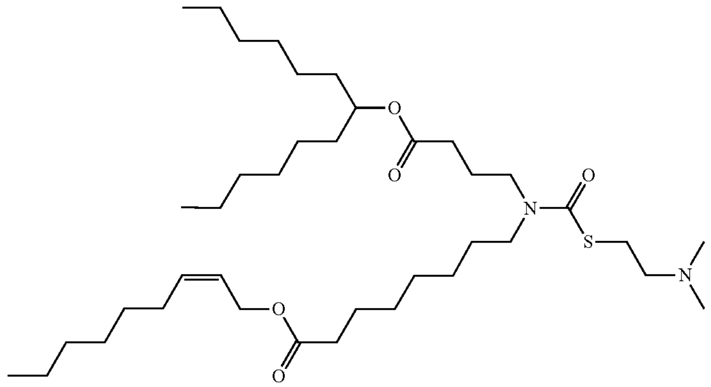 [SMILES: CCCCCC/C=C\COC(=O)CCCCCCCN(CCCC(=O)OC(CCCCCC)CCCCCC)C(=O)SCCN(C)C] | 4,8 (6,6) 2-C $CH_3$ | 12.37 | 8.68 (5.61) | 63 |
| 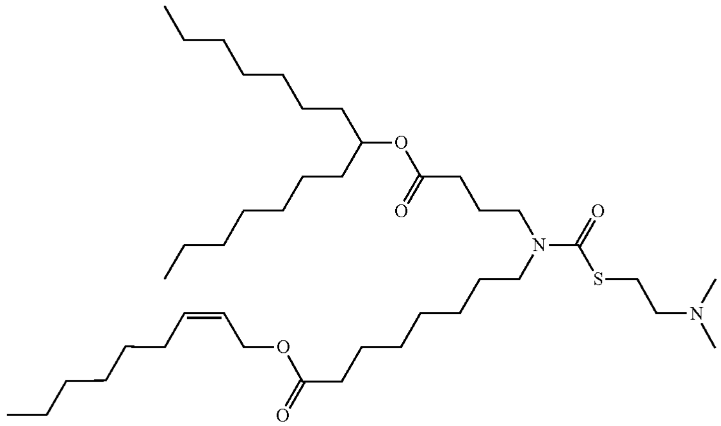 [SMILES: CCCCCC/C=C\COC(=O)CCCCCCCN(CCCC(=O)OC(CCCCCCC)CCCCCCC)C(=O)SCCN(C)C] | 4,8 (7,7) 2-C $CH_3$ | 12.66 | 8.68 (5.38) | 73 |
| 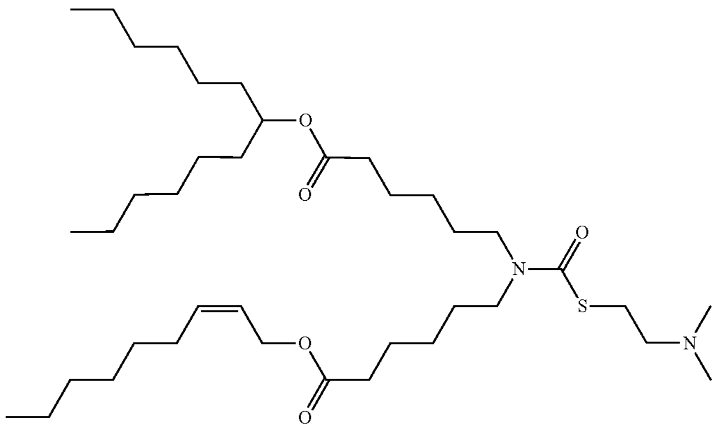 [SMILES: CCCCCC/C=C\COC(=O)CCCCCN(CCCCCC(=O)OC(CCCCCC)CCCCCC)C(=O)SCCN(C)C] | 6,6 (6,6) 2-C $CH_3$ | 11.37 | 8.68 (6.11) | 68 |

TABLE 1-continued
| Compound | Designa-tion | c-LogD | c-pKa (pKa) | Bio-activity |
|---|---|---|---|---|
| 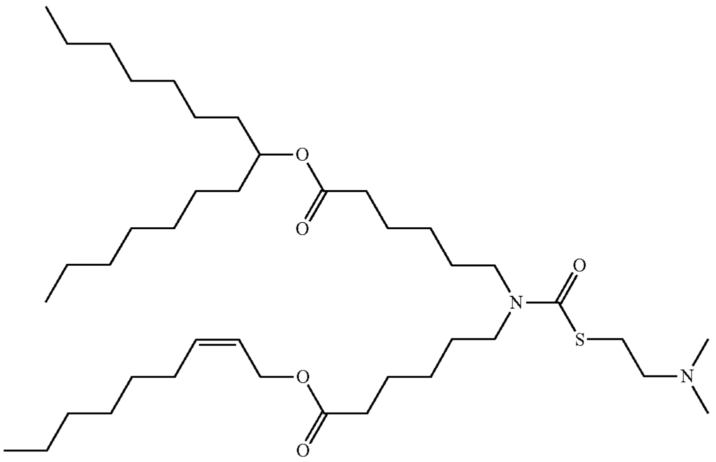 [SMILES: CCCCCC/C=C\COC(=O)CCCCCN(CCCCCC(=O)OC(CCCCCCC)CCCCCCC)C(=O)SCCN(C)C] | 6,6 (7,7) 2-C $CH_3$ | 12.89 | 8.68 (5.93) | 91 |
| 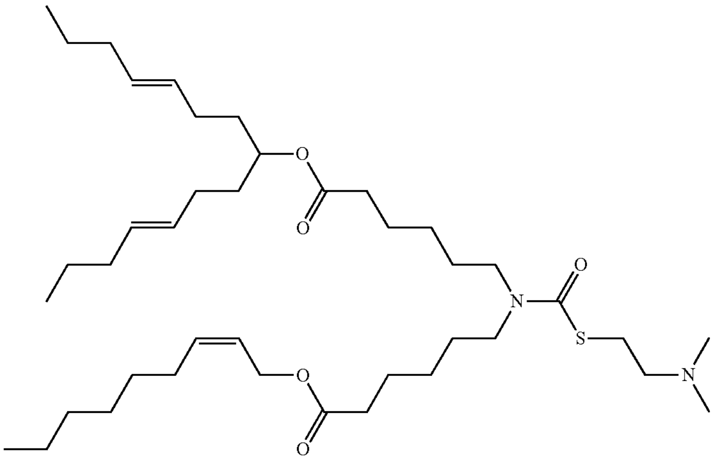 [SMILES: CCC/C=C/CCC(CC/C=C/CCC)OC(=O)CCCCCN(CCCCCC(=O)OC/C=C\CCCCCC)C(=O)SCCN(C)C] | 6,6 (7*,7*) 2-C $CH_3$ | 11.54 | 8.68 (5.94) | 82 |
| 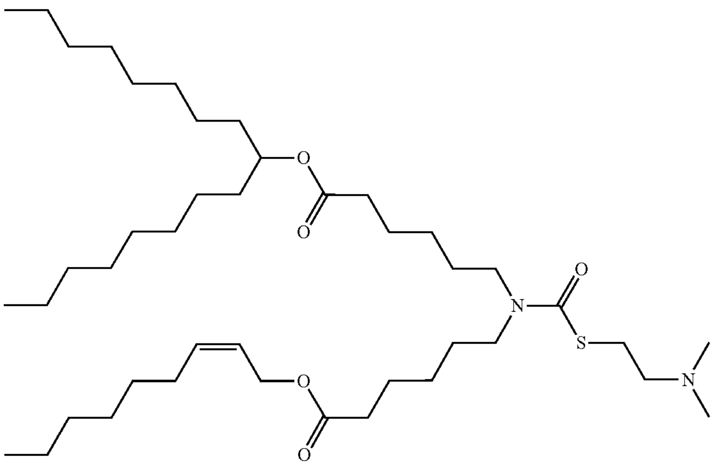 [SMILES: CCCCCC/C=C\COC(=O)CCCCCN(CCCCCC(=O)OC(CCCCCCCC)CCCCCCCC)C(=O)SCCN(C)C] | 6,6 (8,8) 2-C $CH_3$ | 13.41 | 8.68 (5.82) | 85 |

TABLE 1-continued
| Compound | Designation | c-LogD | c-pKa (pKa) | Bio-activity |
|---|---|---|---|---|
| 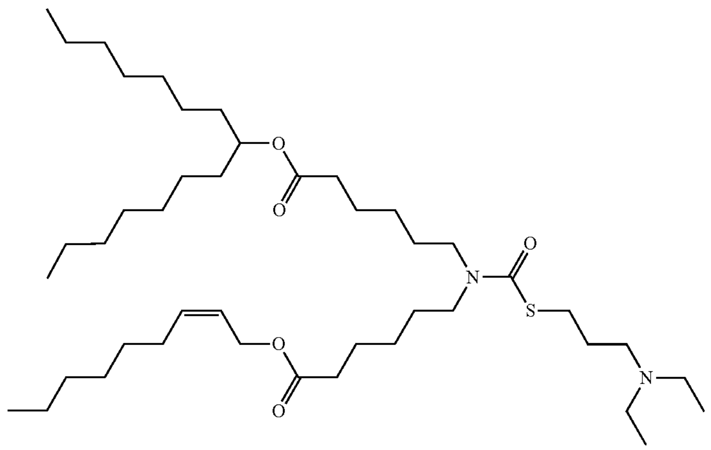 [SMILES: CCCCCC/C=C\COC(=O)CCCCCN(CCCCCC(=O)OC(CCCCCCC)CCCCCCC)C(=O)SCCCN(CC)CC] | 6,6 (7,7) 3-C $NCH_2CH_3$ | 12.41 | 10.20 (6.45) | 95 |
| 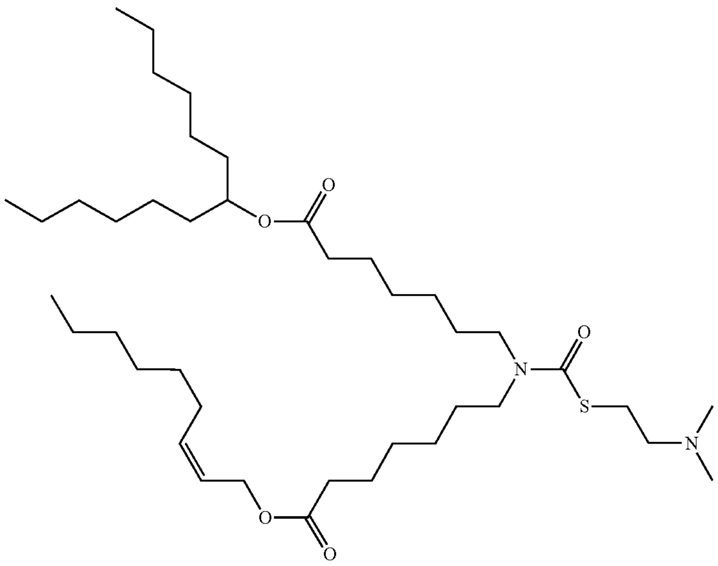 [SMILES: CCCCCC/C=C\COC(=O)CCCCCCN(CCCCCCC(=O)OC(CCCCCC)CCCCCC)C(=O)SCCN(C)C] | 7,7 (6,6) 2-C $CH_3$ | 12.38 | 8.68 (5.67) | 66 |

TABLE 1-continued
| Compound | Designation | c-LogD | c-pKa (pKa) | Bio-activity |
|---|---|---|---|---|
| 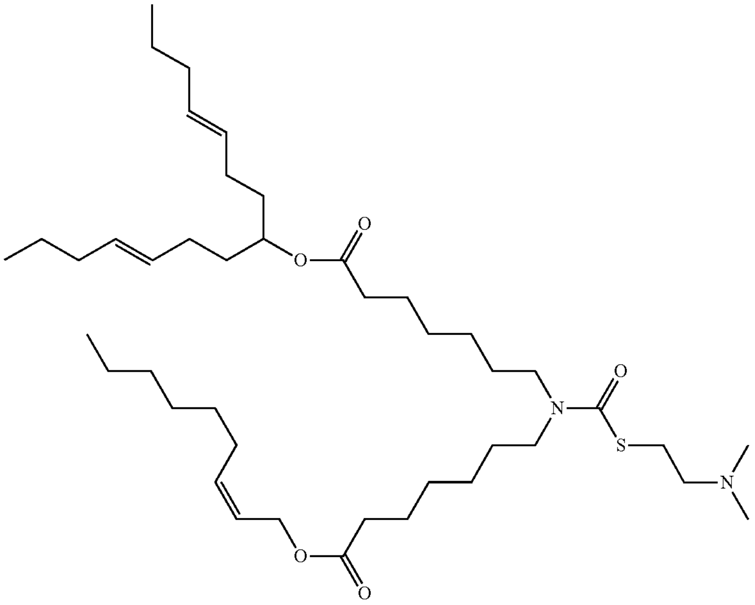 [SMILES: CCC/C=C/CCC(CC/C=C/CCC)OC(=O)CCCCCCN(CCCCCCC(=O)OC/C=C\CCCCCC)C(=O)SCCN(C)C] | 7,7 (7*,7*) 2-C $CH_3$ | 12.56 | 8.68 (5.68) | 67 |
| 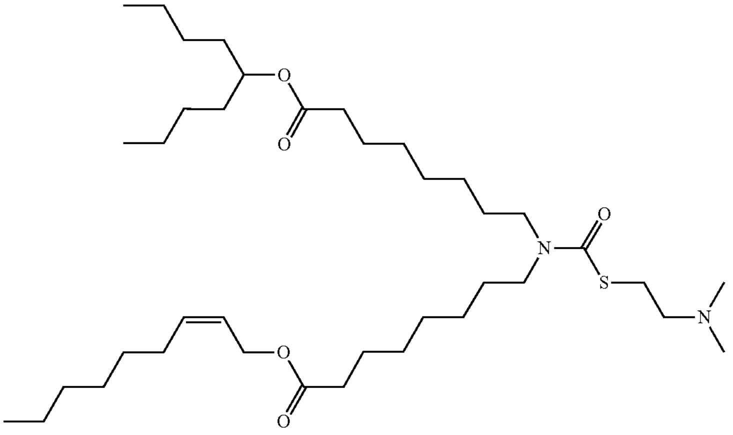 [SMILES: CCCCCC/C=C\COC(=O)CCCCCCCN(CCCCCCCC(=O)OC(CCCC)CCCC)C(=O)SCCN(C)C] | 8,8 (4,4) 2-C $CH_3$ | 11.37 | 8.68 (6.22) | 71 |
| 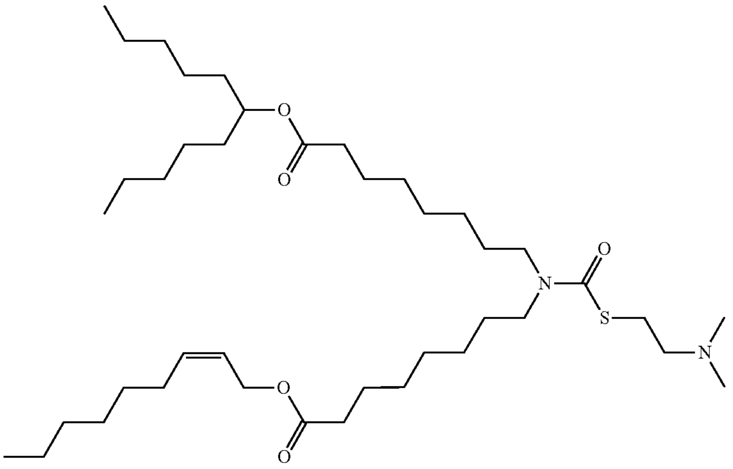 [SMILES: CCCCCC/C=C\COC(=O)CCCCCCCN(CCCCCCCC(=O)OC(CCCCC)CCCCC)C(=O)SCCN(C)C] | 8,8 (5,5) 2-C $CH_3$ | 12.38 | 8.68 (5.81) | 68 |

TABLE 1-continued
| Compound | Designation | c-LogD | c-pKa (pKa) | Bio-activity | |
|---|---|---|---|---|---|
| 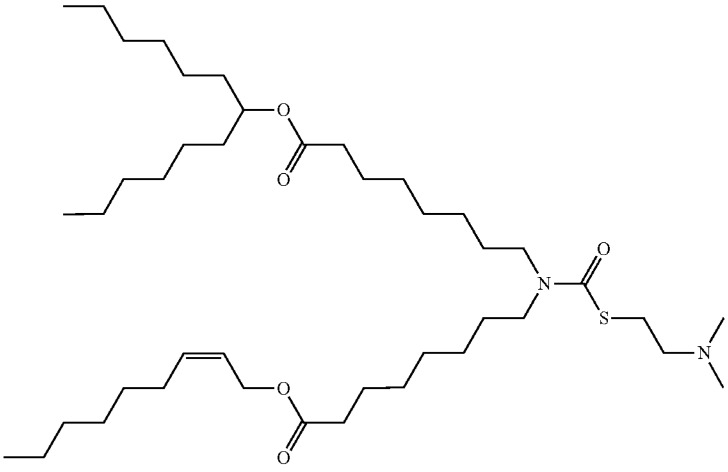 [SMILES: CCCCCC/C=C\COC(=O)CCCCCCCN(CCCCCCCC(=O)OC(CCCCCC)CCCCCC)C(=O)SCCN(C)C] | 8,8 (6,6) 2-C $CH_3$ | 0093 | 13.95 | 8.68 (5.79) | 70 |
| 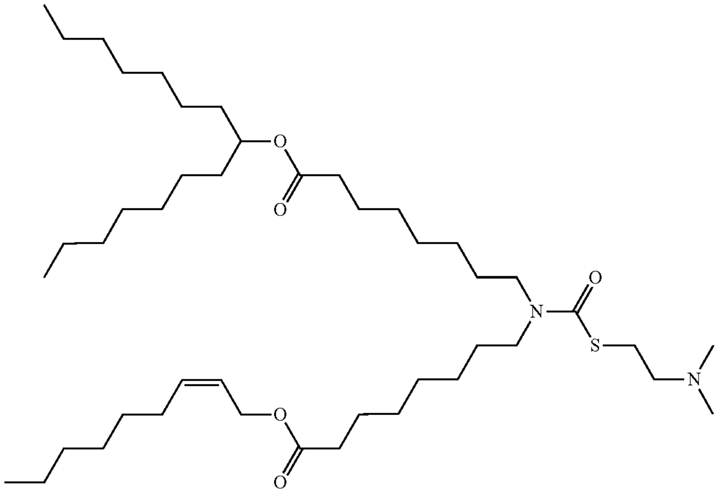 [SMILES: CCCCCC/C=C\COC(=O)CCCCCCCN(CCCCCCCC(=O)OC(CCCCCCC)CCCCCCC)C(=O)SCCN(C)C] | 8,8 (7,7) 2-C $CH_3$ | 0097 | 15.02 | 8.68 (5.89) | 71 |
| 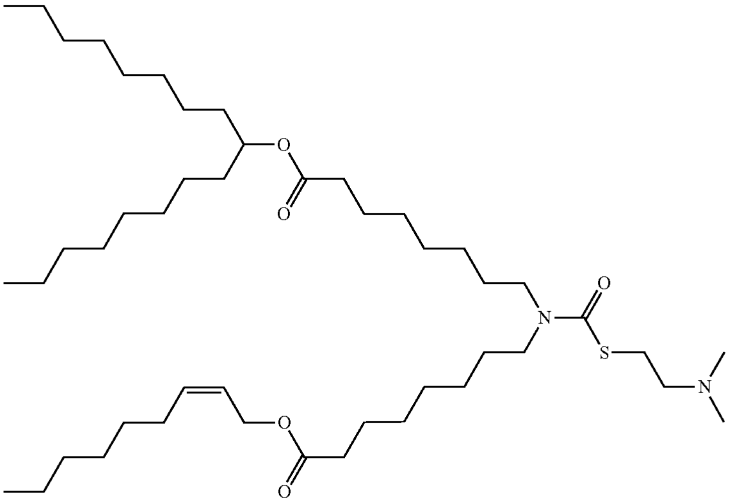 [SMILES: CCCCCC/C=C\COC(=O)CCCCCCCN(CCCCCCCC(=O)OC(CCCCCCCC)CCCCCCCC)C(=O)SCCN(C)C] | 8,8 (8,8) 2-C $CH_3$ | 0096 | 16.08 | 8.68 (5.59) | 40 |

Example 2: Synthesis of ATX-0043

FIG. 1 shows the synthetic pathway of ATX-0043 that is described further as follows.

ATX-0043: Step 1

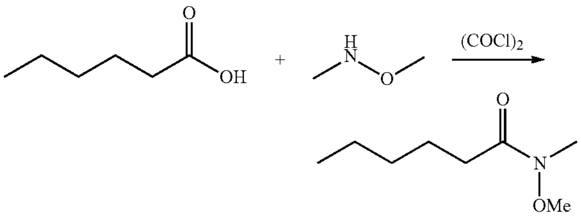

In a 500 mL single neck round bottom flask, 25 g hexanoic acid (SM 1; 1 eq.) dissolved in dichloromethane (DCM; 200 mL) was taken and then added 27.6 ml oxalyl chloride (1.5 eq.) slowly at 0° C., stirring under nitrogen atmosphere and then added 0.5 ml dimethylformamide (DMF; catalytic). The resulting reaction mixture was stirred at room temperature for 2 hours.

In a separate 1 liter two neck found bottom flask, to 31.4 g N,O-dimethylhydroxylamine hydrochloride (1.5 eq.) in DCM (200 ml), was added 89.8 ml triethylamine ($Et_3N$, 3 eq.) using additional funnel, stirred at 0° C. To this resulting solution, the above acid chloride, after concentration under reduced pressure, was added under nitrogen atmosphere by dissolving in DCM (100 ml), dropwise using addition funnel for 20 minutes. The resulting reaction solution was stirred at room temperature for 3 hours under nitrogen atmosphere.

Progress of the reaction was monitored by thin layer chromatography (TLC) (20% ethylacetate (EtOAc)/hexane; Rf: 0.5). Reaction mass was diluted with water (300 ml). Organic layer was separated and the aqueous layer was washed with DCM (3×100 ml). Combined organic layer was concentrated under reduced pressure.

Crude compound was subjected to column chromatography using (60-120 silica gel; 10% EtOAc/hexane). Quantity produced, 20.0 g; yield, 58%.

ATX-0043: Step 2

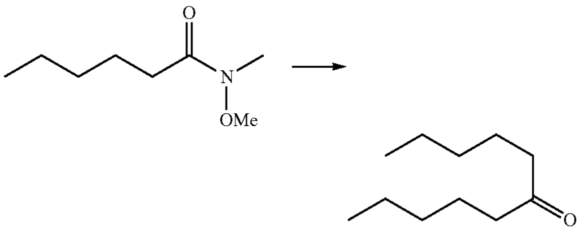

To a solution of 33 g pentyl magnesium bromide (1.5 eq.) in tetrahydrofuran (THF; 100 ml), taken in a 500 ml two neck round bottom flask, stirred at 0° C. under nitrogen atmosphere, was added 20 g N-methoxy-N-methyl hexanamide (1 eq.) solution (dissolved in 200 ml of THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (150 ml) and then EtOAc (300 ml) was added. Organic layer was separated and the aqueous layer was washed with EtOAc (2×100 ml). Combined organic layers were concentrated under reduced pressure.

Crude compound was subjected to column chromatography using (60-120 mesh silica gel; 2% EtOAc/hexane). Quantity produced, 15.0 g; yield, 66%.

ATX-0043: Step 3

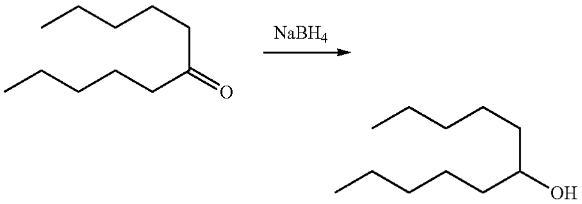

To a solution of 15 g undecan-6-one (1 eq.) dissolved in 25 ml methanol (MeOH) in 150 ml THF, 4.9 g sodium borohydride (1.5 eq.) was added at 0° C. and the resulting solution was stirred at room temperature for 2 hour.

Progress of the reaction was monitored by TLC (10% EtOAc in hexane; Rf: 0.5). Reaction mass was quenched with saturated $NH_4Cl$ solution (100 ml). Solvent was removed under reduced pressure and the resulting crude was portioned between EtOAc (150 ml) and water (150 ml). Organic layer was separated and the aqueous layer was washed with EtOAc (3×100 ml). Combined organic layers were concentrated under reduced pressure to get white solid. Quantity produced, 14.0 g; yield, 93%.

ATX-0043: Step 4

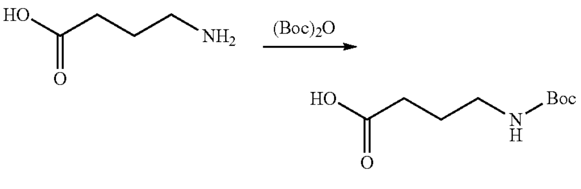

To a solution of 15 g 4-aminobutanoic acid (1 eq.) dissolved in 150 ml THF, 145 ml aqueous 1 N NaOH solution (1 eq.) was added at 0° C., followed by 43.4 ml Boc anhydride (1.3 eq.), sequentially using additional funnel, over a period of 15 minutes each one. The resulting solution was stirred at room temperature for 4 hours.

Progress of the reaction was monitored by TLC (10% MeOH in chloroform ($CHCl_3$); Rf: 0.5). Reaction mass was quenched with 5% HCl (150 ml) and then EtOAc (100 ml) was added. Organic layer was separated and the aqueous layer was washed with EtOAc (2×100 ml). Combined organic layer was concentrated under reduced pressure to get gummy liquid. Quantity produced, 20.0 g; yield, 68%.

ATX-0043: Step 5

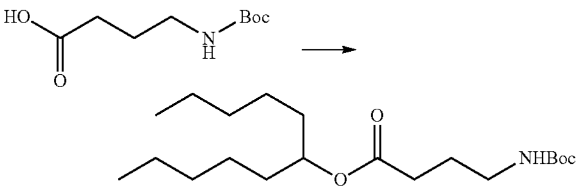

To a solution of 12 g 4-((tert-butoxycarbonyl) amino) butanoic acid (1 eq.) dissolved in DCM (200 ml), cooled to below 0° C. was added 14.7 g 1-ethyl-3-(3-dimethylamino-propyl)carbodiimide (EDC)·HCl (1.3 eq.), 10.6 ml $Et_3N$ (1.3 eq.), and 0.72 g 4-Dimethylaminopyridine (DMAP; 0.1 eq.) sequentially under nitrogen atmosphere with 10-minute intervals. To this resulting solution alcohol was added at the same temperature, by dissolving in DCM (50 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (100 ml) and then organic layer was separated. Aqueous layer was washed with DCM (2×50 ml). Combined organic layer was concentrated under reduced pressure. The resulting crude was washed with saturated $NaHCO_3$ solution (100 ml) and then extracted with EtOAc (2×50 ml). Organic layer was concentrated under reduced pressure and proceeded to next step with crude. Quantity produced, 8.5 g; yield, 48%.

ATX-0043: Step 6

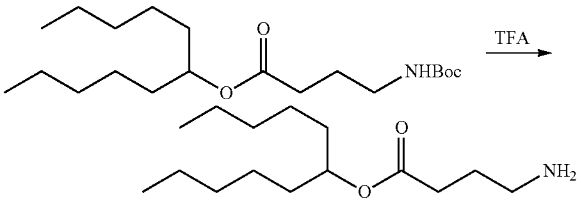

To a solution 8.5 g undecan-6-yl 4-((tert-butoxycarbonyl) amino) butanoate (1 eq.) dissolved in 70 ml DCM, was added trifluoroacetic acid (TFA; 10 eq.) at 0° C. and stirred at room temperature for 4 hours under nitrogen atmosphere.

Progress of the reaction was monitored by TLC (70% EtOAc/hexane; Rf: 0.2). Reaction mass was concentrated under reduced pressure. The resulting crude was washed with saturated $NaHCO_3$ solution (150 ml) and then extracted with EtOAc (2×100 ml). Organic layer was separated and concentrated under reduced pressure.

Crude compound was subjected to column chromatography using (60-120 mesh silica gel; 4% MeOH/$CHCl_3$ and 1 ml of triethylamine), and alcohol was recovered. Quantity produced, 5.0 g; yield, 33% (with respect to alcohol).

ATX-0043: Step 7

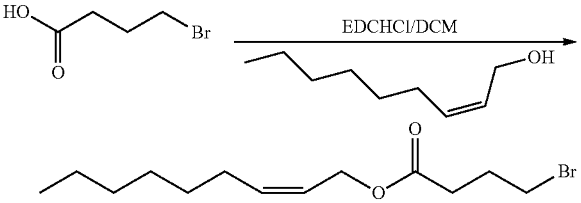

To a solution of 14 g 4-bromo butyric acid (1 eq.) dissolved in DCM (100 ml), cooled to below 0° C. was added 21 g EDC·HCl (1.3 eq.), 15.2 ml $Et_3N$ (1.3 eq.), and 1 g DMAP (0.1 eq.) sequentially under nitrogen atmosphere with 10-minute intervals. To this resulting solution 8.3 g (Z)-non-2-en-1-ol (0.7 eq.) was added, by dissolving in 50 ml of DCM, using additional funnel, and stirred at room temperature for 16 hours under nitrogen atmosphere.

Progress of the reaction was monitored by TLC (10% EtOAc in hexane; Rf: 0.7). Reaction mass was quenched with water (50 ml) and then organic layer was separated. Aqueous layer was washed with DCM (2×50 ml). Combined organic layer was concentrated under reduced pressure. The resulting crude was washed with saturated $NaHCO_3$ solution (100 ml) and then extracted with EtOAc (2×50 ml). Organic layer was separated and concentrated under reduced pressure.

Crude compound was subjected to column chromatography (60-120 mesh silica gel) using 5% EtOAc/hexane. Quantity produced, 11.0 g; yield, 64%.

ATX-0043: Step 8

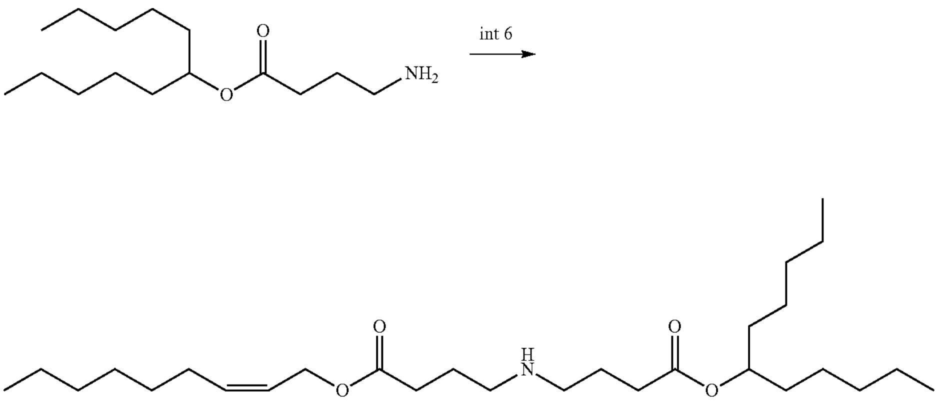

To a 250 ml round bottom flask, 2 g undecan-6-yl 4-aminobutanoate (1 eq.) and 2.2 g (Z)-non-2-en-1-yl 4-bromobutanoate (1 eq.) in DMF, 1.2 g potassium carbonate (1.2 eq.) was added and the resulting mixture was refluxed at 90° C. for 4 hours under nitrogen atmosphere.

Progress of the reaction was monitored by TLC (10% MeOH in $CHCl_3$; Rf 0.5). Ice water was added to the reaction mass and then extracted with EtOAc and dried over sodium sulphate and concentrated under reduced pressure.

Crude compound was subjected to column chromatography (100-200 mesh silica gel) using 15% EtOAc/hexane. Starting amine and bromo compounds were recovered. Quantity produced, 1.45 g; yield, 40%.

ATX-0043: Step 9

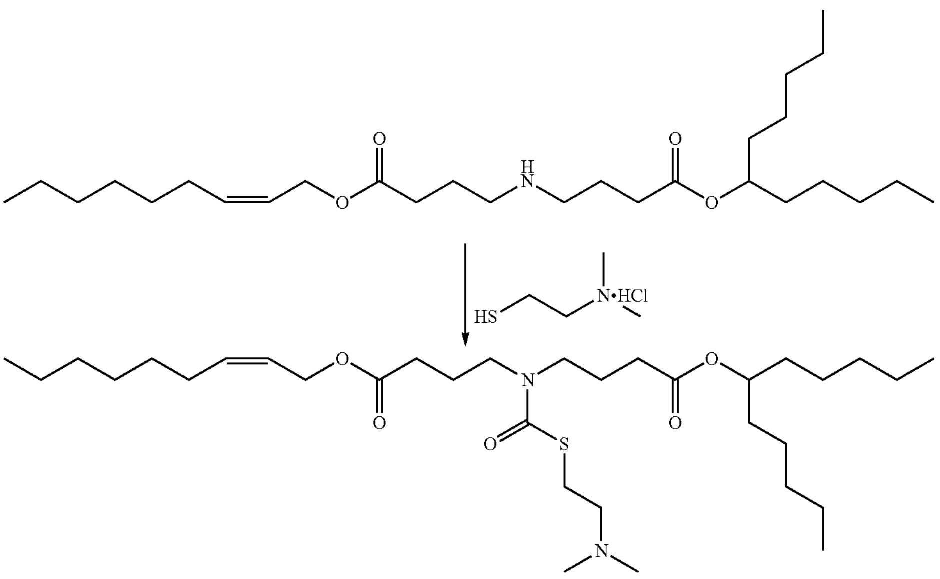

To a solution of 1.45 g (Z)-non-2-en-1-yl 4-((4-oxo-4-(undecan-6-yloxy)butyl)amino)butanoate (1 eq.) dissolved in dry DCM, was added 1.29 ml triethylamine 3 eq.) and 360 mg triphosgene (0.4 eq.) with 5 minute intervals at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 360 mg sodium hydride (5.5 eq.) dissolved in dry THF (20 ml), in a 2 neck 250 ml round bottom flask stirred at 0° C. under nitrogen atmosphere, was added 2.1 g 2-(dimethylamino)ethane-1-thiol hydrochloride (5.5 eq.) in THF (30 ml) and kept stirring for 5 minutes under nitrogen atmosphere. To this resulting solution the above carbonyl chloride dissolved in THF (50 mL) was added using additional funnel slowly for about 15 minutes, added to this resulting solution and stirred at room temperature for 1 hour.

Reaction mass was quenched with saturated $NH_4Cl$ solution (20 ml) and then EtOAc (20 mL) was added. Organic layer was separated and the aqueous layer was washed with EtOAc (2×20 mL). Combined organic layer was concentrated and the resulting crude was subjected to column chromatography. Progress of the reaction was monitored by TLC (60% EtOAc/Hex; Rf: 0.5; PMA charring).

Purification was done using silica gel (100-200 mesh; 18% EtOAc/hexane) chromatography. Quantity produced, 500 mg; yield, 26%; confirmed by $^1$H NMR; HPLC; and mass spectroscopy (Mass).

ATX-0043/RL-43A: $^1$H-NMR (PPM, 400 MHz, $CDCl_3$): δ=5.63 (m, 1), 5.54 (m, 1), 4.87 (m, 1), 4.63 (d, J=7.0, 2), 3.37 (brs, 4), 3.03 (t, J=7.0, 2), 2.27 (s, 6), 2.22-2.32 (4), 2.09 (m, 2), 1.80-1.90 (4), 1.45-1.55 (4), 1.20-1.40 (22), 0.83-0.92 (9).

Example 3: Synthesis of ATX-0057

Figure 2:
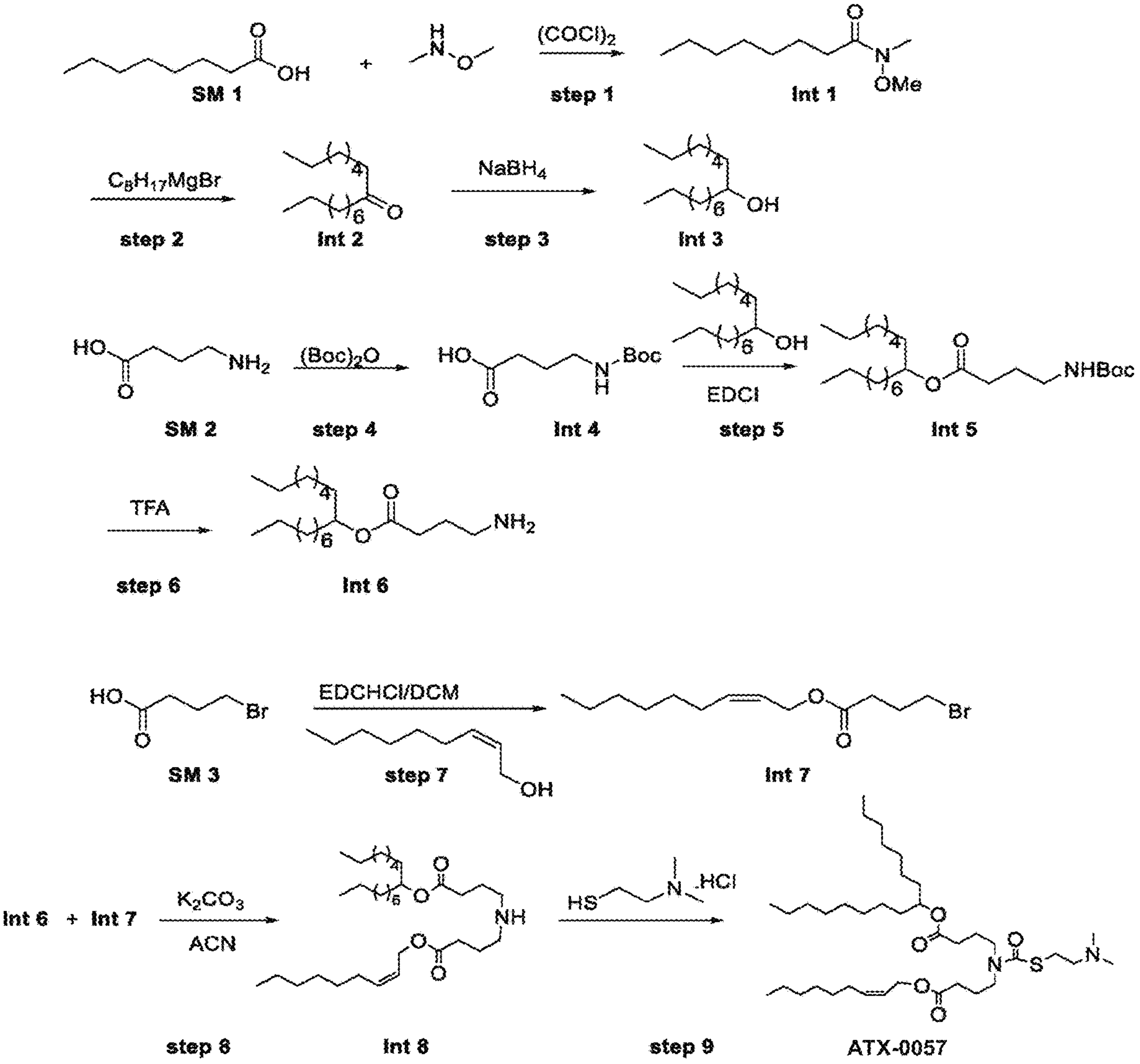
FIG. 2 shows the synthetic pathway of ATX-0057 from octanoate (SM 1), 4-aminobutanoic acid (SM 2), and 4-bromobutyric acid (SM 3). Ints 1-8 and reactions are described in Example 3.

FIG. 2 shows the synthetic pathway of ATX-0057 that is described further as follows.

ATX-0057: Step 1: N-methoxy-N-methyloctanamide

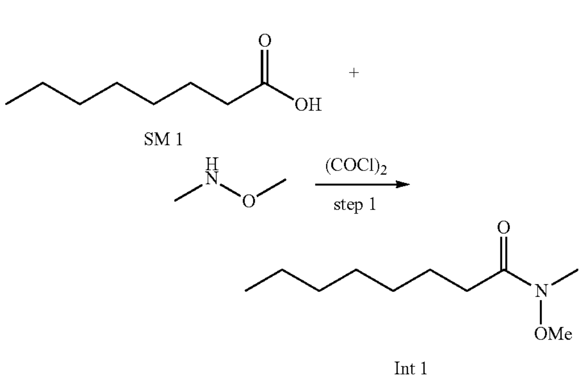

SM 1

Int 1

In a 2 liter, two neck round bottom flask, octanoic acid (1 eq.) dissolved in DCM (300 ml) was taken and then added 1.5 eq. oxalyl chloride slowly at 0° C., stirring under nitrogen atmosphere. The resulting reaction mixture was stirred at room temperature for 2 hours. In a separate 2 liter, two neck round bottom flask, to 2 eq. N,O-dimethylhydroxylamine hydrochloride in DCM (200 ml), was added 3 eq. trimethylamine using additional funnel, stirred at 0° C. To this resulting solution, the above acid chloride, after concentration under reduced pressure, was added under nitrogen atmosphere by dissolving in DCM (150 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure. Crude compound was subjected to column chromatography using (60-120 mesh silica gel; 10% EtOAc/hexane). Quantity produced, 85 g; yield, 65%.

ATX-0057: Step 2: hexadecane-8-one

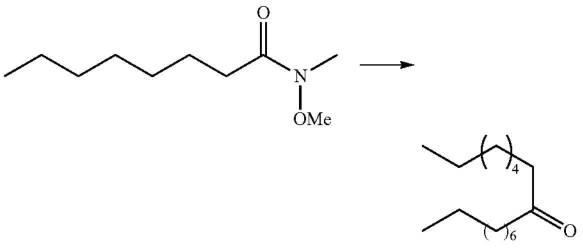

To a solution of octyl magnesium bromide in THF (100 ml), taken in a 1 liter, two neck round bottom flask, stirred at 0° C. under nitrogen atmosphere, was added N-methoxy-N-methyloctanamide solution (dissolved in 200 ml THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (250 ml) and then EtOAc (350 ml) was added. The organic layer was separated and the aqueous layer was washed with EtOAc (2×100 ml). Combined organic layers were concentrated under reduced pressure. Crude compound was subjected to column chromatography using (60-120 mesh silica gel; 2% EtOAc/hexane). Quantity produced, 65 g; yield, 63%.

ATX-0057: Step 3: hexadecane-8-ol

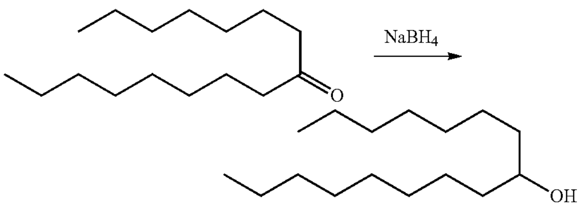

To a solution of hexadecan-8-one (1 eq.) dissolved in MeOH/THF, 1 eq. sodium borohydride was added at 0° C. and the resulting solution was stirred at room temperature for 1.5 hours.

Progress of the reaction was monitored by TLC (10% EtOAc in hexane; Rf: 0.5). Reaction mass was quenched with saturated $NH_4Cl$ solution (75 ml). Solvent was removed under reduced pressure and the resulting crude was portioned between EtOAc (150 ml) and water (100 ml). Organic layer was separated and the aqueous layer was washed with EtOAc (3×100 ml). Combined organic layers were concentrated under reduced pressure to get white solid. Quantity produced, 60 g; yield, 91%.

ATX-0057: Step 4: 4-((tert-butoxycarbonyl) amino)butanoic acid

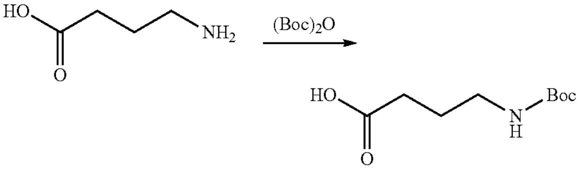

To a solution of 4-aminobutanoic acid, dissolved in THF, aqueous 1 N NaOH solution was added at 0° C., followed by Boc anhydride, sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (250 ml) and then EtOAc (300 ml) was added. Organic layer was separated and the aqueous layer was washed with EtOAc (3×150 ml). Combined organic layer was concentrated under reduced pressure to obtain a gummy liquid. Quantity produced, 80 g; yield, 81%.

ATX-0057: Step 5: hexadecan-8-yl 4-((tert-butoxycarbonyl)amino)butanoate

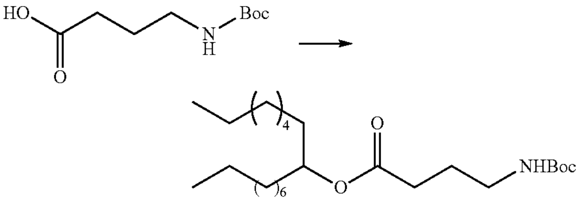

To a solution of 4-((tert-butoxycarbonyl) amino)butanoic acid, dissolved in DCM (200 ml), cooled to below 0° C. was added EDC·HCl, $Et_3N$, and 4-dimethylaminopyridine (DMAP), sequentially under nitrogen atmosphere with 10 minutes interval. To this resulting solution, 1 eq. hexadecane-8-ol alcohol was added at the same temperature, by dissolving in DCM (150 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (150 ml) and then organic layer was separated. Aqueous layer was washed with DCM (2×100 ml). Combined organic layer was concentrated under reduced pressure. The resulting crude was washed with saturated $NaHCO_3$ solution (150 ml) and then EtOAc (200 ml) was added. Organic layer was separated, concentrated under reduced pressure, and proceeded to next step with crude. Quantity produced, 80 g (crude; required compound and alcohol).

ATX-0057: Step 6: hexadecan-8-yl 4-aminobutanoate

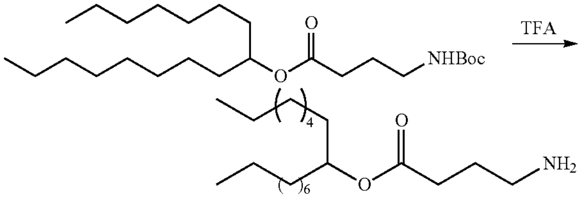

To a solution of hexadecan-8-yl-4-((tert-butoxycarbonyl) amino)butanoate, dissolved in DCM, was added TFA at 0° C. and stirred at room temperature for 3 hours under nitrogen atmosphere. Progress of the reaction was monitored by TLC (10% MeOH in $CHCl_3$; Rf: 0.3). Reaction mass was concentrated under reduced pressure. The resulting crude was washed with a saturated $NaHCO_3$ solution (300 ml) and then extracted with EtOAc (2×200 ml). The organic layer was separated and concentrated under reduced pressure. Crude compound was subjected to column chromatography using (60-120 mesh silica gel; 4% MeOH/$CHCl_3$ and 1 ml of triethylamine), and alcohol was recovered. Quantity produced, 40 g; yield, 59% for two steps; confirmed by Mass.

ATX-0057: Step 7: (Z)-non-2-en-1-yl 4-bromobutanoate

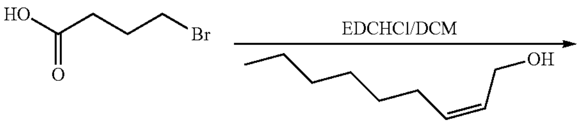

-continued

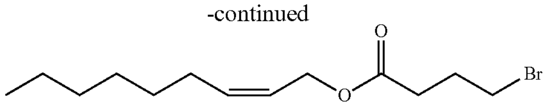

To a solution of 4-bromo butyric acid, dissolved in DCM (400 ml), cooled to below 0° C. was added to EDC·HCl, $Et_3N$, and DMAP sequentially under nitrogen atmosphere with 10-minute intervals. To this resulting solution (Z)-non-2-en-1-ol was added, by dissolving in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (300 ml) and then organic layer was separated. Aqueous layer was washed with DCM (2×150 ml). Combined organic layer was concentrated under reduced pressure. The resulting crude was washed with saturated $NaHCO_3$ solution (200 ml) and then extracted with EtOAc (150 ml). Organic layer was separated and concentrated under reduced pressure. Crude compound was subjected to column chromatography (60-120 mesh silica gel) using 5% EtOAc/hexane. Alcohol was recovered. Quantity produced, 27 g; yield, 51%.

ATX-0057: Step 8: hexadecan-8-yl (Z)-4-((4-(non-2-en-1-yloxy)-4-oxobutyl)amino)butanoate

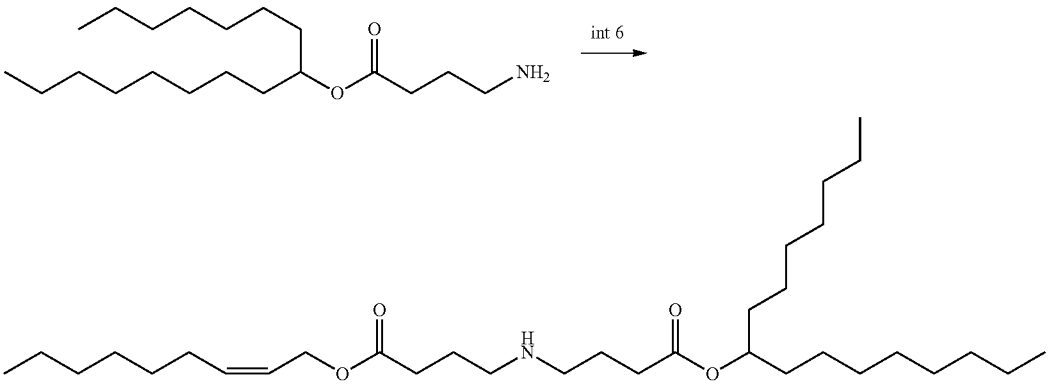

To a solution of hexadecan-8-yl 4-aminobutanoate, (Z)-non-2-en-1-yl 4-bromobutanoate in acetonitrile (ACN), potassium carbonate was added and the resulting mixture was refluxed at 90° C. for 4 hours under nitrogen atmosphere. Progress of the reaction was monitored by TLC (10% MeOH in $CHCl_3$; Rf. 0.5). Reaction mass was filtered, washed with ACN (20 ml), and the filtrate concentrated under reduced pressure. Crude compound was subjected to column chromatography (100-200 mesh silica gel) using 15% EtOAc/hexane. Starting materials, amine and bromo compounds, were recovered. Quantity produced, 20 g; yield, 40%; confirmed by Mass.

ATX-0057: Step 9

Combined organic layer was concentrated and the resulting crude was subjected to column chromatography.

The first purification was done using silica gel (60-120 mesh) 22 g of crude compound was adsorbed on 60 g of silica gel and poured onto 500 g of silica gel taken in the column. Compound was eluted at 35% EtOAc/hexane. The second purification was done using neutral alumina with HPLC grade solvents. Crude compound, 7.5 g, was adsorbed on 18 g of neutral alumina and the resulting was poured onto 130 g of neutral alumina taken in the column. Compound was eluted at 10% EtOAc/hexane. Yield, 29%; confirmed by $^1$H NMR, HPLC, and Mass.

ATX-0057/RL-43C: $^1$H-NMR (PPM, 400 MHz, $CDCl_3$): δ=5.63 (m, 1), 5.51 (m, 1), 4.68 (m, 1), 4.83 (d, J=7.0, 2),

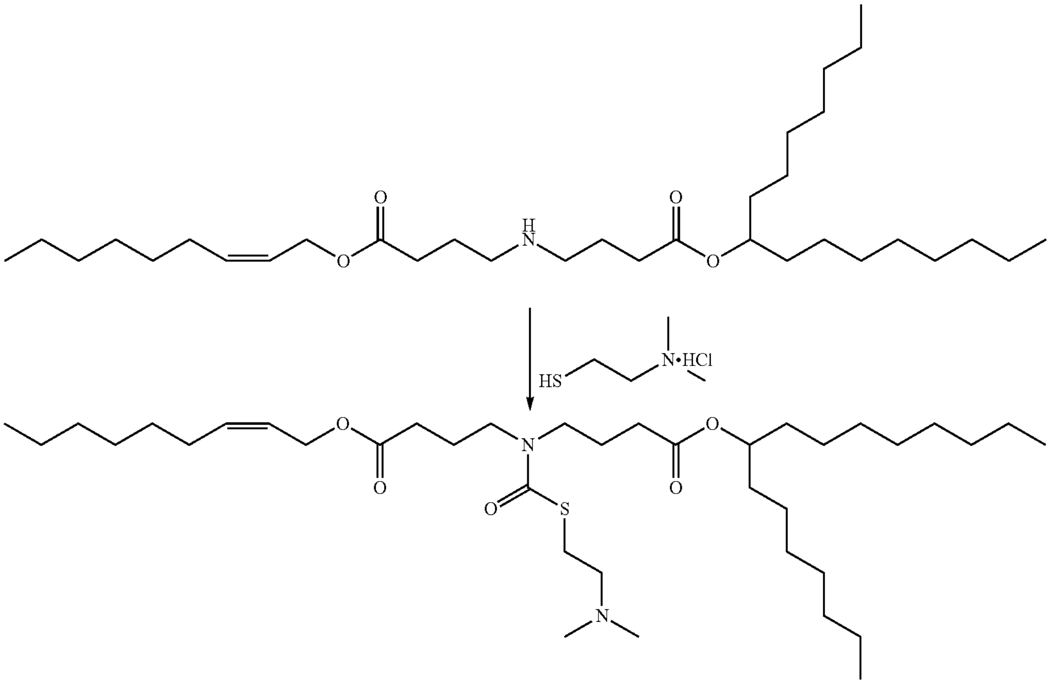

To a solution of hexadecan-8-yl (Z)-4-((4-(non-2-en-1-yloxy)-4-oxobutyl) amino) butanoate, dissolved in dry DCM, was added trimethylamine and triphosgene with 5 minutes interval at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To sodium hydride dissolved in dry THF (50 ml), in a two neck 100 ml round bottom flask stirred at 0° C. under nitrogen atmosphere, was added 2-(dimethylamino)propane-1-thiol hydrochloride and kept stirring for 5 minutes under nitrogen atmosphere. To this resulting solution the above carbamoyl chloride, dissolved in THF (80 ml), was added via syringe slowly for about 10 minutes. The resulting solution was stirred at room temperature for 6 hours under nitrogen atmosphere.

Progress of the reaction was monitored by TLC (60% EtOAC/hexane; Rf: 0.5; PMA charring). Reaction mass was quenched with saturated $NH_4Cl$ solution (75 ml) and then EtOAc (150 ml) was added. Organic layer was separated and the aqueous layer was washed with EtOAc (3×40 ml).

3.19 (brs, 4), 3.22 (m, 2), 2.52 (m, 2), 2.23-2.37 (4), 2.18 (s, 6), 2.08 (m, 2), 1.84-1.93 (4), 1.46-1.54 (4), 1.20-1.40 (30), 0.83-0.91 (9).

Example 4: Synthesis of ATX-0058

Figure 3:
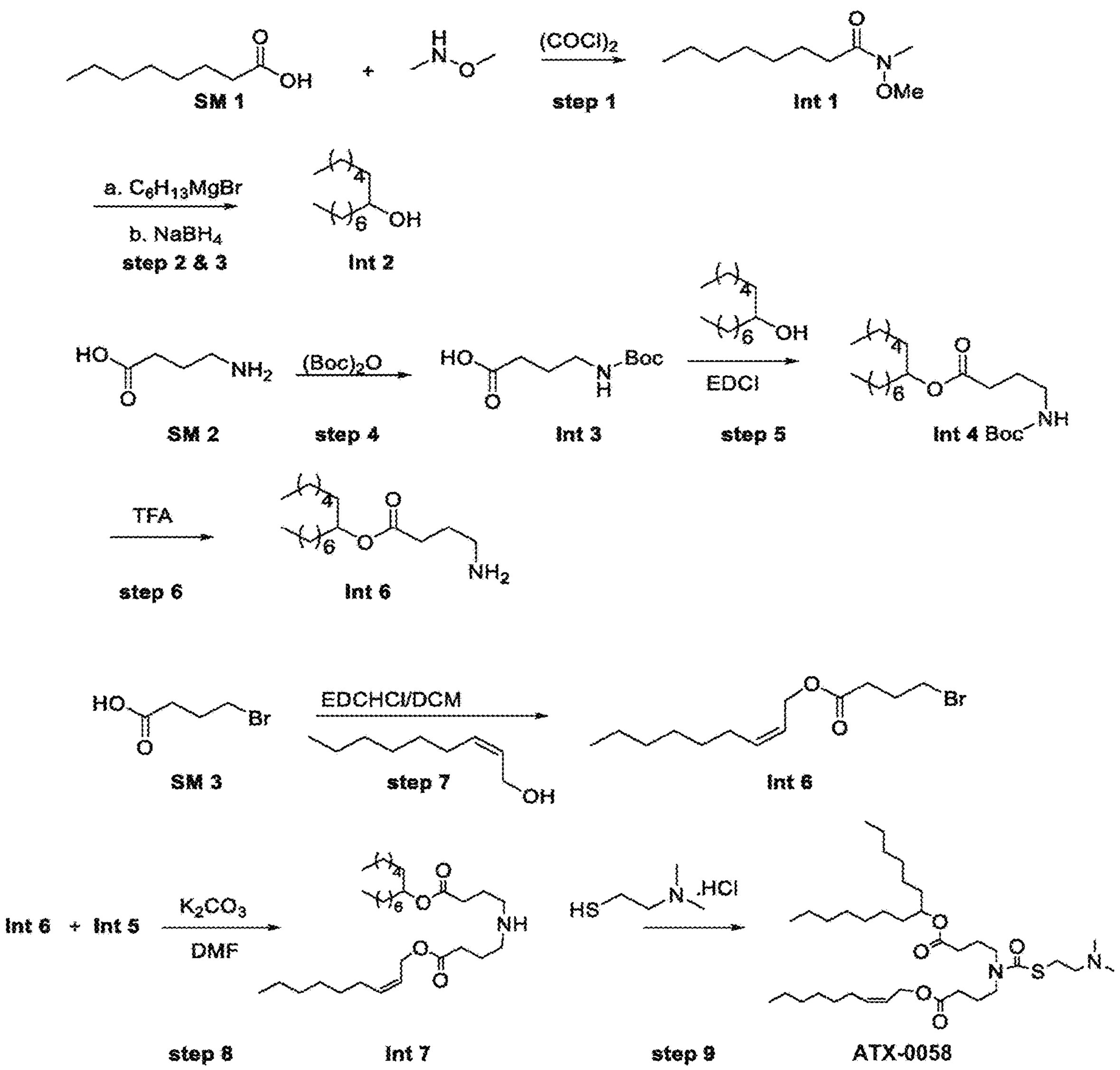
FIG. 3 shows the synthetic pathway of ATX-0058 from SM 1, SM 2 and SM3, which are the same as in FIG. 2. Ints 1-7 and reactions are described in Example 4.

FIG. 3 shows the synthetic pathway of ATX-0058 that is described further as follows.

ATX-0058: Step 1

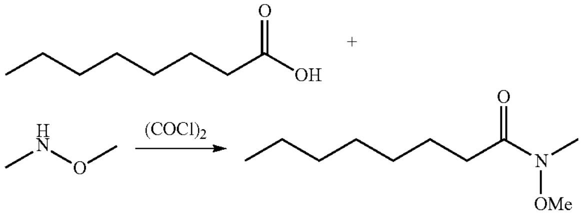

In 500 ml two neck round bottom flask under $N_2$ atmosphere, 30 g 8-bromooctanoic acid (1 eq.) dissolved in 200 ml of DCM was taken and then added slowly to 26.7 ml oxalyl chloride (1.5 eq.) at 0° C., stirring under nitrogen atmosphere. The resulting reaction mixture was stirred at room temperature for 2 hours.

In a separate 1 liter two neck round bottom flask, 40.5 g N,O-dimethylhydroxylamine hydrochloride (2 eq.) in 300 ml DCM was added 87 ml trimethylamine (3 eq.) stirred at 0° C. To this resulting solution, the above acid chloride was added after concentration under reduced pressure, by dissolving in 500 ml DCM, dropwise using addition funnel for 15 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (300 ml). Organic layer was separated and the aqueous layer was washed with DCM (2×100 ml). Combined organic layer was concentrated under reduced pressure.

Crude compound was subjected to column chromatography using (60-120 mesh silica gel; 10% EtOAc/hexane). Quantity produced, 28 g.

ATX-0058: Step 2

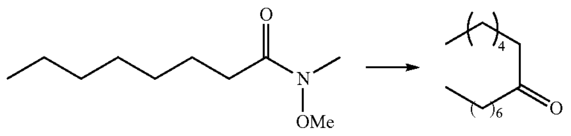

To a solution of 28 g hexyl magnesium bromide (1 eq.) in THF (100 ml), stirred at 0° C. under nitrogen atmosphere, was added 36.8 g N-methoxy-N-methyloctanamide (1.3 eq.) in 200 ml THF and the resulting reaction mixture was stirred at room temperature for 5 hours.

Progress of the reaction was monitored by TLC (10% EtOAc/hexane; Rf: 0.7). Reaction mass was quenched with saturated $NH_4Cl$ solution (100 ml). The organic layer was separated and the aqueous layer was washed with EtOAc (2×100 ml). Combined organic layer was concentrated under reduced pressure.

Crude compound was subjected to column chromatography using (60-120 mesh silica gel; 2% ethyl acetate/hexane). Quantity produced, 24 g; yield, 77%.

ATX-0058: Step 3

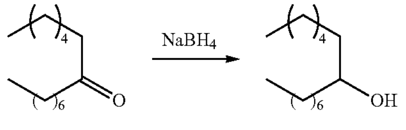

To a solution of 24 g tetradecan-7-one (1 eq.) dissolved in MeOH/THF, 4.27 g sodium borohydride (1 eq.) was added at 0° C. and the resulting solution was stirred at room temperature for 1 hour.

Progress of the reaction was monitored by TLC (10% EtOAc/hexane; Rf: 0.5). Reaction mass was quenched with saturated $NH_4Cl$ solution (50 ml). Methanol was reduced under reduced pressure. The resulting crude was portioned between EtOAc (200 ml) and water. Organic layer was separated and the aqueous layer was washed with EtOAc (2×80 ml). Combined organic layer was concentrated under reduced pressure to obtain a white solid. Quantity produced, 21.5 g; yield, 89%.

ATX-0058: Step 4

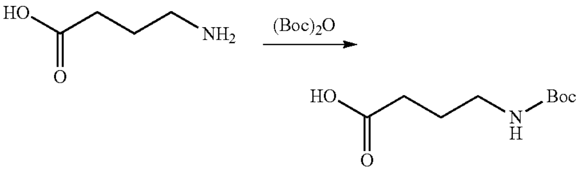

To a solution of 20 g 4-aminobutanoic acid dissolved in 140 ml THF, 196 ml of aqueous 1N NaOH solution was added at 0° C., followed by 36.8 g Boc anhydride, using a funnel. The resulting solution was stirred at room temperature for 4 hours.

Progress of the reaction was monitored by TLC (10% $MeOH/CHCl_3$; Rf: 0.5). Reaction mass was quenched with 5% HCl (100 ml) and then EtOAc (200 ml) was added. The organic layer was separated and the aqueous layer was washed with EtOAc (2×100 ml). Combined organic layer was concentrated under reduced pressure to obtain a gummy liquid. Quantity produced, 30 g; yield, 76%.

ATX-0058: Step 5

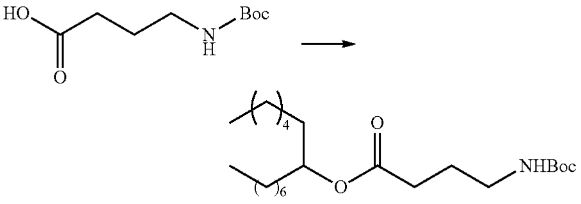

To a solution of 10 g 4-((tert-butoxycarbonyl)amino)butanoic acid (1 eq.) dissolved in DCM (150 ml), cooled to below 0° C. was added 12.2 g EDC·HCl (1.3 eq.), 20.4 ml $Et_3N$ (3 eq.), and 488 mg DMAP (0.1 eq.) sequentially with 10 minutes interval. To this resulting solution alcohol was added, by dissolving in DCM, using additional funnel, and stirred at room temperature for 24 hours under nitrogen atmosphere.

Progress of the reaction was monitored by TLC (10% EtOAc/hexane; Rf: 0.5). Reaction mass was quenched with water (100 ml) and the organic layer was separated. The aqueous layer was washed with DCM (2×50 ml). Combined organic layer was concentrated under reduced pressure. The resulting crude was washed with saturated $NaHCO_3$ solution and EtOAc (100 ml) was added. The organic layer was separated and concentrated under reduced pressure, and proceeded to next step with crude. Quantity produced, 12.7 g (crude).

ATX-0058: Step 6

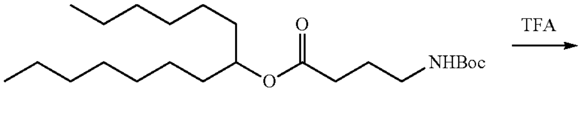

-continued

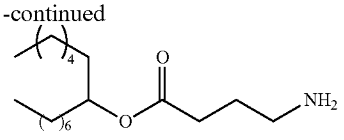

To a solution of 12.5 g tetradecan-7-yl 4-((tert-butoxycarbonyl)amino)butanoate (1 eq.) dissolved in 100 ml DCM, was added 23.9 ml TFA (10 eq.) at 0° C. and stirred at room temperature for 3 hours under nitrogen atmosphere.

Progress of the reaction was monitored by TLC (10% MeOH/$CHCl_3$; Rf: 0.3). Reaction mass was concentrated under reduced pressure. The resulting crude was washed with saturated $NaHCO_3$ solution (100 ml) and EtOAc (100 ml) was added. The organic layer was separated and concentrated under reduced pressure.

Crude compound was subjected to column chromatography using (60-120 mesh silica gel; 4% MeOH/$CHCl_3$) and alcohol was recovered. Quantity produced, 7 g for two steps; yield, 47%; confirmed by Mass.

ATX-0058: Step 7

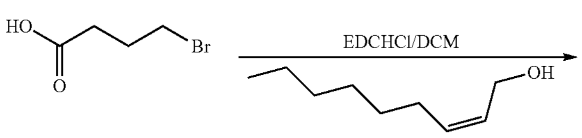

-continued

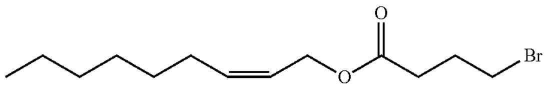

To a solution of 20 g 4-bromo butyric acid (1 eq.) dissolved in DCM (150 ml), cooled to 0° C. was added 1.5 eq. EDC·HCl, 3 eq. $Et_3N$, and 0.1 eq. DMAP sequentially with 10 minutes interval. To this resulting solution 0.7 eq. (Z)-non-2-en-1-ol was added, by dissolving in 100 ml DCM, using a funnel, and stirred at room temperature for 24 hours under nitrogen atmosphere.

Progress of the reaction was monitored by TLC (10% EtOAc/hexane; Rf: 0.7). Reaction mass was quenched with water (100 ml) and then organic layer was separated. Aqueous layer was washed with DCM (2×100 ml). Combined organic layer was concentrated under reduced pressure. The resulting crude was washed with saturated $NaHCO_3$ solution and EtOAc (150 ml) was added. The organic layer was separated and concentrated under reduced pressure.

Crude compound was subjected to column chromatography using (60-120 mesh silica gel; 5% EtOAc/hexane). Quantity produced, 17 g; yield, 69%; confirmed by $^1H$ NMR.

ATX-0058: Step 8

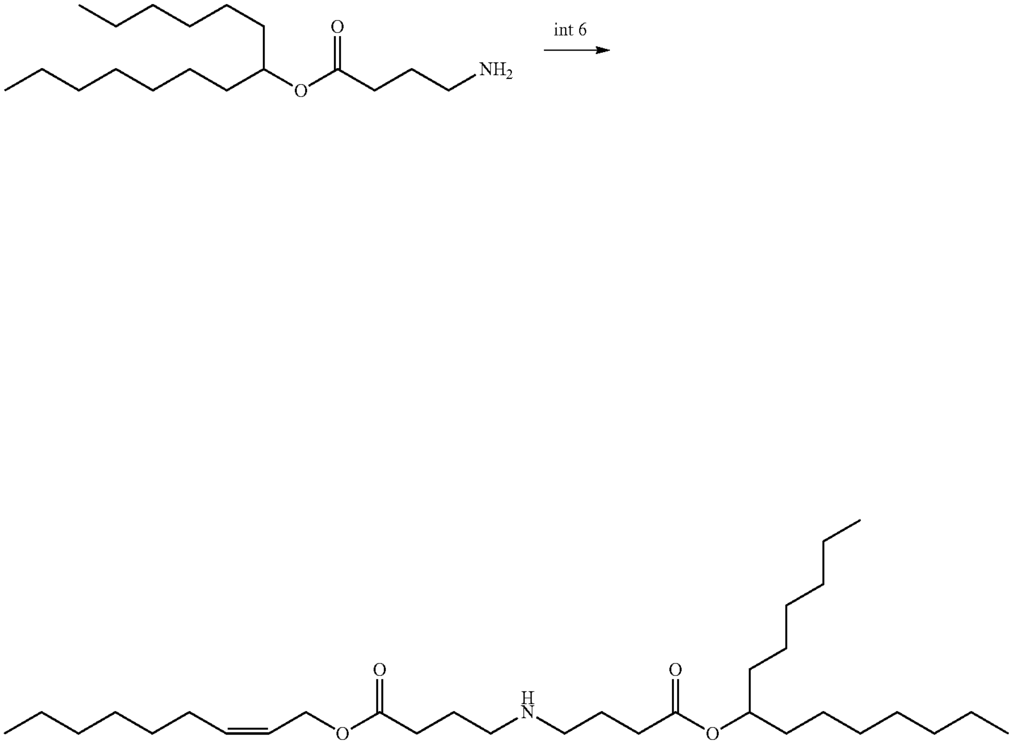

To a solution of 6 g tetradecan-7-yl 4-aminobutanoate (1 eq.), 5.8 g (Z)-non-2-en-1-yl 4-bromobutanoate (1 eq.) in ACN (125 ml), 2.7 g potassium carbonate (1.2 eq.) was added and the resulting was refluxed at 90° C. for 3 hours under nitrogen atmosphere.

Progress of the reaction was monitored by TLC (10% $MeOH/CHCl_3$; Rf: 0.5). Reaction mass was filtered and the filtrate concentrated under reduced pressure.

Crude compound was subjected to column chromatography using (100-200 mesh silica gel; 15% EtOAc/hexane). Quantity produced, 4.5 g; yield, 44%; confirmed by Mass.

ATX-0058: Step 9

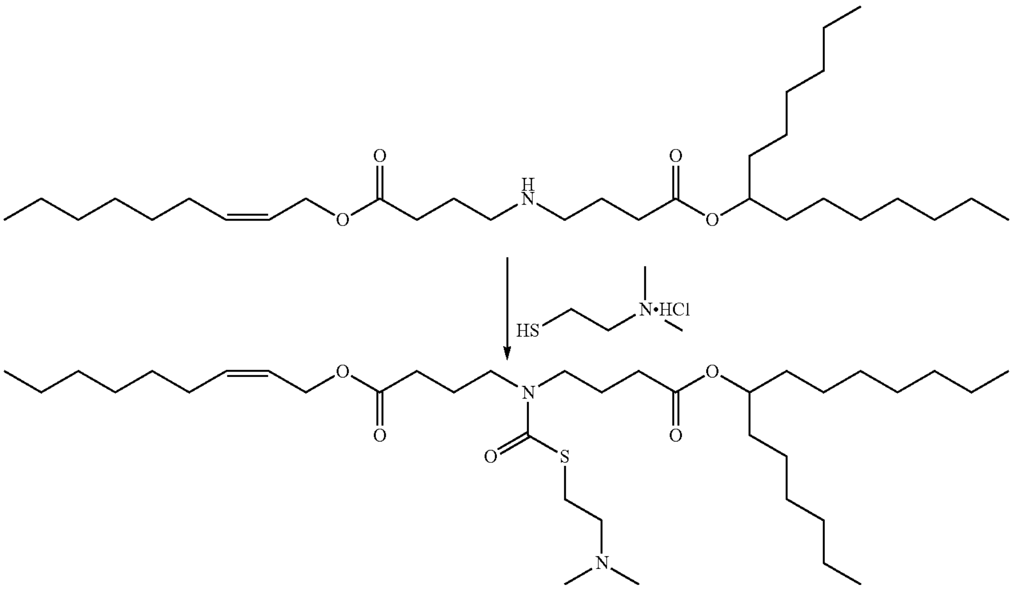

To a solution of 4.4 g (Z)-non-2-en-1-yl 4-((4-oxo-4-(tetradecan-7-yloxy)butyl)amino)butanoate (1 eq.) dissolved in 30 ml dry DCM, was added 0.83 ml trimethylamine (3 eq.) and 418 mg triphosgene (0.5 eq.) with 5 minutes interval, at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 192 mg sodium hydride (10 eq.) dissolved in dry THF (25 ml), in a two neck 100 ml round bottom flask, was added 564 mg 2-(dimethylamino)propane-1-thiol hydrochloride (5 eq.) at 0° C. and kept stirring for 5 minutes under nitrogen atmosphere. To this resulting solution the above carbamoyl chloride, dissolved in THF (35 ml), was added via syringe slowly for about 10 minutes. The resulting solution was stirred at room temperature for 4 hours under nitrogen atmosphere.

Progress of the reaction was monitored by TLC (60% EtOAC/hexane; Rf: 0.5; PMA charring). Reaction mass was quenched with saturated $NH_4Cl$ (30 ml) and then EtOAc (100 ml) was added. The organic layer was separated and the aqueous layer was washed with EtOAc (2×50 ml). Combined organic layer was concentrated and the resulting crude was subjected to column chromatography.

A first purification was done using silica gel (60-120 mesh). 5.0 g of crude compound was adsorbed on 9 g of silica gel and poured onto 90 g of silica gel taken in the column. Compound was eluted at 35% EtOAc/hexane. A second purification was done using neutral alumina with HPLC grade solvents. 1.5 g of crude compound was adsorbed on 4 g of neutral alumina and the resulting was poured onto 40 g of neutral alumina taken in the column. Compound was eluted at 10% EtOAc/hexane. Quantity produced, 1.2 g; yield, 21%; confirmed by $^1H$ NMR; HPLC; Mass.

ATX-0058/RL-43B: $^1H$-NMR (PPM, 400 MHz, $CDCl_3$): δ=5.65 (m, 1), 5.52 (m, 1), 4.86 (m, 1), 4.63 (d, J=7.0, 2), 3.37 (brs, 4), 3.02 (t, J=6.0, 2), 2.53 (t, J=6.0, 2), 2.27-2.36 (4), 2.27 (s, 6), 2.09 (m, 2), 1.83-1.96 (4), 1.46-1.54 (4), 1.20-1.40 (26), 0.84-0.91 (9).

Example 5: Synthesis of ATX-0081

Figure 4:
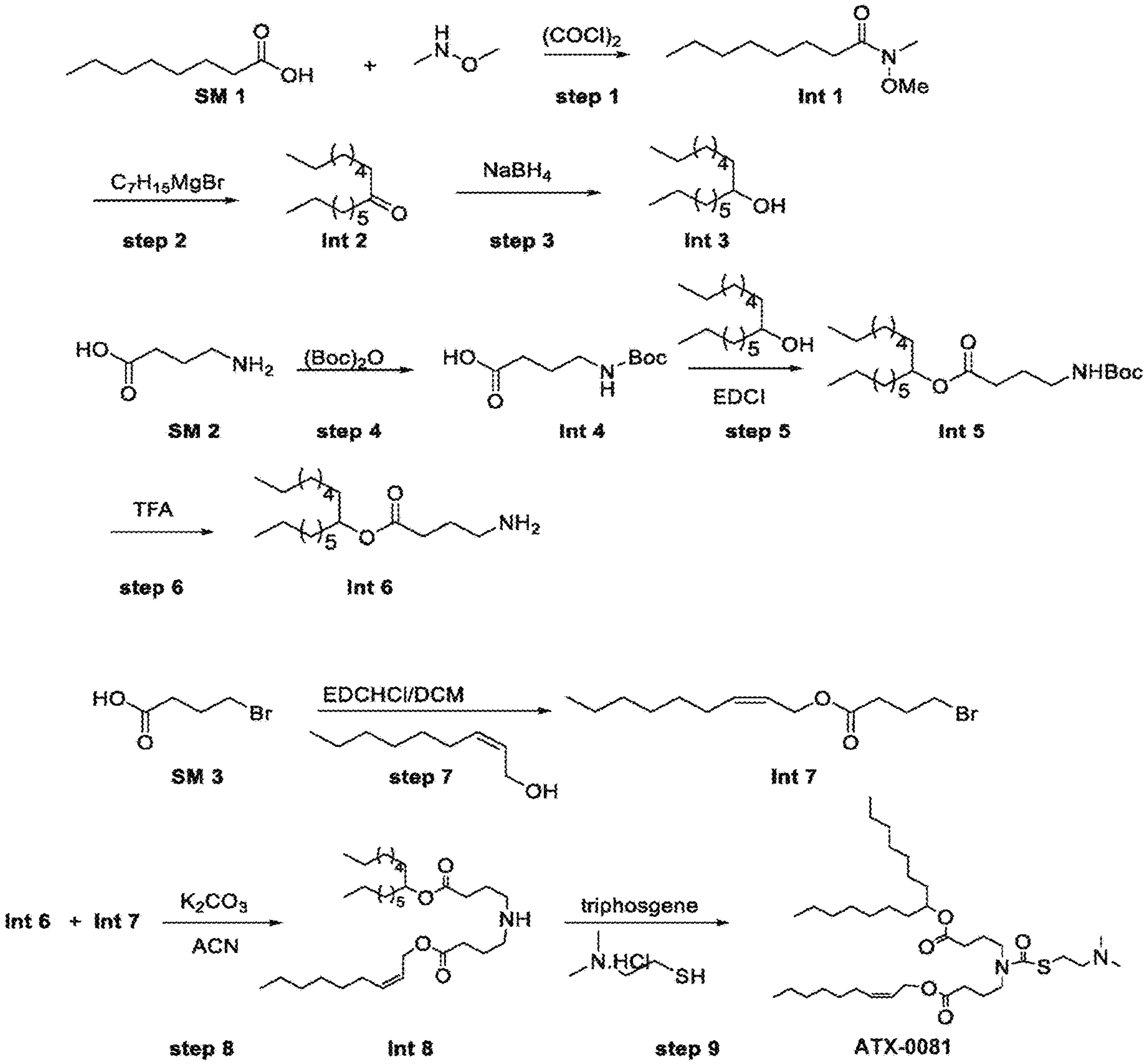
FIG. 4 shows the synthetic pathway of ATX-0081 from SM 1, SM 2 and SM3, which are the same as in FIG. 2. Ints 1-8 and reactions are described in Example 5.

FIG. 4 shows the synthetic pathway of ATX-0081 that is described further as follows.

ATX-0081: Step 1

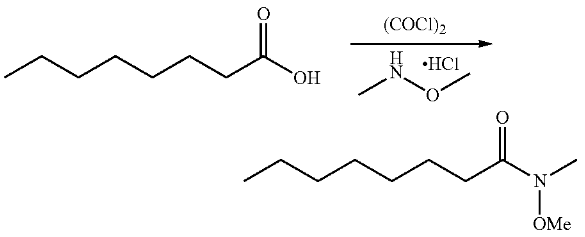

In a 2 L, two neck round bottom flask, octanoic acid dissolved in DCM (200 ml) was taken and then added 1.5 eq. oxalyl chloride slowly at 0° C., stirring under nitrogen atmosphere. The resulting reaction mixture was stirred at room temperature for 2 hours. In a separate 2 liter, two neck round bottom flask, to 2 eq. N,O-dimethylhydroxylamine hydrochloride in DCM (200 ml), was added 3 eq. trimethylamine using additional funnel, stirred at 0° C. To this resulting solution, the above acid chloride, after concentration under reduced pressure, was added under nitrogen atmosphere by dissolving in DCM (150 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure. Crude compound was subjected to column chromatography using (60-120 mesh silica gel; 10% EtOAc/hexane). Quantity produced, 33 g; yield, 84%.

ATX-0081: Step 2

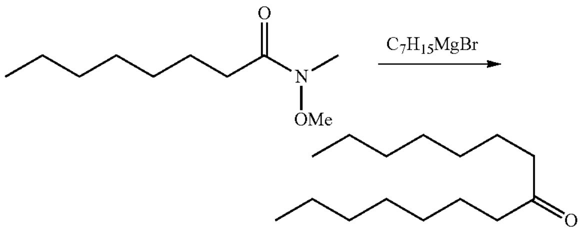

To a solution of 22 g heptyl magnesium bromide (1.5 eq.) in THF (100 ml), taken in a 1 liter, two neck round bottom flask, stirred at 0° C. under nitrogen atmosphere, was added N-methoxy-N-methyloctanamide (1 eq.) solution (dissolved in 200 ml THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (250 ml) and then EtOAc (350 ml) was added. The organic layer was separated and the aqueous layer was washed with EtOAc (2×100 ml). Combined organic layers were concentrated under reduced pressure. Crude compound was subjected to column chromatography using (60-120 mesh silica gel; 2% EtOAc/hexane). Quantity produced, 22 g; yield, 65%.

ATX-0081: Step 3

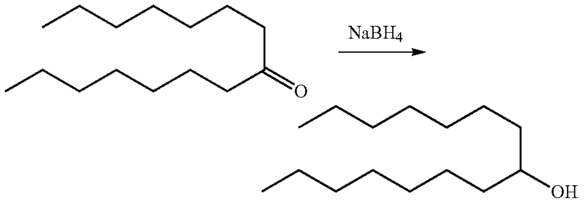

To a solution of 22 g pentadecan-8-one (1 eq.) dissolved in MeOH/THF, 1.5 eq. sodium borohydride was added at 0° C. and the resulting solution was stirred at room temperature for 1 hour.

Progress of the reaction was monitored by TLC (10% EtOAc in hexane; Rf: 0.5). Reaction mass was quenched with saturated $NH_4Cl$ solution (75 ml). Solvent was removed under reduced pressure and the resulting crude was portioned between EtOAc (150 ml) and water (100 ml). Organic layer was separated and the aqueous layer was washed with EtOAc (3×100 ml). Combined organic layers were concentrated under reduced pressure to get white solid. Quantity produced, 20 g; yield, 90%.

ATX-0081: Step 4

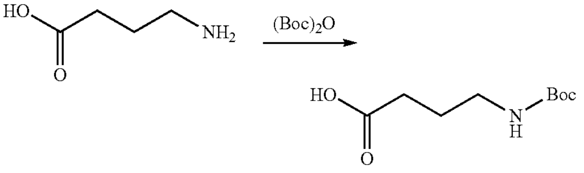

To a solution of 50 g 4-aminobutanoic acid dissolved in 350 ml THF, 490 ml aqueous 1 N NaOH solution was added at 0° C., followed by 140 ml Boc anhydride, sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (250 ml) and then EtOAc (300 ml) was added. Organic layer was separated and the aqueous layer was washed with EtOAc (3×150 ml). Combined organic layer was concentrated under reduced pressure to obtain a gummy liquid. Quantity produced, 80 g; yield, 81%.

ATX-0081: Step 5

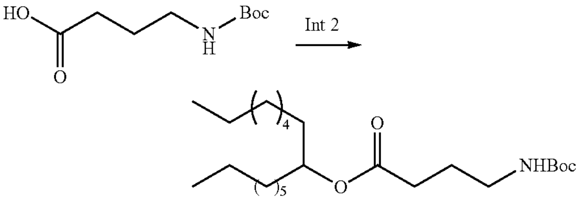

To a solution of 10 g 4-((tert-butoxycarbonyl) amino) butanoic acid, dissolved in DCM (250 ml), cooled to below 0° C. was added 1.3 eq. EDC·HCl, $Et_3N$, and 4-dimethylaminopyridine (DMAP), sequentially under nitrogen atmosphere with 10 minutes interval. To this resulting solution, 1 eq. pentadecane-7-ol alcohol was added at the same temperature, by dissolving in DCM (150 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (150 ml) and then organic layer was separated. Aqueous layer was washed with DCM (2×100 ml). Combined organic layer was concentrated under reduced pressure. The resulting crude was washed with saturated $NaHCO_3$ solution (150 ml) and then EtOAc (200 ml) was added. Organic layer was separated, concentrated under reduced pressure, and proceeded to next step with crude. Quantity produced, 8.5 g (crude; required compound and alcohol).

ATX-0081: Step 6

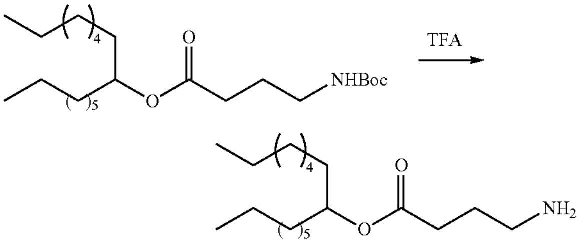

To a solution of 8.5 g pentadecan-8-yl 4-((tert-butoxycarbonyl)amino)butanoate dissolved in 65 ml DCM, was added 10 eq. TFA at 0° C. and stirred at room temperature for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with a saturated $NaHCO_3$ solution (300 ml) and then extracted with EtOAc (2×200 ml). The organic layer was separated and concentrated under reduced pressure. Crude compound was subjected to column chromatography using (60-120 mesh silica gel; 4% MeOH/$CHCl_3$ and 1 ml of triethylamine), and alcohol was recovered. Quantity produced, 4 g for two steps; yield, 25%; confirmed by Mass.

ATX-0081: Step 7

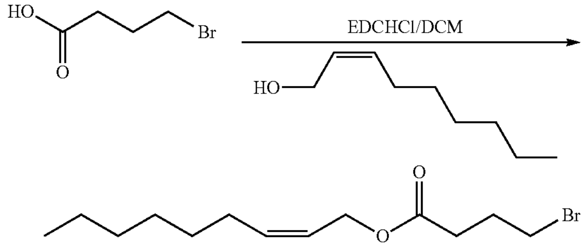

To a solution of 4-bromo butyric acid, dissolved in DCM (300 ml), cooled to below 0° C. was added to EDC·HCl, $Et_3N$, and DMAP sequentially under nitrogen atmosphere with 10-minute intervals. To this resulting solution 20 g (Z)-non-2-en-1-ol was added, by dissolving in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (300 ml) and then organic layer was separated. Aqueous layer was washed with DCM (2×150 ml). Combined organic layer was concentrated under reduced pressure. The resulting crude was washed with saturated $NaHCO_3$ solution (200 ml) and then extracted with EtOAc (150 ml). Organic layer was separated and concentrated under reduced pressure. Crude compound was subjected to column chromatography (60-120 mesh silica gel) using 5% EtOAc/hexane. Alcohol was recovered. Quantity produced, 19 g; yield, 55%.

ATX-0081: Step 8

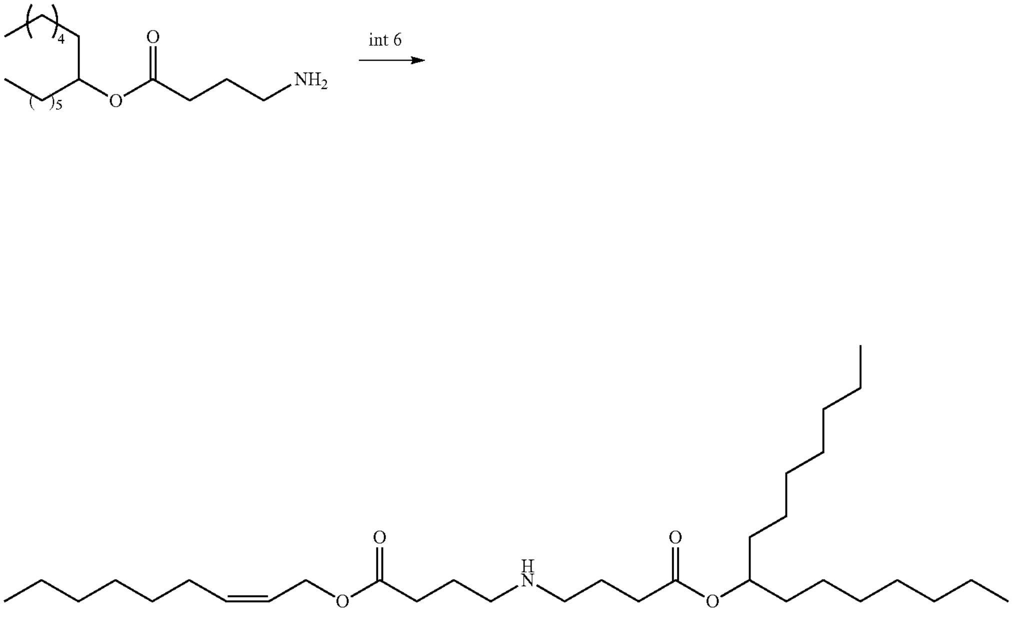

To a solution of 4.5 g pentadecan-8-yl 4-aminobutanoate, 1 eq. (Z)-non-2-en-1-yl 4-bromobutanoate in 70 ml acetonitrile (ACN), 1.4 eq. potassium carbonate was added and the resulting mixture was refluxed at 90° C. for 4 hours under nitrogen atmosphere.

Progress of the reaction was monitored by TLC (10% MeOH in $CHCl_3$; Rf: 0.5). Reaction mass was filtered, washed with ACN (20 ml), and the filtrate concentrated under reduced pressure. Crude compound was subjected to column chromatography (100-200 mesh silica gel) using 15% EtOAc/hexane. Starting materials, amine and bromo compounds, were recovered. Quantity produced, 2.1 g; yield, 27%; confirmed by Mass.

ATX-0081: Step 9

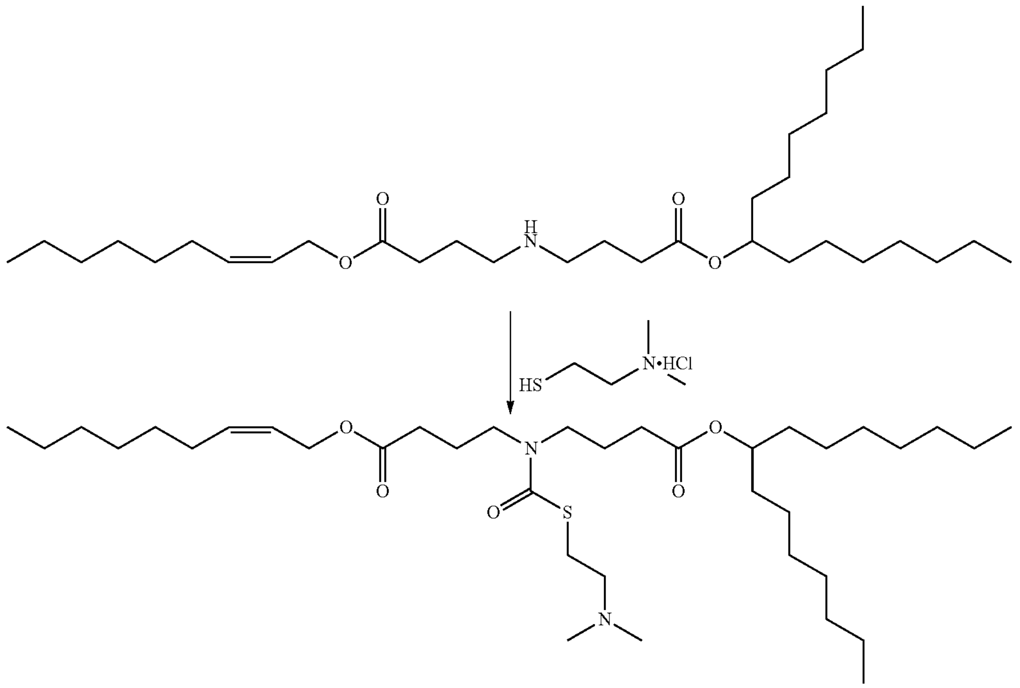

To a solution of 2.1 g pentadecan-8-yl (Z)-4-((4-(non-2-en-1-yloxy)-4-oxobutyl) amino) butanoate, dissolved in 150 ml dry DCM, was added 3 eq. triethylamine and triphosgene with 5 minutes interval at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 7 eq. sodium hydride dissolved in dry THF (80 ml), in a two neck 100 ml round bottom flask stirred at 0° C. under nitrogen atmosphere, was added 3.5 eq. 2-(dimethylamino) propane-1-thiol hydrochloride and kept stirring for 5 minutes under nitrogen atmosphere. To this resulting solution the above carbamoyl chloride, dissolved in THF (80 ml), was added via syringe slowly for about 10 minutes. The resulting solution was stirred at 0° C. to room temperature overnight under nitrogen atmosphere.

Progress of the reaction was monitored by TLC (60% EtOAC/hexane; Rf: 0.5; PMA charring). Reaction mass was quenched with saturated $NH_4Cl$ solution (75 ml) and then EtOAc (150 ml) was added. Organic layer was separated and the aqueous layer was washed with EtOAc (3×40 ml). Combined organic layer was concentrated and the resulting crude was subjected to column chromatography.

The first purification was done using silica gel (60-120 mesh) of crude compound was adsorbed on 60 g of silica gel and poured onto 500 g of silica gel taken in the column. Compound was eluted at 35% EtOAc/hexane. The second purification was done using neutral alumina with HPLC grade solvents. Crude compound was adsorbed on 18 g of neutral alumina and the resulting was poured onto 130 g of neutral alumina taken in the column. Compound was eluted at 10% EtOAc/hexane. Quantity produced, 1.5 g; yield, 45%; confirmed by $^1$H NMR, HPLC, and Mass.

ATX-0081/RL-48B: $^1$H-NMR (PPM, 500 MHz, $CDCl_3$): δ=5.64 (m, 1), 5.52 (m, 1), 4.86 (m, 1), 4.63 (d, J=7.0, 2), 3.31-3.44 (4), 3.02 (t, J=7.0, 2), 2.52 (t, J=7.0, 2), 2.26-2.36 (4), 2.27 (s, 6), 2.10 (m, 2), 1.84-1.95 (4), 1.46-1.54 (4), 1.20-1.40 (26), 0.85-0.94 (9).

Example 6: Synthesis of ATX-0082

Figure 5:
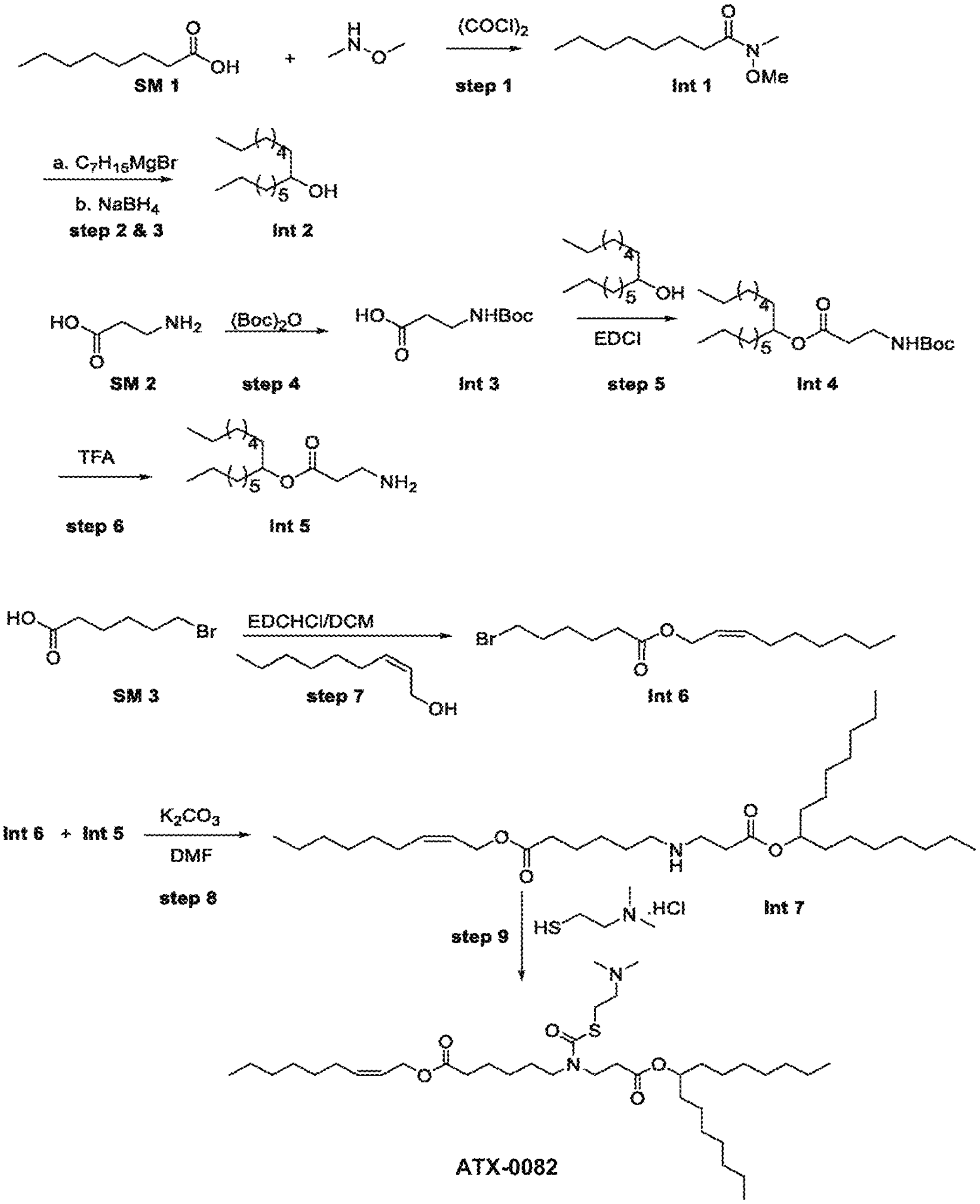
FIG. 5 shows the synthetic pathway of ATX-0082 from SM 1, SM 2 and SM3, which are the same as in FIG. 2. Ints 1-7 and reactions are described in Example 6.

FIG. 5 shows the synthetic pathway of ATX-0082 that is described further as follows.

ATX-0082: Step 1

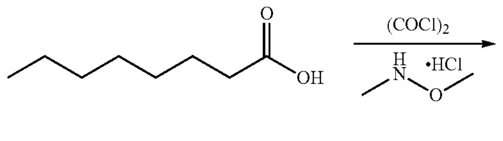

-continued

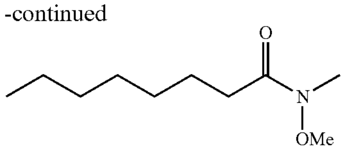

In a 2 liter, two neck round bottom flask, 30 g octanoic acid dissolved in DCM (200 ml) was taken and then added 1.5 eq. oxalyl chloride slowly at 0° C., stirring under nitrogen atmosphere. The resulting reaction mixture was stirred at room temperature for 2 hours. In a separate 2 liter, two neck round bottom flask, to 2 eq. N,O-dimethylhydroxylamine hydrochloride in DCM (200 ml), was added 3 eq. trimethylamine using additional funnel, stirred at 0° C. To this resulting solution, the above acid chloride, after concentration under reduced pressure, was added under nitrogen atmosphere by dissolving in DCM (150 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure. Crude compound was subjected to column chromatography using (60-120 mesh silica gel; 10% EtOAc/hexane). Quantity produced, 33 g; yield, 84%.

ATX-0082: Step 2

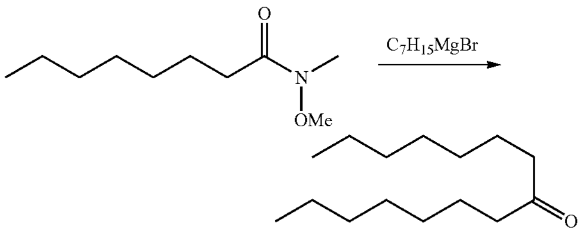

To a solution of heptyl magnesium bromide (1.5 eq.) in THF (100 ml), taken in a 1 liter, two neck round bottom flask, stirred at 0° C. under nitrogen atmosphere, was added 28 g N-methoxy-N-methyloctanamide (1 eq.) solution (dissolved in 200 ml THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (250 ml) and then EtOAc (350 ml) was added. The organic layer was separated and the aqueous layer was washed with EtOAc (2×100 ml). Combined organic layers were concentrated under reduced pressure. Crude compound was subjected to column chromatography using (60-120 mesh silica gel; 2% EtOAc/hexane). Quantity produced, 22 g; yield, 65%.

ATX-0082: Step 3

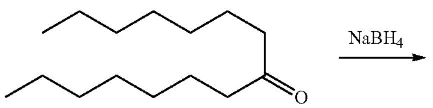

-continued

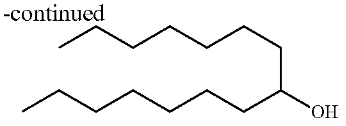

To a solution of 22 g pentadecan-8-one (1 eq.) dissolved in MeOH/THF, 1.5 eq. sodium borohydride was added at 0° C. and the resulting solution was stirred at room temperature for 1 hour.

Progress of the reaction was monitored by TLC (10% EtOAc in hexane; Rf: 0.5). Reaction mass was quenched with saturated $NH_4Cl$ solution (75 ml). Solvent was removed under reduced pressure and the resulting crude was portioned between EtOAc (150 ml) and water (100 ml). Organic layer was separated and the aqueous layer was washed with EtOAc (3×100 ml). Combined organic layers were concentrated under reduced pressure to get white solid. Quantity produced, 20 g; yield, 90%.

ATX-0082: Step 4

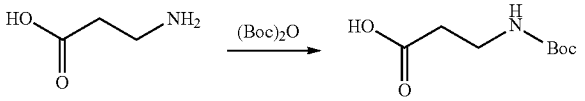 [SMILES: "(Boc)2O" ; NCCC(=O)O ; CC(C)(C)OC(=O)NCCC(=O)O]

To a solution of 15 g 4-aminobutanoic acid dissolved in 120 ml THF, 185 ml aqueous 1 N NaOH solution was added at 0° C., followed by 50 ml Boc anhydride, sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (250 ml) and then EtOAc (300 ml) was added. Organic layer was separated and the aqueous layer was washed with EtOAc (3×150 ml). Combined organic layer was concentrated under reduced pressure to obtain a gummy liquid. Quantity produced, 27 g; yield, 85%.

ATX-0082: Step 5

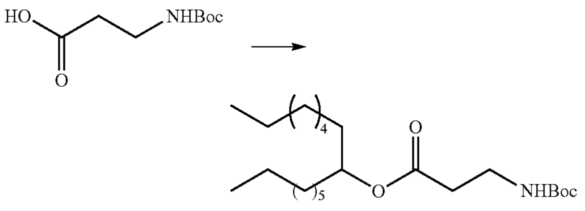

To a solution of 10 g 4-((tert-butoxycarbonyl) amino) butanoic acid, dissolved in DCM (250 ml), cooled to below 0° C. was added 1.3 eq. EDC·HCl, $Et_3N$, and 4-dimethylaminopyridine (DMAP), sequentially under nitrogen atmosphere with 10 minutes interval. To this resulting solution, 1 eq. pentadecane-7-ol alcohol was added at the same temperature, by dissolving in DCM (150 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (150 ml) and then organic layer was separated. Aqueous layer was washed with DCM (2×100 ml). Combined organic layer was concentrated under reduced pressure. The resulting crude was washed with saturated $NaHCO_3$ solution (150 ml) and then EtOAc (200 ml) was added. Organic layer was separated, concentrated under reduced pressure, and proceeded to next step with crude. Quantity produced, 8 g (crude; required compound and alcohol).

ATX-0082: Step 6

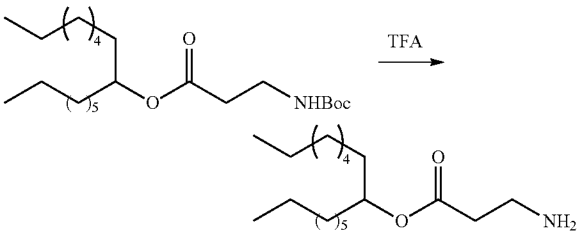

To a solution of 8.0 g pentadecan-8-yl 4-((tert-butoxycarbonyl)amino)butanoate dissolved in 60 ml DCM, was added 10 eq. TFA at 0° C. and stirred at room temperature for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with a saturated $NaHCO_3$ solution (300 ml) and then extracted with EtOAc (2×200 ml). The organic layer was separated and concentrated under reduced pressure. Crude compound was subjected to column chromatography using (60-120 mesh silica gel; 4% MeOH/$CHCl_3$ and 1 ml of triethylamine), and alcohol was recovered. Quantity produced, 4 g; yield, 25% for two steps; confirmed by Mass.

ATX-0082: Step 7

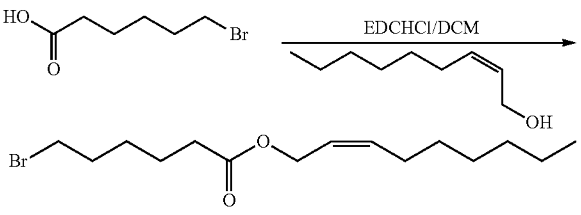

To a solution of 4-bromo butyric acid, dissolved in DCM (400 ml), cooled to below 0° C. was added to 1.5 eq. EDC·HCl, 3 eq. $Et_3N$, and DMAP sequentially under nitrogen atmosphere with 10-minute intervals. To this resulting solution 20 g (Z)-non-2-en-1-ol was added, by dissolving in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (300 ml) and then organic layer was separated. Aqueous layer was washed with DCM (2×150 ml). Combined organic layer was concentrated under reduced pressure. The resulting crude was washed with saturated $NaHCO_3$ solution (200 ml) and then extracted with EtOAc (150 ml). Organic layer was separated and concentrated under reduced pressure. Crude compound was subjected to column chromatography (60-120 mesh silica gel) using 5% EtOAc/hexane. Alcohol was recovered. Quantity produced, 18 g; yield, 55%.

ATX-0082: Step 8

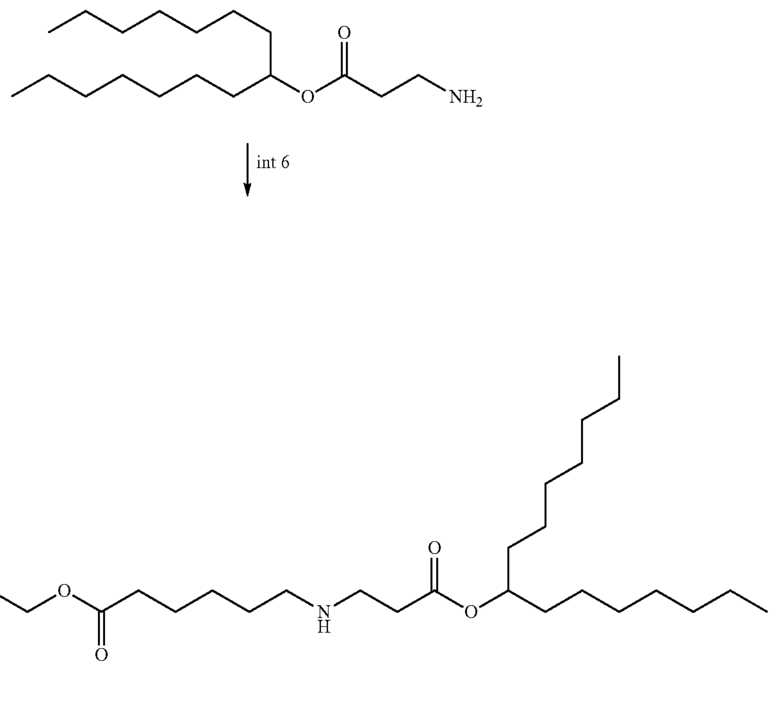

To a solution of 4.0 g pentadecan-8-yl 4-aminobutanoate, 1 eq. (Z)-non-2-en-1-yl 4-bromobutanoate in 90 ml ACN, 1.4 eq. potassium carbonate was added and the resulting mixture was refluxed at 90° C. for 4 hours under nitrogen atmosphere.

Progress of the reaction was monitored by TLC (10% MeOH in $CHCl_3$; Rf: 0.5). Reaction mass was filtered, washed with ACN (20 ml), and the filtrate concentrated under reduced pressure. Crude compound was subjected to column chromatography (100-200 mesh silica gel) using 15% EtOAc/hexane. Starting materials (amine and bromo compounds) were recovered. Quantity produced, 2.2 g; yield, 30%; confirmed by Mass.

ATX-0082: Step 9

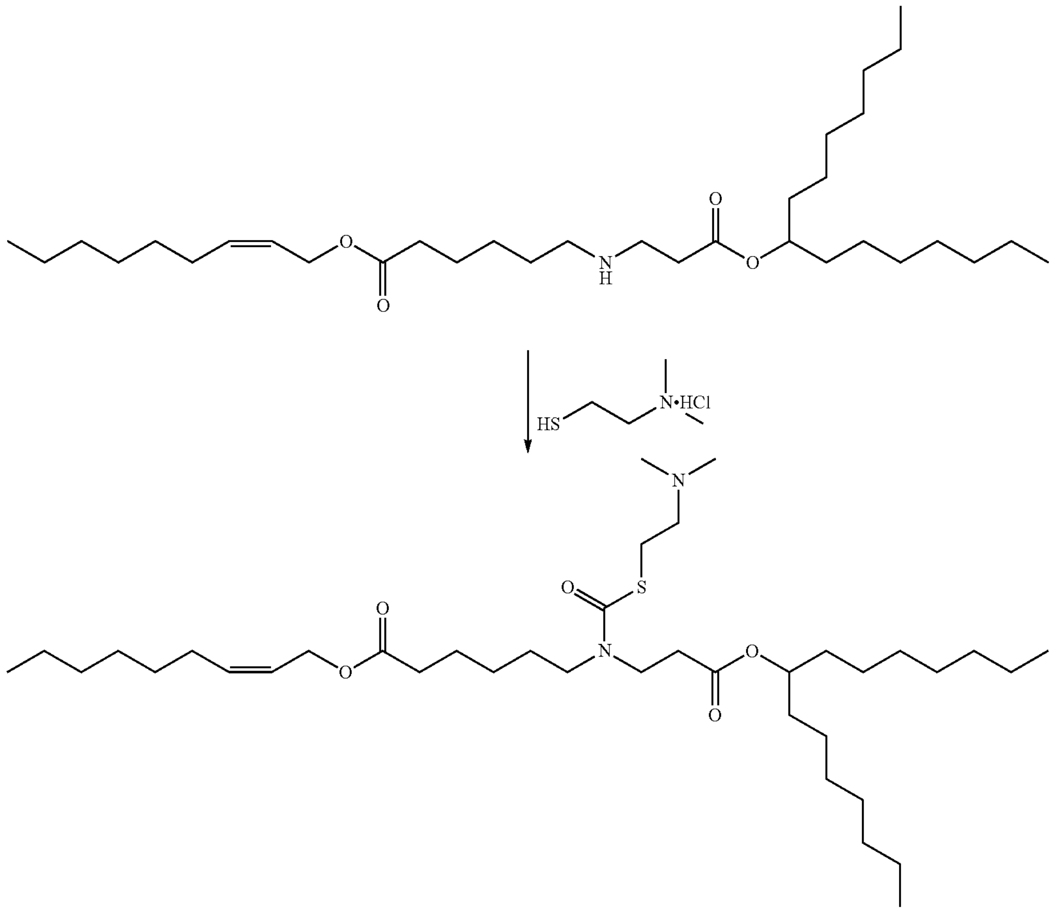

To a solution of 2.2 g pentadecan-8-yl (Z)-4-((4-(non-2-en-1-yloxy)-4-oxobutyl) amino) butanoate, dissolved in 25 ml dry DCM, was added 3 eq. triethylamine and triphosgene with 5 minutes interval at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 7 eq. sodium hydride dissolved in dry THF (100 ml), in a two neck 100 ml round bottom flask stirred at 0° C. under nitrogen atmosphere, was added 3.5 eq. 2-(dimethylamino)propane-1-thiol hydrochloride and kept stirring for 5 minutes under nitrogen atmosphere. To this resulting solution the above carbamoyl chloride, dissolved in THF (100 ml), was added via syringe slowly for about 10 minutes. The resulting solution was stirred at 0° C. to room temperature overnight under nitrogen atmosphere.

Progress of the reaction was monitored by TLC (60% EtOAc/hexane; Rf: 0.5; PMA charring). Reaction mass was quenched with saturated $NH_4Cl$ solution (75 ml) and then EtOAc (150 ml) was added. Organic layer was separated and the aqueous layer was washed with EtOAc (3×40 ml). Combined organic layer was concentrated and the resulting crude was subjected to column chromatography.

The first purification was done using silica gel (60-120 mesh) of crude compound was adsorbed on 60 g of silica gel and poured onto 500 g of silica gel taken in the column. Compound was eluted at 35% EtOAc/hexane. The second purification was done using neutral alumina with HPLC grade solvents. Crude compound was adsorbed on 18 g of neutral alumina and the resulting was poured onto 130 g of neutral alumina taken in the column. Compound was eluted at 10% EtOAc/hexane. Quantity produced, 1.2 g; yield, 43%; confirmed by $^1H$ NMR, HPLC, and Mass.

ATX-0082/RL-47A: $^1H$-NMR (PPM, 500 MHz, $CDCl_3$): δ=5.64 (m, 1), 5.52 (m, 1), 4.87 (m, 1), 4.62 (d, J=7.0, 2), 3.61 (t, J=7.0, 2), 3.28-3.37 (2), 3.02 (t, J=7.0, 2), 2.61 (m, 2), 2.52 (t, J=7.0, 2), 2.31 (m, 2), 2.27 (s, 6), 2.10 (m, 2), 1.62-1.70 (6), 1.21-1.40 (32), 0.85-0.91 (9).

Example 7: Synthesis of ATX-0086

Figure 6:
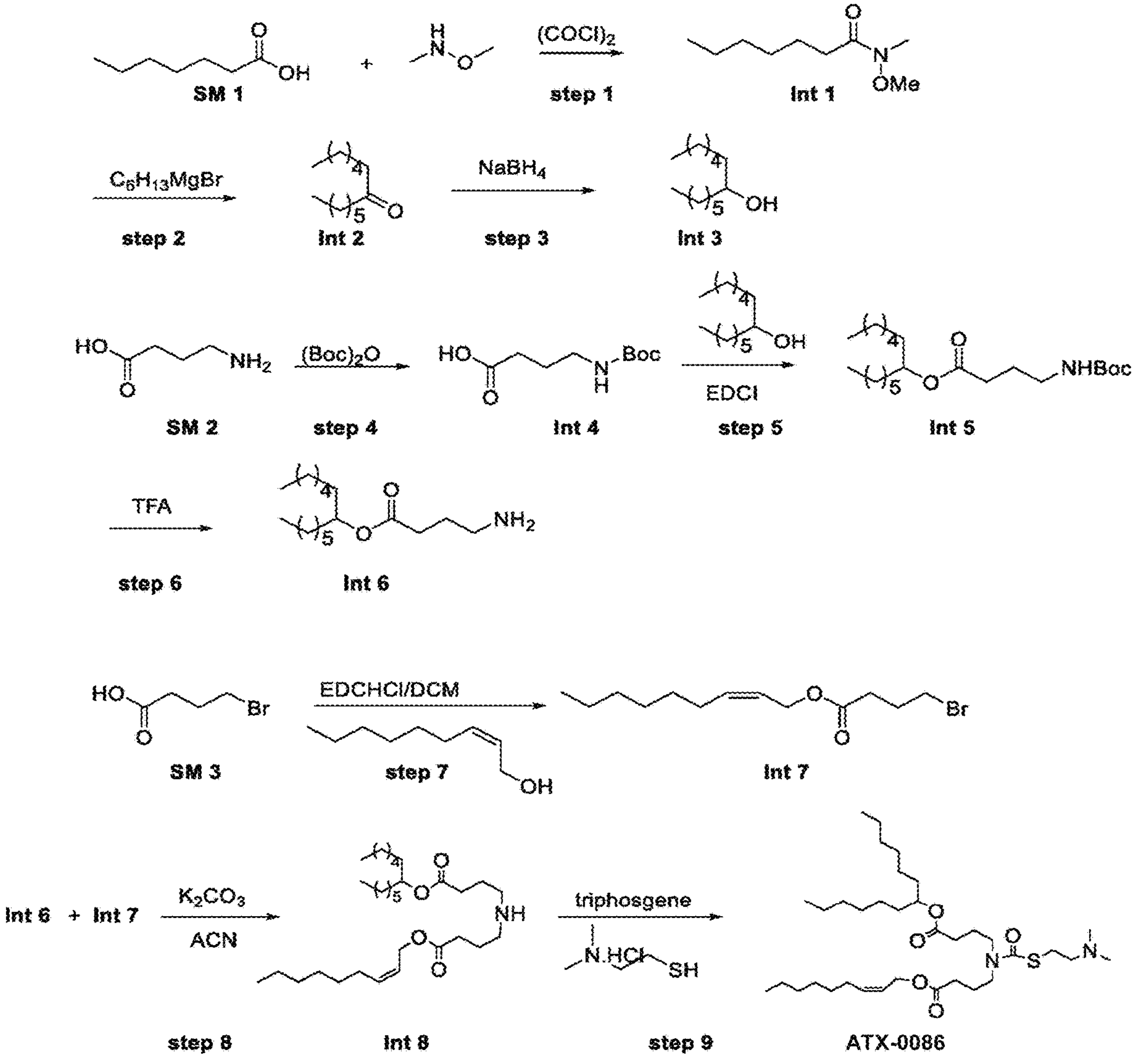
FIG. 6 shows the synthetic pathway of ATX-0086 from SM 1, SM 2 and SM3, which are the same as in FIG. 2. Ints 1-8 and reactions are described in Example 7.

FIG. 6 shows the synthetic pathway of ATX-0086 that is described further as follows.

ATX-0086: Step 1

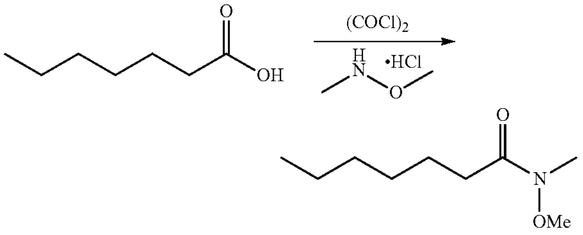

In a 2 liter, two neck round bottom flask, 30 g octanoic acid dissolved in DCM (200 ml) was taken and then added 1.5 eq. oxalyl chloride slowly at 0° C., stirring under nitrogen atmosphere. The resulting reaction mixture was stirred at room temperature for 2 hours. In a separate 2 liter, two neck round bottom flask, to 2 eq. N,O-dimethylhydroxylamine hydrochloride in DCM (200 ml), was added 3 eq. trimethylamine using additional funnel, stirred at 0° C. To this resulting solution, the above acid chloride, after concentration under reduced pressure, was added under nitrogen atmosphere by dissolving in DCM (150 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure. Crude compound was subjected to column chromatography using (60-120 mesh silica gel; 10% EtOAc/hexane). Quantity produced, 38 g; yield, 84%; confirmed by Mass.

ATX-0086: Step 2

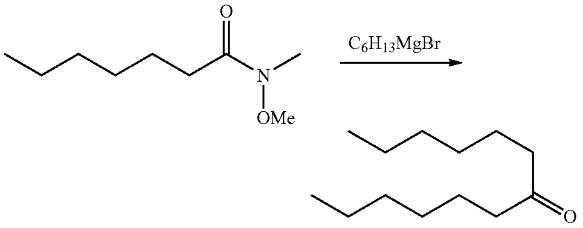

To a solution of hexyl magnesium bromide (1.5 eq.) in THF (100 ml), taken in a 1 liter, two neck round bottom flask, stirred at 0° C. under nitrogen atmosphere, was added 38 g N-methoxy-N-methyloctanamide (1 eq.) solution (dissolved in 200 ml THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (250 ml) and then EtOAc (350 ml) was added. The organic layer was separated and the aqueous layer was washed with EtOAc (2×100 ml). Combined organic layers were concentrated under reduced pressure. Crude compound was subjected to column chromatography using (60-120 mesh silica gel; 2% EtOAc/hexane). Quantity produced, 44 g; yield, 65%; confirmed by Mass.

ATX-0086: Step 3

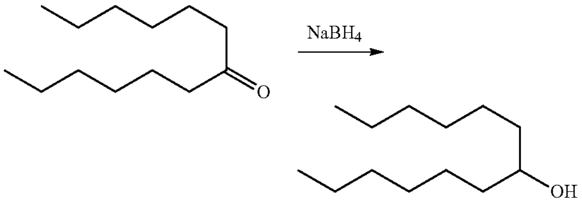

To a solution of 44 g tridecane-7-one (1 eq) dissolved in MeOH/THF, 1.5 eq. sodium borohydride was added at 0° C. and the resulting solution was stirred at room temperature for 1 hour.

Progress of the reaction was monitored by TLC (10% EtOAc in hexane; Rf: 0.5). Reaction mass was quenched with saturated $NH_4Cl$ solution (75 ml). Solvent was removed under reduced pressure and the resulting crude was portioned between EtOAc (150 ml) and water (100 ml). Organic layer was separated and the aqueous layer was washed with EtOAc (3×100 ml). Combined organic layers were concentrated under reduced pressure to get white solid. Quantity produced, 40 g; yield, 90%; confirmed by Mass.

ATX-0086: Step 4

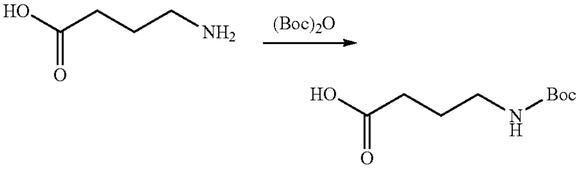

To a solution of 50 g 4-aminobutanoic acid dissolved in 350 ml THF, 490 ml aqueous 1 N NaOH solution was added at 0° C., followed by 140 ml Boc anhydride, sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (250 ml) and then EtOAc (300 ml) was added. Organic layer was separated and the aqueous layer was washed with EtOAc (3×150 ml). Combined organic layer was concentrated under reduced pressure to obtain a gummy liquid. Quantity produced, 80 g; yield, 81%; confirmed by Mass.

ATX-0086: Step 5

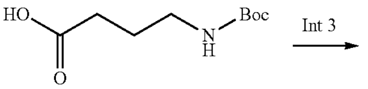

-continued

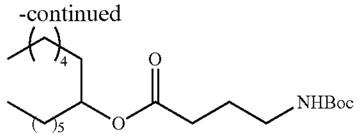

To a solution of 10 g 4-((tert-butoxycarbonyl) amino) butanoic acid, dissolved in DCM (250 ml), cooled to below 0° C. was added 1.3 eq. EDC·HCl, $Et_3N$, and 4-dimethylaminopyridine (DMAP), sequentially under nitrogen atmosphere with 10 minutes interval. To this resulting solution, 1 eq. pentadecane-7-ol alcohol was added at the same temperature, by dissolving in DCM (150 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (150 ml) and then organic layer was separated. Aqueous layer was washed with DCM (2×100 ml). Combined organic layer was concentrated under reduced pressure. The resulting crude was washed with saturated $NaHCO_3$ solution (150 ml) and then EtOAc (200 ml) was added. Organic layer was separated, concentrated under reduced pressure, and proceeded to next step with crude. Quantity produced, 8 g (crude; required compound and alcohol).

ATX-0086: Step 6

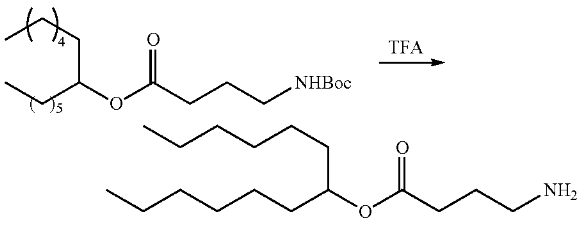

To a solution of 8.0 g pentadecan-8-yl 4-((tert-butoxycarbonyl)amino)butanoate dissolved in 60 ml DCM, was added 10 eq. TFA at 0° C. and stirred at room temperature for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with a saturated $NaHCO_3$ solution (300 ml) and then extracted with EtOAc (2×200 ml). The organic layer was separated and concentrated under reduced pressure. Crude compound was subjected to column chromatography using (60-120 mesh silica gel; 4% MeOH/$CHCl_3$ and 1 mL of triethylamine), and alcohol was recovered. Quantity produced, 3.5 g; yield, 52% for two steps; confirmed by Mass.

ATX-0086: Step 7

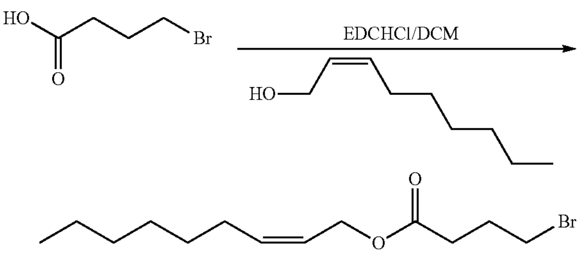

To a solution of 4-bromo butyric acid, dissolved in DCM (400 ml), cooled to below 0° C. was added to 1.5 eq. EDC·HCl, 2 eq. $Et_3N$, and DMAP sequentially under nitrogen atmosphere with 10-minute intervals. To this resulting solution 20 g (Z)-non-2-en-1-ol was added, by dissolving in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (300 ml) and then organic layer was separated. Aqueous layer was washed with DCM (2×150 ml). Combined organic layer was concentrated under reduced pressure. The resulting crude was washed with saturated $NaHCO_3$ solution (200 ml) and then extracted with EtOAc (150 ml). Organic layer was separated and concentrated under reduced pressure. Crude compound was subjected to column chromatography (60-120 mesh silica gel) using 5% EtOAc/hexane. Alcohol was recovered. Quantity produced, 18 g; yield, 55%.

ATX-0086: Step 8

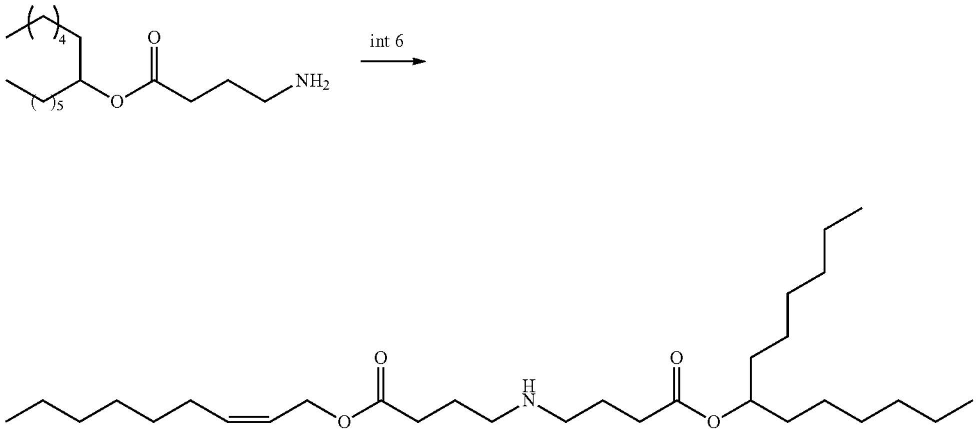

To a solution of 4.0 g tridecan-7-yl 4-aminobutanoate, 1 eq. (Z)-non-2-en-1-yl 4-bromobutanoate in 90 ml ACN, 1.4 eq. potassium carbonate was added and the resulting mixture was refluxed at 90° C. for 4 hours under nitrogen atmosphere.

Progress of the reaction was monitored by TLC (10% MeOH in $CHCl_3$; Rf: 0.5). Reaction mass was filtered, washed with ACN (20 ml), and the filtrate concentrated under reduced pressure. Crude compound was subjected to column chromatography (100-200 mesh silica gel) using 15% EtOAc/hexane. Starting materials, amine and bromo compounds, were recovered. Quantity produced, 2.2 g; yield, 30%; confirmed by Mass.

ATX-0086: Step 9

Progress of the reaction was monitored by TLC (60% EtOAC/hexane; Rf: 0.5; PMA charring). Reaction mass was quenched with saturated $NH_4Cl$ solution (75 ml) and then EtOAc (150 ml) was added. Organic layer was separated and the aqueous layer was washed with EtOAc (3×40 ml). Combined organic layer was concentrated and the resulting crude was subjected to column chromatography.

The first purification was done using silica gel (60-120 mesh) of crude compound was adsorbed on 60 g of silica gel and poured onto 500 g of silica gel taken in the column. Compound was eluted at 35% EtOAc/hexane. The second purification was done using neutral alumina with HPLC grade solvents. Crude compound was adsorbed on 18 g of neutral alumina and the resulting was poured onto 130 g of neutral alumina taken in the column. Compound was eluted

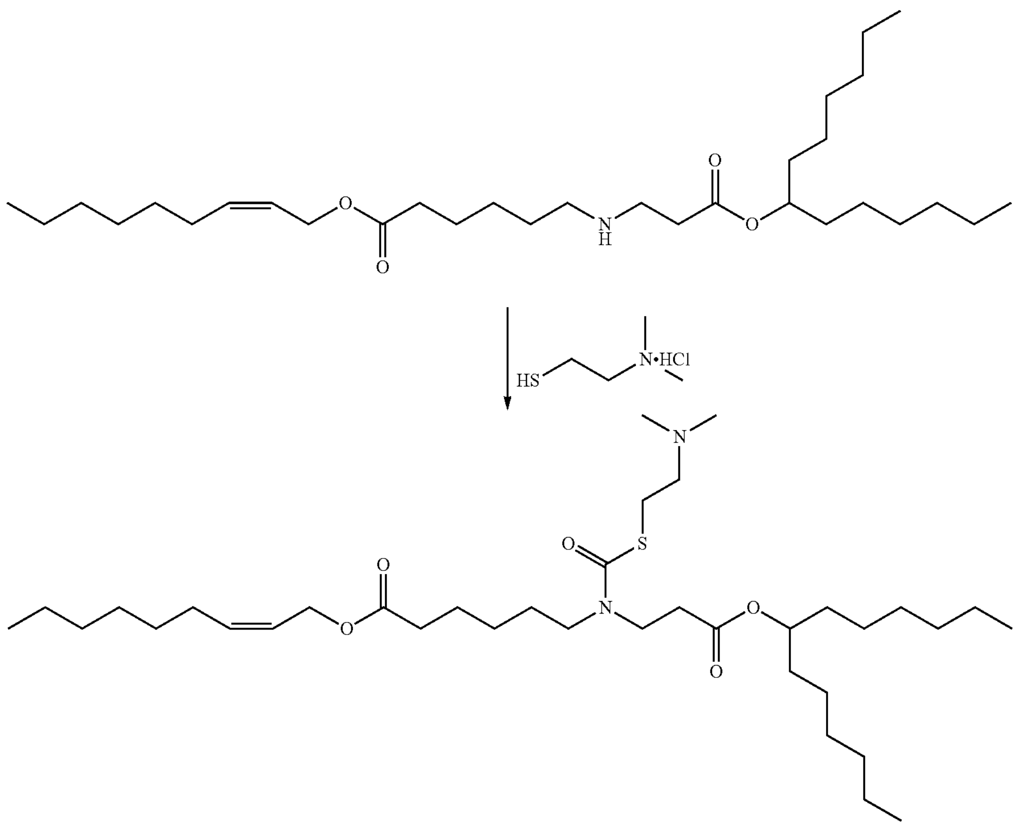

To a solution of 2.2 g tridecan-7-yl (Z)-4-((4-(non-2-en-1-yloxy)-4-oxobutyl) amino) butanoate, dissolved in 25 ml dry DCM, was added 3 eq. triethylamine and triphosgene with 5 minutes interval at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 7 eq. sodium hydride dissolved in dry THF (100 ml), in a two neck 100 ml round bottom flask stirred at 0° C. under nitrogen atmosphere, was added 3.5 eq. 2-(dimethylamino)propane-1-thiol hydrochloride and kept stirring for 5 minutes under nitrogen atmosphere. To this resulting solution the above carbamoyl chloride, dissolved in THF (100 ml), was added via syringe slowly for about 10 minutes. The resulting solution was stirred at 0° C. to room temperature overnight under nitrogen atmosphere.

at 10% EtOAc/hexane. Quantity produced, 1.2 g; yield, 43%; confirmed by $^1$H NMR, HPLC, and Mass.

ATX-0086/RL-48A: $^1$H-NMR (PPM, 500 MHz, $CDCl_3$): δ=5.64 (m, 1), 5.51 (m, 10, 4.87 (m, 1), 4.63 (d, J=7.0, 2), 3.30-3.44 (4), 3.02 (t, J=7.0, 2), 2.52 (t, J=7.0, 2), 2.26-2.36 (4), 2.27 (s, 6), 2.09 (m, 2), 1.82-1.96 (4), 1.46-1.54 (4), 1.21-1.40 (24), 0.84-0.91 (9).

Example 8: Synthesis of ATX-0087

Figure 7:
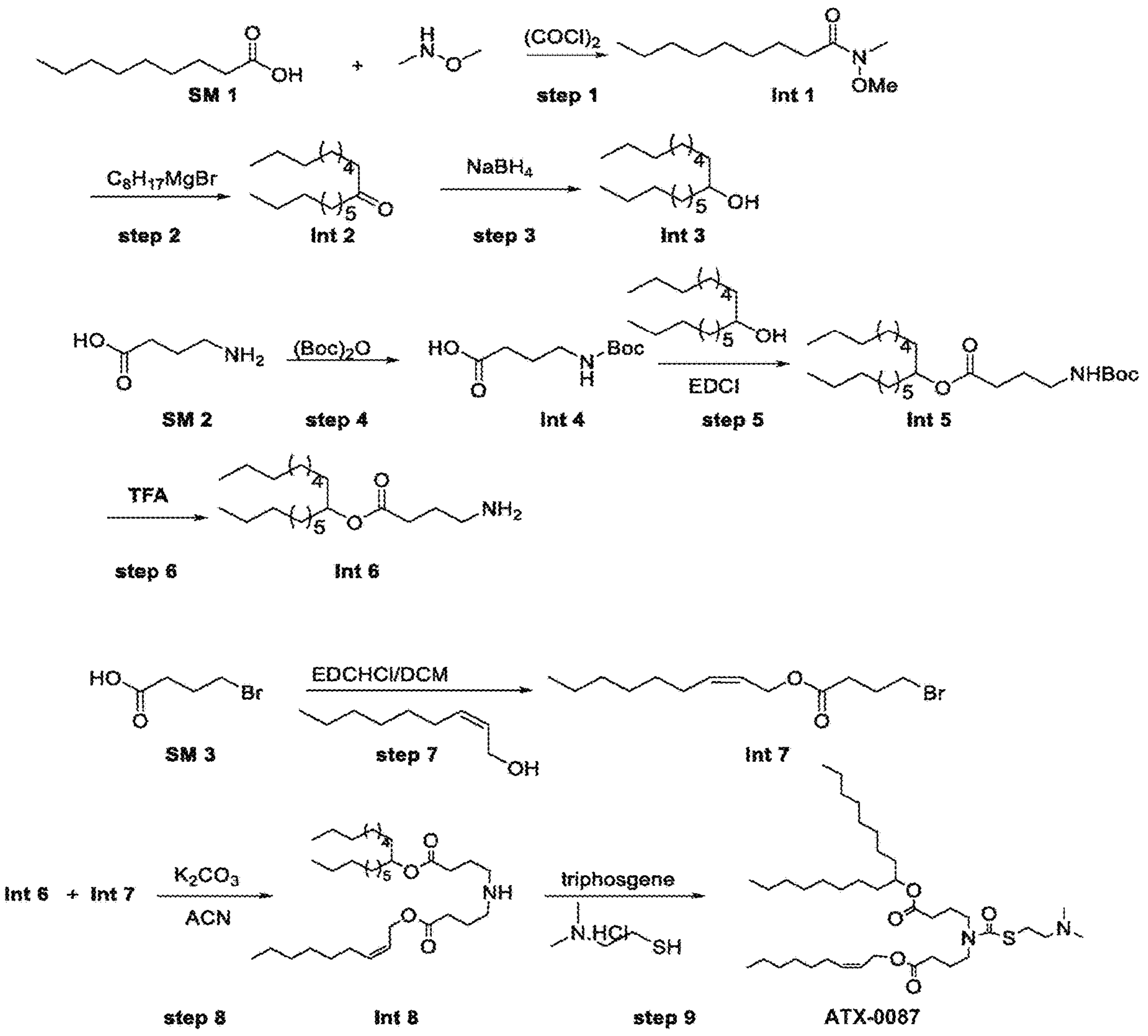
FIG. 7 shows the synthetic pathway of ATX-0087 from SM 1, SM 2 and SM3, which are the same as in FIG. 2. Ints 1-8 and reactions are described in Example 8.

FIG. 7 shows the synthetic pathway of ATX-0087 that involves nine steps.

ATX-0087: Step 1

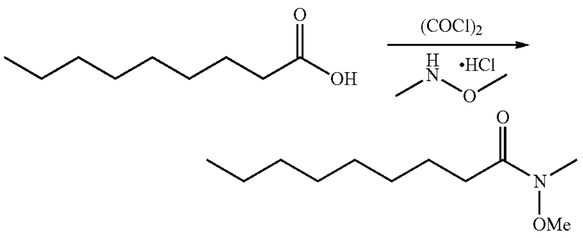

In a 2 liter, two neck round bottom flask, 20 g octanoic acid dissolved in DCM (200 ml) was taken and then added 1.5 eq. oxalyl chloride slowly at 0° C., stirring under nitrogen atmosphere. The resulting reaction mixture was stirred at room temperature for 2 hours. In a separate 2 liter, two neck round bottom flask, to 2 eq. N,O-dimethylhydroxylamine hydrochloride in DCM (200 ml), was added 3 eq. trimethylamine using additional funnel, stirred at 0° C. To this resulting solution, the above acid chloride, after concentration under reduced pressure, was added under nitrogen atmosphere by dissolving in DCM (150 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure. Crude compound was subjected to column chromatography using (60-120 mesh silica gel; 10% EtOAc/hexane). Quantity produced, 20 g; yield, 84%.

ATX-0087: Step 2

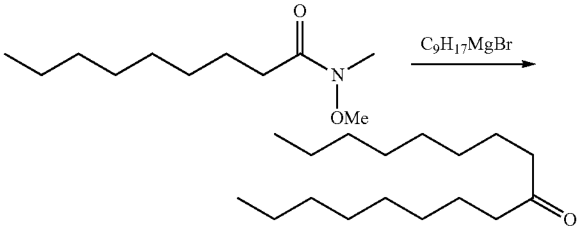

To a solution of hexyl magnesium bromide (1.5 eq.) in THF (100 ml), taken in a 1 liter, two neck round bottom flask, stirred at 0° C. under nitrogen atmosphere, was added 20 g N-methoxy-N-methyloctanamide (1 eq.) solution (dissolved in 200 ml THF) and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (250 ml) and then EtOAc (350 ml) was added. The organic layer was separated and the aqueous layer was washed with EtOAc (2×100 ml). Combined organic layers were concentrated under reduced pressure. Crude compound was subjected to column chromatography using (60-120 mesh silica gel; 2% EtOAc/hexane). Quantity produced, 25 g; yield, 65%.

ATX-0087: Step 3

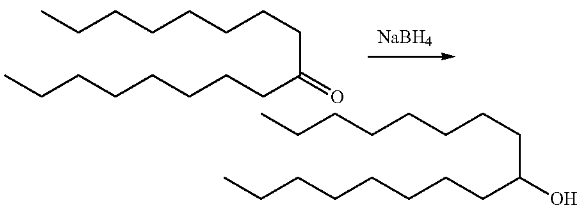

To a solution of 25 g tridecane-7-one (1 eq) dissolved in MeOH/THF, 1.5 eq. sodium borohydride was added at 0° C. and the resulting solution was stirred at room temperature for 1 hour.

Progress of the reaction was monitored by TLC (10% EtOAc in hexane; Rf: 0.5). Reaction mass was quenched with saturated $NH_4Cl$ solution (75 ml). Solvent was removed under reduced pressure and the resulting crude was portioned between EtOAc (150 ml) and water (100 ml). Organic layer was separated and the aqueous layer was washed with EtOAc (3×100 ml). Combined organic layers were concentrated under reduced pressure to get white solid. Quantity produced, 22 g; yield, 90%.

ATX-0087: Step 4

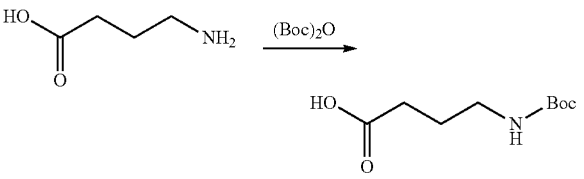

To a solution of 50 g 4-aminobutanoic acid dissolved in 350 ml THF, 490 ml aqueous 1 N NaOH solution was added at 0° C., followed by 140 ml Boc anhydride, sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (250 ml) and then EtOAc (300 ml) was added. Organic layer was separated and the aqueous layer was washed with EtOAc (3×150 ml). Combined organic layer was concentrated under reduced pressure to obtain a gummy liquid. Quantity produced, 80 g; yield, 81%.

ATX-0087: Step 5

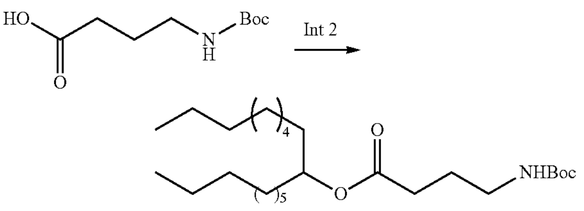

To a solution of 17 g 4-((tert-butoxycarbonyl) amino) butanoic acid, dissolved in DCM (250 ml), cooled to below 0° C. was added 1.3 eq. EDC·HCl, $Et_3N$, and 4-dimethylaminopyridine (DMAP), sequentially under nitrogen atmosphere with 10 minutes interval. To this resulting solution, 1 eq. tridecane-7-ol was added at the same temperature, by dissolving in DCM (150 ml), using additional funnel, and stirred at room temperature for 24 hours under nitrogen atmosphere.

Progress of the reaction was monitored by TLC (10% EtOAc in hexane; Rf: 0.5). Reaction mass was quenched with water (150 ml) and then organic layer was separated. Aqueous layer was washed with DCM (2×100 ml). Combined organic layer was concentrated under reduced pressure. The resulting crude was washed with saturated $NaHCO_3$ solution (150 ml) and then EtOAc (200 ml) was added. Organic layer was separated, concentrated under reduced pressure, and proceeded to next step with crude. Quantity produced, 15 g (crude; required compound and alcohol).

ATX-0087: Step 6

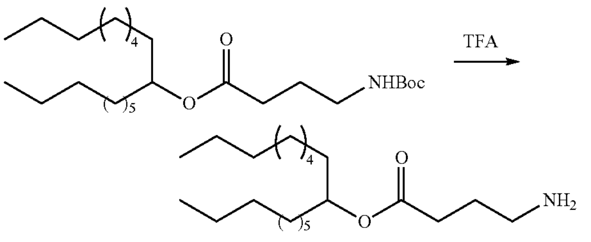

To a solution of 15.0 g pentadecan-8-yl 4-((tert-butoxycarbonyl)amino)butanoate dissolved in 80 ml DCM, was added 10 eq. TFA at 0° C. and stirred at room temperature for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with a saturated $NaHCO_3$ solution (300 ml) and then extracted with EtOAc (2×200 ml). The organic layer was separated and concentrated under reduced pressure. Crude compound was subjected to column chromatography using (60-120 mesh silica gel; 4% MeOH/$CHCl_3$ and 1 mL of triethylamine), and alcohol was recovered. Quantity produced, 7 g; yield, 24% for two steps; confirmed by Mass.

ATX-0087: Step 7

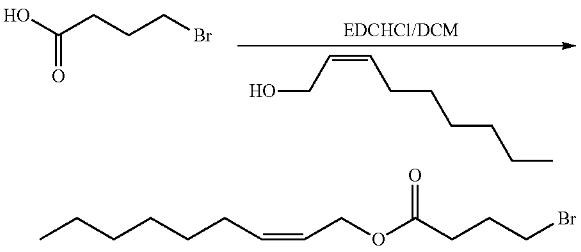

To a solution of 4-bromo butyric acid, dissolved in DCM (400 ml), cooled to below 0° C. was added to 1.5 eq. EDC·HCl, 2 eq. $Et_3N$, and DMAP sequentially under nitrogen atmosphere with 10-minute intervals. To this resulting solution 20 g (Z)-non-2-en-1-ol was added, by dissolving in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (300 ml) and then organic layer was separated. Aqueous layer was washed with DCM (2×150 ml). Combined organic layer was concentrated under reduced pressure. The resulting crude was washed with saturated $NaHCO_3$ solution (200 ml) and then extracted with EtOAc (150 ml). Organic layer was separated and concentrated under reduced pressure. Crude compound was subjected to column chromatography (60-120 mesh silica gel) using 5% EtOAc/hexane. Alcohol was recovered. Quantity produced, 19 g; yield, 55%.

ATX-0087: Steps 8

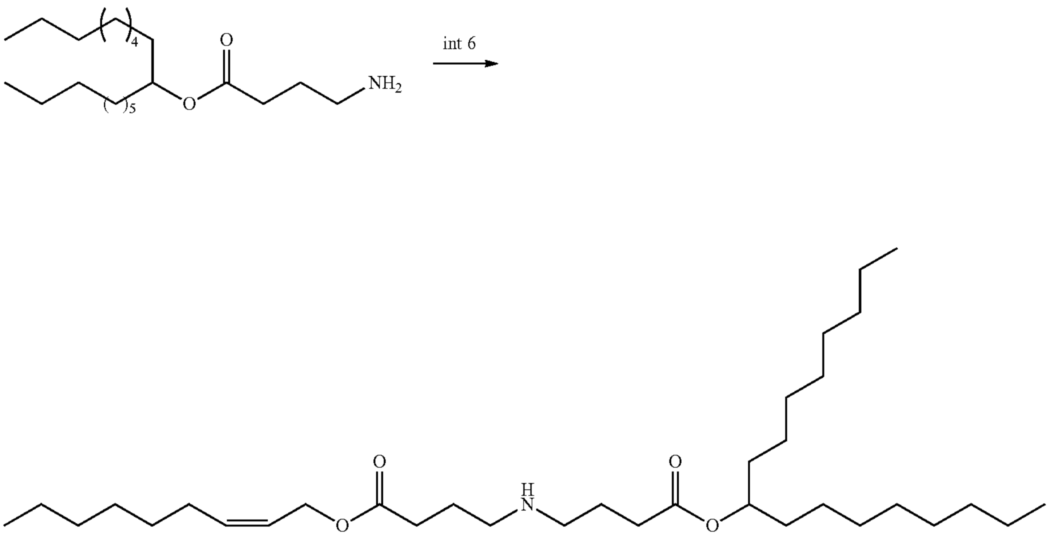

To a solution of 4.0 g tridecan-7-yl 4-aminobutanoate, 1 eq. (Z)-non-2-en-1-yl 4-bromobutanoate in 90 ml ACN, 1.4 eq. potassium carbonate was added and the resulting mixture was refluxed at 90° C. for 4 hours under nitrogen atmosphere.

Progress of the reaction was monitored by TLC (10% MeOH in $CHCl_3$; Rf: 0.5). Reaction mass was filtered, washed with ACN (20 ml), and the filtrate concentrated under reduced pressure. Crude compound was subjected to column chromatography (100-200 mesh silica gel) using 15% EtOAc/hexane. Starting materials, amine and bromo compounds, were recovered. Quantity produced, 2.2 g; yield, 30%; confirmed by Mass.

ATX-0087: Step 9

To 7 eq. sodium hydride dissolved in dry THF (100 ml), in a two neck 100 ml round bottom flask stirred at 0° C. under nitrogen atmosphere, was added 3.5 eq. 2-(dimethylamino)propane-1-thiol hydrochloride and kept stirring for 5 minutes under nitrogen atmosphere. To this resulting solution the above carbamoyl chloride, dissolved in THF (100 ml), was added via syringe slowly for about 10 minutes. The resulting solution was stirred at 0° C. to room temperature overnight under nitrogen atmosphere.

Progress of the reaction was monitored by TLC (60% EtOAc/hexane; Rf. 0.5; PMA charring). Reaction mass was quenched with saturated $NH_4Cl$ solution (75 ml) and then EtOAc (150 ml) was added. Organic layer was separated and the aqueous layer was washed with EtOAc (3×40 ml). Combined organic layer was concentrated and the resulting crude was subjected to column chromatography.

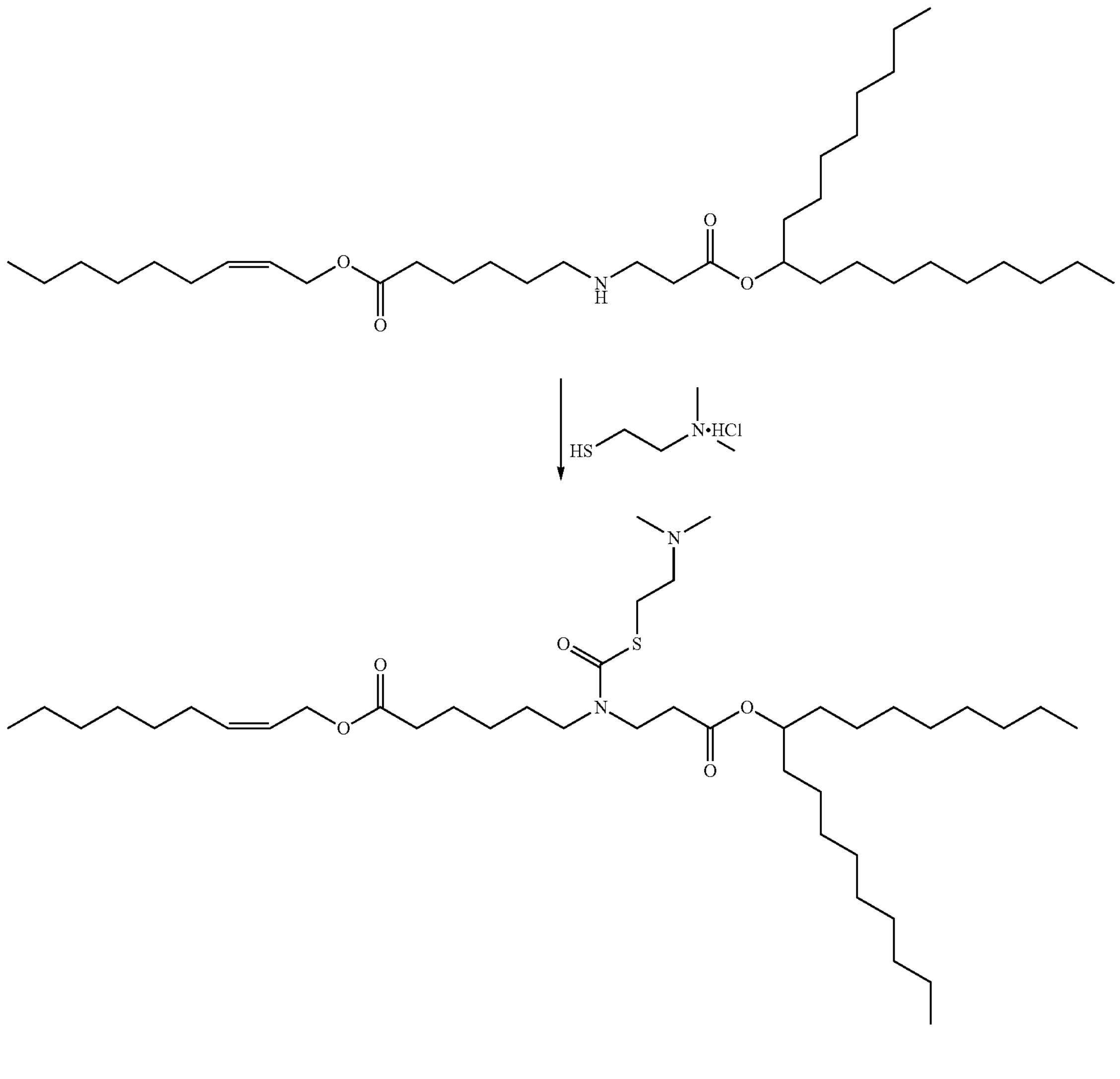

To a solution of 2.2 g tridecan-7-yl (Z)-4-((4-(non-2-en-1-yloxy)-4-oxobutyl) amino) butanoate, dissolved in 25 ml dry DCM, was added 3 eq. triethylamine and triphosgene with 5 minutes interval at 0° C. under nitrogen atmosphere. The resulting solution was stirred at room temperature, under nitrogen atmosphere for 1 hour. The resulting reaction mass was concentrated under reduced pressure and kept under nitrogen atmosphere.

The first purification was done using silica gel (60-120 mesh) of crude compound was adsorbed on 60 g of silica gel and poured onto 500 g of silica gel taken in the column. Compound was eluted at 35% EtOAc/hexane. The second purification was done using neutral alumina with HPLC grade solvents. Crude compound was adsorbed on 18 g of neutral alumina and the resulting was poured onto 130 g of neutral alumina taken in the column. Compound was eluted at 10% EtOAc/hexane. Quantity produced, 1.2 g; yield, 43%; confirmed by $^1$H NMR, HPLC, and Mass.

ATX-0087/RL-48C: $^1$H-NMR (PPM, 500 MHz, $CDCl_3$): δ=5.64 (m, 1), 5.52 (m, 1), 4.87 (m, 1), 4.63 (d, J=7.0, 2), 3.30-3.44 (4), 3.02 (t, J=7.0, 2), 2.52 (t, J=7.0, 2), 2.26-2.36 (4), 2.27 (s, 6), 2.09 (m, 2), 1.83-1.96 (4), 1.46-1.54 (4), 1.21-1.40 (32), 0.85-0.90 (9).

Example 9: Synthesis of ATX-0088

Figure 8:
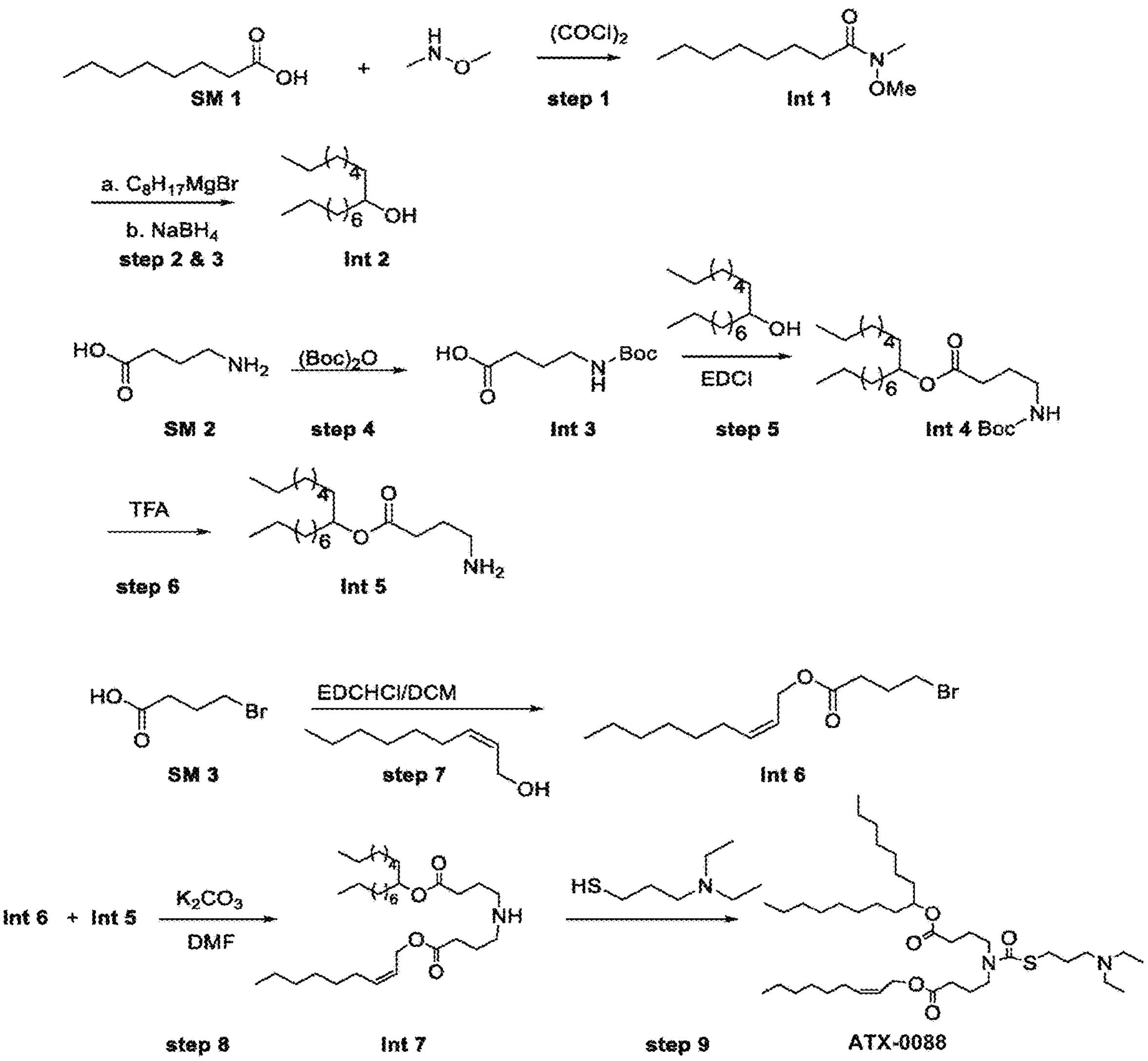
FIG. 8 shows the synthetic pathway of ATX-0088 from SM 1, SM 2 and SM3, which are the same as in FIG. 2. Ints 1-8 and reactions are described in Example 9.

FIG. 8 shows the synthetic pathway of ATX-0088 that is described further as follows.

ATX-0088: Step 1

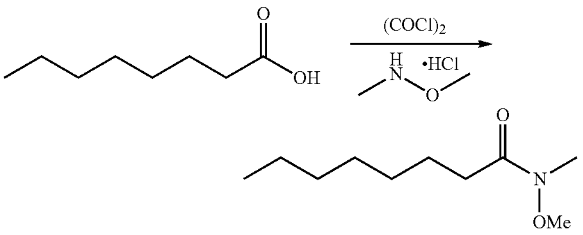

In 500 ml two neck round bottom flask under $N_2$ atmosphere, 25 g 8-bromooctanoic acid (1 eq.) dissolved in 200 ml of DCM was taken and then added slowly to oxalyl chloride, 1.5 eq., at 0° C., stirring under nitrogen atmosphere. The resulting reaction mixture was stirred at room temperature for 2 hours.

In a separate 1 liter two neck round bottom flask, 2 eq. N,O-dimethylhydroxylamine hydrochloride in 300 ml DCM was added 3 eq. trimethylamine and stirred at 0° C. To this resulting solution, the above acid chloride was added after concentration under reduced pressure, by dissolving in 500 ml DCM, dropwise using addition funnel for 15 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (300 ml). Organic layer was separated and the aqueous layer was washed with DCM (2×100 ml). Combined organic layer was concentrated under reduced pressure.

Crude compound was subjected to column chromatography using (60-120 mesh silica gel; 10% EtOAC/hexane). Quantity produced, 21 g; yield, 66%.

ATX-0088: Step 2

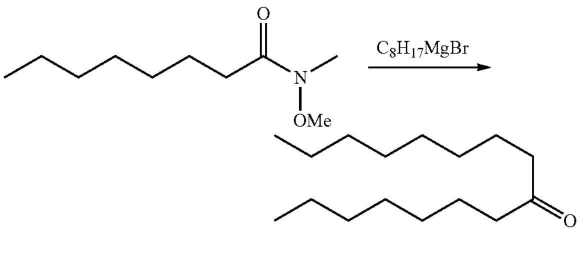

To a solution of 1.3 eq. octyl magnesium bromide in THF (100 ml), stirred at 0° C. under nitrogen atmosphere, was added 20 g N-methoxy-N-methyloctanamide in 100 ml THF and the resulting reaction mixture was stirred at room temperature for 4 hours.

Progress of the reaction was monitored by TLC (10% EtOAc/hexane; Rf: 0.7). Reaction mass was quenched with saturated $NH_4Cl$ solution (100 ml). The organic layer was separated and the aqueous layer was washed with EtOAc (2×100 ml). Combined organic layer was concentrated under reduced pressure.

Crude compound was subjected to column chromatography using (60-120 mesh silica gel; 2% ethyl acetate/hexane). Quantity yield was 17.4 g; 68%.

ATX-0088: Step 3

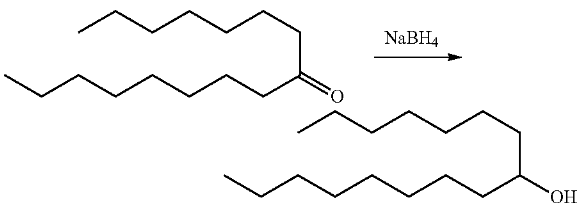

To a solution of 17 g hexadecan-7-one (1 eq.) dissolved in 135 ml MeOH/THF, 1.5 eq. sodium borohydride was added at 0° C. and the resulting solution was stirred at room temperature for 1 hour.

Progress of the reaction was monitored by TLC (10% EtOAc/hexane; Rf: 0.5). Reaction mass was quenched with saturated $NH_4Cl$ solution (50 ml). Methanol was reduced under reduced pressure. The resulting crude was portioned between EtOAc (200 ml) and water. Organic layer was separated and the aqueous layer was washed with EtOAc (2×80 ml). Combined organic layer was concentrated under reduced pressure to obtain a white solid. Quantity produced, 14.5 g; yield, 85%.

ATX-0088: Step 4

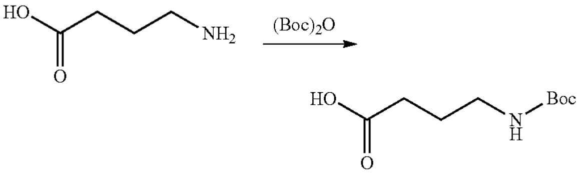

To a solution of 50 g 4-aminobutanoic acid dissolved in 350 ml THF, 490 ml of aqueous 1N NaOH solution was added at 0° C., followed by 140 ml Boc anhydride, using a funnel. The resulting solution was stirred at room temperature for 4 hours.

Progress of the reaction was monitored by TLC (10% MeOH/$CHCl_3$; Rf: 0.5). Reaction mass was quenched with 5% HCl (100 ml) and then EtOAc (200 ml) was added. The organic layer was separated and the aqueous layer was washed with EtOAc (2×100 ml). Combined organic layer was concentrated under reduced pressure to obtain a gummy liquid. Quantity produced, 80 g; yield, 81%.

ATX-0088: Step 5

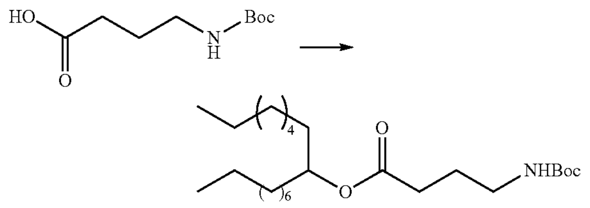

To a solution of 1 eq. 4-((tert-butoxycarbonyl)amino) butanoic acid dissolved in DCM (200 ml), cooled to below 0° C. was added 3 eq. EDC·HCl, $Et_3N$ (3 eq.), and DMAP (0.1 eq.) sequentially with 10 minutes interval. To this resulting solution alcohol was added, by dissolving in DCM, using additional funnel, and stirred at room temperature for 24 hours under nitrogen atmosphere.

Progress of the reaction was monitored by TLC (10% EtOAc/hexane; Rf: 0.5). Reaction mass was quenched with water (100 ml) and the organic layer was separated. The aqueous layer was washed with DCM (2×50 ml). Combined organic layer was concentrated under reduced pressure. The resulting crude was washed with saturated $NaHCO_3$ solution and EtOAc (100 ml) was added. The organic layer was separated and concentrated under reduced pressure, and proceeded to next step with crude. Quantity produced, 19 g (crude).

ATX-0088: Step 6

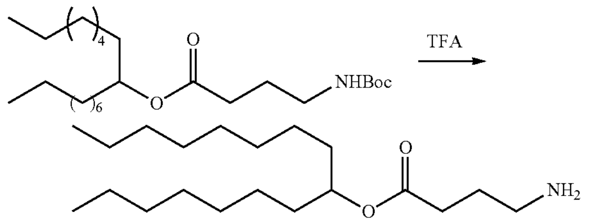

To a solution of 19 g hexadecan-7-yl 4-((tert-butoxycarbonyl)amino)butanoate (1 eq.) dissolved in 140 ml DCM, was added 10 eq. TFA at 0° C. and stirred at room temperature for 3 hours under nitrogen atmosphere.

Progress of the reaction was monitored by TLC (10% $MeOH/CHCl_3$; Rf: 0.3). Reaction mass was concentrated under reduced pressure. The resulting crude was washed with saturated $NaHCO_3$ solution (100 ml) and EtOAc (100 ml) was added. The organic layer was separated and concentrated under reduced pressure.

Crude compound was subjected to column chromatography using (60-120 mesh silica gel; 4% $MeOH/CHCl_3$) and alcohol was recovered. Quantity produced, 9.4 g; yield, 50% for two steps; confirmed by Mass.

ATX-0088: Step 7

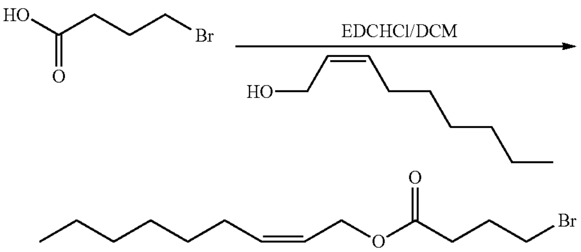

To a solution of 30 g 4-bromo butyric acid (1 eq.) dissolved in DCM (500 ml), cooled to 0° C. was added 1.5 eq. EDC·HCl, 3 eq. $Et_3N$, and 0.1 eq. DMAP sequentially with 10 minutes interval. To this resulting solution 0.7 eq. (Z)-non-2-en-1-ol was added, by dissolving in 100 ml DCM, using a funnel, and stirred at room temperature for 24 hours under nitrogen atmosphere.

Progress of the reaction was monitored by TLC (10% EtOAc/hexane; Rf: 0.7). Reaction mass was quenched with water (100 ml) and then organic layer was separated. Aqueous layer was washed with DCM (2×100 ml). Combined organic layer was concentrated under reduced pressure. The resulting crude was washed with saturated $NaHCO_3$ solution and EtOAc (150 ml) was added. The organic layer was separated and concentrated under reduced pressure.

Crude compound was subjected to column chromatography using (60-120 mesh silica gel; 5% EtOAc/hexane). Quantity produced, 27 g; yield, 51%; confirmed by $^1H$ NMR.

ATX-0088: Step 8

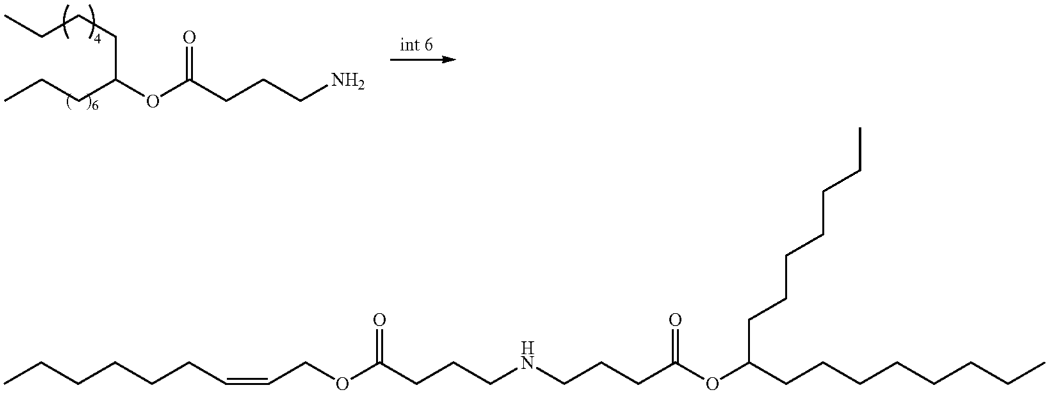

To a solution of 6 g hexadecan-8-yl 4-aminobutanoate (1 eq.), 1 eq. 5 (Z)-non-2-en-1-yl 4-bromobutanoate in ACN (70 ml), 1.2 eq. potassium carbonate was added and the resulting was refluxed at 90° C. for 3 hours under nitrogen atmosphere.

Progress of the reaction was monitored by TLC (10% $MeOH/CHCl_3$; Rf: 0.5). Reaction mass was filtered and the filtrate concentrated under reduced pressure.

Crude compound was subjected to column chromatography using (100-200 mesh silica gel; 15% EtOAc/hexane). Quantity produced, 4.5 g; yield, 44%; confirmed by Mass.

ATX-0088: Step 9

EtOAc (100 ml) was added. The organic layer was separated and the aqueous layer was washed with EtOAc (2×50 ml). Combined organic layer was concentrated and the resulting crude was subjected to column chromatography.

A first purification was done using silica gel (60-120 mesh). 5.0 g of crude compound was adsorbed on 9 g of silica gel and poured onto 90 g of silica gel taken in the column. Compound was eluted at 35% EtOAc/hexane. A second purification was done using neutral alumina with HPLC grade solvents. Crude compound, 1.5 g, was adsorbed on 4 g of neutral alumina and the resulting was poured onto 40 g of neutral alumina taken in the column. Compound was eluted at 10% EtOAc/hexane. Quantity produced, 1.2 g; yield, 21%; confirmed by $^1H$ NMR; HPLC; Mass.

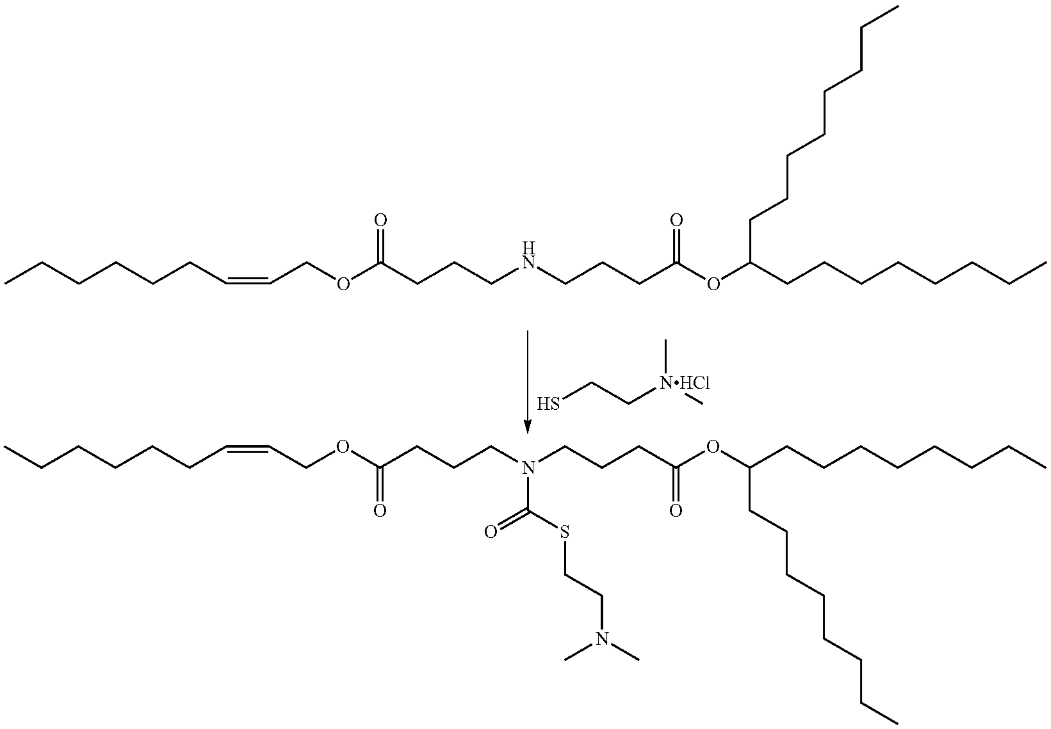

To a solution of 4.4 g (Z)-non-2-en-1-yl 4-((4-oxo-4-(tetradecan-7-yloxy)butyl)amino)butanoate (1 eq.) dissolved in 30 ml dry DCM, was added 0.83 ml trimethylamine (3 eq.) and 418 mg triphosgene (0.5 eq.) with 5 minutes interval, at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To 192 mg sodium hydride (10 eq.) dissolved in dry THF (25 ml), in a two neck 100 ml round bottom flask, was added 564 mg 2-(dimethylamino)propane-1-thiol hydrochloride (5 eq.) at 0° C. and kept stirring for 5 minutes under nitrogen atmosphere. To this resulting solution the above carbamoyl chloride, dissolved in THF (35 ml), was added via syringe slowly for about 10 minutes. The resulting solution was stirred at room temperature for 4 hours under nitrogen atmosphere.

Progress of the reaction was monitored by TLC (60% EtOAC/hexane; Rf. 0.5; PMA charring). Reaction mass was quenched with saturated $NH_4Cl$ solution (30 ml) and then ATX-0088/RL-48D: $^1H$-NMR (PPM, 500 MHz, $CDCl_3$): δ=5.64 (m, 1), 5.51 (m, 1), 4.87 (m, 1), 4.63 (d, J=7.0, 2), 3.30-3.44 (4), 2.90 (t, J=7.0, 2), 2.46-2.55 (6), 2.26-2.37 (4), 2.09 (m, 2), 1.71-1.80 (4), 1.46-1.55 (4), 1.21-1.41 (32), 1.01 (t, J=7.0, 6), 00.85-0.91 (9).

Example 10: Synthesis of ATX-0083

Figure 9:
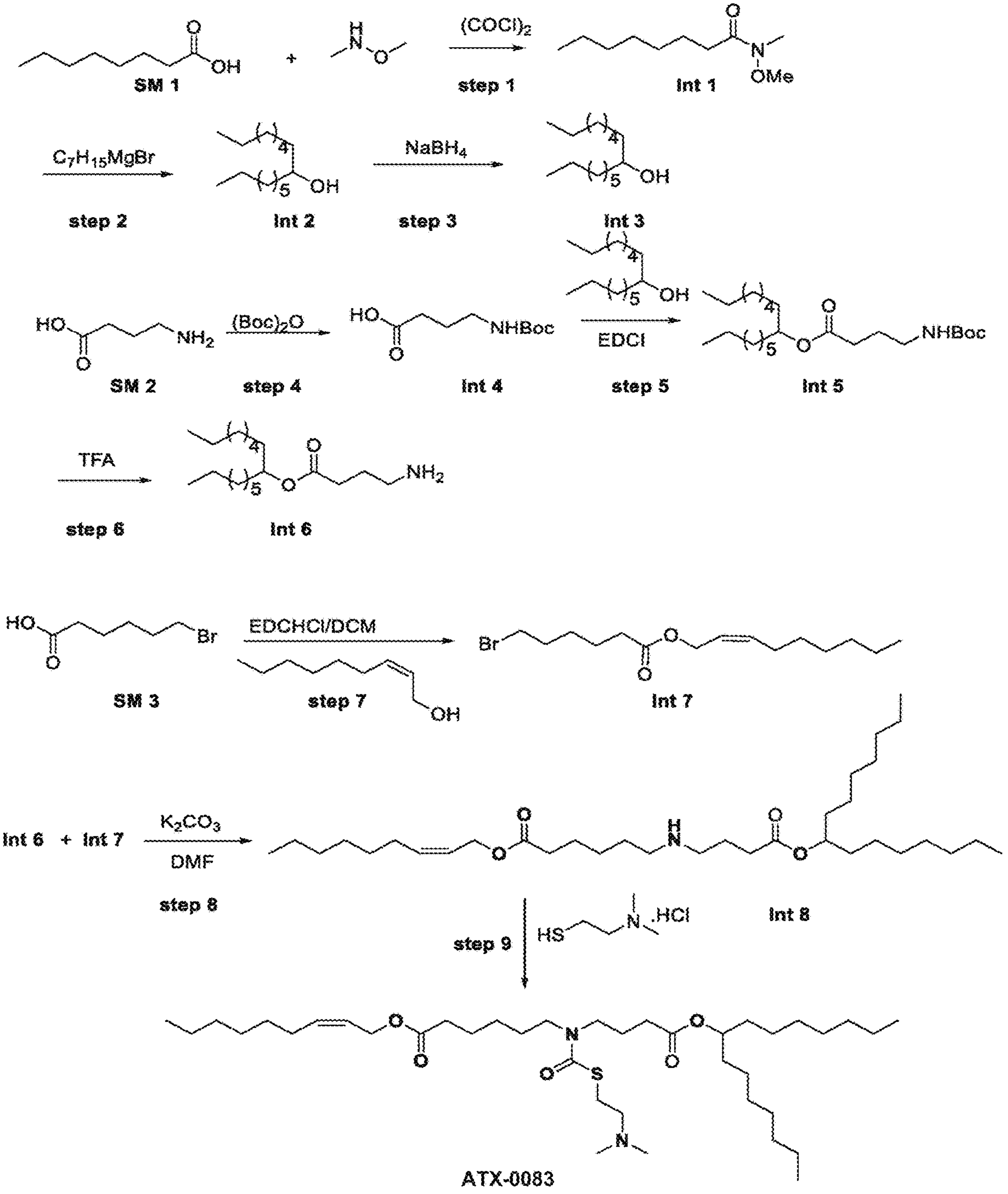
FIG. 9 shows the synthetic pathway of ATX-0083 from SM 1, SM 2 and SM3, which are the same as in FIG. 2. Ints 1-8 and reactions are described in Example 10.

FIG. 9 shows the synthetic pathway of ATX-0083 that is described further as follows.

ATX-0083: Step 1

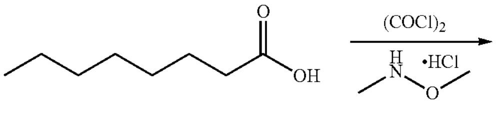

-continued

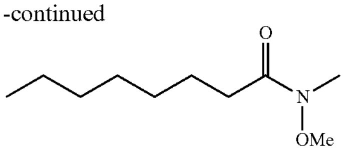

In a 500 ml single neck round bottom flask, 50 g octanoic acid (1 eq.) dissolved in of DCM (200 ml) was taken and then added 44.6 ml oxalyl chloride (1.5 eq.) slowly at 0° C., via additional funnel, stirring under nitrogen atmosphere and then added 1 ml DMF (catalytic). The resulting reaction mixture was stirred at room temperature for 2 hours.

In a separate 2 lit two neck round bottom flask to 67.4 g N,O-dimethylhydroxylamine hydrochloride (2 eq.) in DCM (300 ml), was added 144 ml triethylamine (3 eq.) using additional funnel, stirred at 0° C. To this resulting solution, the above acid chloride, after concentration under reduced pressure, was added under nitrogen atmosphere by dissolving in DCM (350 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5; PMA charring). Reaction mass was diluted with water (300 ml). Organic layer was separated and the aqueous layer was washed with DCM (3×100 ml). Combined organic layer was dried over anhydrous $Na_2SO_4$ and concentrated under reduced pressure.

Crude compound was subjected to column chromatography (60-120 mesh silica gel) using 10% EtOAc/hexane. Quantity produced, 55.0 g; yield, 84%.

ATX-0083: Step 2

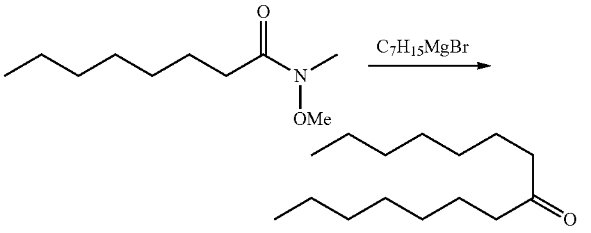

To a solution of 55 g heptyl magnesium bromide (1 eq.) in ether, taken in a 2 l two neck round bottom flask, stirred at 0° C. under nitrogen atmosphere, was added 89.6 g N-methoxy-N-methyloctanamide solution (1.5 eq.) dissolved in 400 ml of dry ether and the resulting reaction solution was stirred at room temperature for 4 hours.

Progress of the reaction was monitored by TLC (10% EtOAc in hexane; Rf: 0.7; PMA charring). Reaction mass was quenched with saturated $NH_4Cl$ solution (250 ml). Organic layer was separated and the aqueous layer was washed with ether (2×100 ml). Combined organic layer was dried over anhydrous $Na_2SO_4$ and concentrated under reduced pressure.

Crude compound was subjected to column chromatography (60-120 mesh silica gel) using 2% EtOAc/hexane. Quantity produced, 50.0 g; yield, 75%.

ATX-0083: Step 3

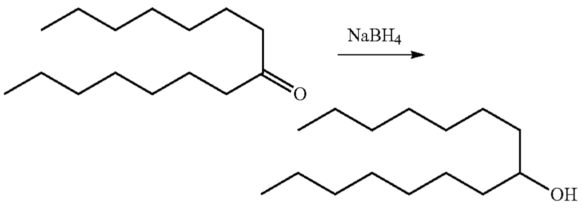

To a solution of 50 g pentadecan-8-one (1 eq.) dissolved in 290 ml MeOH/THF, 12.5 g sodium borohydride (1.5 eq.) was added at 0° C. and the resulting solution was stirred at room temperature for 2 hours.

Progress of the reaction was monitored by TLC (10% EtOAc in hexane; Rf: 0.5; PMA charring). Reaction mass was quenched with saturated $NH_4Cl$ solution (80 ml). Solvent was removed under reduced pressure and the resulting crude was partitioned between EtOAc (250 ml) and water (100 ml). Organic layer was separated and the aqueous layer was washed with EtOAc (3×80 ml). Combined organic layer was dried over anhydrous $Na_2SO_4$ concentrated under reduced pressure and dried under vacuum to get white solid. Quantity produced, 46.0 g; yield, 90%.

ATX-0083: Step 4

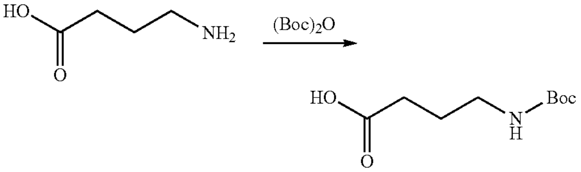

To a solution of 50 g 4-aminobutanoic acid (1 eq.) dissolved in THF, 490 ml 1 N aqueous NaOH solution (1 eq.) was added at 0° C., followed by 140 ml Boc anhydride (1.3 eq.), sequentially using additional funnel, over a period of 15 minutes. The resulting solution was stirred at room temperature for 4 hours.

Progress of the reaction was monitored by TLC (10% MeOH in $CHCl_3$; Rf: 0.5). Reaction mass was quenched with 5% HCl (350 ml) and then EtOAc (300 ml) was added. Organic layer was separated and the aqueous layer was washed with EtOAc (3×150 ml). Combined organic layer was dried over anhydrous $Na_2SO_4$ and concentrated under reduced pressure to get gummy liquid. Quantity produced, 77.0 g; yield, 78%.

ATX-0083: Step 5

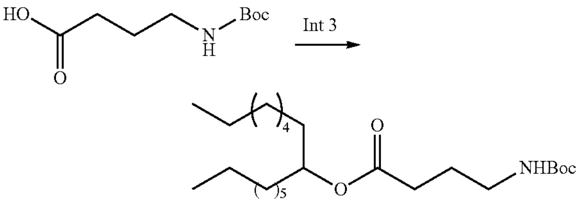

Synthesis was done in 4 batches. In each, to a solution of 23 g 4-((tert-butoxycarbonyl) amino)butanoic acid (1 eq.) in DCM (400 ml), cooled to below 0° C., were added 32.3 g EDC·HCl (1.5 eq.), 47 ml $Et_3N$ (3 eq.), and 1.3 g DMAP (0.1 eq.) sequentially under nitrogen atmosphere with 10 min interval. To this resulting solution 20 g pentadecan-8-ol (0.77 eq.) was added, by dissolving in DCM (200 ml), using additional funnel, and stirred at room temperature for 24 hours under nitrogen atmosphere.

Progress of the reaction was monitored by TLC (10% EtOAc in hexane; Rf: 0.4). Reaction mass was quenched with water (250 ml) and then organic layer was separated. Aqueous layer was washed with DCM (2×100 ml). Combined organic layer was concentrated under reduced pressure. To this resulting crude was washed saturated $NaHCO_3$ solution (150 ml) and EtOAc (250 ml) was added. Organic layer was separated, dried over anhydrous $Na_2SO_4$ and concentrated under reduced pressure and then proceeded to next step with crude. Quantity produced, 105 g (crude; required compound and alcohol).

ATX-0083: Step 6

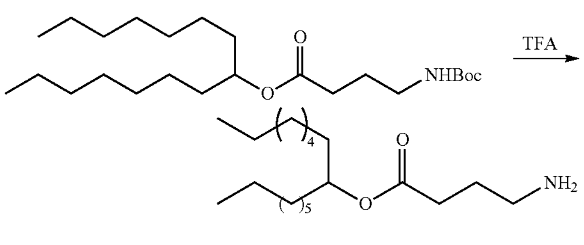

To a solution of 105 g pentadecan-8-yl 4-((tert-butoxycarbonyl)amino)butanoate (1 eq.) dissolved in 450 ml DCM, was added 194 ml TFA (10 eq.) at 0° C. and stirred at room temperature for 3 hours under nitrogen atmosphere.

Progress of the reaction was monitored by TLC (10% MeOH in $CHCl_3$; Rf: 0.3).

Reaction mass was concentrated under reduced pressure. The resulting crude was stirred with saturated $NaHCO_3$ solution (200 ml) for 10 minutes and then EtOAc (300 ml). Organic layer was separated and the aqueous layer was washed with EtOAc (2×100 ml). Combined organic layer was dried over anhydrous $Na_2SO_4$ and concentrated under reduced pressure.

Crude compound was subjected to column chromatography (silica gel 60-120 mesh) using 4% MeOH/$CHCl_3$ and 1 ml of triethylamine. Quantity produced, 60.0 g for two steps; yield, 54%.

ATX-0083: Step 7

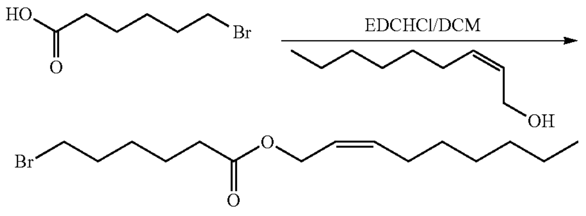

Reaction was done in two batches, In each, to a solution of 20 g 6-bromohexanoic acid (1 eq.) dissolved in DCM (300 ml), cooled to below 0° C. was added 29.3 g EDC·HCl (1.5 eq.), 42.8 ml $Et_3N$ (3 eq.), and 1.2 g DMAP (0.1 eq.) sequentially under nitrogen atmosphere with 10-minute intervals. To this resulting solution 14.5 g (Z)-non-2-en-1-ol (1 eq.) was added (by dissolving in 100 ml of DCM) using additional funnel, and stirred at room temperature for 24 hours under nitrogen atmosphere.

Progress of the reaction was monitored by TLC (10% EtOAc in hexane; Rf: 0.7). Reaction mass was quenched with water (200 ml) and then organic layer was separated. Aqueous layer was washed with DCM (2×100 ml). Combined organic layer was concentrated under reduced pressure. The resulting crude was washed with saturated $NaHCO_3$ solution (150 ml) and then extracted with EtOAc (2×150 ml). Organic layer was separated, dried over anhydrous $Na_2SO_4$ and concentrated under reduced pressure.

Crude compound was subjected to column chromatography (60-120 mesh silica gel) using 4% EtOAc/hexane. Alcohol reactant was recovered. Quantity produced, 36.0 g; yield, 55%.

ATX-0083: Step 8

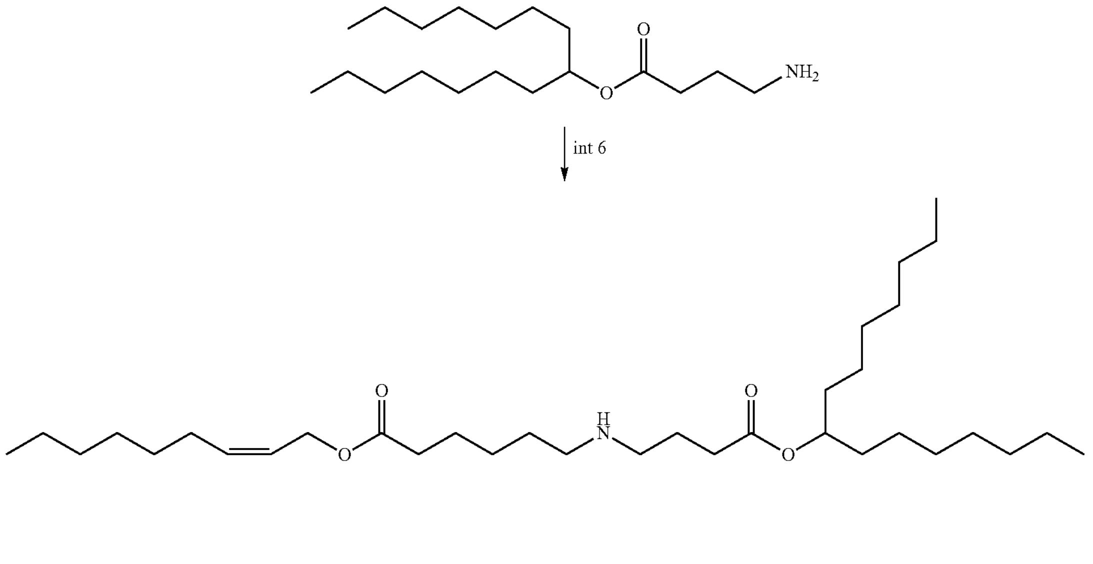

The reaction was done in six batches. In each, to a solution of 10 g pentadecan-8-yl 4-aminobutanoate (Int 6, 1 eq.), 10.1 g (Z)-non-2-en-1-yl 6-bromohexanoate (Int 7, 1 eq.) in 120 ml ACN, 6.1 g anhydrous potassium carbonate (1.4 eq.) was added and the resulting mixture was refluxed at 90° C. for 4 hours under nitrogen atmosphere.

Progress of the reaction was monitored by TLC (10% MeOH in $CHCl_3$; Rf: 0.5). Reaction mass was filtered, washed with ACN (2×20 ml), and the filtrate concentrated under reduced pressure.

Crude compound was subjected to column chromatography (silica gel 100-200 mesh) using 20-80% EtOAc/hexane. Starting materials were recovered. Quantity produced, 36.9 g; yield, 35%.

ATX-0083: Step 9

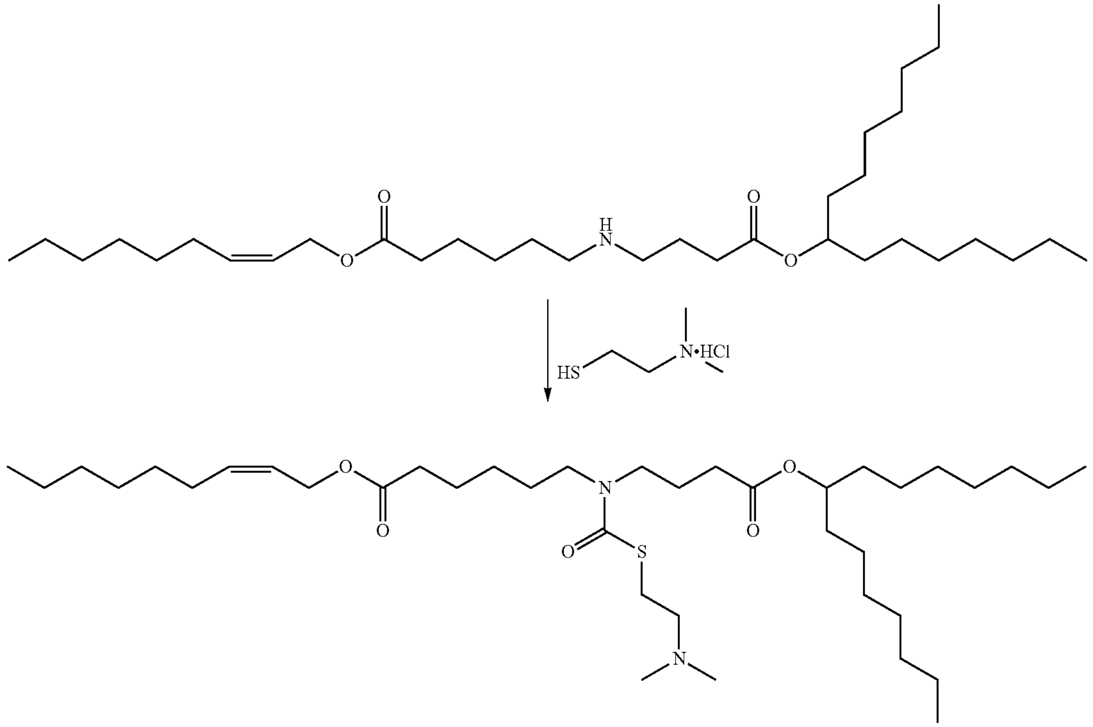

The reaction was done in three batches. In each, to a solution of 10 g (Z)-non-2-en-1-yl 6-((4-oxo-4-(pentadecan-8-yloxy)butyl)amino)hexanoate (1 eq.) dissolved in 100 ml dry DCM, was added 7.5 ml triethylamine (3 eq.) and 2.68 g triphosgene (0.5 eq.) with 5 minute intervals at 0° C. under nitrogen atmosphere. The resulting solution was stirred at room temperature, under nitrogen atmosphere for 1 hour. The resulting reaction mass was concentrated under reduced pressure and kept under nitrogen atmosphere.

To a suspension of 3 g sodium hydride (7 eq.) in dry THF (100 ml), in a 2 neck 500 ml RB flask stirred at 0° C. under nitrogen atmosphere, was added 8.9 g 2-(dimethylamino) ethane-1-thiol hydrochloride (3.5 eq.) and kept stirring for 5 minutes under nitrogen atmosphere. To this resulting solution the above carbamoyl chloride, dissolved in dry THF (200 ml), was added via syringe slowly for about 10 minutes. The resulting solution was stirred at room temperature overnight under nitrogen atmosphere.

Progress of the reaction was monitored by TLC (10% EtOAc/hexane; Rf: 0.5; PMA charring). Reaction mass was quenched with saturated $NH_4Cl$ solution (100 ml) and then EtOAc (350 ml) was added. Organic layer was separated and the aqueous layer was washed with EtOAc (2×80 ml). Combined organic layer was dried over anhydrous $Na_2SO_4$ and concentrated under reduced pressure.

A first purification was done using neutral alumina. Crude compound, dissolved in hexane, was loaded at the top of neutral alumina (700 g loaded in the column). Compound was eluted at 8-10% EtOAc/hexane. A second purification was done using silica gel (100-200 mesh). Compound, dissolved in hexane, was loaded at the top of silica gel (500 g loaded in the column). Compound was eluted at 20-25% EtOAc/hexane. Final Compound (dissolved in hexane) was subjected to charcoal treatment (200 mg/g) and filtered through celite bed (after stirred for 20 minutes), and then passed through syringe end membrane filter (PTFE; 0.2 micron, 25 mm diameter). The resulting filtrate was concentrated under reduced pressure. Quantity produced, 15.5 g; yield, 41%.

ATX-0083/RL-47B: $^1$H-NMR (PPM, 500 MHz, $CDCl_3$): δ=5.64 (m, 1), 5.52 (m, 1), 4.87 (m, 1), 4.62 (d, J=7.0, 2), 3.24-3.42 (4), 3.02 (t, J=7.0, 2), 2.53 (t, J=7.0, 2), 2.26-2.34 (4), 2.26 (s, 6), 2.10 (m, 2), 1.45-1.70 (6), 1.20-1.41 (34), 0.84-0.92 (9).

Example 11: Synthesis of ATX-0084

Figure 10:
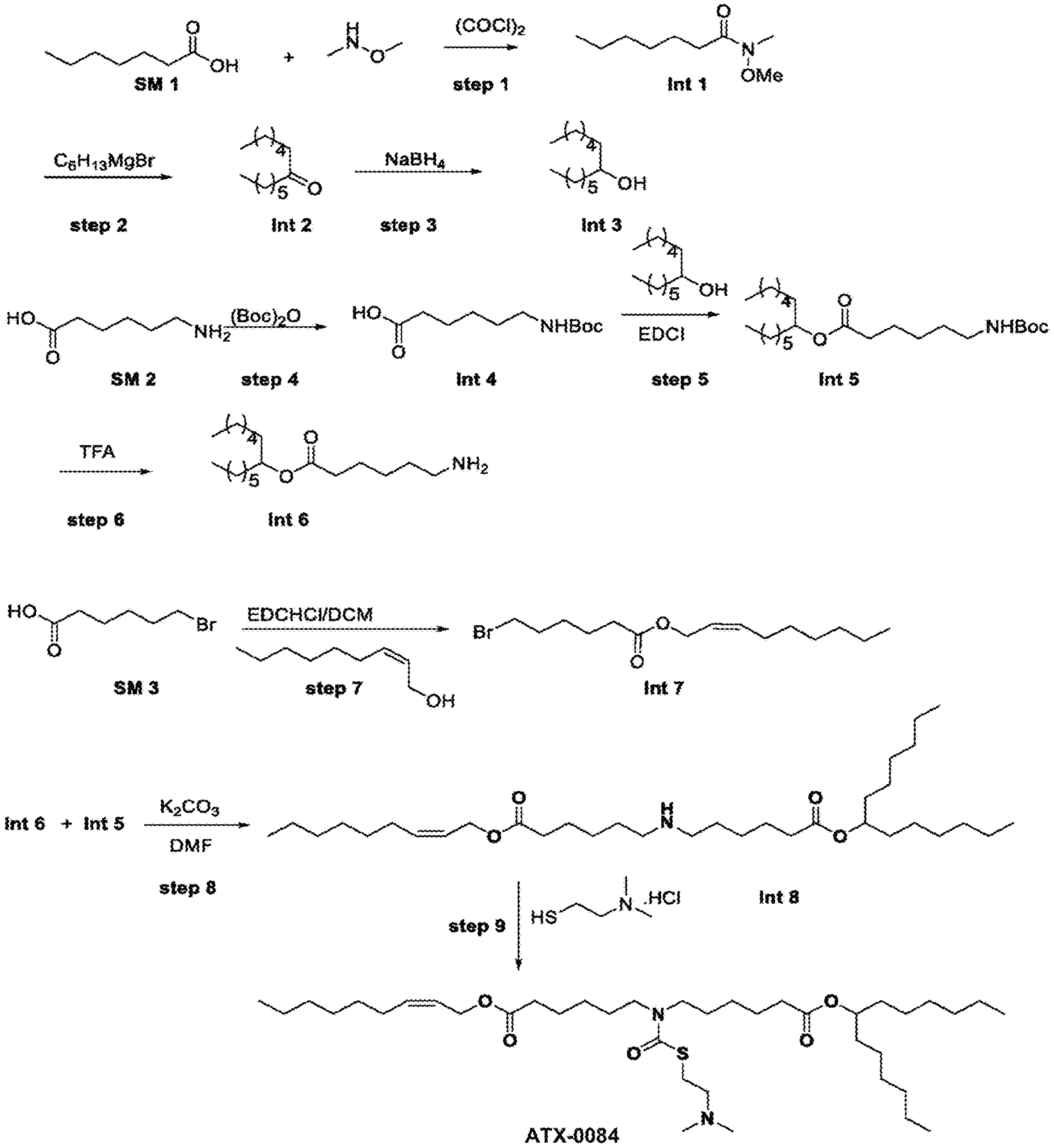
FIG. 10 shows the synthetic pathway of ATX-0084 from SM 1, SM 2 and SM3, which are the same as in FIG. 2. Ints 1-8 and reactions are described in Example 11.

FIG. 10 shows the synthetic pathway of ATX-0084 that is described further as follows.

ATX-0084: Step 1

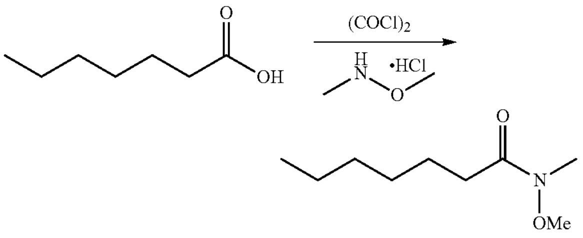

In a 500 ml single neck round bottom flask, 30 g heptanoic acid (1 eq.) dissolved in of DCM (200 ml) was taken and then added 26.7 g oxalyl chloride (1.5 eq.) slowly at 0° C., stirring under nitrogen atmosphere and then added 1 ml DMF (catalytic). The resulting reaction mixture was stirred at room temperature for 2 hours.

In a separate 1 l two neck round bottom flask, to 40.5 g N,O-dimethylhydroxylamine hydrochloride (2 eq.), in DCM (250 ml), was added 86.6 ml trimethylamine (3 eq.) using additional funnel, stirred at 0° C. To this resulting solution, the above acid chloride, after concentration under reduced pressure, was added under nitrogen atmosphere by dissolving in DCM (100 ml), dropwise using addition funnel for 20 minutes. The resulting reaction solution was stirred at room temperature for 3 hours under nitrogen atmosphere.

Progress of the reaction was monitored by TLC (20% EtOAc/hexane; Rf: 0.5). Reaction mass was diluted with water (250 ml). Organic layer was separated and the aqueous layer was washed with DCM (3×100 ml). Combined organic layer was concentrated under reduced pressure.

Crude compound was subjected to column chromatography using (60-120 silica gel) using 10% EtOAc/hexane. Quantity produced, 38.0 g; yield, 84%.

ATX-0084: Step 2

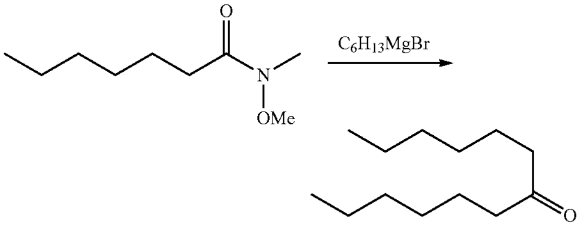

To a solution of 8 g hexyl magnesium bromide (1 eq.) in 250 ml dry ether, taken in a 1 liter two neck round bottom flask, stirred at 0° C. under nitrogen atmosphere, was added 2.3 g N-methoxy-N-methyheptanamide (0.5 eq.) dissolved in 250 ml of ether and the resulting reaction mixture was stirred at room temperature for 4 hours.

Progress of the reaction was monitored by TLC (10% EtOAc in hexane; Rf: 0.7). Reaction mass was quenched with saturated $NH_4Cl$ solution (200 ml). Organic layer was separated and the aqueous layer was washed with ether (2×100 ml). Combined organic layer was dried over anhydrous $Na_2SO_4$ and concentrated under reduced pressure.

Crude compound was subjected to column chromatography using (60-120 mesh silica gel) using 2% EtOAc/hexane. Quantity produced, 30.8 g; yield, 71%.

ATX-0084: Step 3

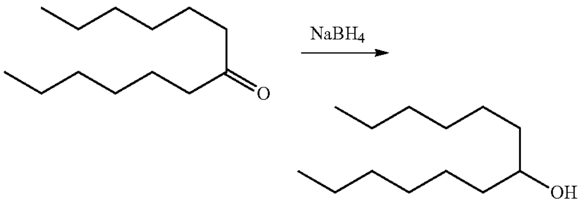

To a solution of 30 g tridecan-7-one (1 eq.) dissolved in 200 ml MeOH/THF, 8.5 g sodium borohydride (0.5 eq.) was added at 0° C. and the resulting solution was stirred at room temperature for 2 hours.

Progress of the reaction was monitored by TLC (10% EtOAc/hexane; Rf: 0.5). Reaction mass was quenched with saturated $NH_4Cl$ solution (80 ml). Solvent was removed under reduced pressure and the resulting crude was partitioned between EtOAc (200 ml) and water (100 ml). Organic layer was separated and the aqueous layer was washed with EtOAc (2×70 ml). Combined organic layers were concentrated under reduced pressure to get white solid. Quantity produced, 27.2 g; yield, 90%.

ATX-0084: Step 4

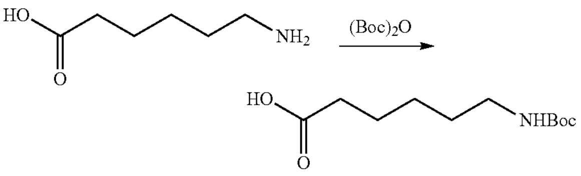

To a solution of 5 g 6-aminohexanoic acid (1 eq.), dissolved in 120 ml THF, 125 ml of 1N aqueous NaOH solution was added at 0° C., followed by 34 ml Boc anhydride (1.3 eq.), sequentially using additional funnel, over a period of 15 min. The resulting solution was stirred at room temperature for 4 hours.

Progress of the reaction was monitored by TLC (10% MeOH in $CHCl_3$; Rf. 0.5). Reaction mass was quenched with 5% HCl (100 ml) and then EtOAc (150 ml) was added. Organic layer was separated and the aqueous layer was washed with EtOAc (2×100 ml). Combined organic layer was concentrated under reduced pressure to get gummy liquid. Quantity produced, 22.4 g; yield, 85%.

ATX-0084: Step 5

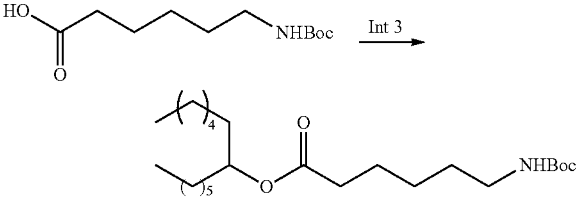

To a solution of 10 g 6-((tert-butoxycarbonyl)amino) hexanoic acid (1 eq.) dissolved in DCM (200 ml), cooled to below 0° C. was added 10.7 g EDC·HCl (1.3 eq.), 18 ml $Et_3N$ (3 eq.), and 525 mg DMAP (0.1 eq.) sequentially under nitrogen atmosphere with 10-minute interval. To this resulting solution 6 g tridecan-7-ol (Int 3, 0.7 eq.) was added at the same temperature, by dissolving in DCM (50 ml), using additional funnel, and stirred at room temperature for 24 hours under nitrogen atmosphere.

Progress of the reaction was monitored by TLC (10% EtOAc in hexane; Rf: 0.4). Reaction mass was quenched with water (150 ml) and then organic layer was separated. Aqueous layer was washed with DCM (2×75 ml). Combined organic layer was concentrated under reduced pressure. The resulting crude was washed with saturated $NaHCO_3$ solution (100 ml) and then extracted with EtOAc (2×100 ml) was added. Organic layer was separated and concentrated under reduced pressure, and proceeded to next step with crude. Quantity produced, 8.5 g (crude; required compound and alcohol).

ATX-0084: Step 6

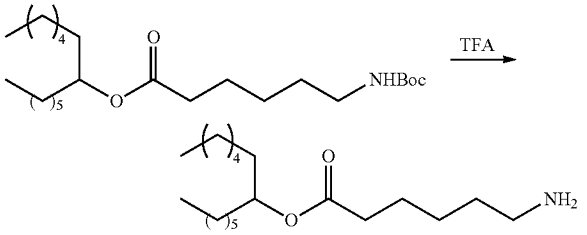

To a solution of 10 g tridecan-7-yl 6-((tert-butoxycarbonyl)amino)hexanoate (1 eq.) dissolved in 65 ml DCM, was added 18.5 ml TFA (10 eq.) at 0° C. and stirred at room temperature for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with saturated $NaHCO_3$ solution (100 ml) and then extracted with EtOAc (3×100 ml). Organic layer was separated and concentrated under reduced pressure.

Crude compound was subjected to column chromatography using (60-120 mesh silica gel; 4% MeOH/$CHCl_3$ and 1 ml triethylamine), and alcohol starting material was recovered. Quantity, 4.5 g in two steps; yield, 33%.

ATX-0084: Step 7

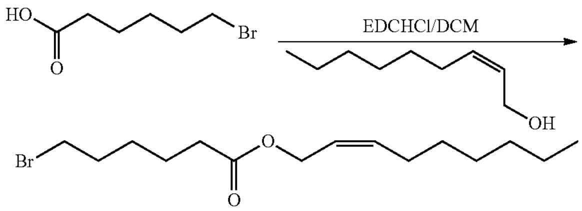

To a solution of 20 g 6-bromohexanoic acid (1 eq.) dissolved in DCM (300 ml), cooled to below 0° C. was added 29.3 g EDC·HCl (1.5 eq.), 42.8 ml $Et_3N$ (3 eq.), and 1.2 g DMAP (0.1 eq.) sequentially under nitrogen atmosphere with 10-minute interval. To this resulting solution 14.5 g (Z)-non-2-en-1-ol (1 eq.) was added, dissolved in 100 ml of DCM, using additional funnel, and stirred at room temperature for 24 hours under nitrogen atmosphere.

Progress of the reaction was monitored by TLC (10% EtOAc in hexane; Rf: 0.7). Reaction mass was quenched with water (200 ml) and then organic layer was separated. Aqueous layer was washed with DCM (2×100 ml). Combined organic layer was concentrated under reduced pressure. The resulting crude was washed with saturated $NaHCO_3$ solution (150 ml) and then extracted with EtOAc (2×150 ml). Organic layer was separated, dried over anhydrous $Na_2SO_4$ and concentrated under reduced pressure.

Crude compound was subjected to column chromatography (60-120 mesh silica gel) using 4% EtOAc/hexane. Alcohol starting material was recovered. Quantity produced, 18.0 g; yield, 55%.

ATX-0084: Step 8

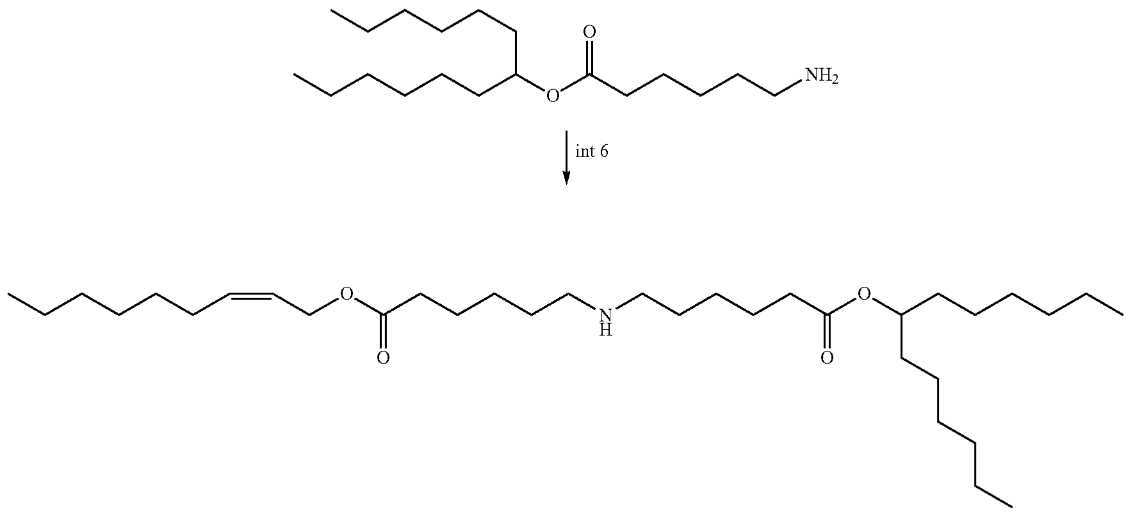

To a solution of 4.5 g tridecan-7-yl 6-aminohexanoate (Int 6, 1 eq.) and 4.5 g (Z)-non-2-en-1-yl 6-bromohexanoate (Int 7, 1 eq.) in 90 ml ACN, 2.7 g potassium carbonate (1.4 eq.) was added and the resulting mixture was refluxed at 90° C. for 4 hour under nitrogen atmosphere.

Progress of the reaction was monitored by TLC (10% MeOH in $CHCl_3$; Rf: 0.5). Reaction mass was filtered, washed with ACN (2×20 ml), and the filtrate concentrated under reduced pressure.

Crude compound was subjected to column chromatography (100-200 mesh silica gel) using 20% EtOAc/hexane. Starting materials were recovered. Quantity produced, 3.0 g; yield, 37%.

ATX-0084: Step 9

A first purification was done using silica gel (100-200 mesh). 4.6 g of crude compound was adsorbed on 10.0 g of silica gel and poured onto 90.0 g of silica gel taken in the column. Compound was eluted at 50% EtOAc/hexane. A second purification was done using neutral alumina with HPLC grade solvents. 2.0 g of crude compound was adsorbed on 6.0 g of neutral alumina and the resulting was poured onto 40.0 g of neutral alumina taken in the column. Compound was eluted at 20% EtOAc/hexane. Quantity produced, 1.2 g; yield, 38% (300 mg mixture).

ATX-0084/RL-47C: $^1$H-NMR (PPM, 500 MHz, $CDCl_3$): δ=5.64 (m, 1), 5.52 (m, 1), 4.86 (m, 1), 4.62 (d, J=7.0, 2), 3.22-3.35 (4), 3.01 (t, J=7.0, 2), 2.53 (t, J=7.0, 2), 2.25-2.34 (4), 2.27 (s, 6), 2.10 (m, 2), 1.45-1-73 (10), 1.20-1.40 (30), 00.84-0.91 (9).

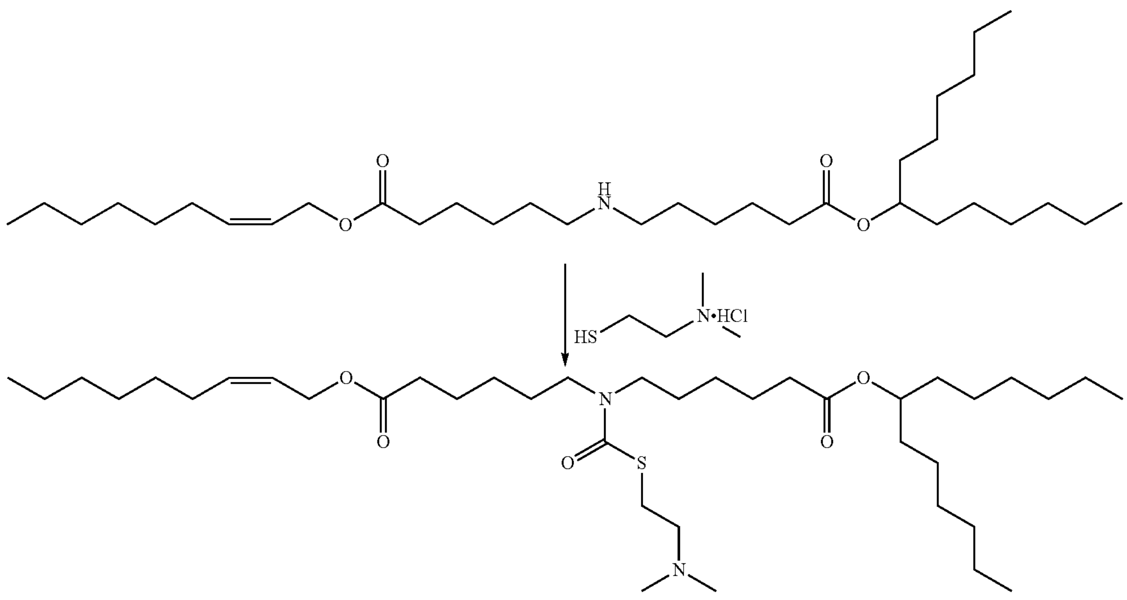

To a solution of 2.5 g (Z)-non-2-en-1-yl 6-((6-oxo-6-(tridecan-7-yloxy)hexyl)amino)hexanoate (1 eq.) dissolved in 30 ml dry DCM, was added 1.8 ml triethylamine (3 eq.) and 672 mg triphosgene (0.5 eq.) with 5 minute interval at 0° C. under nitrogen atmosphere. The resulting solution was stirred at room temperature under nitrogen atmosphere for 1 hour. The resulting reaction mass was concentrated under reduced pressure and kept under nitrogen atmosphere.

To a suspension of 761 mg sodium hydride in dry THF (50 ml), in a 2 neck 250 ml round bottom flask stirred at 0° C. under nitrogen atmosphere, was added 2.2 g 2-(dimethylamino)ethane-1-thiol hydrochloride (3.5 eq.) and kept stirring for 5 minutes under nitrogen atmosphere. To the resulting solution the above carbamoyl chloride, dissolved in THF (60 ml), was added via syringe slowly for about 10 minutes. The resulting solution was stirred at room temperature overnight under nitrogen atmosphere.

Progress of the reaction was monitored by TLC (10% EtOAc/hexane; Rf. 0.5; PMA charring). Reaction mass was quenched with saturated $NH_4Cl$ solution (60 ml) and then EtOAc (130 ml) was added. Organic layer was separated and the aqueous layer was washed with EtOAc (3×40 ml). Combined organic layer was concentrated and the resulting crude was subjected to column chromatography.

Example 12: Synthesis of ATX-0061

Figure 11:
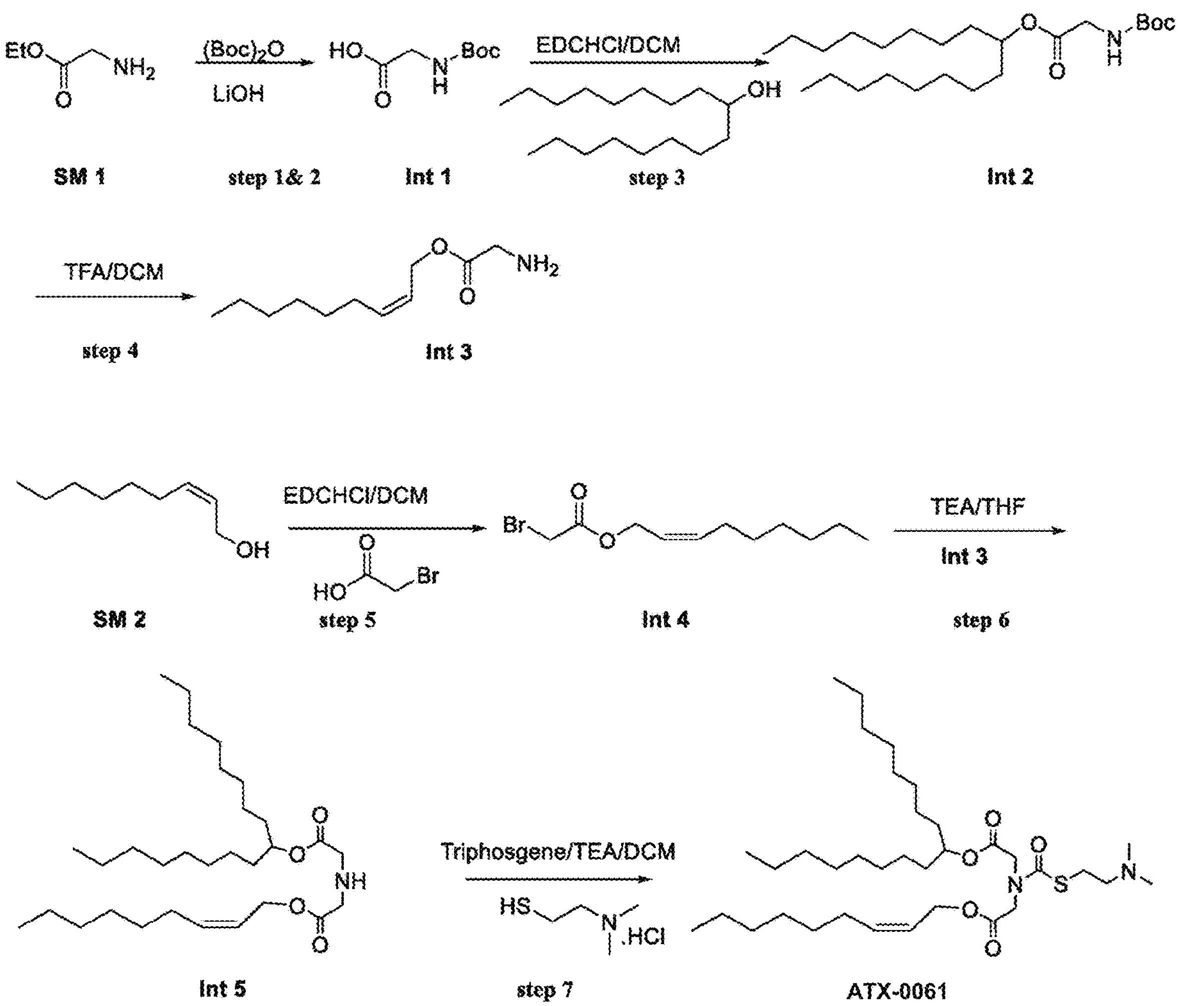
FIG. 11 shows the synthetic pathway of ATX-0061 from SM 1 and SM 2, which are the same as in FIG. 1. Ints 1-5 and reactions are described in Example 12.

FIG. 11 shows the synthetic pathway of ATX-0061 that is described further as follows ATX-0061: Step 1

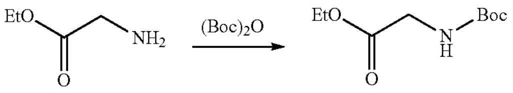 [SMILES: "(Boc)2O" ; CCOC(=O)CN ; CCOC(=O)CNC(=O)OC(C)(C)C]

12 g glycine ester (1 eq.) was dissolved in THF (100 ml) and cooled to below 0° C. To this solution, 24.2 ml triethylamine (1.5 eq.) and 38.11 g Boc anhydride (1.5 eq.) through an additional funnel were added sequentially.

Progress of the reaction was monitored by TLC using 50% EtOAc/hexane; Rf: 0.4.

Reaction mass was quenched with water and EtOAc (100 ml) was added, after 16 hours. Organic layer was separated, aqueous layer was washed with EtOAc (2×40 ml) and combined organic layers were dried over sodium sulphate and concentrated under reduced pressure.

Crude product was subjected to 60-120 silica gel (25% EtOAc/hexane). Quantity produced, 20.8; yield, 88%.

ATX-0061: Step 2

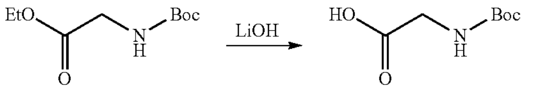 [SMILES: CCOC(=O)CNC(=O)OC(C)(C)C ; "LiOH" ; CC(C)(C)OC(=O)NCC(=O)O]

To a solution of 18.9 g N-Boc glycine ester (1 eq.) dissolved in THF (130 ml) was added aqueous solution of 5.85 g LiOH (1.5 eq.) and the resulting solution was stirred at room temperature for 4 hours.

The reaction was monitored by TLC (60% EtOAc/hexane; Rf: 0.3), SM is absent.

Reaction mass was concentrated and crude mass was quenched with 5% HCl (pH 3) and then extracted with EtOAc (4×80 ml), dried over sodium sulphate and concentrated under reduced pressure to get the compound. Quantity produced, 15 g; yield, 92%; confirmed by Mass.

ATX-0061: Step 3

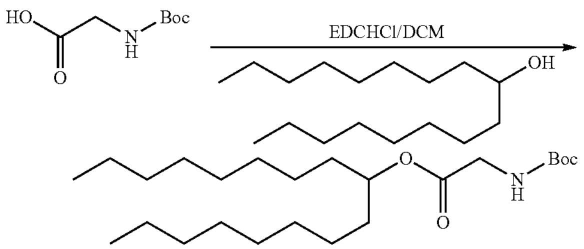

To a solution of 5 g N-Boc-glycine ester (Int 1, 1 eq.) dissolved in DCM (30 ml), cooled to below 0° C. was added 4.5 ml $Et_3N$ (1.2 eq.) and 6.44 g EDC·HCl (1.2 eq.). To this reaction solution 5.12 g heptaden-9-ol (0.7 eq.) in 20 ml DCM was added and stirred at room temperature overnight.

Starting material observed to be absent by TLC (10% EtOAc/hexane; Rf: 0.6). Reaction mass was diluted with saturated $NaHCO_3$ solution, organic layer was separated, aqueous layer was washed with DCM (2×30 ml) and dried over sodium sulphate and concentrated under reduced pressure. Proceeded to next step with crude (6.8 g; mixture of product and alcohol).

ATX-0061: Step 4

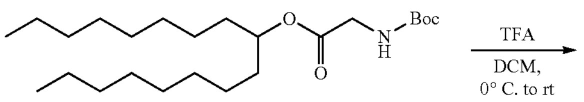

-continued

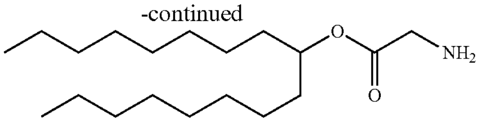

4 g heptadecan-9-yl (tert-butoxycarbonyl)glycinate (Int 2, 1 eq.) was dissolved in DCM (40 ml) and cooled 0° C., added 7.4 ml TFA (10 eq.) and stirred at room temperature for 1 hour.

Completion of reaction was checked in 2 hour by TLC (10% EtOAc/hexane; Rf: 0.5).

Reaction mass was concentrated under reduced pressure, residual mass was washed with saturated sodium bicarbonate solution (30 ml) and extracted with EtOAc (3×30 ml), organic layer dried over sodium sulphate and concentrated under reduced pressure to get Int 3.

Crude product was subjected to column chromatography (silica, 60-120) using 1-3% $MeOH/CHCl_3$ and 2 mL of $Et_3N$. Quantity produced, 1 g; confirmed by $^1H$-NMR and Mass.

ATX-0061: Step 5

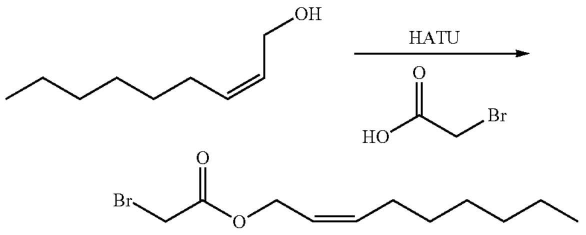

To a solution of 4 g bromo acetic acid (1 eq.) dissolved in DCM (35 ml), cooled to below 0° C. was added 4.7 ml $Et_3N$ (1.2 eq.) and 354 mg DMAP (0.1 eq.), followed by 13.23 g HATU (1.2 eq.). To this reaction solution 2.88 g (Z)-non-2-en-1-ol (0.7 eq.) in 20 ml of DCM was added and stirred at room temperature overnight.

Reaction was monitored by TLC (10% EtOAc/hexane; Rf: 0.7).

Reaction mass was diluted with saturated $NaHCO_3$ solution (80 ml), organic layer was separated, aqueous layer was washed with DCM (40 ml), dried over sodium sulphate and concentrated under reduced pressure. The residual mass was purified by silica gel (60-120) column chromatography (1.5% EtOAc/hexane). Quantity produced, 4 g; yield, 52%.

ATX-0061: Step 6

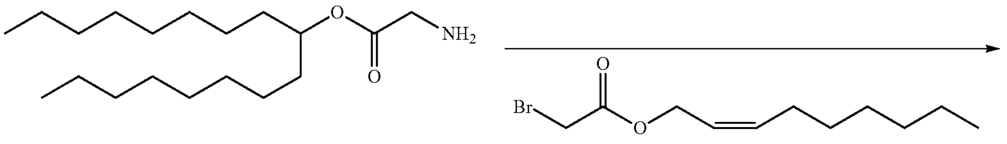

-continued

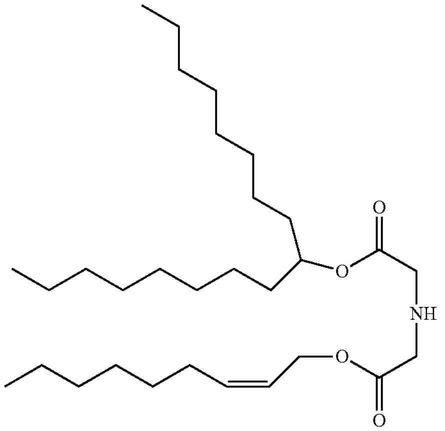

1 g heptadecan-9-yl glycinate (Int 3, 1 eq.) was dissolved in THF (25 ml), added 0.5 ml TEA (1.3 eq.) and 1.08 g (Z)-non-2-en-1-yl 2-bromoacetate derivative (Int 4, 1.3 eq.), and stirred at room temperature for overnight.

Progress of the reaction was monitored by TLC (10% EtOAc/hexane; Rf: 0.4). Reaction mixture was diluted with water (30 ml) and extracted with EtOAc (20 ml×2), combined organic layer was dried over sodium sulphate and concentrated under reduced pressure.

The residual mass was purified by column (silica gel; 100-200) chromatography (2% EtOAc/hexane). Quantity produced, 700 mg; yield, 47%; confirmed by Mass.

ATX-0061: Step 7

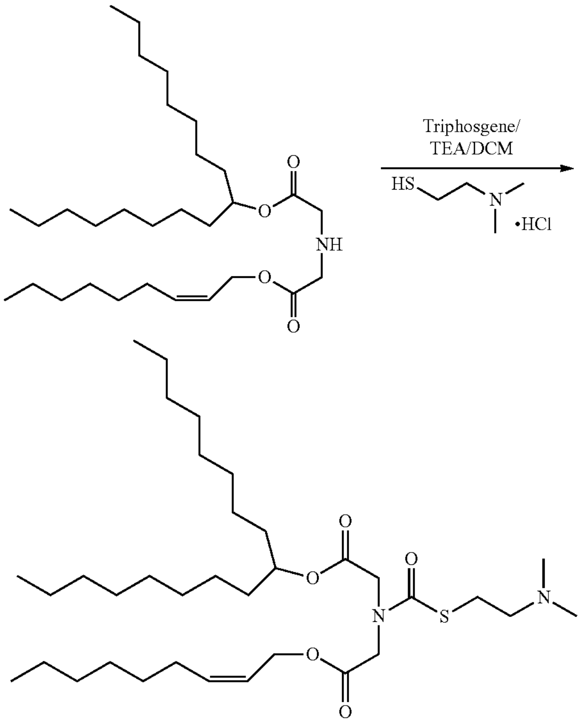

To a solution of 700 mg heptadecan-9-yl (Z)-(2-(non-2-en-1-yloxy)-2-oxoethyl)glycinate) (1 eq.) dissolved in 15 ml DCM, cooled to below 5° C. was added 0.4 ml $Et_3N$ (3 eq.), followed by 209 mg triphosgene (0.5 eq.) portion-wise for 10 minutes.

Progress of the reaction mixture monitored by TLC, reaction was completed for 0.5 hours, reaction mass was concentrated under reduced pressure.

To a solution of 423 mg N, N-dimethyl ethanethiol hydrochloride (3 eq.) in dry THF (10 ml) and DMF (3 ml), stirred at 0° C. under nitrogen atmosphere was added 144 mg sodium hydride (6 eq.). After 10 minutes, to this reaction mass was added the above solution, by dissolving in THF (15 ml). The resulting solution was stirred at room temperature for 1 hour.

Completion of the reaction was observed by TLC (10% $MeOH/CHCl_3$; Rf: 0.5), after 1 hour.

Reaction mass was quenched with saturated $NH_4Cl$ solution (20 ml), water (20 ml) and EtOAc (30 ml) was added. Aqueous layer was washed with EtOAc (2×20 ml), and the combined organic layer was washed with brine solution (20 ml). Organic layer was dried over $Na_2SO_4$ and concentrated under reduced pressure.

Crude was subjected to column chromatography using silica gel (100-200) with 15% EtOAC/hexane, and then with neutral alumina with 15% EtOAc/hexane, to get pure compound. Quantity produced, 520 mg; yield, 58%; confirmed by $^1$H-NMR, HPLC and Mass.

ATX-0061/RL-42D: 1H-NMR (PPM, 400 MHz, $CDCl_3$): δ=5.67 (m, 1), 5.51 (m, 1), 4.92 (m, 1), 4.70 (m, 2), 4.16-4.27 (4), 3.07 (m, 2), 2.53 (m, 2), 2.27 (s, 6), 2.10 (m, 2), 1-47-1.57 (4), 1.19-1.40 (32), 0.83-0.92 (9).

Example 13: Synthesis of ATX-0063

Figure 12:
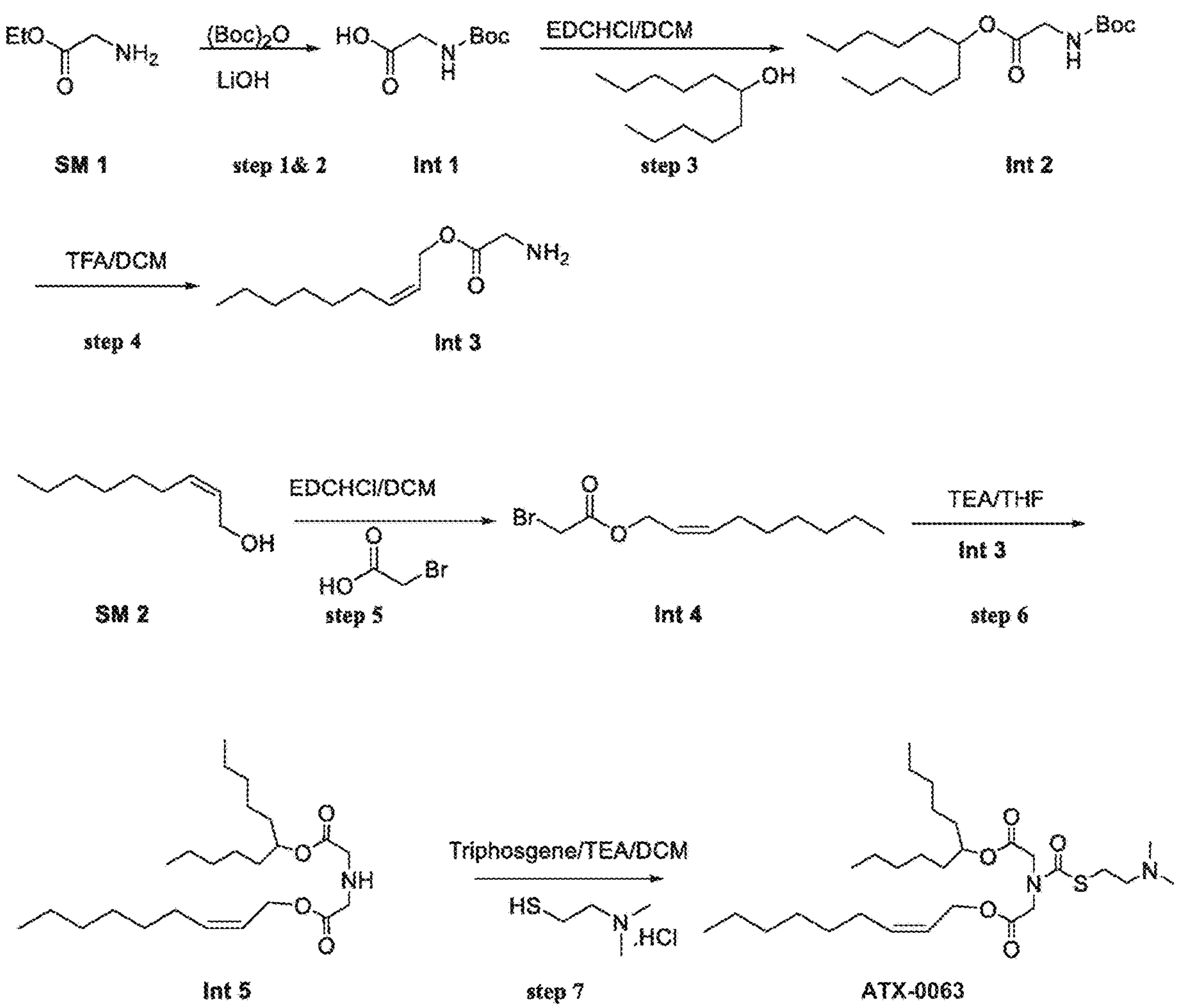
FIG. 12 shows the synthetic pathway of ATX-0063 from SM 1 and SM 2, which are the same as in FIG. 1. Ints 1-5 and reactions are described in Example 13.

FIG. 12 shows the synthetic pathway of ATX-0063 that is described further as follows.

ATX-0063: Step 1

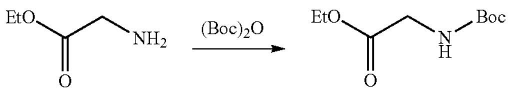

ethyl glycinate 12 g glycine ester (1 eq.) was dissolved in THF (100 mL) and cooled to below 0° C. To this solution, 24.2 ml triethylamine (1.5 eq.) and 38.11 g Boc anhydride (1.5 eq.) through an additional funnel were added sequentially.

Progress of the reaction was monitored by TLC using 50% EtOAc/hexane; Rf: 0.4.

Reaction mass was quenched with water and EtOAc (100 ml) was added, after 16 hours. Organic layer was separated, aqueous layer was washed with EtOAc (2×40 ml) and combined organic layers were dried over sodium sulphate and concentrated under reduced pressure.

Crude product was subjected to 60-120 silica gel (25% EtOAc/hexane). Quantity produced, 20.8; yield, 88%.

ATX-0063: Step 2

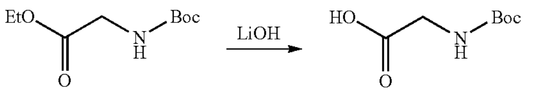 [SMILES: CCOC(=O)CNC(=O)OC(C)(C)C ; "LiOH" ; CC(C)(C)OC(=O)NCC(=O)O]

To a solution of 18.9 g N-Boc glycine ester (1 eq.) dissolved in THF (130 ml) was added aqueous solution of 5.85 g LiOH (1.5 eq.) and the resulting solution was stirred at room temperature for 4 hours.

The reaction was monitored by TLC (60% EtOAc/hexane; Rf: 0.3), starting was absent from reaction product.

The reaction mass was concentrated and crude mass was quenched with 5% HCl (pH 3) and then extracted with EtOAc (4×80 ml), dried over sodium sulphate and concentrated under reduced pressure to get the compound. Quantity produced, 15 g; yield, 92%; confirmed by Mass.

AT-X-0063: Step 3

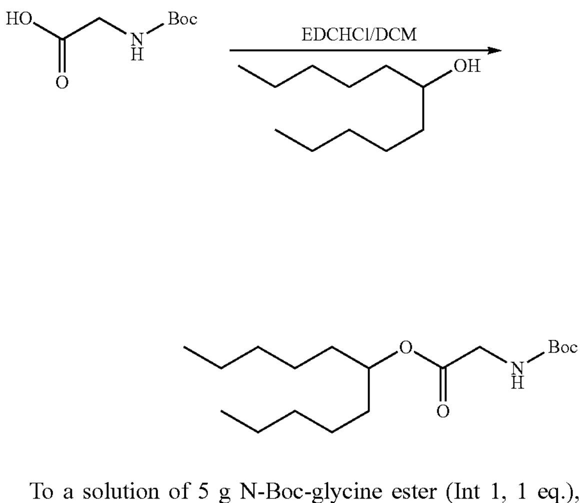

To a solution of 5 g N-Boc-glycine ester (Int 1, 1 eq.), dissolved in DCM (50 ml), cooled to below 0° C. was added 4.5 ml $Et_3N$ (1.2 eq.) and 6.4 g EDC·HCl (1.2 eq.). To this reaction solution 3.4 g undecan-6-ol (0.7 eq.) in 20 ml of DCM was added and stirred at room temperature overnight.

Starting material observed to be absent by TLC (15% EtOAc/hexane; Rf: 0.6). Reaction mass was diluted with saturated $NaHCO_3$ solution (20 ml), organic layer was separated, aqueous layer was washed with DCM (2×40 mL) and dried over sodium sulphate and concentrated under reduced pressure. Proceeded to next step with crude (5.5 g; mixture of product and alcohol), after column filtration.

ATX-0063: Step 4

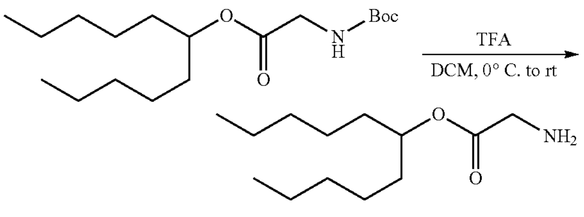

3.3 g crude undecan-6-yl (tert-butoxycarbonyl)glycinate (Int 2, 1 eq.) was dissolved in DCM (20 ml) and cooled to 0° C., added 7.6 ml TFA (10 eq.) and stirred at room temperature for 1 hour.

Completion of reaction was checked in 2 hours by TLC (10% MeOH/DCM; Rf: 0.5). Reaction mass was concentrated under reduced pressure, residual mass was washed with saturated sodium bicarbonate solution (50 ml) and extracted with EtOAc (3×25 ml), organic layer dried over sodium sulphate and concentrated under reduced pressure to get Int 3.

Crude product was subjected to column chromatography (silica, 60-120) using 1-3% $MeOH/CHCl_3$ and 2 ml $Et_3N$. Quantity produced, 1.2 g; yield, 40%; confirmed by $^1H$-NMR and Mass.

ATX-0063: Step 5

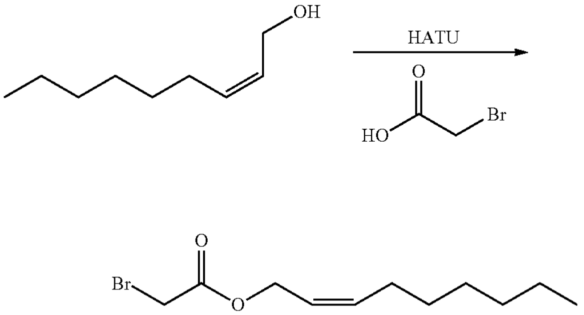

To a solution of 4 g bromo acetic acid (1 eq.) dissolved in DCM (35 mL), cooled to below 0° C. was added 4.7 ml $Et_3N$ (1.2 eq.) followed by 13.23 g HATU (1.2 eq.) and 354 mg DMAP (0.1 eq.). To this reaction solution 2.88 g (Z)-non-2-en-1-ol (0.7 eq.) in 20 mL of DCM was added and stirred at room temperature overnight.

Reaction was monitored by TLC (10% EtOAc/hexane; Rf: 0.7).

Reaction mass was diluted with saturated $NaHCO_3$ solution (80 ml), organic layer was separated, aqueous layer was washed with DCM (40 ml), dried over sodium sulphate and concentrated under reduced pressure. The residual mass was purified by silica gel (60-120) column chromatography (1.5% EtOAc/hexane). Quantity produced, 4 g; yield, 52%.

ATX-0063: Step 6

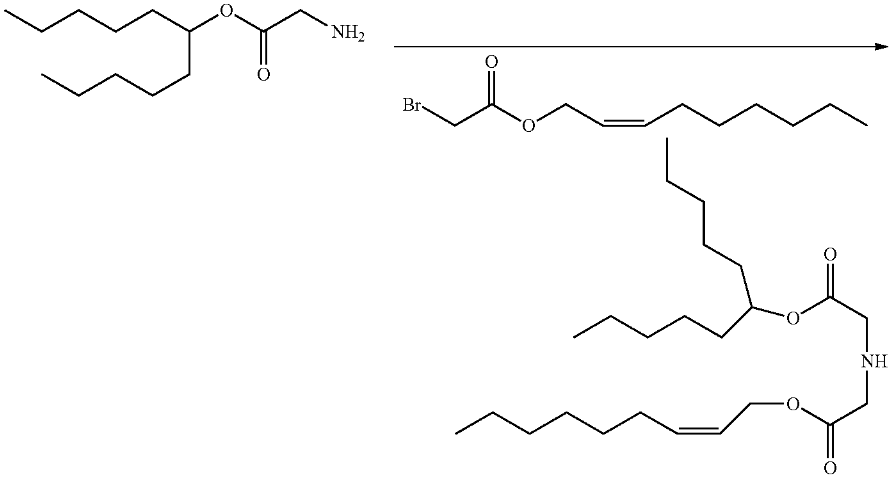

1.2 g undecan-6-yl glycinate (Int 3, 1 eq.) was dissolved in 25 ml THF, added 0.9 ml TEA (1.3 eq.) and 1.37 g (Z)-non-2-en-1-yl 2-bromoacetate (Int 4, 1 eq.), and stirred at room temperature overnight.

Progress of the reaction was monitored by TLC (10% EtOAc/hexane; Rf: 0.5). Reaction mixture was diluted with water (30 ml) and extracted with EtOAc (20 ml×2), combined organic layer was dried over sodium sulphate and concentrated under reduced pressure.

The residual mass was purified by column (silica gel; 100-200) chromatography (3% EtOAc/hexane). Quantity produce, 800 mg; yield, 37%; confirmed by Mass.

ATX-0063: Step 7

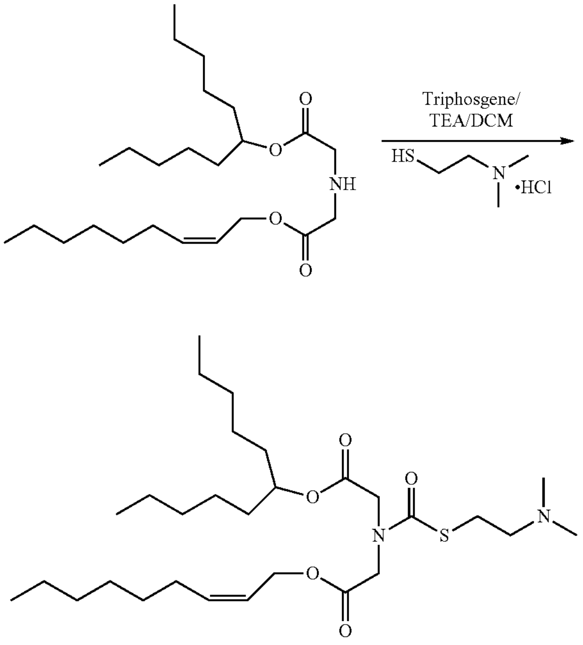

To a solution of 800 mg (Z)-non-2-en-1-yl (2-oxo-2-(undecan-6-yloxy)ethyl)glycinate (1 eq.) dissolved in DCM, cooled to below 5° C. was added 0.4 ml $Et_3N$ (3 eq.), followed by 209 mg triphosgene (0.5 eq.) portion-wise for 10 minutes.

Progress of the reaction mixture monitored by TLC, reaction was completed for 1 hour, reaction mass was concentrated under reduced pressure.

To a solution of 423 mg N, N-dimethyl ethanethiol hydrochloride (3 eq.) in dry THF and DMF (10 ml and 5 ml, respectively), stirred at 0° C. under nitrogen atmosphere was added 144 mg sodium hydride (6 eq.). After 10 minutes, to this reaction mass was added the above solution, by dissolving in THF. The resulting solution was stirred at room temperature for 1 hour.

Completion of the reaction was observed by TLC (70% EtOAc/hexane; Rf: 0.4), after 1 hour. Reaction mass was quenched with saturated $NH_4Cl$ solution (25 ml), water (20 ml) and EtOAc (20 ml) was added. Aqueous layer was washed with EtOAc (2×20 ml), and the combined organic layer was washed with brine solution (20 ml). Organic layer was dried over $Na_2SO_4$ and concentrated under reduced pressure.

Crude was subjected to column chromatography using silica gel (100-200) with 20% EtOAc/hexane, and then with neutral alumina with 5% EtOAc/hexane, to get pure compound. Quantity produced, 510 mg; yield, 48%; confirmed by $^1$H-NMR, HPLC and Mass.

ATX-0063/RL-42A: $^1$H-NMR (PPM, 400 MHz, $CDCl_3$): δ=5.67 (m, 1), 5.52 (m, 1), 4.92 (m, 1), 4.70 (m, 2), 4.15-4.27 (4), 3.06 (m, 2), 2.53 (m, 2), 2.27 (s, 6), 2.09 (m, 2), 1.47-1.57 (4), 1.20-1.41 (20), 0.82-0.92 (9).

Example 14: Synthesis of ATX-0064

Figure 13:
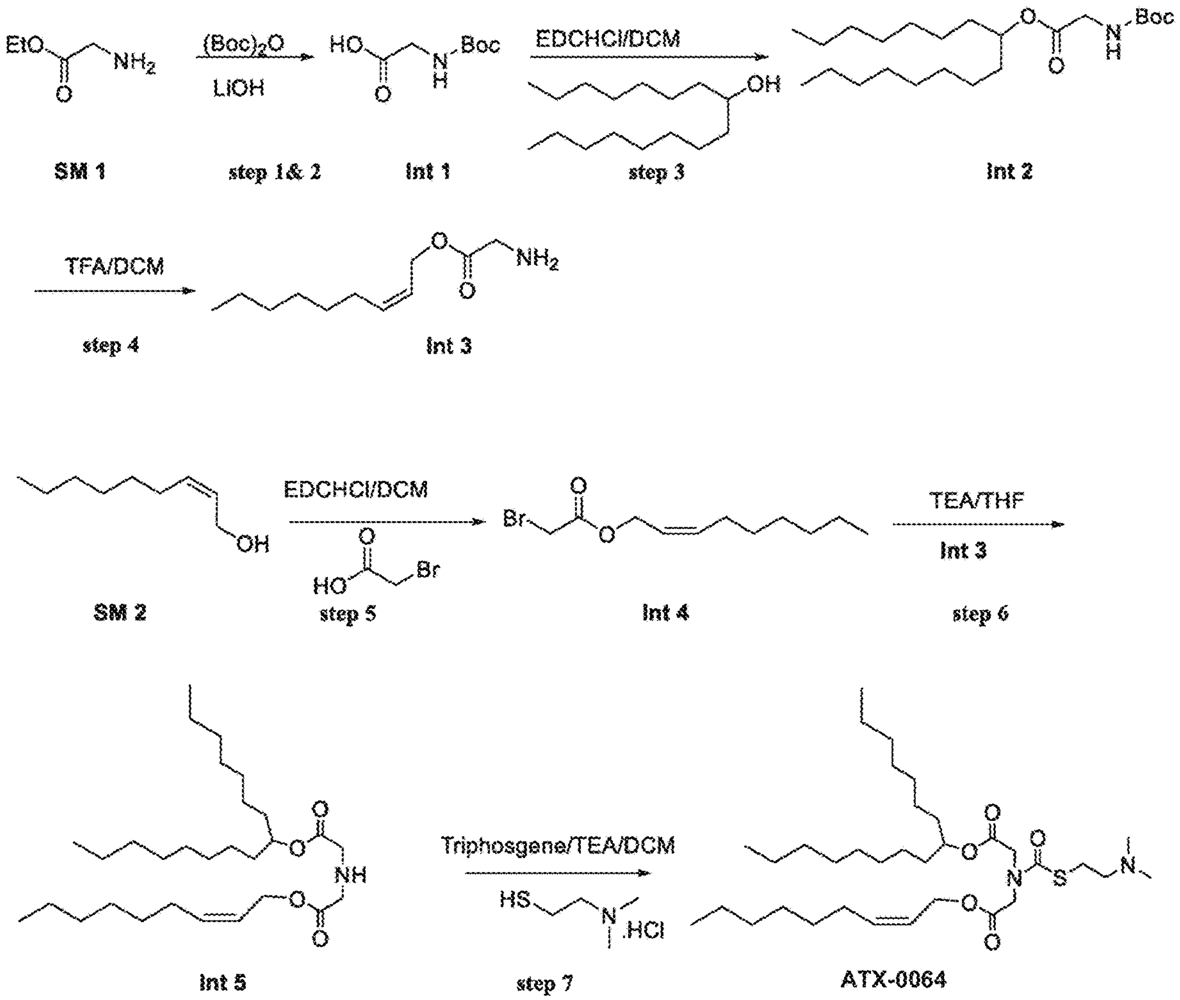
FIG. 13 shows the synthetic pathway of ATX-0064 from SM 1 and SM 2, which are the same as in FIG. 1. Ints 1-5 and reactions are described in Example 14.

FIG. 13 shows the synthetic pathway of ATX-0064 that is described further as follows.

ATX-0064: Step 1

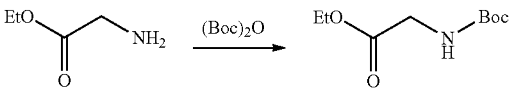

ethyl glycinate 12 g ethyl glycinate (1 eq.) was dissolved in THF (100 ml) and cooled to below 0° C. To this resulting solution, 24.2 ml triethylamine (1.5 eq.) and 38.11 g Boc anhydride (1.5 eq.) through an additional funnel were added sequentially.

Progress of the reaction was monitored by TLC using 50% EtOAc/hexane; Rf: 0.4.

Reaction mass was quenched with water and EtOAc (100 m) was added, after 16 hour. Organic layer was separated, aqueous layer was washed with EtOAc (2×40 ml) and combined organic layers were dried over sodium sulphate and concentrated under reduced pressure.

Crude product was subjected to 60-120 silica gel (25% EtOAc/hexane). Quantity produced, 20.8; yield, 88%.

ATX-0064: Step 2

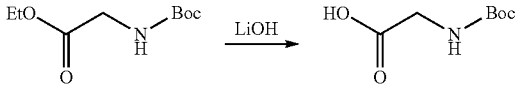

To a solution of 18.9 g N-Boc glycine ester (1 eq.) dissolved in THF (130 ml) was added aqueous solution of 5.85 g LiOH (1.5 eq.) and the resulting solution was stirred at room temperature for 4 hours.

The reaction was monitored by TLC (60% EtOAc/hexane; Rf: 0.3), starting material was absent from the reaction product.

Reaction mass was concentrated and crude mass was quenched with 5% HCl (pH 3) and then extracted with EtOAc (4×80 ml), dried over sodium sulphate and concentrated under reduced pressure to get the compound. Quantity produced, 15 g; yield, 92%; confirmed by Mass.

ATX-0064: Step 3

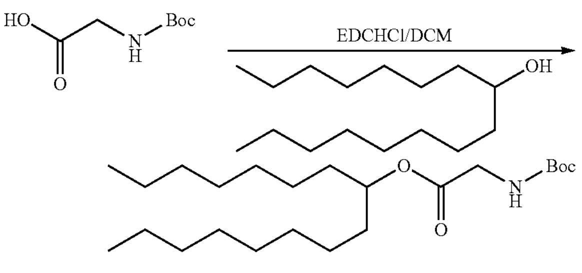

To a solution of 5 g N-Boc-glycine ester (Int 1, 1 eq.), dissolved in DCM (50 mL), cooled to below 0° C. was added 4.5 ml $Et_3N$ (1.2 eq.) and 6.4 g EDC·HCl (1.2 eq.). To this reaction solution 4.84 g hexadecan-10-ol (0.7 eq.) in 15 ml of DCM was added and stirred at room temperature overnight.

Starting material observed to be absent by TLC (15% EtOAc/hexane; Rf: 0.6). Reaction mass was diluted with saturated $NaHCO_3$ solution, organic layer was separated, aqueous layer was washed with DCM (2×30 ml) and dried over sodium sulphate and concentrated under reduced pressure.

Proceeded to next step with crude (5.5 g; mixture of product and alcohol) after column filtration.

ATX-0064: Step 4

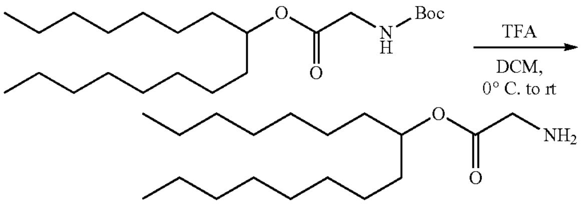

3.85 g crude heptadecan-9-yl (tert-butoxycarbonyl)glycinate (Int 2, 1 eq.) was dissolved in 30 ml DCM and cooled 0° C., added 7.4 ml TFA (10 eq.), and stirred at room temperature for 1 hour.

Completion of reaction was checked in 2 hours by TLC (10% MeOH/DCM; Rf: 0.5).

Reaction mass was concentrated under reduced pressure, residual mass was washed with saturated sodium bicarbonate solution (30 ml) and extracted with EtOAc (3×30 ml), organic layer dried over sodium sulphate and concentrated under reduced pressure to afford Int 3.

Crude product was subjected to column chromatography (silica, 60-120) using 1-3% MeOH/$CHCl_3$ and 2 ml of $Et_3N$. Quantity produced, 2.2 g; confirmed by $^1H$-NMR and Mass.

ATX-0064: Step 5

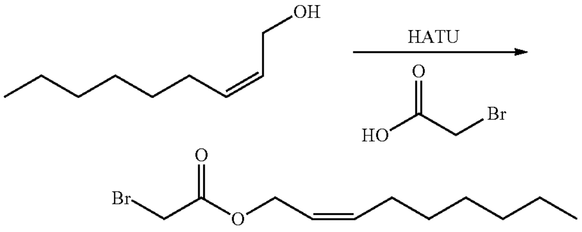

To a solution of 4 g bromo acetic acid (1 eq.) dissolved in DCM (35 mL), cooled to below 0° C. was added 4.7 ml $Et_3N$ (1.2 eq.) followed by 13.23 g HATU (1.2 eq.) and 354 mg DMAP (0.1 eq.). To this reaction solution 2.88 g (Z)-non-2-en-1-ol (0.7 eq.) in 20 ml of DCM was added and stirred at room temperature overnight.

Reaction was monitored by TLC (10% EtOAc/hexane; Rf: 0.7).

Reaction mass was diluted with saturated $NaHCO_3$ solution (80 ml), organic layer was separated, aqueous layer was washed with DCM (40 ml), dried over sodium sulphate and concentrated under reduced pressure.

The residual mass was purified by silica gel (60-120) column chromatography (1.5% EtOAc/hexane). Quantity produced, 4 g; yield, 52%.

ATX-0064: Step 6

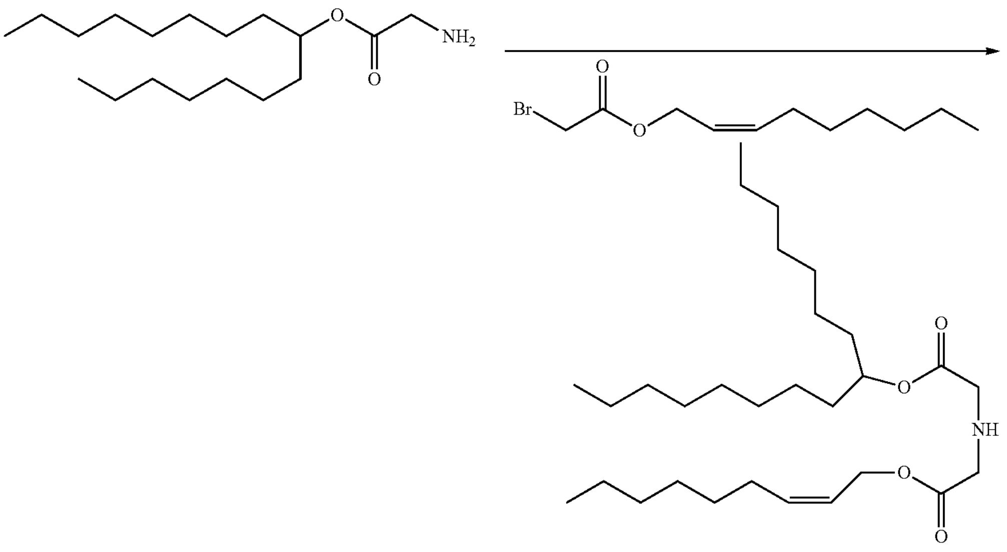

2.1 g hexadecan-8-yl glycinate (Int 3, 1 eq.) was dissolved in 50 ml THF, added 1.2 ml TEA (1.3 eq.) and 2.39 g (Z)-non-2-en-1-yl 2-bromoacetate (Int 4, 1.3 eq.), and stirred at room temperature overnight.

Progress of the reaction was monitored by TLC (10% EtOAc/hexane; Rf. 0.5). Reaction mixture was diluted with water (30 ml) and extracted with EtOAc (2×30 ml), combined organic layer was dried over sodium sulphate and concentrated under reduced pressure.

The residual mass was purified by column (silica gel; 100-200) chromatography (3% EtOAc/hexane). Quantity produced, 2.2 g; yield, 65%; confirmed by Mass.

ATX-0064: Step 7

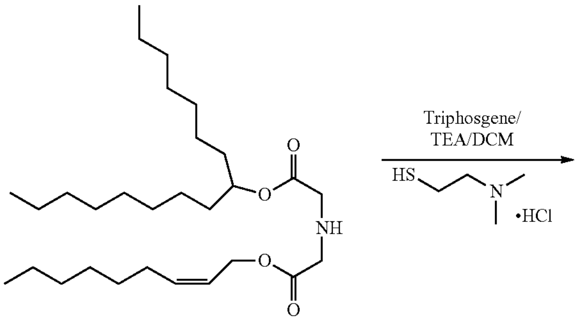

-continued

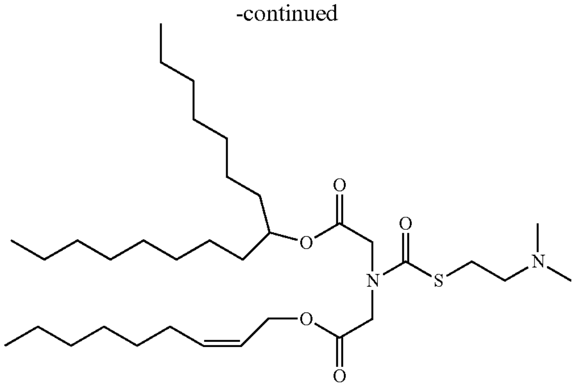

To a solution of 2.2 g heptadecan-9-yl (Z)-(2-(non-2-en-1-yloxy)-2-oxoethyl)glycinate) (1 eq.) dissolved in 15 ml DCM, cooled to below 5° C. was added 1.6 ml $Et_3N$ (3 eq.), followed by 678 mg triphosgene (0.5 eq.) portion-wise for 10 minutes.

Progress of the reaction mixture monitored by TLC, reaction was completed for 1 hour, reaction mass was concentrated under reduced pressure.

To a solution of 3.94 g N, N-dimethyl ethanethiol hydrochloride (7 eq.) in dry THF and DMF (35 ml and 15 ml, respectively), stirred at 0° C. under nitrogen atmosphere was added 672 mg sodium hydride (7 eq.). After 10 minutes, to this reaction mass was added the above solution, by dissolving in THF. The resulting solution was stirred at room temperature for 1 hour.

Completion of the reaction was observed by TLC (70% EtOAc/hexane; Rf: 0.4), after 1 hour. Reaction mass was quenched with saturated $NH_4Cl$ solution (25 ml), water (20 ml) and EtOAc (20 ml) was added. Aqueous layer was washed with EtOAc (20 ml×2), and the combined organic layer was washed with brine solution (20 ml). Organic layer was dried over $Na_2SO_4$ and concentrated under reduced pressure.

Crude was subjected to column chromatography using silica gel (100-200) with 25% EtOAc/hexane, and then with neutral alumina with 15-20% EtOAc/hexane, to get pure compound. Quantity produced, 1.0 mg; yield, 40%; confirmed by $^1$H-NMR, HPLC and Mass.

ATX-0064/RL-42C: $^1$H-NMR (PPM, 400 MHz, $CDCl_3$): δ=5.67 (m, 1), 5.50 (m, 1), 4.92 (m, 1), 4.70 (t, J=7.0, 2), 3.06 (m, 2), 2.53 (m, 2), 2.27 (s, 6), 1.47-1.57 (4), 1.17-1.40 (30), 0.82-0.93 (9).

Example 15: Synthesis of ATX-0081

Figure 14:
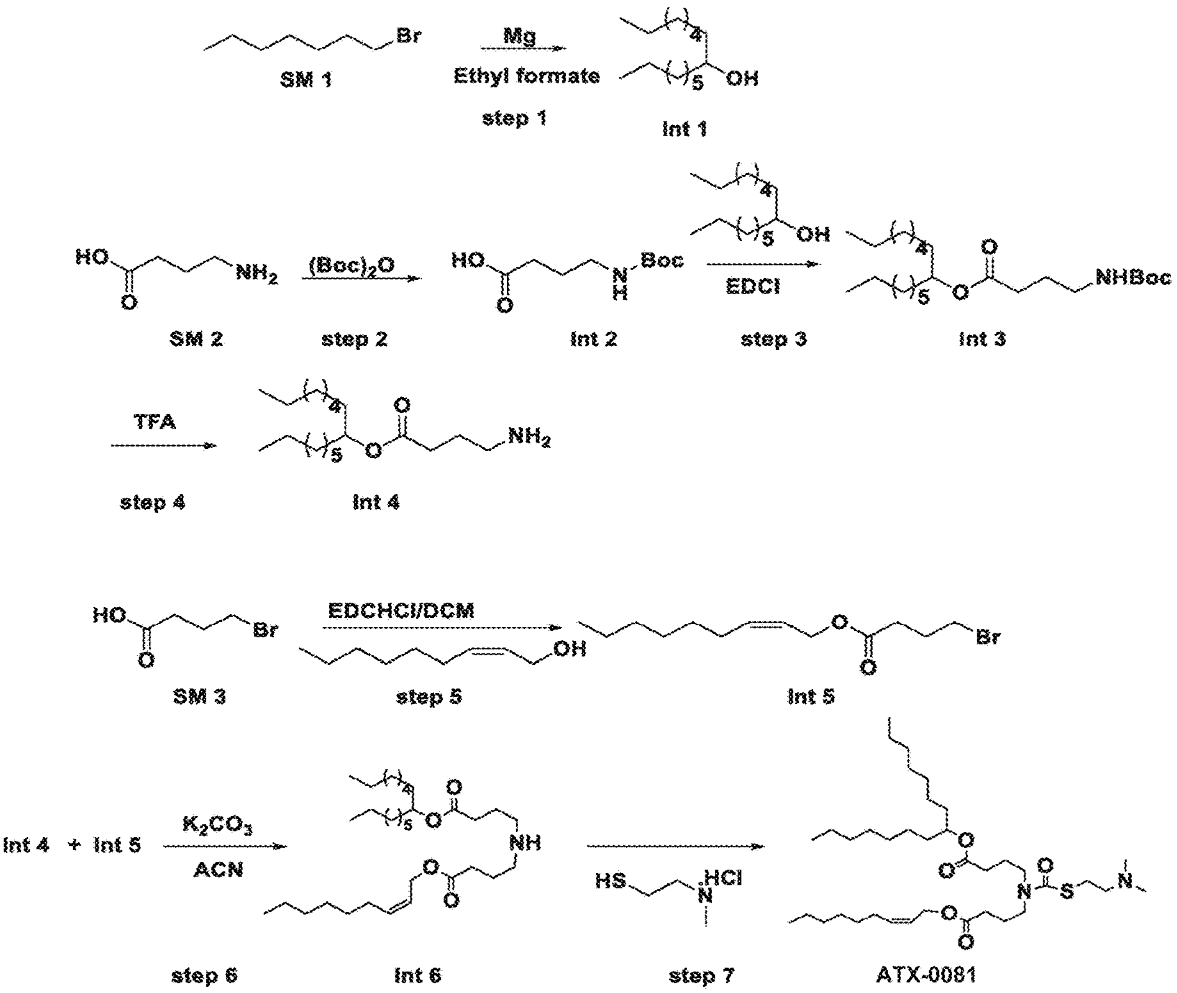
FIG. 14 shows the synthetic pathway of ATX-0081. Ints 1-6 and reactions are described in Example 15.

FIG. 14 shows the synthetic pathway of ATX-0081 that is described further as follows.

ATX-0081: Step 1

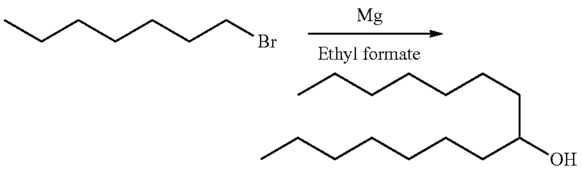

To a solution of heptyl magnesium bromide in 370 mL dry THF (in situ generated) (1.5 eq.), cooled to −15° C. under nitrogen atmosphere, was added ethylformate dissolved in 80 mL of THF (0.5 eq.) dropwise via addition funnel over 20 min, and the resulting reaction mixture was warmed to room temperature and stirred overnight.

Progress of the reaction was monitored by TLC (10% EtOAc in Hexane; Rf: 0.5).

Reaction mass was quenched with saturated $NH_4Cl$ solution (500 mL). The organic layer was separated and the aqueous layer was washed with EtOAc (3×100 mL). Combined organic layer was dried over anhydrous $Na_2SO_4$ and concentrated under reduced pressure.

Crude compound was subjected to column chromatography on silica gel (60-120 mesh) using 20% EtOAc/Hex. Quantity produced, 169.0 g; yield 60%.

ATX-0081: Step 2

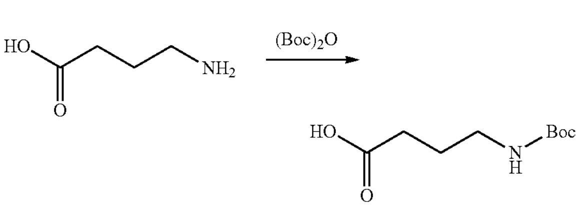

To a solution of 100 g 4-aminobutanoic acid (1 eq.) in THF, was added 1N. aq. NaOH solution (1.065 lit) (1.1 eq.) in an ice bath, followed by 1.3 eq. Boc anhydride, sequentially using addition funnel over a period of 15 min. The resulting solution was allowed to warm to RT and stirred for 4 hours.

Progress of the reaction was monitored by TLC (10% $MeOH/CHCl_3$; Rf: 0.5).

Reaction mass was quenched with 5% HCl (1 Lit) and then EtOAc (300 mL) was added. The organic layer was separated and the aqueous layer was washed with EtOAc (3×200 mL). The combined organic layers were concentrated under reduced pressure to get gummy liquid.

Crude compound was subjected to column chromatography on silica gel (60-120 mesh) using 80-100% EtOAc/Hex. Quantity produced, 161.0 g; yield, 82%.

ATX-0081: Step 3

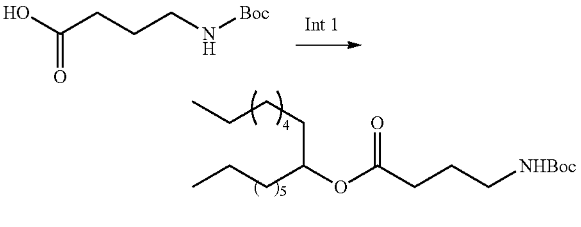

To a solution of 3×17.8 g 4-((tert-butoxycarbonyl) amino) butanoic acid in DCM (350 mL) (1 eq.), cooled in an ice bath was added 2×25.1 g EDC·HCl (1.5 eq), $Et_3N$ (2.0 eq.), and 3×1.0 g DMAP (0.1 eq) sequentially under nitrogen atmosphere with 10 min interval. To this resulting solution 3×20.0 g alcohol (1.0 eq.) was added (in 150 mL of DCM) dropwise via additional funnel, at the same temperature, and the resulting reaction mass was allowed to warm to RT and stirred for 24 hours under nitrogen atmosphere.

Progress of the reaction was monitored by TLC (10% EtOAc in Hex; Rf: 0.5).

The reaction mass was quenched with water (450 mL) and the organic layer was separated. Aqueous layer was washed with DCM (3×100 mL). The combined organic layers were concentrated under reduced pressure. The resulting crude was stirred with saturated $NaHCO_3$ solution (300 mL), for 5 min, and the aqueous phase was extracted with EtOAc (3×150 mL). The organic layer was separated, dried over anhydrous $Na_2SO_4$ and concentrated under reduced pressure, and proceeded to next step with crude. Quantity produced, 69.0 g (crude; required compound and alcohol);

ATX-0081: Step 4

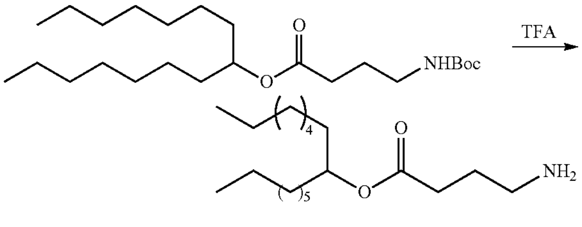

To a solution of 69.0 g pentadecan-8-yl 4-((tert-butoxycarbonyl) amino) butanoate (1 eq.) dissolved in DCM, was added TFA (10 eq.) in an ice bath and the resulting reaction solution was allowed to warm to RT and stirred for 3 hours under nitrogen atmosphere.

Progress of the reaction was monitored by TLC (10% MeOH in $CHCl_3$; Rf: 0.3). Reaction mass was concentrated under reduced pressure. The resulting crude was washed with saturated $NaHCO_3$ solution (450 mL) and then extracted with EtOAc (3×150 mL). Combined organic layer was dried over anhydrous $Na_2SO_4$ and concentrated under reduced pressure.

Crude compound was subjected to column chromatography using (60-120 mesh silica gel; 4% $MeOH/CHCl_3$ and 1 mL of triethylamine), and alcohol was recovered. Quantity produced, 47.0 g; yield, 57% for two steps ATX-0081: Step 5

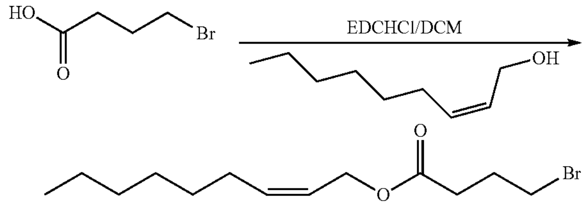

To a solution of 50.0 g 4-bromo butyric acid in DCM (450 mL) (1.0 eq.), taken in a 2 L RB flask, cooled to below 0° C. was added 86.0 g EDC·HCl (1.5 eq.), 83.3 mL $Et_3N$ (2.0 eq.), and 3.6 g DMAP (0.1 eq.) sequentially under nitrogen atmosphere with 10 min interval. To this resulting solution 42.5 g alcohol (1.0 eq.) was added (by dissolving in 200 mL of DCM) using additional funnel and resulting solution was warmed to RT and stirred for 24 h under nitrogen atmosphere.

Progress of the reaction was monitored by TLC (10% EtOAc in Hex; Rf: 0.7).

The reaction mass was quenched with water (250 mL) and the organic layer was separated. The aqueous layer was washed with DCM (2×150 mL). The combined organic layers were concentrated under reduced pressure. The resulting crude was washed with saturated $NaHCO_3$ solution (150 mL) and then extracted with EtOAc (2×150 mL). The organic layer was separated and concentrated under reduced pressure.

Crude compound was subjected to column chromatography on silica gel (60-120 mesh silica gel) using 5% EtOAc/Hex. Quantity produced, 55.0 g; yield, 63%

ATX-0081: Step 6

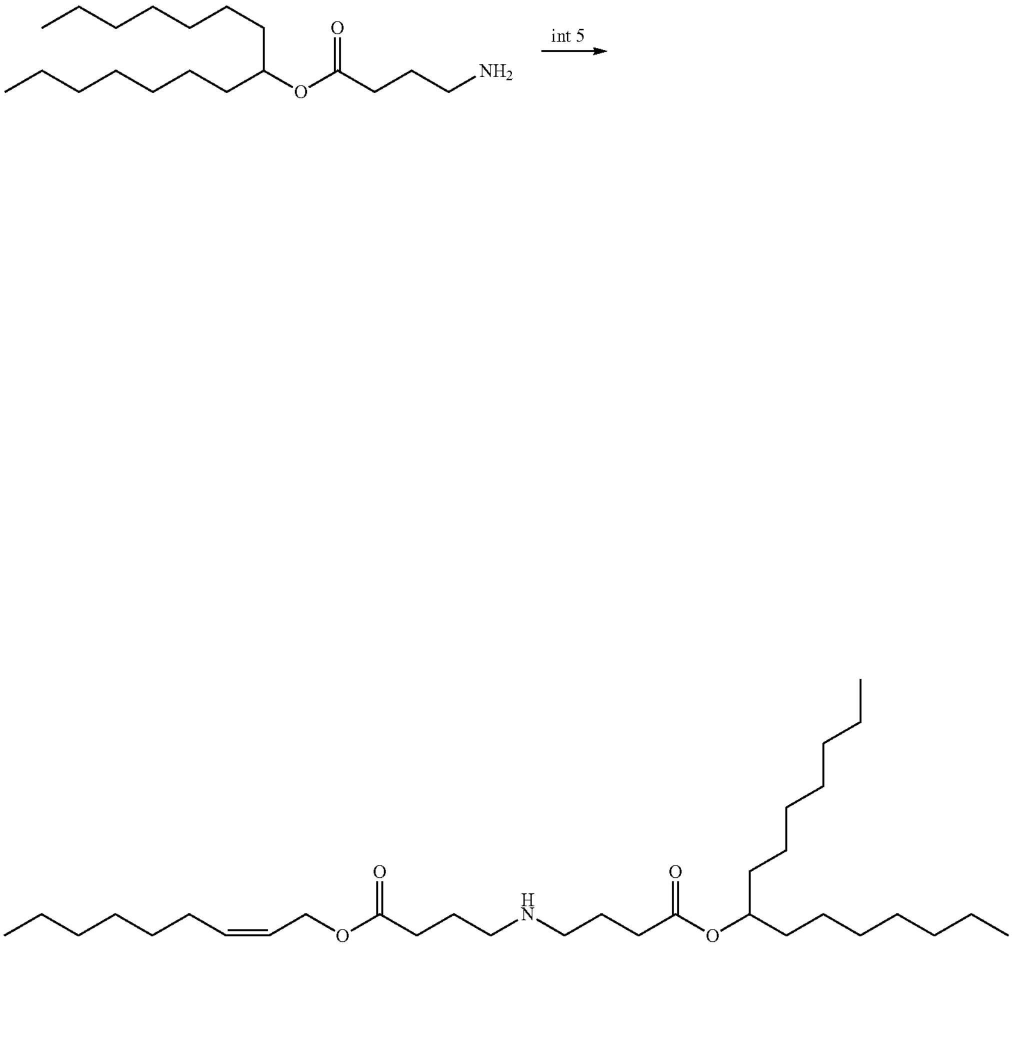

To a solution of 2×20.0 g pentadecan-8-yl 4-aminobutanoate (1 eq.), 2×18.5 g (Z)-non-2-en-1-yl 4-bromobutanoate (1 eq.) in 180 ml of ACN, 2×17.6 g potassium carbonate (2 eq.) was added and the resulting mixture was refluxed at 70° C. for 5 h under nitrogen atmosphere.

Progress of the reaction was monitored by TLC (10% MeOH/$CHCl_3$; Rf: 0.4). Reaction mass was filtered, washed with ACN (2×20 mL), and the filtrate concentrated under reduced pressure.

Crude compound was subjected to column chromatography (100-200 mesh silica gel) using 30% EtOAc/Hex. SMs (Amine) was recovered. Quantity produced, 24.0 g; yield, 36%.

ATX-0081: Step 7

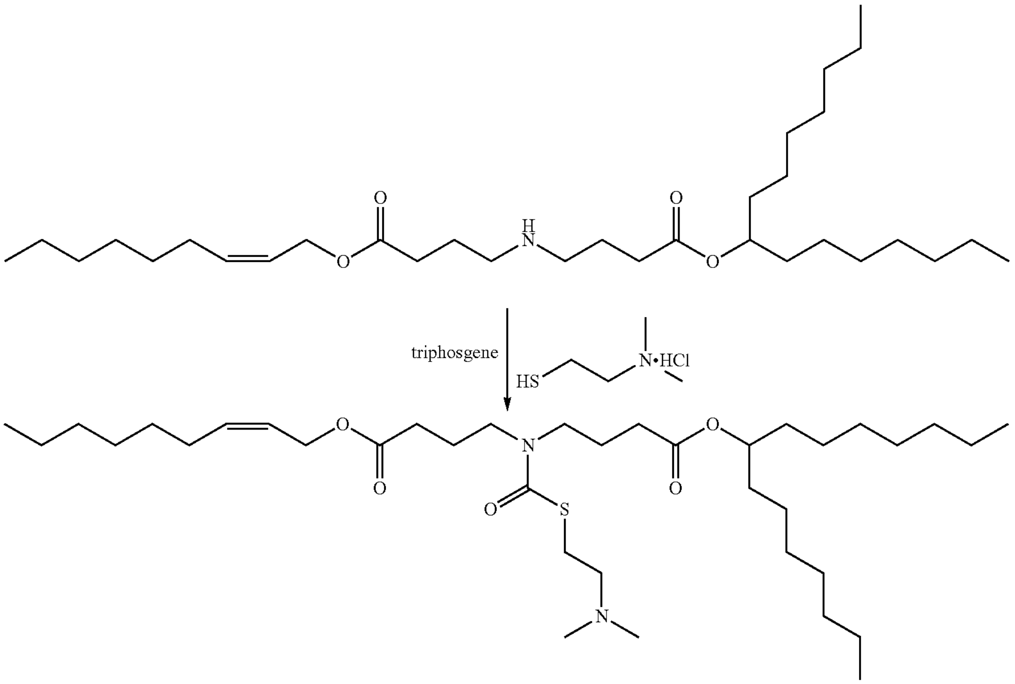

To a solution of 24.0 g (Z)-non-2-en-1-yl 4-((4-oxo-4-(pentadecan-8-yloxy)butyl)amino)butanoate (1 eq.), dissolved in 250 mL dry DCM, 13.5 g triphosgene (1 eq.) was added and the reaction mixture was cooled to 0° C., and 18.4 mL pyridine (5 eq.) was added dropwise over a period of 10 min. The reaction mixture was stirred at 20° C. for 4 h.

DCM was removed under reduced pressure and the mixture was taken up with pyridine (300 mL). After cooled to 0° C., 32.3 g dimethylaminoethanethiol hydrochloride salt (5 eq.) was added portion wise and the resulting solution was stirred for overnight at 20° C. under nitrogen atmosphere.

The reaction mass, after TLC checking, was concentrated under reduced pressure to dryness. To this residue was added 250 mL EA and 200 mL (10%) citric acid. The organic phase was separated and then organic layer was washed again with 10% citric acid (100 mL) for one time and again 10% brine (200 mL) for one time. The resulting organic layer was dried over anhydrous $Na_2SO_4$ and concentrated under reduced pressure to get crude product.

A first purification was done on silica gel (100-200 mesh; 500 g). In gradient elution, compound was eluted at 70% EtOAc/Hex. After concentration compound (22.0 g) appeared in reddish color. A second purification was done using neutral alumina (400 g) with HPLC grade solvents. Compound was eluted at 15% EtOAc/Hex and pure fractions were concentrated under reduced pressure to get 19.0 g of yellow liquid.

The product (14.0 g) was diluted with 200 mL EtOH (HPLC grade), then added charcoal (50% W/W) 7.0 g to the solution and continued stirring at room temperature for overnight. The resulting solution was filtered through a pad of celite and the filtrate was concentrated. Finally, compound dissolved in 120 mL of 50% EtOAc/Hex and filtered (to remove alumina and silica particles) through cotton plug and concentrated under reduced pressure. Final compound (11.5 g) appeared in light yellow color.

A second batch (5.0 g) was diluted with 80 mL EtOH (HPLC grade), then added charcoal (50% W/W) 2.5 g to the solution and continued stirring at room temperature for overnight. The resulting solution was filtered through a pad of celite and the filtrate was concentrated. Finally, compound dissolved in 60 mL of 50% EtOAc/Hex and filtered (to remove alumina and silica particles) through cotton plug and concentrated under reduced pressure. Final compound (4.0 g) appeared in reddish yellow color. Quantity produced, 15.5 g; yield, 510%.

ATX-0081: $^1H$-NMR (PPM, 400 MHz, $CDCl_3$): δ=5.62 (m, 1), 5.51 (m, 1), 4.86 (m, 1), 4.62 (d, J=6.0 Hz, 2), 3.37 (brs, 4), 3.01 (t, J=7.1 Hz, 2), 2.51 (t, J=7.1 Hz, 2), 2.31 (m, 4), 2.26 (s, 6), 2.07 (m, 2), 1.89 (brs, 4), 1.42-1.57 (4), 1.16-1.40 (28), 0.82-0.91 (9)

Example 15A: Synthesis of ATX-0085

Figure 15:
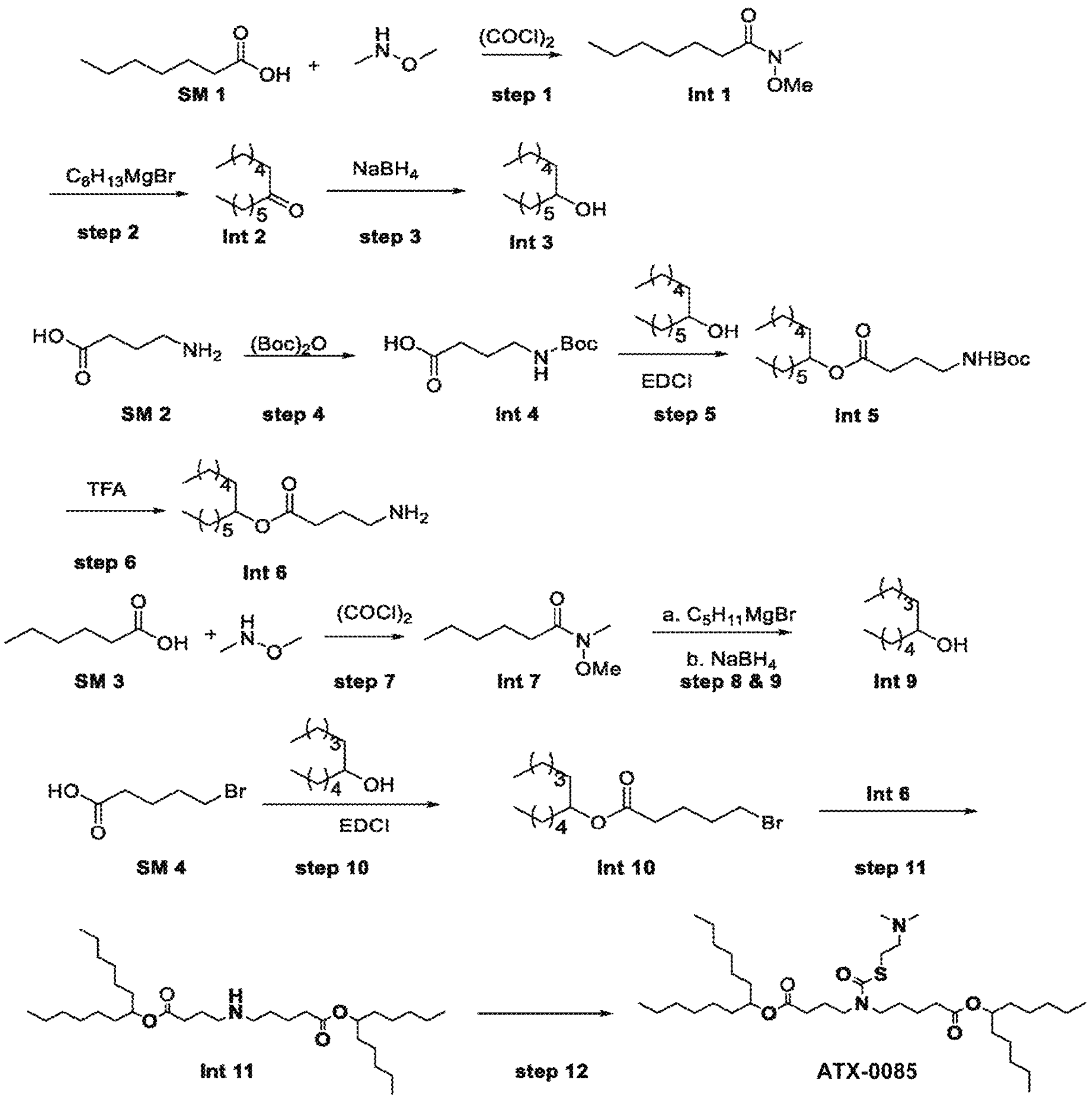
FIG. 15 shows the synthetic pathway of ATX-0085 from SM 1, SM 2 and SM3, which are the same as in FIG. 2. Ints 1-11 and reactions are described in Example 15A.

FIG. 15 shows the synthetic pathway of ATX-0085 that is described further as follows.

ATX-0085: Step 1

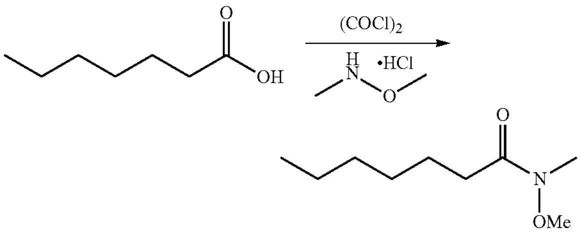

In a 500 mL lit single neck RB flask, 30.0 g heptanoic acid (1 eq.) dissolved in of DCM (200 mL) was taken and then added 26.7 mL oxalyl chloride (1.5 eq.) slowly at 0° C., stirring under nitrogen atmosphere and then added 1 ml DMF (catalytic). The resulting reaction mixture was stirred at RT for 2 h.

In a separate 1 lit two neck RB flask, to 40.5 g N,O-dimethylhydroxylamine hydrochloride (2 eq.) in DCM (250 mL), was added 86.6 mL trimethylamine (3 eq.) using additional funnel, stirred at 0° C. To this resulting solution, the above acid chloride, after concentration under reduced pressure, was added under nitrogen atmosphere by dissolving in DCM (100 mL), dropwise using addition funnel for 20 min. The resulting reaction solution was stirred at RT for 3 h under nitrogen atmosphere.

Progress of the reaction was monitored by TLC (20% EtOAc/Hexane; Rf: 0.5). Reaction mass was diluted with water (250 mL).

The organic layer was separated and the aqueous layer was washed with DCM (3×100 mL). The combined organic layers were concentrated under reduced pressure.

Crude compound was subjected to column chromatography using (60-120 silica gel) using 10% EtOAc/Hex. Quantity produced, 38.0 g; yield, 84%.

ATX-0085: Step 2

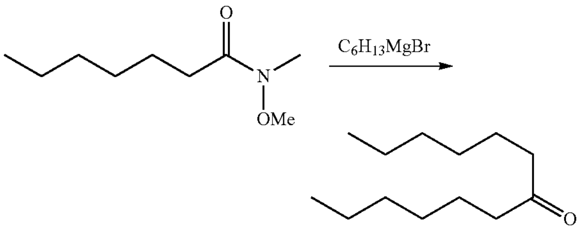

To a solution of 62.3 g hexylmagnesium bromide (1.5 eq.) in ether, taken in a 1 L two neck RB flask, stirred at 0° C. under nitrogen atmosphere, was added 38.0 g N-methoxy-N-methylheptanamide (1 eq.) dissolved in 250 mL of ether and the resulting reaction mixture was stirred at RT for 4 h.

Progress of the reaction was monitored by TLC (10% EtOAc in Hexane; Rf: 0.7).

Reaction mass was quenched with saturated $NH_4Cl$ solution (200 mL). The organic layer was separated and the aqueous layer was washed with ether (2×100 mL). The combined organic layers were dried over anhydrous $Na_2SO_4$ and concentrated under reduced pressure.

Crude compound was subjected to column chromatography using (60-120 mesh silica gel) using 2% EtOAc/Hex. Quantity produced, 30.8 g; yield, 71%.

ATX-0085: Step 3

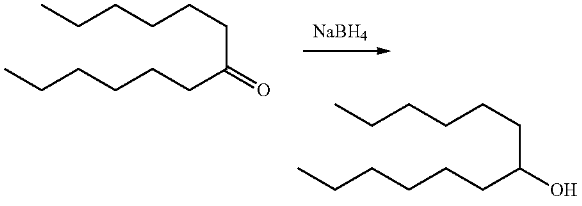

To a solution of 30.0 g tridecan-7-one (1 eq.), dissolved in 200 MeOH/THF (10:1, v:v), 8.5 g sodium borohydride (1.5 eq.) was added at 0° C. and the resulting solution was stirred at RT for 2 h.

Progress of the reaction was monitored by TLC (10% EtOAc/Hexane; Rf: 0.5).

Reaction mass was quenched with saturated $NH_4Cl$ solution (80 mL). Solvent was removed under reduced pressure and the resulting crude was partitioned between EtOAc (200 mL) and water (100 mL). Organic layer was separated and the aqueous layer was washed with EtOAc (2×70 mL). Combined organic layers were concentrated under reduced pressure to get white solid. Quantity produced, 27.2 g; yield, 90%.

ATX-0085: Step 4

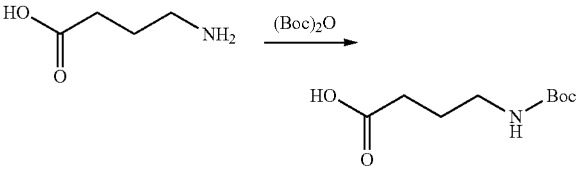

To a solution of 50.0 g 4-aminobutanoic acid (1 eq.) dissolved in THF/aq. NaOH solution (490 mL) was added at 0° C., followed by 140 mL Boc anhydride (1.3 eq.), sequentially using additional funnel, over a period of 15 min. The resulting solution was stirred at RT for 4 hours.

Progress of the reaction was monitored by TLC (10% MeOH in $CHCl_3$; Rf: 0.5).

Reaction mass was quenched with 5% HCl (250 mL) and then EtOAc (300 mL) was added. Organic layer was separated and the aqueous layer was washed with EtOAc (3×150 mL). Combined organic layer was concentrated under reduced pressure to get gummy liquid. Quantity produced, 80.0 g; yield, 81%. Confirmed by 1H NMR. Note: Since Boc-Acid (Int 4) is having some impurity (20-30%) observed in the 1H NMR, it was reflected in step 5 & step 6 yields ATX-0085: Step 5

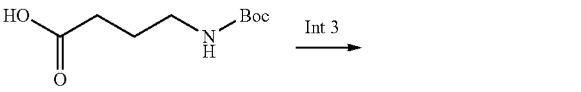

-continued

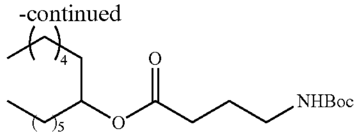

To a solution of 10.0 g 4-((tert-butoxycarbonyl) amino) butanoic acid (1 eq.) dissolved in DCM (200 mL), cooled to below 0° C. was added 12.2 g EDC·HCl (1.3 eq.), 20.4 mL $Et_3N$ (3 eq.), and 601 mg DMAP (0.1 eq.) sequentially under nitrogen atmosphere with 10 min interval. To this resulting solution alcohol was added at the same temperature, by dissolving in DCM (150 mL), using additional funnel, and stirred at RT for 24 hours under nitrogen atmosphere.

Progress of the reaction was monitored by TLC (10% EtOAc in Hex; Rf: 0.5).

Reaction mass was quenched with water (150 mL) and then organic layer was separated. Aqueous layer was washed with DCM (2×75 mL). Combined organic layer was concentrated under reduced pressure. The resulting crude was washed with saturated $NaHCO_3$ solution (100 mL) and then EtOAc (200 mL) was added. Organic layer was separated and concentrated under reduced pressure, and proceeded to next step with crude. Quantity produced, 8.0 g (crude; required compound and alcohol).

ATX-0085: Step 6

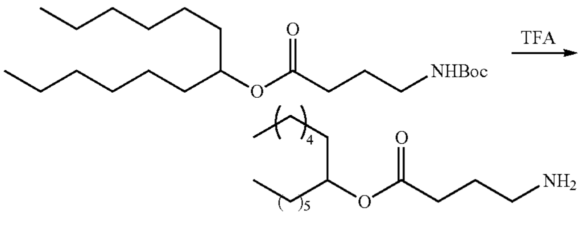

To a solution of 8.0 g tridecan-7-yl 4-((tert-butoxycarbonyl)amino)butanoate (1 eq.) dissolved in 65 mL DCM, was added 15.7 mL TFA (10 eq.) at 0° C. and stirred at RT for 3 hours under nitrogen atmosphere.

Progress of the reaction was monitored by TLC (10% MeOH in $CHCl_3$; Rf: 0.3).

Reaction mass was concentrated under reduced pressure. The resulting crude was washed with saturated $NaHCO_3$ solution (100 mL) and then extracted with EtOAc (3×100 mL). Organic layer was separated and concentrated under reduced pressure. Crude compound was subjected to column chromatography using (60-120 mesh silicagel; 4% MeOH/$CHCl_3$ and 1 mL of triethylamine), and alcohol was recovered. Quantity produced, 3.5 g; yield, 25% for two steps. Confirmed by Mass.

ATX-0085: Step 7

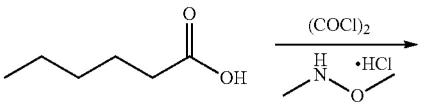

-continued

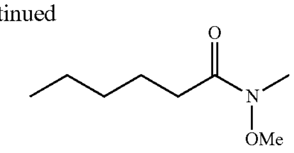

To 20.0 g hexanoic acid (1 eq.) dissolved in of DCM (150 mL) was added slowly 22.1 mL oxalyl chloride (1.5 eq.) at 0° C., stirring under nitrogen atmosphere and then added 1 mL DMF (catalytic). The resulting reaction mixture was stirred at RT for 2 hours.

In a separate flask, to 33.5 g N,O-dimethylhydroxylamine hydrochloride (2 eq.) in DCM (250 mL), was added 71.7 mL trimethylamine (3 eq.) using an addition funnel, stirred at 0° C. To this resulting solution, the above acid chloride, after concentration under reduced pressure, was added under nitrogen atmosphere by dissolving in DCM (100 mL), dropwise using addition funnel for 20 min. The resulting reaction solution was stirred at RT for 3 hours under nitrogen atmosphere.

Progress of the reaction was monitored by TLC (20% EtOAc/Hexane; Rf: 0.5). Reaction mass was diluted with water (250 mL). Organic layer was separated and the aqueous layer was washed with DCM (2×100 mL). Combined organic layer was concentrated under reduced pressure.

Crude compound was subjected to column chromatography using (60-120 silica gel) using 10% EtOAc/Hex. Quantity produced, 21.0 g; yield, 76%.

ATX-0085: Step 8

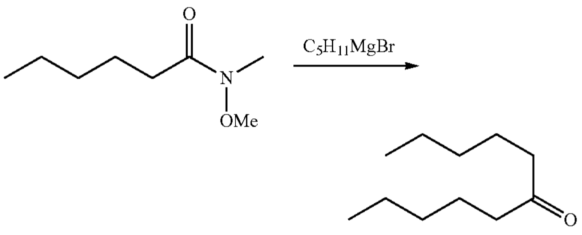

To a solution of 33.0 g pentylmagnesium bromide (1.5 eq.) in ether at 0° C. under nitrogen atmosphere, was added 20.0 g N-methoxy-N-methylhexanamide (1 eq.) dissolved in 220 mL of ether and the resulting reaction mixture was stirred at RT for 4 hours.

Progress of the reaction was monitored by TLC (10% EtOAc in Hexane; Rf: 0.6).

Reaction mass was quenched with saturated $NH_4Cl$ solution (200 mL). Organic layer was separated and the aqueous layer was washed with ether (2×100 mL). Combined organic layers were dried over anhydrous $Na_2SO_4$ and concentrated under reduced pressure. Crude compound was subjected to column chromatography using (60-120 mesh silica gel) using 2% EtOAc/Hex. Quantity produced, 15.4 g; yield, 72%.

ATX-0085: Step 9

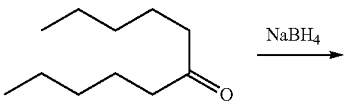

-continued

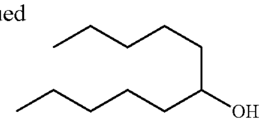

To a solution 15.0 g of undecan-6-one (1 eq.) dissolved in 100 mL MeOH/15 mL THF, 4.9 g sodium borohydride (1.5 eq.) was added at 0° C. and the resulting solution was stirred at RT for 2 h.

Progress of the reaction was monitored by TLC (10% EtOAc/Hexane; Rf: 0.5).

Reaction mass was quenched with saturated $NH_4Cl$ solution (80 mL). Solvent was removed under reduced pressure and the resulting crude was partitioned between EtOAc (200 mL) and water (100 mL). Organic layer was separated and the aqueous layer was washed with EtOAc (2×70 mL). Combined organic layers were concentrated under reduced pressure to get white solid. Quantity produced, 13.9 g; white solid; yield, 92%

ATX-0085: Step 10

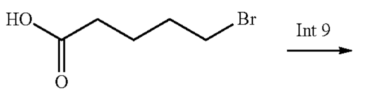

-continued

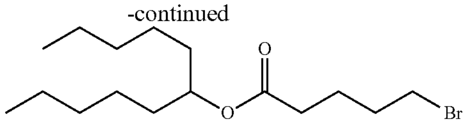

To a solution of 10.0 g 5-bromopentanoic acid (1 eq.), dissolved in DCM (300 mL), cooled to below 0° C. was added 13.7 g EDC·HCl (1.3 eq.), 23.0 mL $Et_3N$ (3 eq.), and 674 mg DMAP sequentially under nitrogen atmosphere with 10 min interval. To this resulting solution 9.5 g alcohol (1 eq.) was added at the same temperature, by dissolving in DCM (150 mL), using additional funnel, and stirred at RT for 24 hours under nitrogen atmosphere.

Progress of the reaction was monitored by TLC (10% EtOAc in Hex; Rf: 0.7).

Reaction mass was quenched with water (200 mL) and then organic layer was separated. Aqueous layer was washed with DCM (2×100 mL). Combined organic layer was concentrated under reduced pressure. The resulting crude was washed with saturated $NaHCO_3$ solution (100 mL) and then EtOAc (3×100 mL) was added. The organic layers were separated and concentrated under reduced pressure and proceeded to next step with crude. Crude compound was subjected to column chromatography using (60-120 mesh silica gel) using 5% EtOAc/Hex, and SM (alcohol) was recovered. Quantity produce, 11.6 g; yield, 62%.

ATX-0085: Step 11

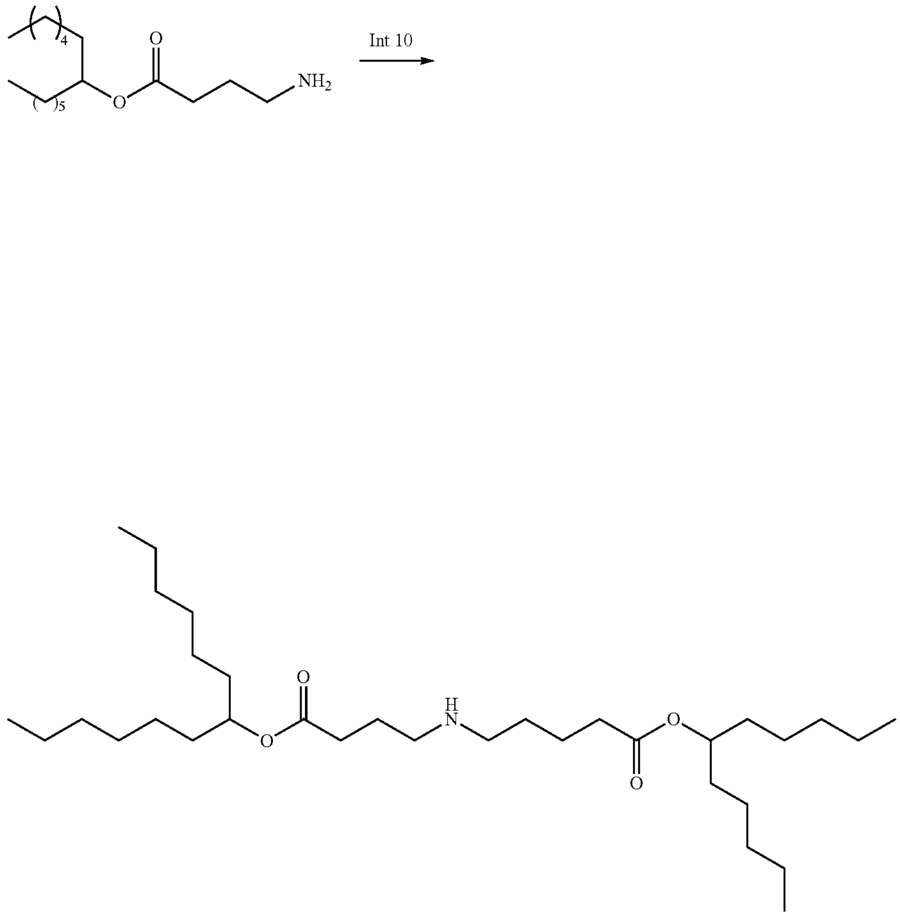

To a solution of 4.5 g tridecan-7-yl 4-aminobutanoate (1 eq.), 5.2 g undecan-6-yl 5-bromopentanoate (1 eq.) in ACN, 3.0 g potassium carbonate (1.4 eq.) was added and the resulting mixture was refluxed at 90° C. for 4 hours under nitrogen atmosphere.

Progress of the reaction was monitored by TLC (10% MeOH/$CHCl_3$; Rf: 0.45).

Reaction mass was filtered, washed with ACN (2×20 mL), and the filtrate concentrated under reduced pressure. Crude compound was subjected to column chromatography (100-200 mesh silica gel) using 20% EtOAc/Hex. SMs (Amine and Bromo compound) were recovered. Quantity produced, 2.2 grams of the pure compound; yield, 25%; and 1.1 gram of the mixture. Confirmed by Mass.

ATX-0085: Step 12

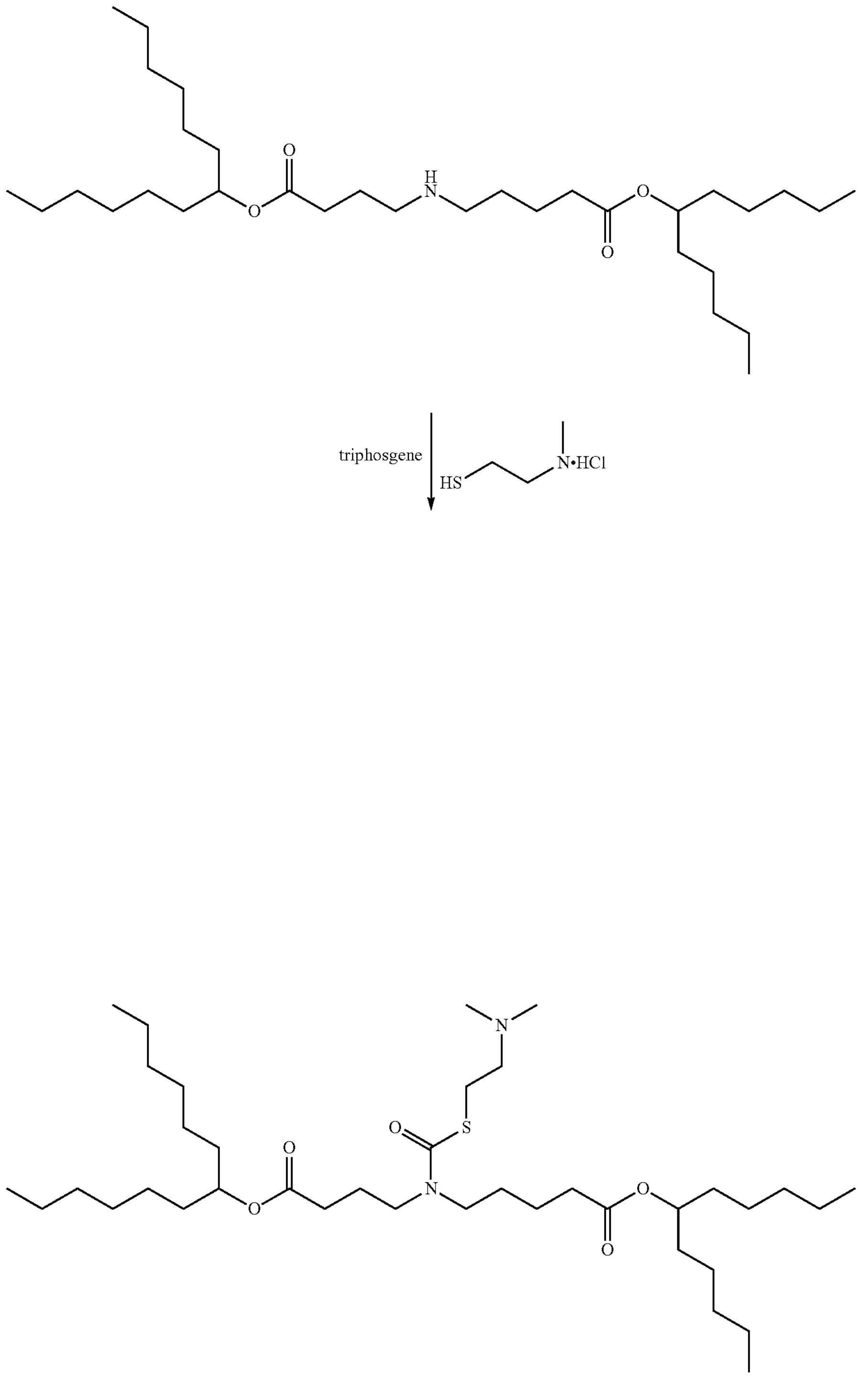

To a solution 2.2 g of undecan-6-yl 5-((4-oxo-4-(tridecan-7-yloxy)butyl)amino)pentanoate (1 eq.) dissolved in dry DCM, was added 1.6 mL trimethylamine (3 eq.) and 604 mg triphosgene (0.5 eq.) with 5 min interval at 0° C. under nitrogen atmosphere. The resulting solution was stirred at RT, under nitrogen atmosphere for 1 hr. The resulting reaction mass was concentrated under reduced pressure and kept under nitrogen atmosphere.

To a suspension of 684 mg sodium hydride (7 eq.) in dry THF (30 mL), in a flask stirred at 0° C. under nitrogen atmosphere, was added 2.0 g 2-(dimethylamino)ethane-1-thiol hydrochloride (3.5 eq.) and kept stirring for 5 min under nitrogen atmosphere. To this resulting solution the above carbamoyl chloride, dissolved in THF (50 mL), was added via syringe slowly for about 10 min. The resulting solution was stirred at RT overnight under nitrogen atmosphere.

Progress of the reaction was monitored by TLC (10% $MeOH/CHCl_3$; Rf: 0.5; PMA charring).

Reaction mass was quenched with sat $NH_4Cl$ (40 mL) and then EtOAc (100 mL) was added. Organic layer was separated and the aqueous layer was washed with EtOAc (2×40 mL). The combined organic layers were concentrated and the resulting crude was subjected to column chromatography. A first purification was done using silica gel (100-200 mesh). 5.0 g of crude compound was adsorbed on 9.0 g of silica gel and poured onto 70 g of silica gel taken in the column. Compound was eluted at 50% EtOAc/Hex. A second purification was done using neutral alumina with HPLC grade solvents. 2.0 g of crude compound was adsorbed on 7.0 g of neutral alumina and the resulting was poured onto 40 g of neutral alumina taken in the column. Compound was eluted at 25% EtOAc/Hex. Quantity: 1.4 g; yield: 51%. Confirmed by $^1H$ NMR.

ATX-0085 $^1H$-NMR (PPM, 400 MHz, $CDCl_3$): δ=4.87 (m, 2), 3.36 (brs, 4), 3.02 (t, J=7.1 Hz, 2), 2.52 (t, J=7.1 Hz, 2), 2.31 (m, 4), 2.27 (s, 6), 1.88 (brs, 2), 1.56-1.66 (4), 1.46-1.54 (8), 1.21-1.34 (30), 0.89 (m, 12).

Example 15B: Synthesis of ATX-0134

Figure 16:
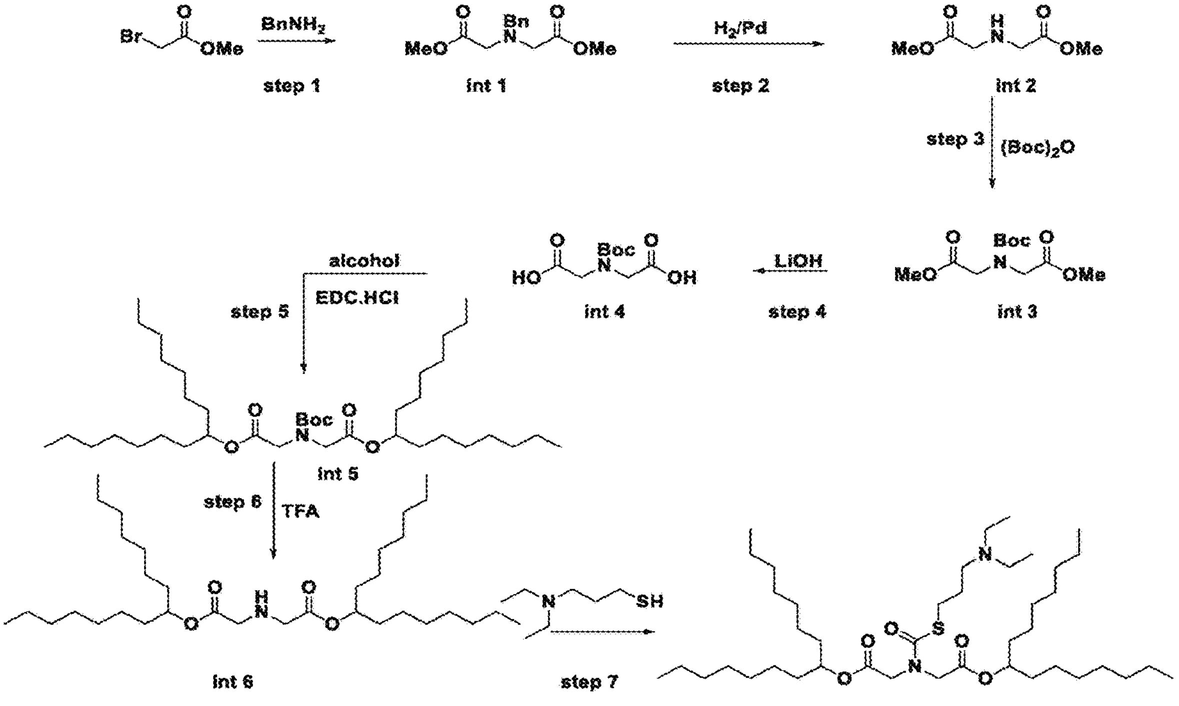
FIG. 16 shows the synthetic pathway of ATX-0134. Ints 1-6 and reactions are described in Example 15B.

FIG. 16 shows the synthetic pathway of ATX-0134 that is described further as follows.

ATX-0134: Step 1

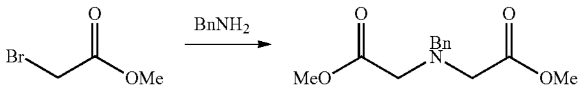 [SMILES: COC(=O)CBr ; "BnNH2" ; COC(=O)CN(CC(=O)OC)Cc1ccccc1]

In a 1 L single neck RB flask, to a stirred solution of 50.0 g methyl 2-bromoacetate (1 eq.) in 400 mL of DMF, was added 90.3 g potassium carbonate (2 eq.) followed by 17.5 g benzyl amine (0.5 eq.), at ice bath temperature under nitrogen atmosphere, and the resulting reaction mixture was allowed to warm to RT and continued stirring for 36 h.

Progress of the reaction was monitored by TLC (20% EtOAc/Hexane; Rf: 0.4; ninhydrin charring).

Reaction mass was diluted with ice water (1 L) and then EtOAc (250 mL) was added. Organic layer was separated and aqueous layer was washed with EtOAc (3×100 mL). Combined organic layer was again washed with ice water (500 mL) and the resultant organic layer was dried over anhydrous $Na_2SO_4$ and concentrated under reduced pressure.

Crude compound was subjected to column chromatography on silica gel (60-120 mesh) using 15-20% EtOAc/Hex. Quantity produced, 35.0 g; yield, 85%.

ATX-0134: Step 2

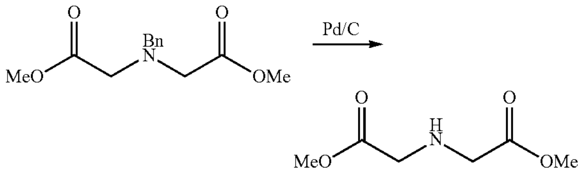

10.5 g 10% Pd/C was added to the reaction 500 mL hydrogenation flask, containing 35.0 g dimethyl 2,2'-(benzylazanediyl)diacetate in EtOAc, and the reaction mass was subjected to hydrogenation using Parr shaker (60 psi) until starting material disappeared (2 h).

Progress of the reaction was monitored by TLC (5% $MeOH/CHCl_3$; Rf: 0.5; ninhydrin charring).

Reaction mass was filtered through a pad of celite and was washed with EtOAc (2×60 mL). The combined filtrate was concentrated under reduced pressure. Quantity produced, 30.0 g (crude).

ATX-0134: Step 3

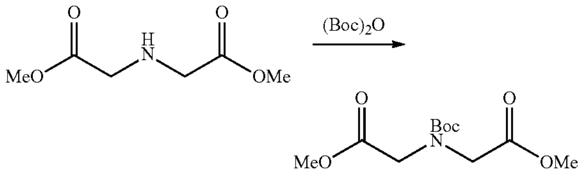

To a solution of 30.0 g dimethyl 2,2'-azanediyldiacetate (1.0 eq.) in THF, was added 38.7 mL triethylamine (1.5 eq.) followed by 55.5 mL Boc anhydride (1.3 eq.), under ice bath temperature, sequentially using an addition funnel. The resulting reaction solution was stirred at RT overnight under nitrogen atmosphere.

Progress of the reaction was monitored by TLC (40% EtOAc/Hexane; Rf: 0.5).

Reaction mass was diluted with water (250 mL) and then EtOAc (150 mL) was added. Organic layer was separated and aqueous layer was washed with EtOAc (2×100 mL). Combined organic layer was dried over anhydrous $Na_2SO_4$ and concentrated under reduced pressure. Crude compound was subjected to column chromatography on silica gel (60-120 mesh) using 15%-20% EtOAc/Hex. Quantity produced, 35.0 g; yield, 96%.

ATX-0134: Step 4

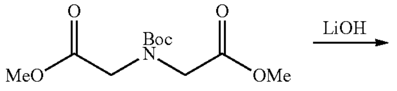

-continued

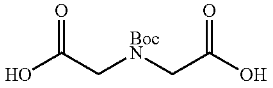

To a solution of 35.0 g dimethyl 2,2'-((tert-butoxycarbonyl)azanediyl)diacetate (1.0 eq.) in THF stirred under ice bath temperature, was added aq. solution of 16.8 g lithium hydroxide (75 mL of 5.3 M) (3 eq.). The resulting reaction solution was stirred at RT for 5 hours under nitrogen atmosphere.

Progress of the reaction was monitored by TLC (10% MeOH/$CHCl_3$; Rf: 0.2).

Reaction mass was quenched with 5% HCl (400 mL) and then EtOAc (200 mL) was added. Organic layer was separated and aqueous layer was washed with EtOAc (2×100 mL). Combined organic layer was dried over anhydrous $Na_2SO_4$ and concentrated under reduced pressure. Crude compound was subjected to column chromatography on silica gel (60-120 mesh) using 100% EtOAc. Quantity produced, 29.0 g; yield, 93%.

ATX-0134: Step 5

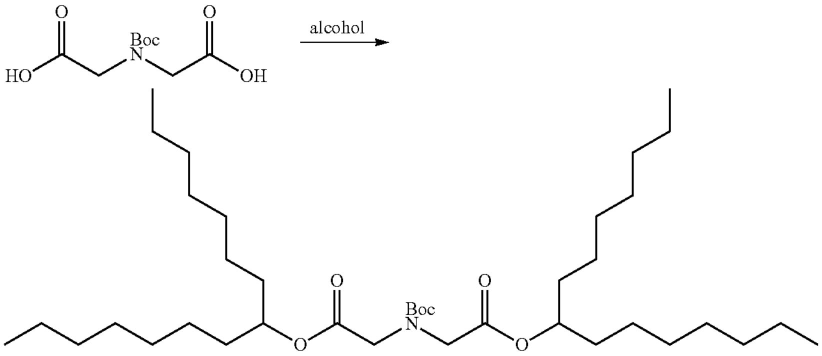

To a solution of 12.0 g 42,2'-((tert-butoxycarbonyl)azanediyl)diacetic acid (1 eq.) in 250 mL of DCM, cooled to between 0° C. to 50° C. (ice bath), was added 29.5 g EDC·HCl (3 eq.), 21.4 mL $Et_3N$ (3 eq.), and 628 mg DMAP (0.1 eq.) sequentially under nitrogen atmosphere with 10 min interval. To this resulting solution 23.5 g alcohol (in 150 mL of DCM) (2 eq.) was added at the same temperature via addition funnel and the resulting reaction mass was allowed to warm to RT and stirred for 24 hours under nitrogen atmosphere.

Progress of the reaction was monitored by TLC (10% EtOAc in Hex; Rf: 0.6; PMA charring).

Reaction mass was quenched with water (100 mL) and then organic layer was separated. Aqueous layer was washed with DCM (2×80 mL). Combined organic layer was concentrated under reduced pressure. The resulting crude was stirred with saturated $NaHCO_3$ solution (100 mL) for 5 min, to remove unreacted acid, and then EtOAc (2×80 mL) was added. Organic layer was dried over anhydrous $Na_2SO_4$ and concentrated under reduced pressure. Crude compound was subjected to column chromatography on silica gel (60-120 mesh) using 2-3% EtOAc/Hex. Quantity produced, 15.0 g; yield, 44%.

ATX-0134: Step 6

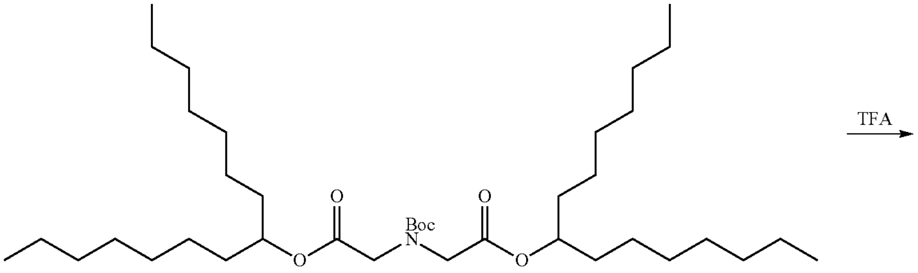

-continued

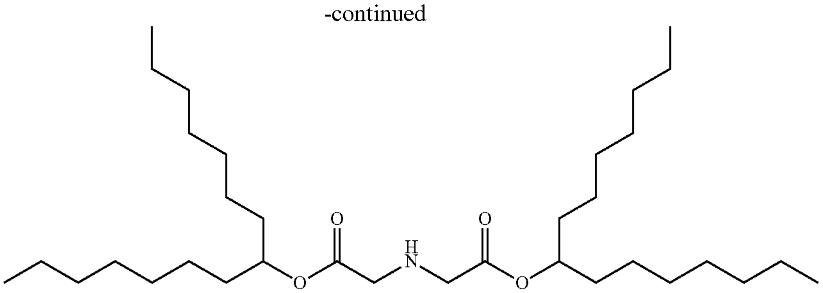

To a solution of 15.0 g di(pentadecan-8-yl) 2,2'-((tert-butoxycarbonyl)azanediyl)diacetate (1 eq.) in 120 mL of DCM, was added 17.7 mL TFA (10 eq.), between 0° C. to 50° C. (ice bath), and the reaction mass was allowed to warm to RT and stirred for 4 hours under nitrogen atmosphere.

Progress of the reaction was monitored by TLC (10% ETOAc/Hex; Rf. 0.5).

Reaction mass was concentrated under reduced pressure and the resulting crude was stirred with saturated $NaHCO_3$ solution (100 mL) for 5 min (to remove traces of TFA) and the aqueous phase was extracted with EtOAc (3×100 mL). Organic layer was separated and concentrated under reduced pressure. Crude compound was subjected to column chromatography on silica gel (60-120 mesh) and compound was eluted with 10% EtOAc/Hex. Quantity produced, 10.4 g; yield, 82%.

ATX-0134: Step 7

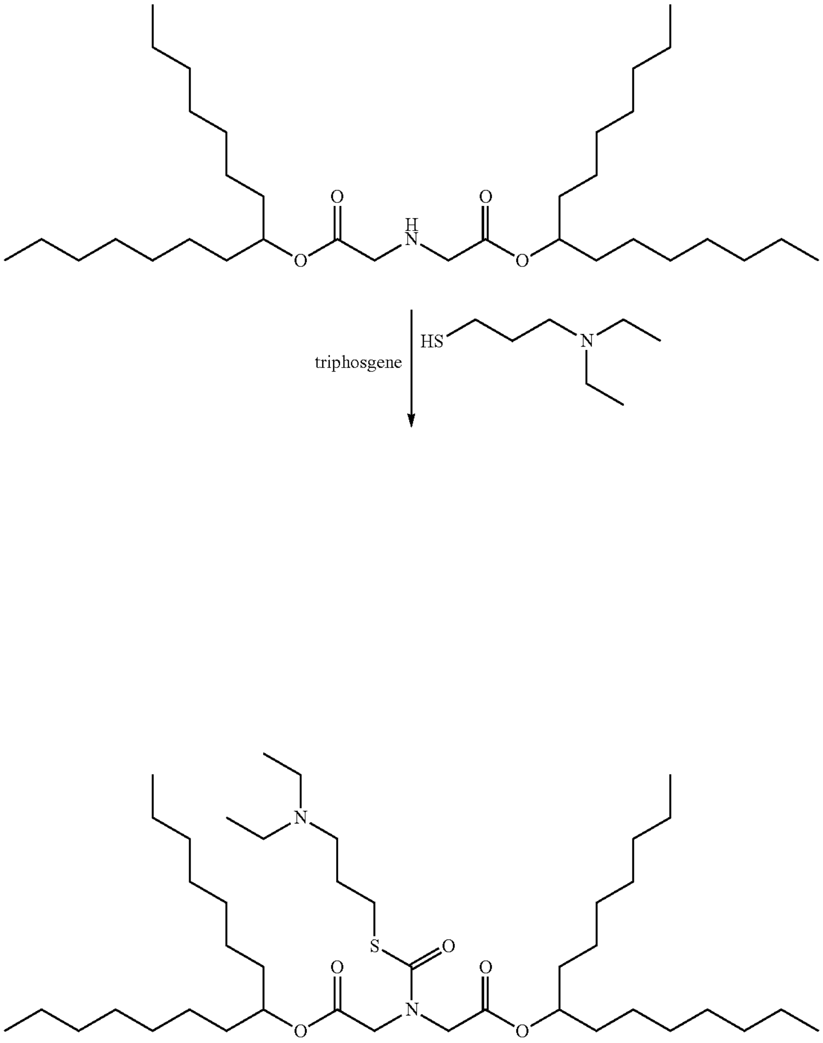

To a solution of 1.5 g di(pentadecan-8-yl) 2,2'-azanediyldiacetate (1 eq.) in 20 mL of dry DCM, was added 1.1 mL trimethylamine (3 eq.) and 401 mg triphosgene (0.5 eq.) with 5 min interval under ice bath temperature and nitrogen atmosphere. The resulting solution was then allowed to warm to RT and stirred for 1 h under nitrogen atmosphere. After completion of starting material (checked by TLC), the resulting reaction mass was concentrated under reduced pressure and kept under nitrogen atmosphere. 1.1 g 3-(diethylamino)propane-1-thiol (3 eq.), dissolved in 10 mL of THF, was added to a suspension of 129 mg sodium hydride (2 eq.) in dry THF (10 mL), cooled to between 0° C. to 50° C. under nitrogen atmosphere, and stirring was continued for 5 min. To this resulting solution the above carbamoyl chloride, dissolved in THF (30 mL), was added at the same temperature via addition funnel for about 5 min. The resulting solution was warmed to RT and continued stirring overnight under nitrogen atmosphere.

Progress of the reaction was monitored by TLC (10% $MeOH/CHCl_3$; Rf: 0.5; PMA charring).

Reaction mass was quenched with sat $NH_4Cl$ (30 mL) and then EtOAc (50 mL) was added. Organic layer was separated and the aqueous layer was washed with EtOAc (2×40 mL). Combined organic layer was concentrated and the resulting crude was subjected to column chromatography. First purification was done using neutral alumina (100 g). In gradient elution, compound was eluted at 20% EtOAc/Hex. Second purification was done using silica gel (100-200 mesh; 80 g) with HPLC grade solvents. Compound was eluted at 50% EtOAc/Hex. Quantity: 680 mg; yield: 34%.

ATX-0134 $^1$H-NMR (PPM, 400 MHz, $CDCl_3$): δ=4.91 (m, 2), 4.21 (s, 2), 4.16 (s, 2), 2.95 (t, J=7.1 Hz, 2), 2.54 (m, 6), 1.79 (m, 2), 1.46-1.52 (8), 1.17-1.36 (40), 1.03 (t, J=7.8 Hz, 6), 0.87 (t, J=7.1 Hz, 12).

Example 15: Synthesis of ATX-0044 and ATX-0091 to ATX-0133

ATX-0044, ATX-0085, ATX-0111, ATX-0132, ATX-0100, ATX-0117, ATX-0114, ATX-0115, ATX-0101, ATX-0106, ATX-0116, ATX-0122, ATX-0123, ATX-0124, ATX-0126, ATX-0129, and ATX-0133 were synthesized using the methods of the previous examples.

Example 16: pKa Values $pK_a$ of cationic lipids in LNP or micellar Formulations were measured by the procedure of Jayaraman, 2012, *Angew. Chem. Int. Ed.,* 51:8529-33, hereby incorporated by reference. Lipid micelles or LNPs are diluted to 1 mM total lipids in universal buffer with a pH range between 3 and 12 in presence of 0.06 mg/mL 6-(p-toluidino)-2-naphthalenesulfonic acid sodium salt (TNS) reagent (Sigma Aldrich), a pH sensitive fluorescence probe. The anionic TNS molecule fluoresces when associated with the surface of positively charged membranes but is not fluorescent when free in solution, allowing measurement of pKa. The TNS signal is measured on a spectral plate reader. The TNS signal is plotted as function of the pH and analyzed using a non-linear (Boltzman) to determine the $pK_a$.

Reagents used in the assay include

- Hepes free acid, CAS: 7365-45-9 (VWR, 0511-1KG or equivalent)
- MES, HPLC grade: (Sigma 105228-100G or equivalent)
- Ammonium acetate, HPLC grade: (Sigma 90335-100 mL or equivalent)
- Sodium chloride, HPLC grade (VWR EM-MX0475-1 or equivalent)
- TNS (Sigma-Aldrich T9792-250 mg or equivalent)
- Hydrochloric acid
- DMSO
- DPBS without calcium and magnesium (GE, SH30028.02 or equivalent)
- $H_2O$, HPLC grade (OmniSolv, WX0004-1 or equivalent)

To prepare a stock solution of Universal Buffer (UB) in a polystyrene sterile storage bottle, prepare 1 L using the following table.

| Component | MW (g/mol) | [Final] (mM) |
|---|---|---|
| Hepes | 238.3 | 10 |
| MES | 213.2 | 10 |
| Ammonium acetate | 77.1 | 10 |
| NaCl | 58.4 | 130 |

Reagents are sterile filtered through a 0.2 μm filter. Preparation of UB solution includes adding 5 mL of 1 M HCl to a 350 mL stock solution.

To prepare a pH ladder, centrifuge tubes (50 mL) with 20 mL UB buffer are used. (pH ~3) and differing amounts of 2 N NaOH. Stock solutions of TNS at 1 mg/mL in DMSO. 60 μL of TNS at 1 mg/mL is added to 940 μL water to reach a working solution concentration of 0.06 mg/mL. Five test samples, 1 mL of LNP sample in PBS at 1 mM total lipid, and 1 reference sample are analyzed per plate. Samples at different pH values are prepared in in wells in which 25 μL of 0.06 mg/mL TNS is added. 15 μL of test samples is added per well. The microplate is incubated for 15 minutes at room temperature in the dark. TNS template can be used to format data from the plate reader. Perform non-linear (Boltzman) regression analysis of the samples in Origin Pro 8 or equivalent software.

The results are shown in Table 1. In general, increasing lipophilicity via the ester near the ionizable head group lowers the measured pKa while making the calculated pKa more basic. Adding lipophilicity in the alcohol while shortening the length of the ester chain can have a major impact on measured pKa. For example, shortening the ester to butanoate has no impact when the lipophilicity of the alcohol is increased to a branched alkyl group (see: ATX-0057 and ATX-0058 vs ATX-0002). A major impact is seen when shortening the ester to an acetate, e.g., ATX-0061/ATX-0064 (Δ=−0.90) and ATX-0063 (Δ=−0.7) for 1-branched/1-Z-2-nonenol ester; and ATX-0062/ATX-0065 (Δ=−3.20) for acetate/bis-branched ester with a Δ c Log P+4.0 vs ATX-0002.

Without conceding to be bound by theory, the results show the importance of increased lipophilicity (measured by c Log P) combined with chain shortening in lowering the measured pKa compared to predicted, and to increasing the bioactivity of the lipid nanoparticles.

Example 17: In Vivo EPO mRNA Stability

Figure 17:
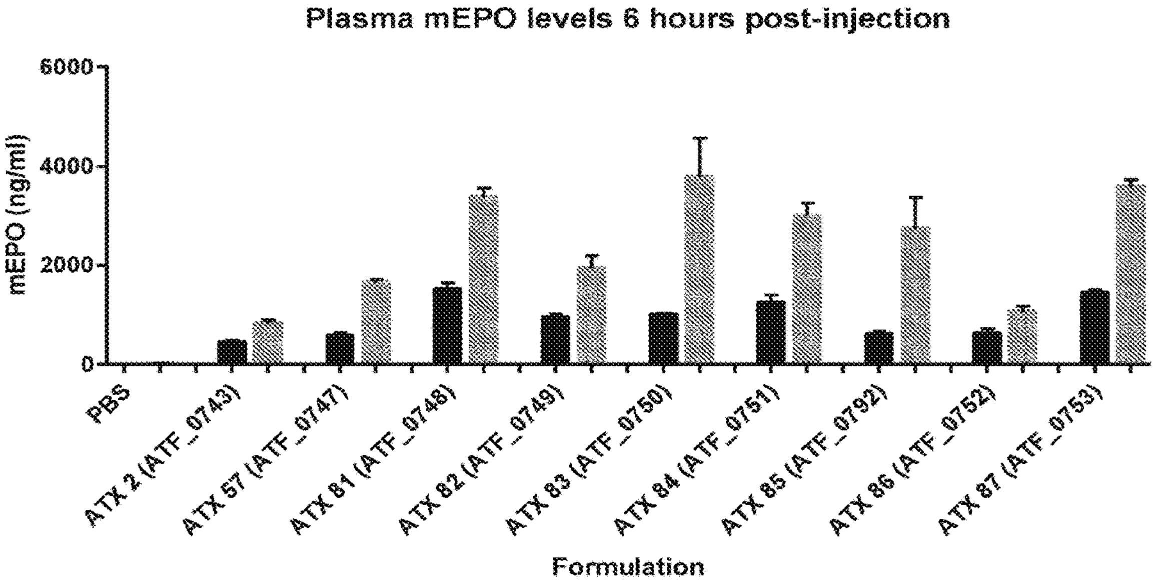
FIG. 17 shows the EPO mRNA levels (ng/ml) following injection of 0.03 mg/kg and 0.1 mg/kg mRNA in nanoparticles comprising ATX-002, ATX-0057, ATX-0081, ATX-0082, ATX-0083, ATX-0084, ATX-0085, ATX-0086, or ATX-0087 cationic lipid into mice.

Levels of mRNA in plasma were measured and compared following injection of nanoparticles comprising different cationic lipids. Female Balb/c mice (6-8 week old) were used for evaluation of plasma erythropoietin (epo) levels in vivo following injection of lipid encapsulated mouse epo mRNA. All Formulations were administered intravenously via tail vein injection at a dose of 0.03 and 0.1 mg/kg at a dosing volume of 5 ml/kg. Terminal blood collection was performed via cardiac puncture under 2% isoflurane at 6 hours after Formulation injections. Blood was collected into 0.109 M citrate buffer tube and processed by centrifugation at 5000 rpm for 10 minutes. Serum was collected and epo mRNA levels were analyzed. Results are shown at FIG. 17. Results show a substantial improvement over ATX-0002 for ATX-0057, ATX-0081, ATX-0082, ATX-0083, ATX-0084, ATX-0085, ATX-0086, and ATX-0087.

Example 18: In Vivo Mouse Factor VII Silencing and EPO Expression

Using a liver-directed in vivo screen of the liposome libraries, a series of compounds were tested that facilitate high levels of siRNA mediated gene silencing in hepatocytes, the cells comprising the liver parenchyma. Factor VII, a blood-clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). Compositions with siRNA directed to Factor VIII were Formulated with the lipid, and comparator sample phosphate-buffered saline (PBS). Female $C_{57}$BL/6 mice (6-8 week old) were used for FVII siRNA knockdown (KD) experiments.

Figure 18:
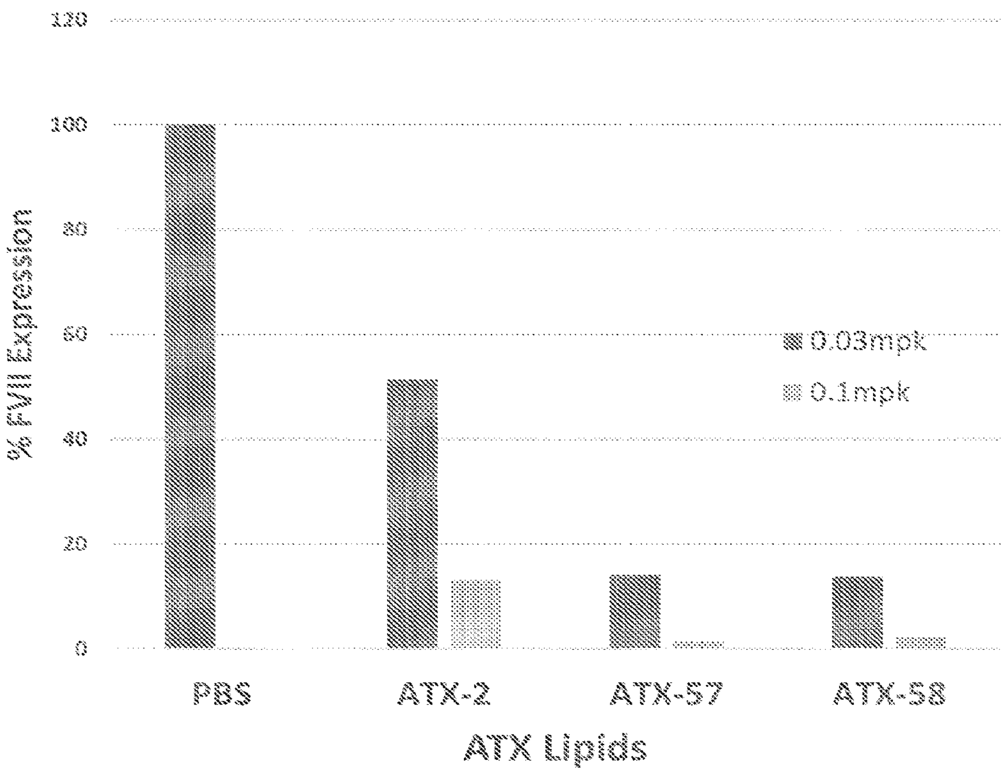
FIG. 18 shows the anti-Factor VII knockdown activity of liposomes with ATX-0057 and ATX-0058 vs. the activity of ATX-002 and control (PBS alone).

All Formulations were administered intravenously via tail vein injection at a dose of 0.03 and 0.1 mg/kg at a dosing volume of 5 mg/kg. Terminal blood collection was performed via cardiac puncture under 2% isoflurane at 48 hours after Formulation injections. Blood was collected into 0.109 M citrate buffer tube and processed by centrifugation at 1200 G for 10 min. Plasma was collected and Factor VII protein levels were analyzed by chromogenic assay (Biophen FVII, Aniara Corporation). A standard curve was constructed using samples from PBS-injected mice and relative Factor VII expression was determined by comparing treated groups to untreated PBS control. The results showed that ATX-0057 and ATX-0058 were substantially more effective than ATX-002 both at 0.03 and 0.1 mg/kg (FIG. 18).

Table 1 shows knockdown resulting from lipid nanoparticles comprising the lipids disclosed herein.

Epo expression following delivery of mRNA using lipid nanoparticles comprising the lipids described herein was measured.

Figure 19:
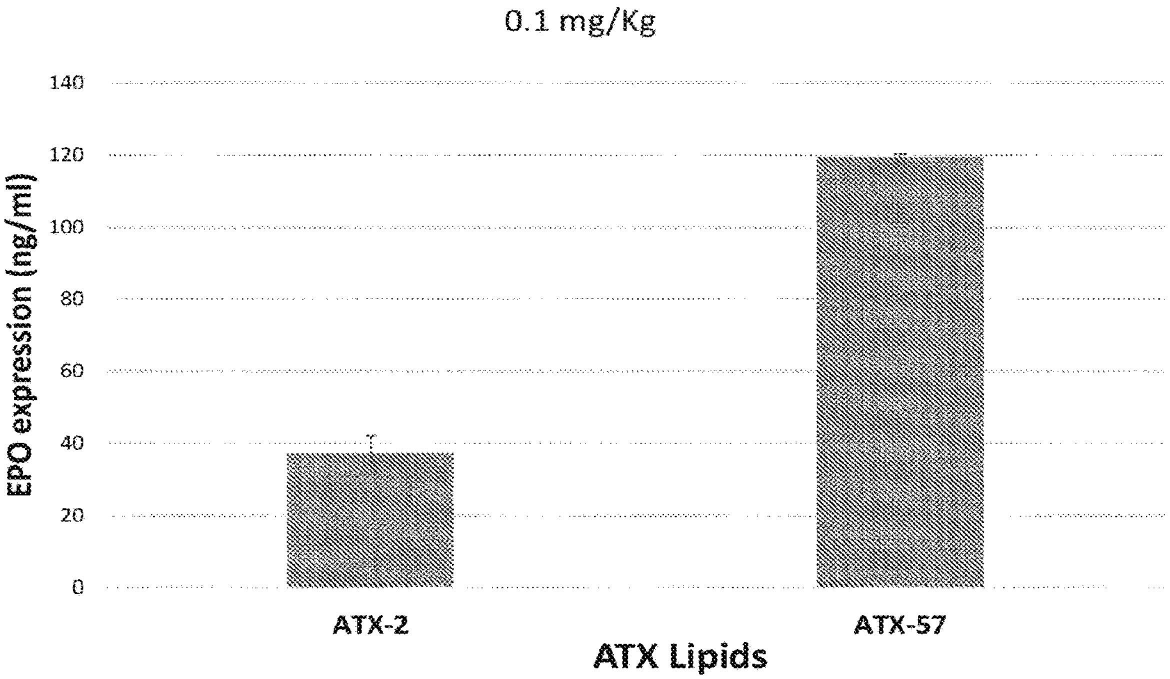
FIG. 19 shows the anti-EPO knockdown activity of liposomes with ATX-0057 vs. the activity of ATX-002.

Female Balb/c mice (6-8 weeks old) were used for evaluation of epo protein expression in vivo following delivery of lipid encapsulated mouse epo mRNA. All formulations were administered intravenously via tail vein injection at a dose of 0.03 and 0.1 mg/kg at a dosing volume of 5 mL/kg. Terminal blood collection was performed via cardiac puncture under 2% isoflurane at 6 hours after Formulation injections. Blood was collected into 0.109 M citrate buffer tube and processed by centrifugation at 5000 rpm for 10 minutes. Serum was collected and epo protein levels were analyzed by epo ELISA assay (R&D systems). A standard curve was constructed using samples from PBS-injected mice and relative Factor VII expression was determined by comparing treated groups to untreated PBS control. The results showed that epo mRNA is expressed at substantially higher amounts in ATX-0057 nanoparticles than ATX-002 at 0.1 mg/ml (FIG. 19).

What is claimed is:

1. A pharmaceutical composition comprising a lipid nanoparticle encapsulating a nucleic acid, wherein the lipid nanoparticle comprises a cationic lipid selected from the group consisting of:

ATX-0085

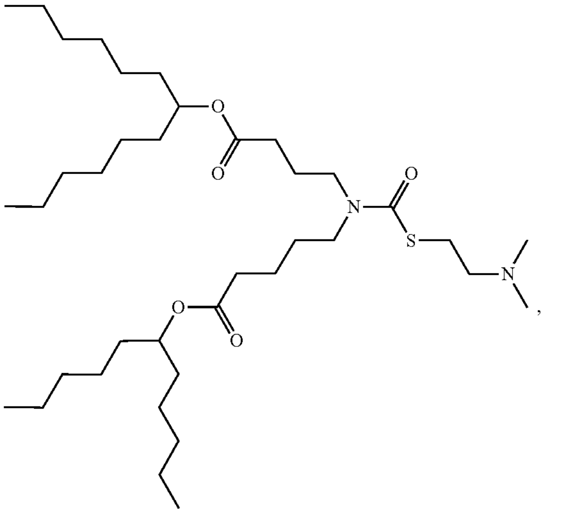

ATX-0121

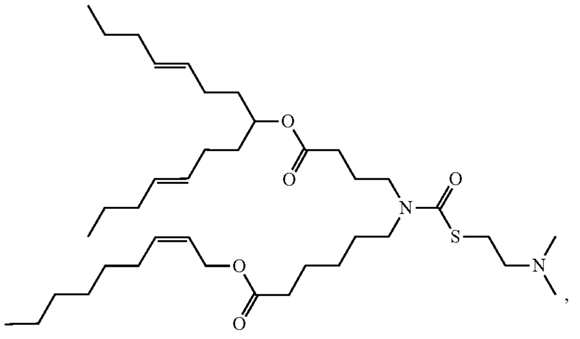

-continued
ATX-0091
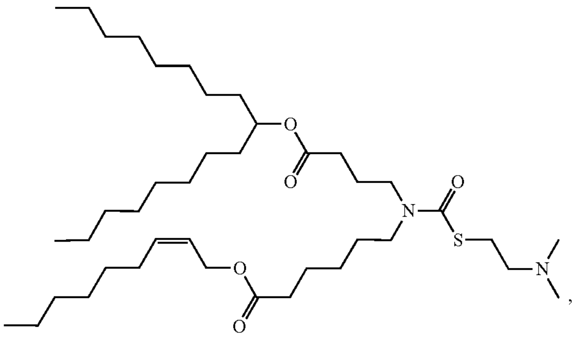
ATX-0102
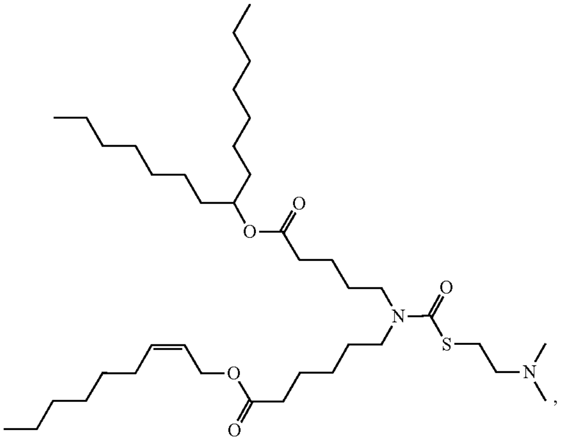
ATX-0098
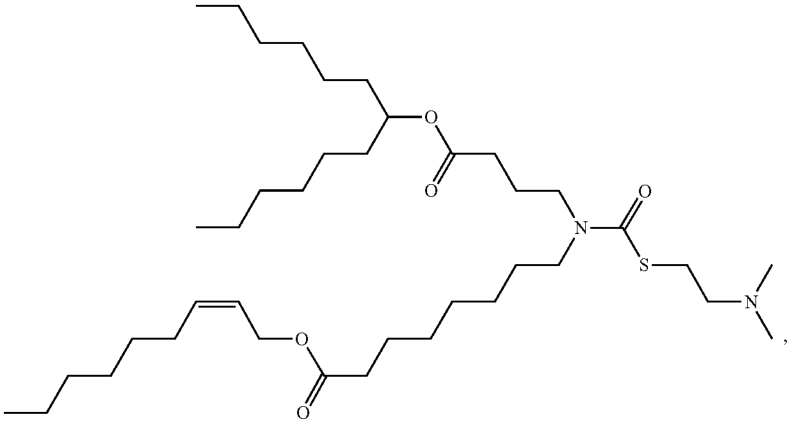
ATX-0092
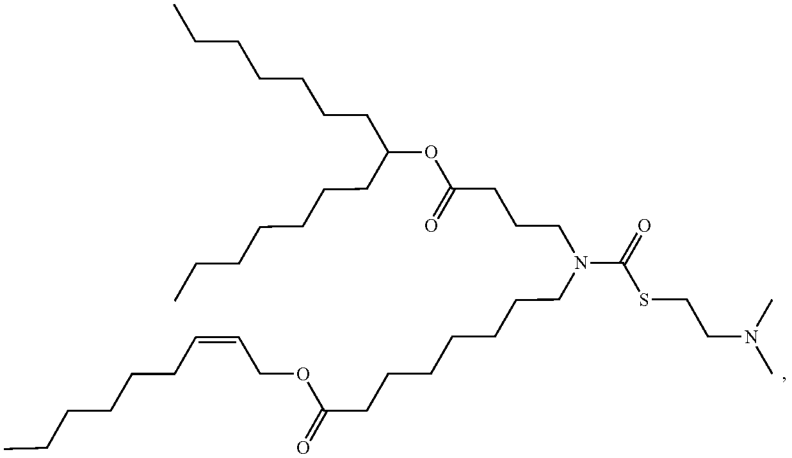

-continued
ATX-0095
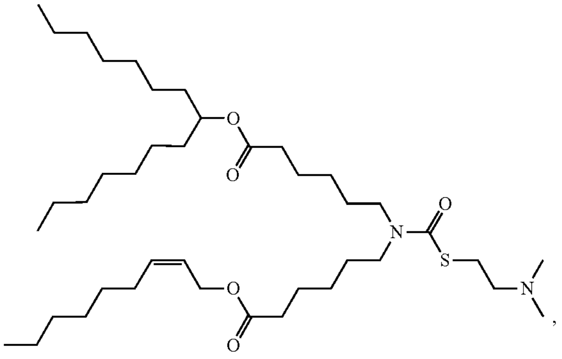
ATX-0125
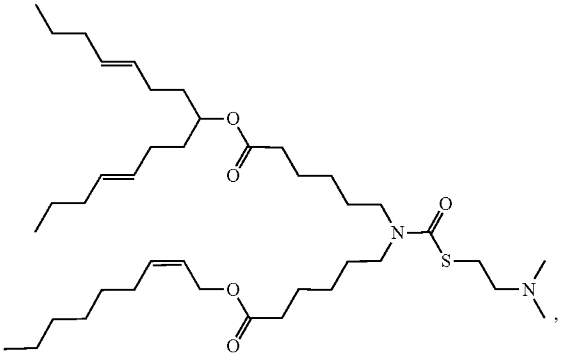
ATX-0094
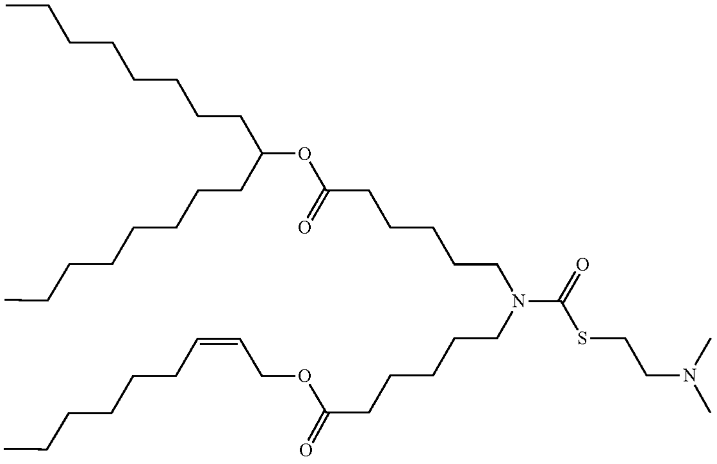
ATX-0109
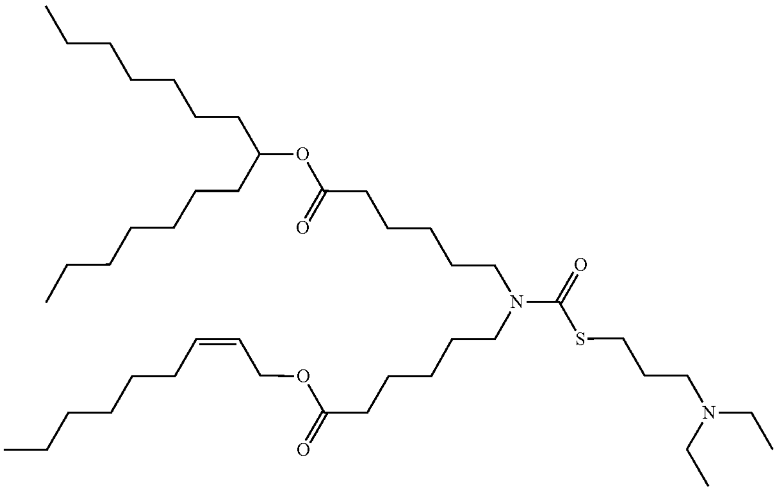

-continued
ATX-0110
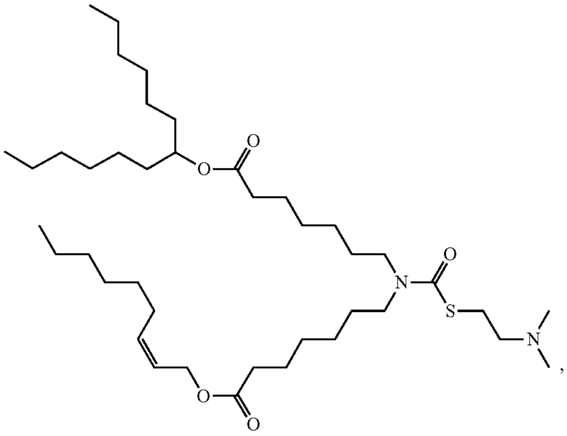
ATX-0118
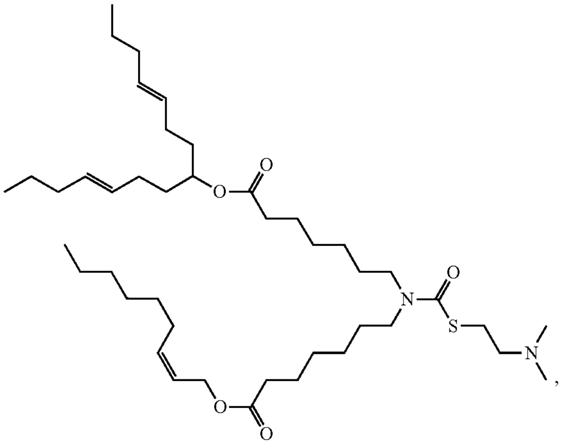
ATX-0108
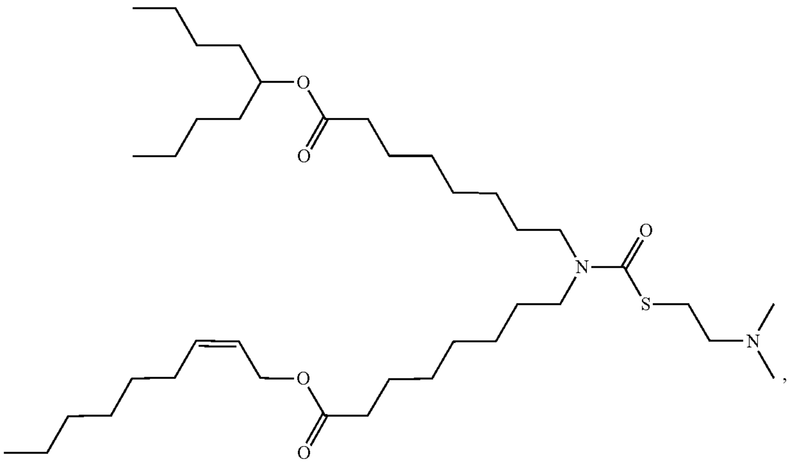
ATX-0107
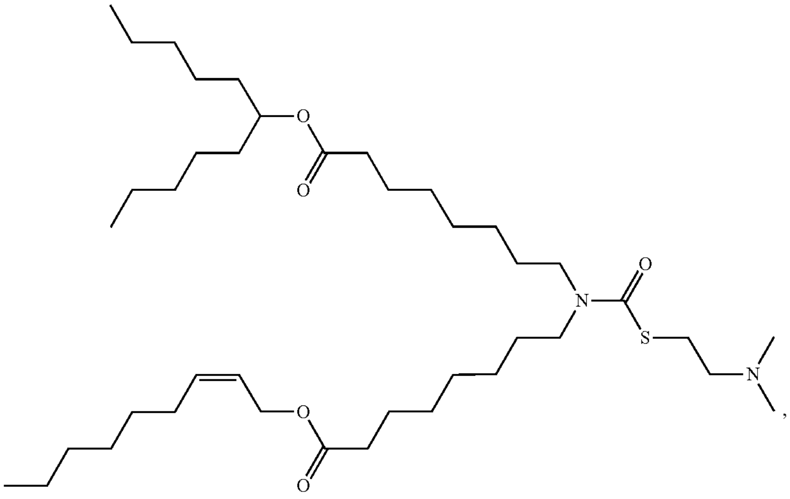

-continued
ATX-0093
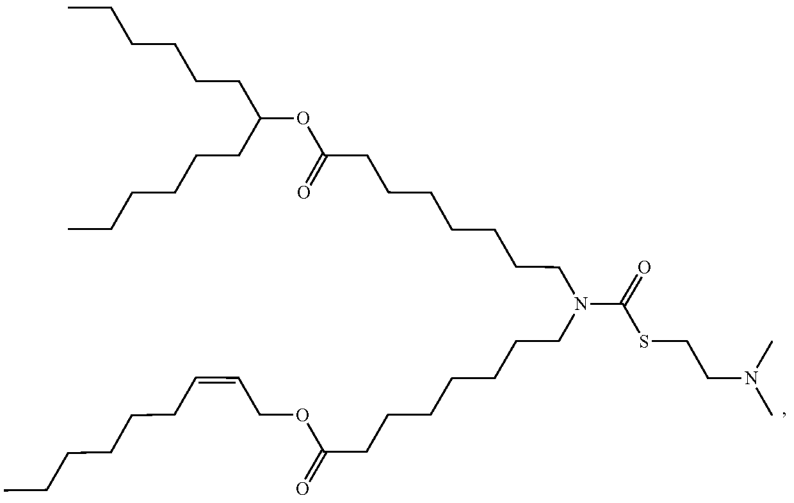
ATX-0097
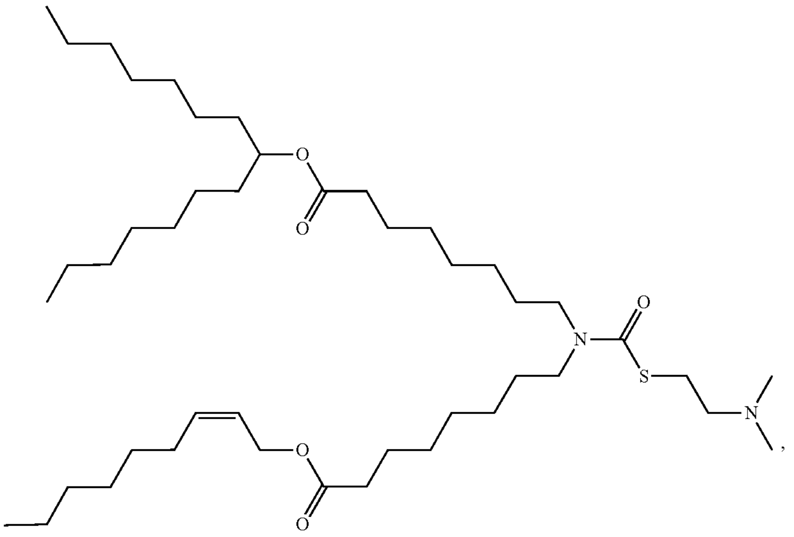
ATX-0096
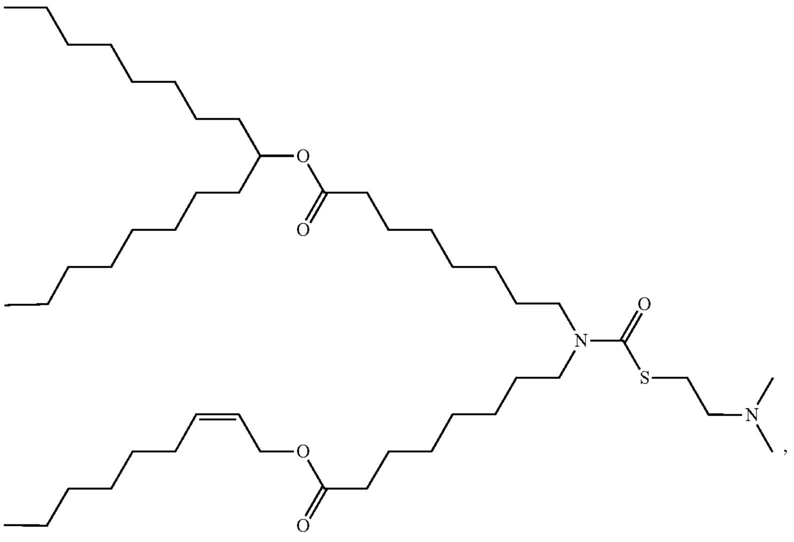

-continued
ATX-0111
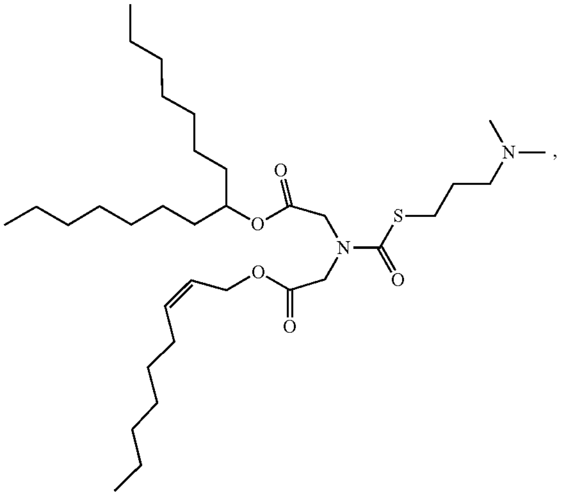
ATX-0132
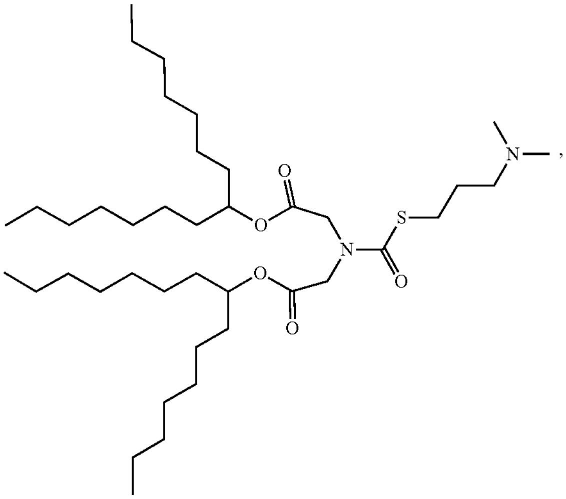
ATX-0134
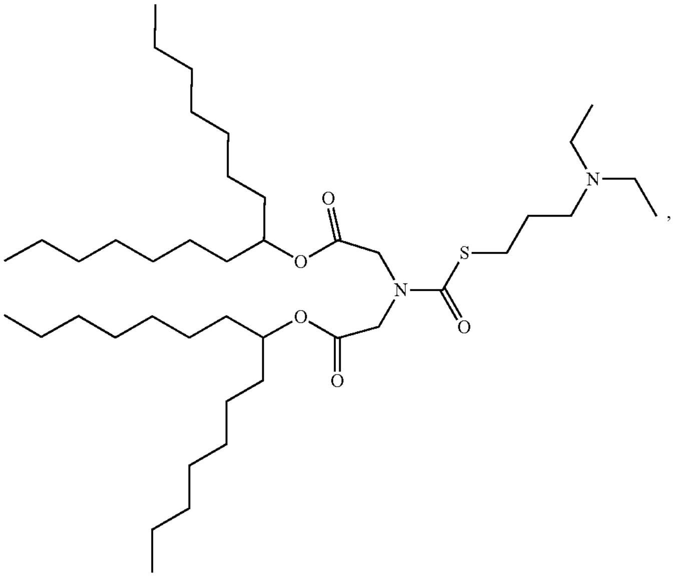

ATX-0100
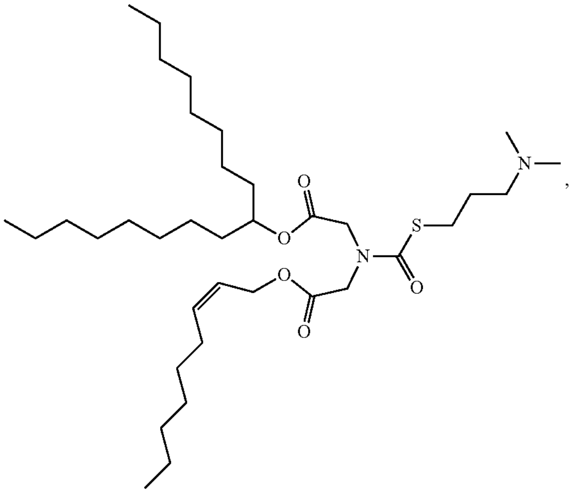
,
ATX-0117
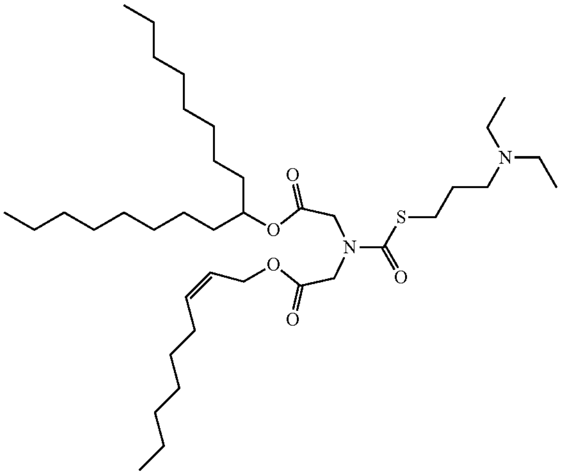
,
ATX-0114
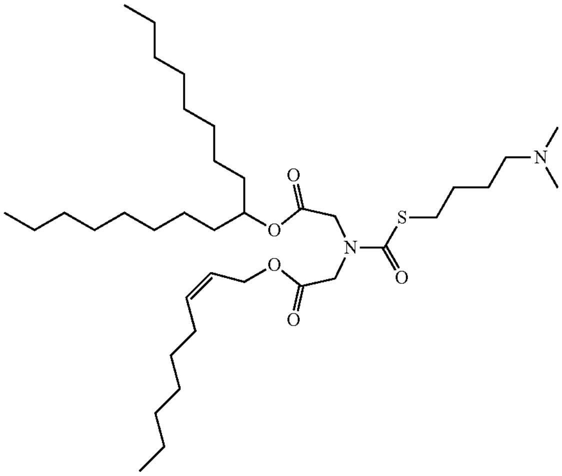
,
ATX-0115
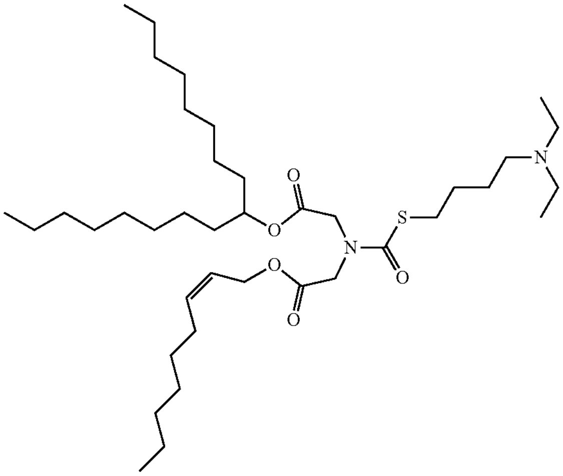
,
ATX-0101
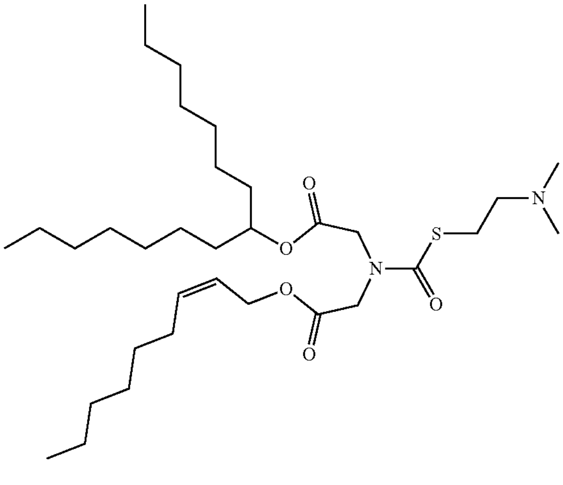
,
ATX-0106
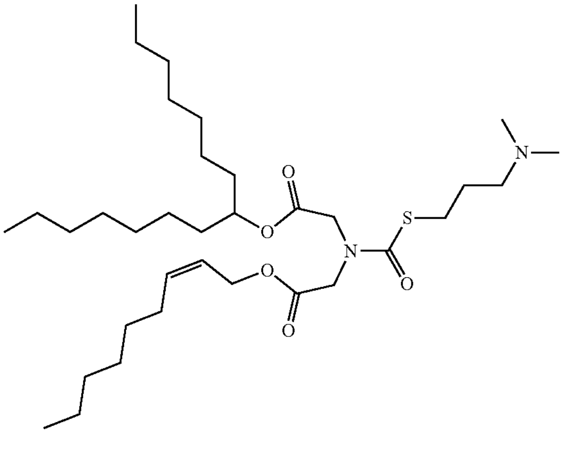
, -continued
ATX-0116
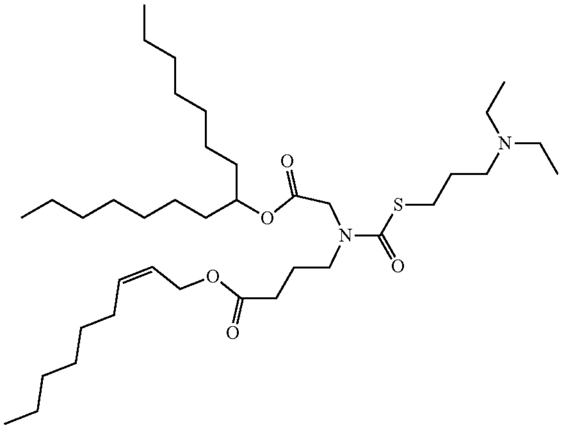
,
ATX-0123
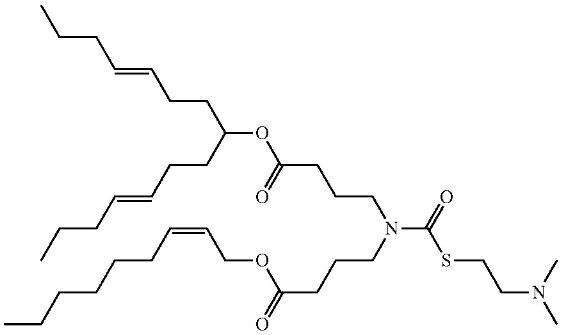
,
ATX-0122
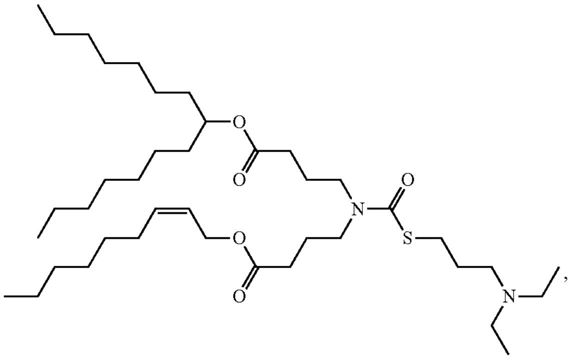
,
ATX-0124
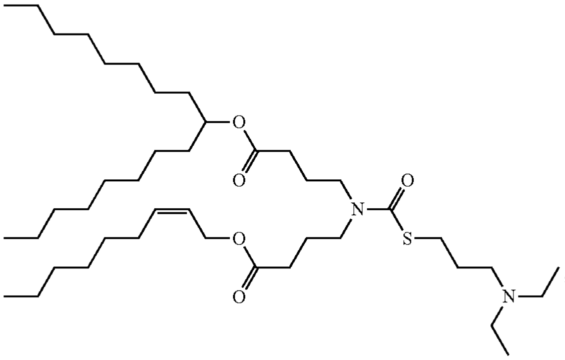
,
ATX-0126
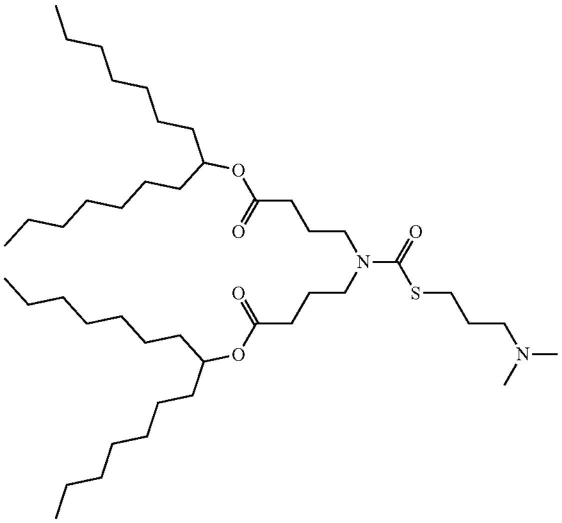
,
ATX-0129
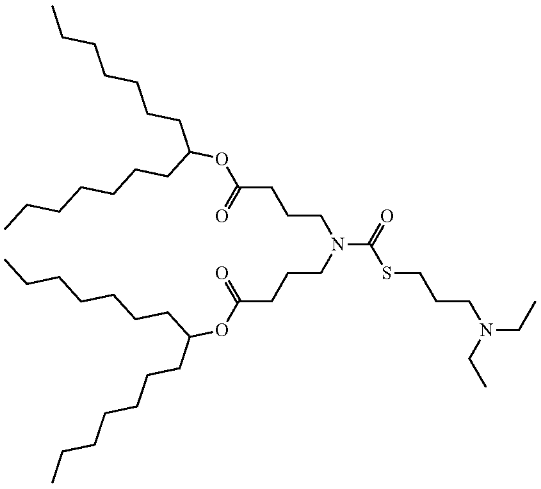
, and -continued

ATX-0123

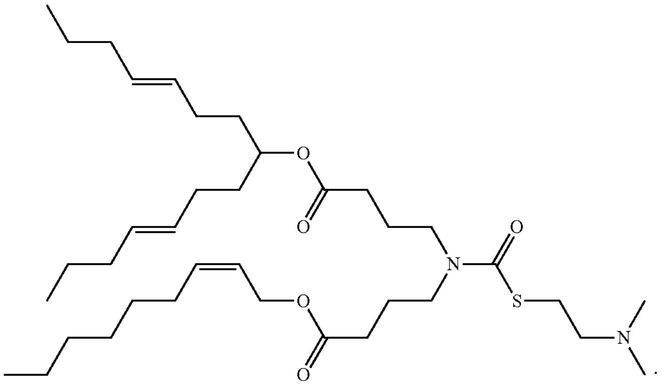

2. The pharmaceutical composition of claim 1, wherein the nucleic acid is RNA or DNA.

3. The pharmaceutical composition of claim 2, wherein the RNA is selected from small interfering RNA (siRNA), antisense RNA, single stranded RNA, microRNA, messenger RNA (mRNA), noncoding RNA, and multivalent RNA.

4. The pharmaceutical composition of claim 3, wherein the RNA is mRNA.

5. The pharmaceutical composition of claim 3, wherein the RNA is siRNA.

6. The pharmaceutical composition of claim 1, wherein the lipid nanoparticle further comprises cholesterol.

7. The pharmaceutical composition of claim 6, wherein the cholesterol comprises 25 mol % to 45 mol % of the total lipid present in the lipid nanoparticle.

8. The pharmaceutical composition of claim 1, wherein the lipid nanoparticle further comprises a helper lipid.

9. The pharmaceutical composition of claim 8, wherein the helper lipid is selected from lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, and dilinoleoylphosphatidylcholine.

10. The pharmaceutical composition of claim 9, wherein the helper lipid is DSPC.

11. The pharmaceutical composition of claim 8, wherein the helper lipid comprises 2 mol % to 30 mol % of the total lipid present in the lipid nanoparticle.

12. The pharmaceutical composition of claim 1, wherein the lipid nanoparticle further comprises a lipid conjugate.

13. The pharmaceutical composition of claim 12, wherein the lipid conjugate is a polyethylene glycol (PEG) lipid conjugate.

14. The pharmaceutical composition of claim 13, wherein the PEG-lipid conjugate is selected from PEG coupled to dialkyloxypropyls (PEG-DAA), PEG coupled to diacylglycerol (PEG-DAG), PEG coupled to phospholipids, PEG conjugated to ceramides, and PEG conjugated to a sterol.

15. The pharmaceutical composition of claim 13, wherein the PEG of the PEG-lipid conjugate has a molecular weight from 750 daltons to 5,000 daltons.

16. The pharmaceutical composition of claim 13, wherein the lipid conjugate comprises 0.1 mol % to 2 mol % of the total lipids present in the lipid nanoparticle.

17. The pharmaceutical composition of claim 1, wherein the cationic lipid comprises 30 mol % to 70 mol % of the total lipids present in the lipid nanoparticle.

18. A pharmaceutical composition comprising a lipid nanoparticle encapsulating a nucleic acid, wherein the lipid nanoparticle comprises i. a cationic lipid in an amount of 30 mol % to 70 mol % of the total lipids present in the lipid nanoparticle, wherein the cationic lipid is selected from the group consisting of:

ATX-0085
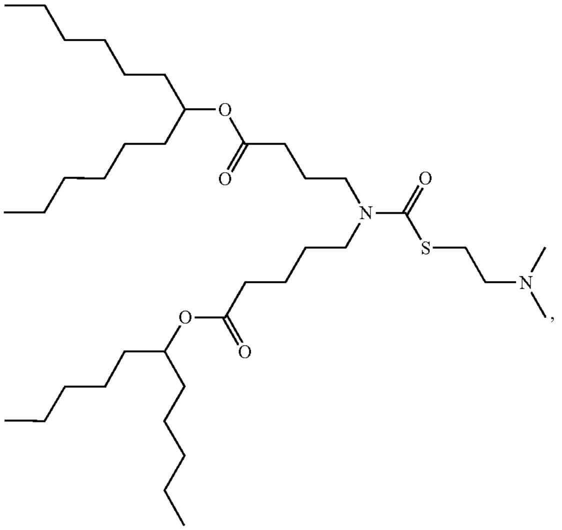
ATX-0121
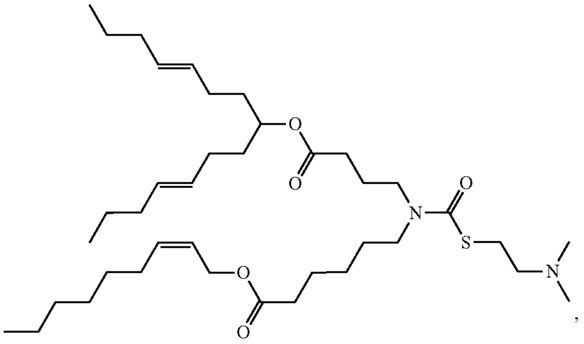
ATX-0091
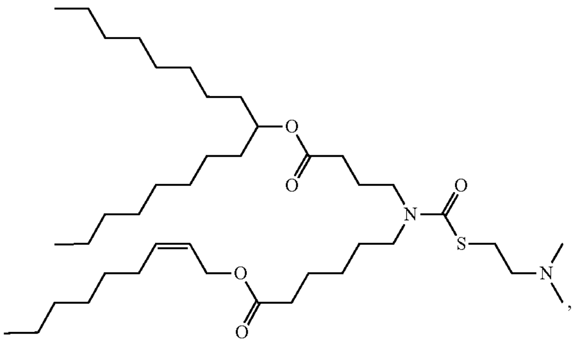
ATX-0102
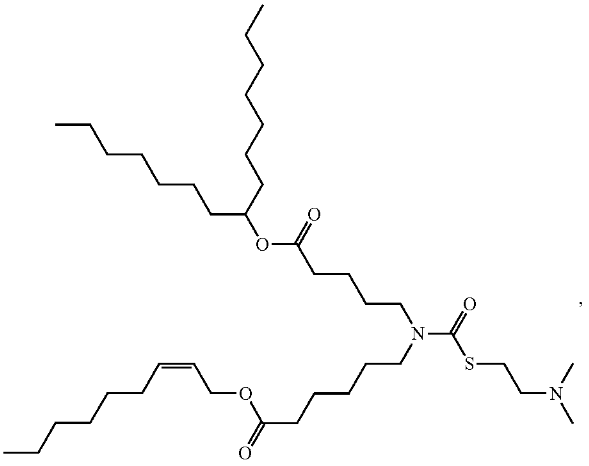
ATX-0098
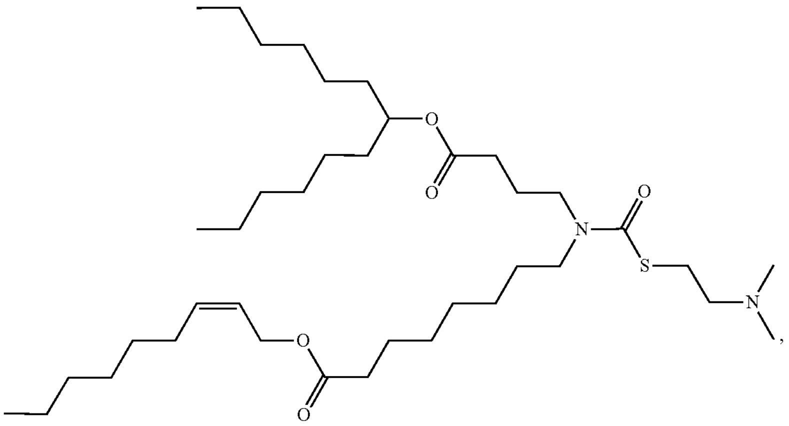

-continued
ATX-0092
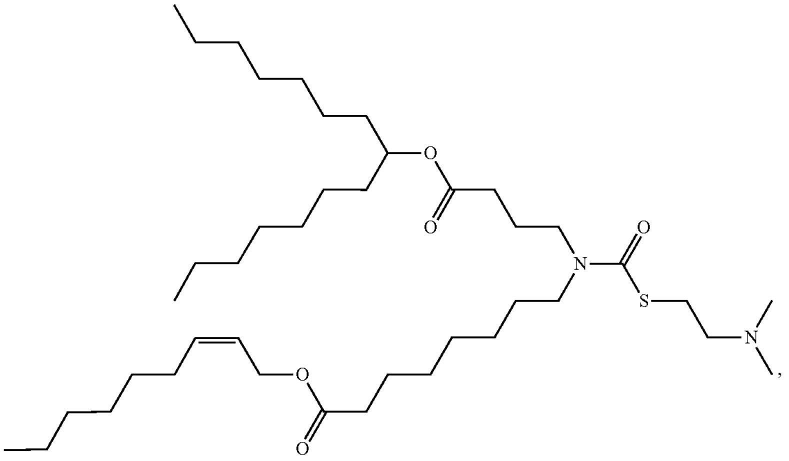
ATX-0095
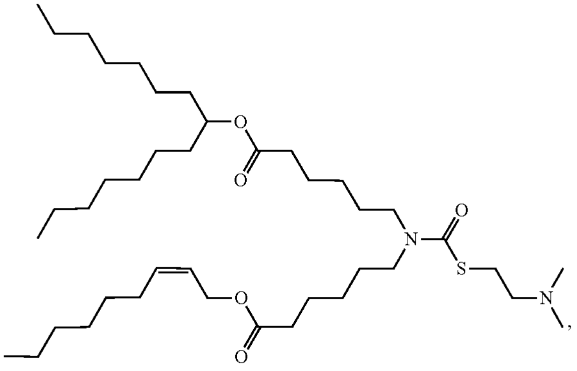
ATX-0125
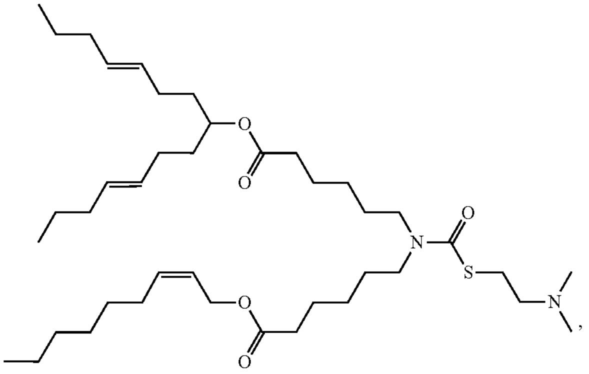
ATX-0094
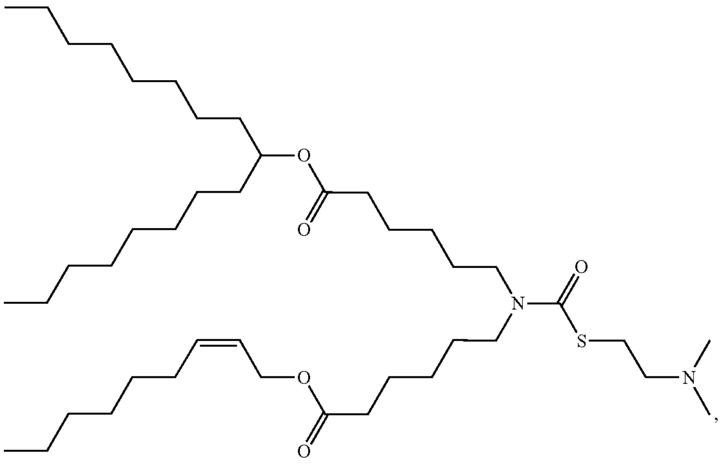

-continued
ATX-0109
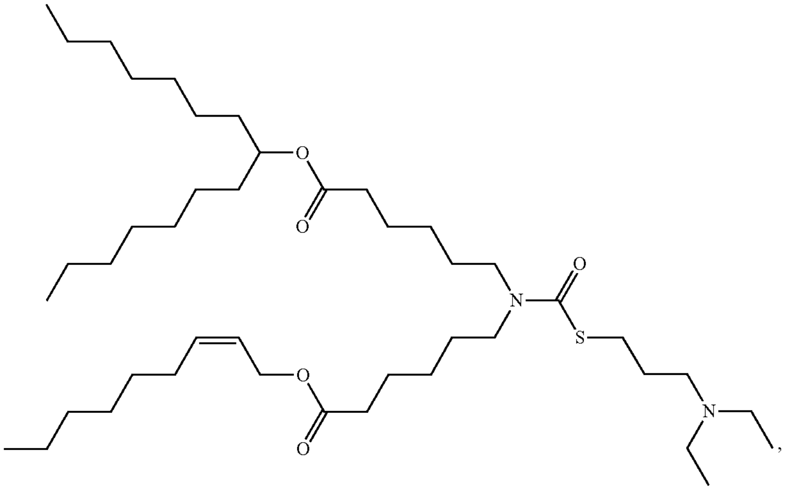
ATX-0110
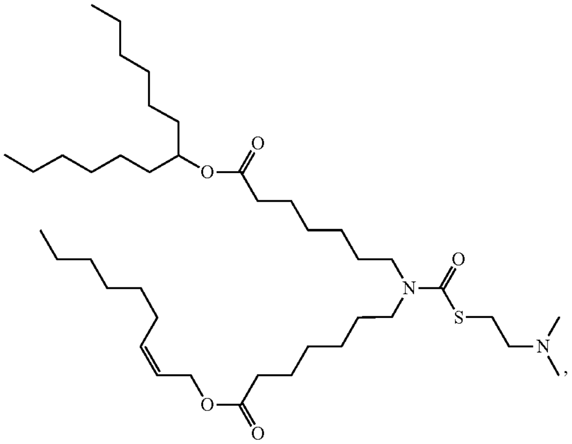
ATX-0118
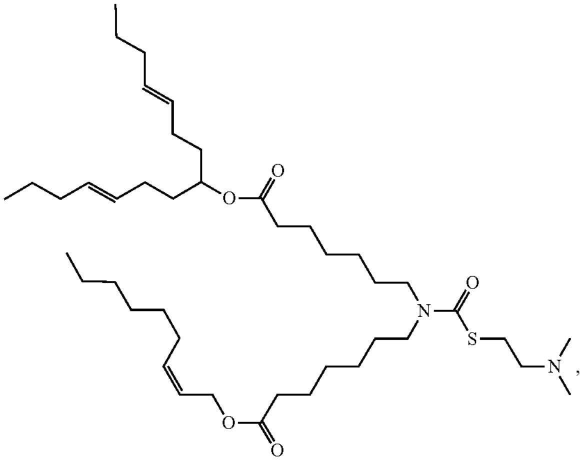
ATX-0108
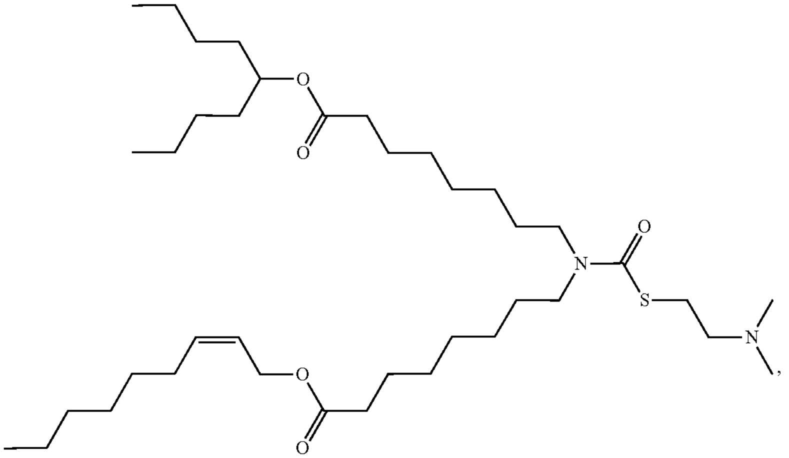

-continued
ATX-0107
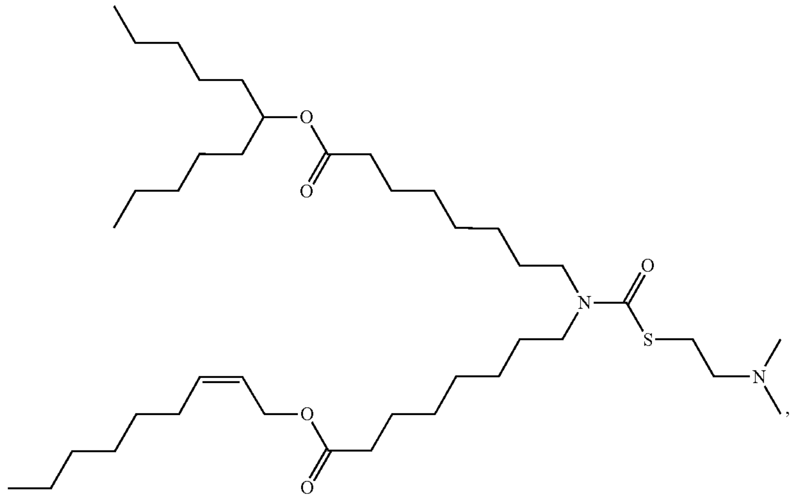
ATX-0093
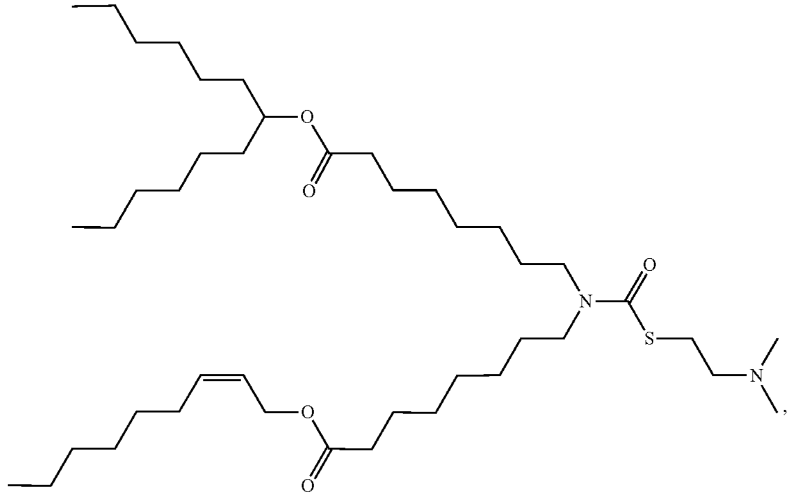
ATX-0097
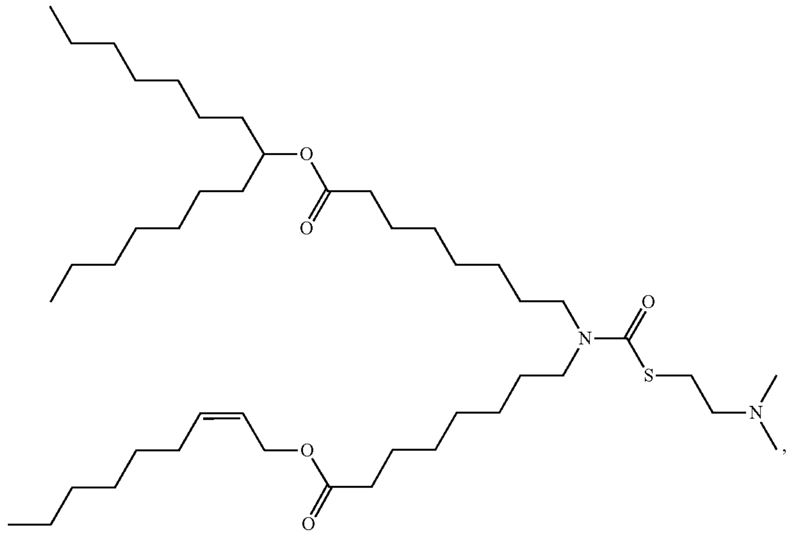

-continued
ATX-0096
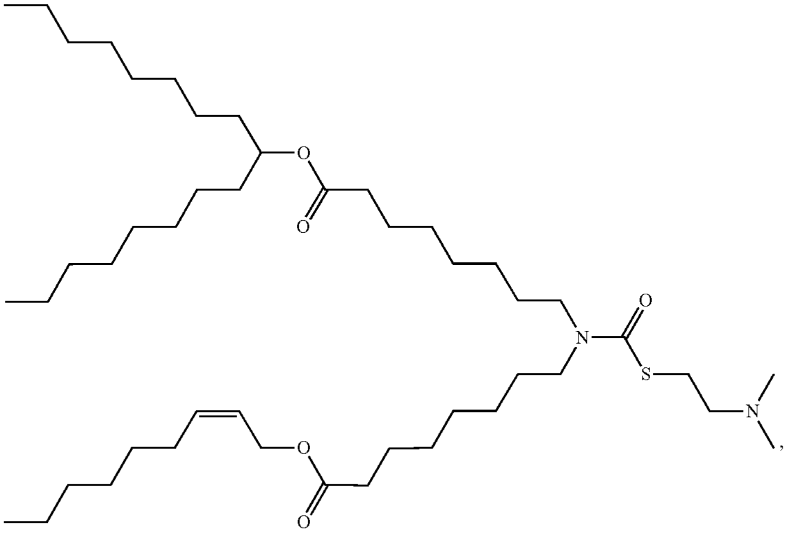
ATX-0111
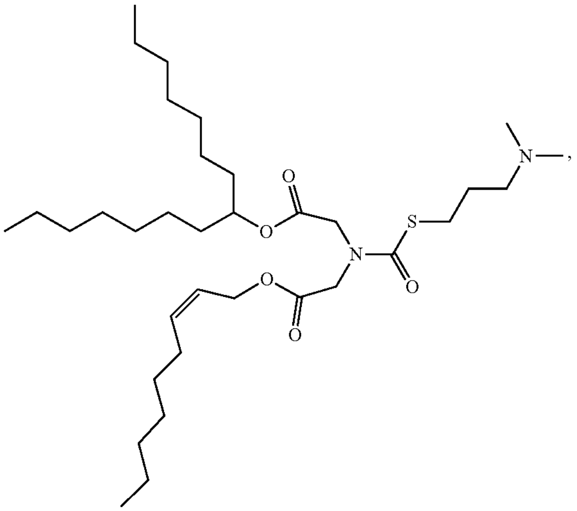
ATX-0132
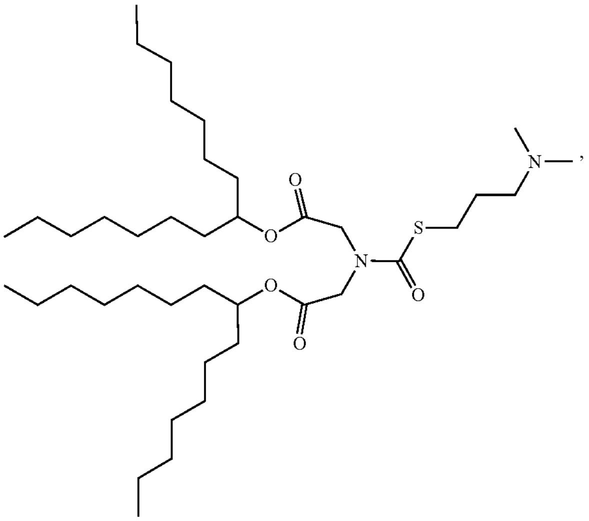
ATX-0134
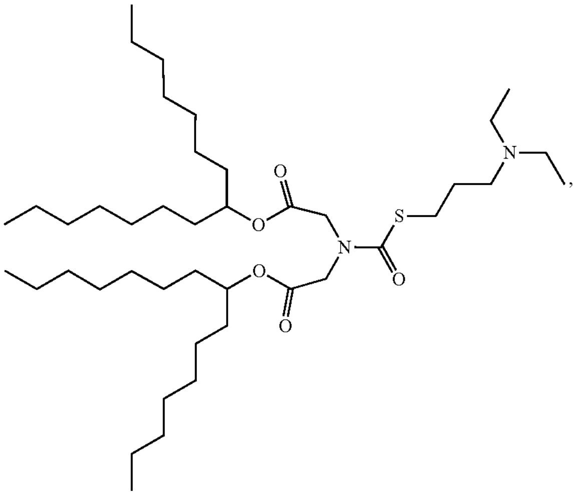
ATX-0100
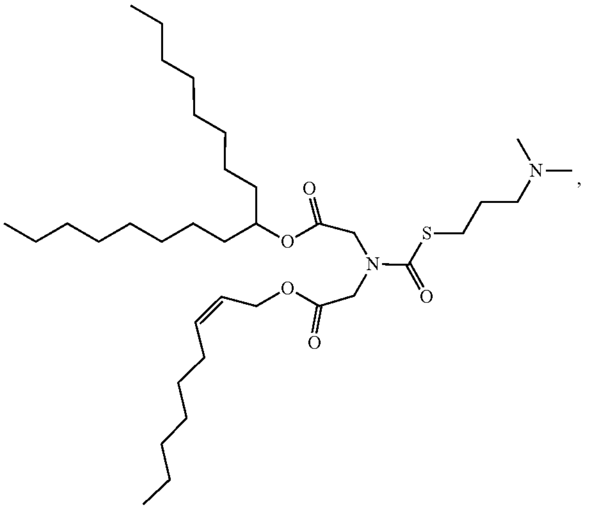

ATX-0117
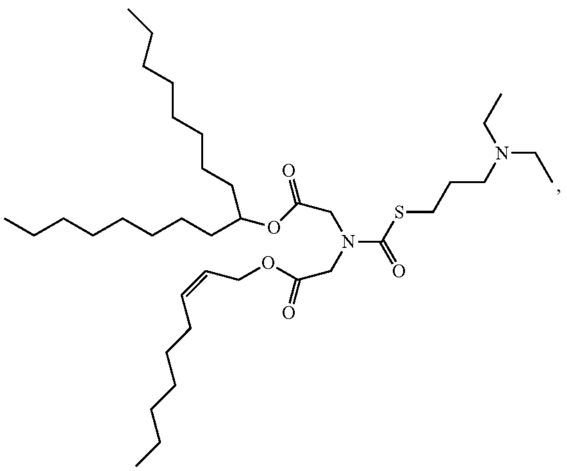
ATX-0114
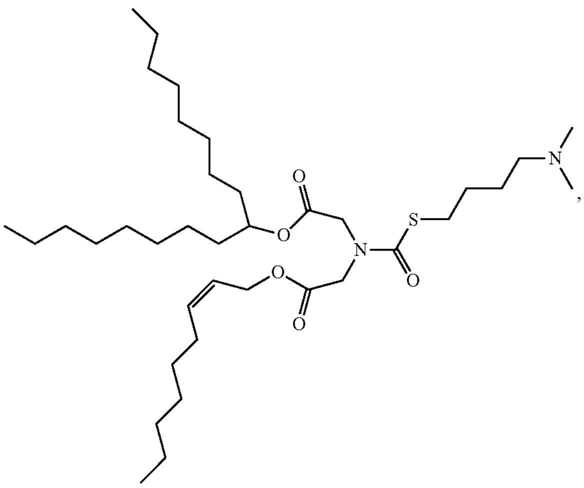
ATX-0115
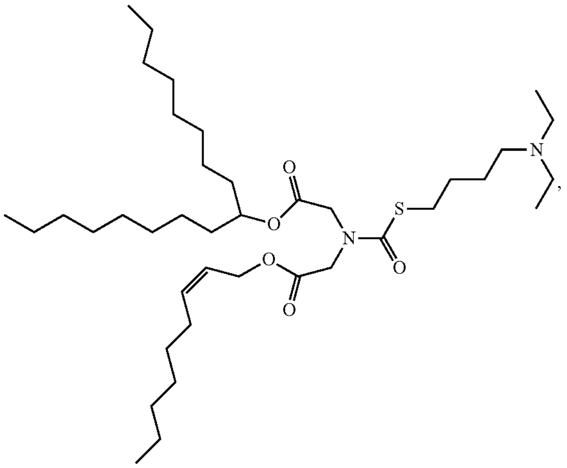
ATX-0101
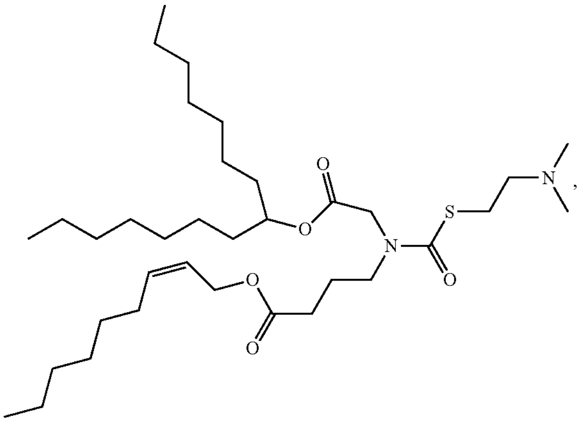
ATX-0106
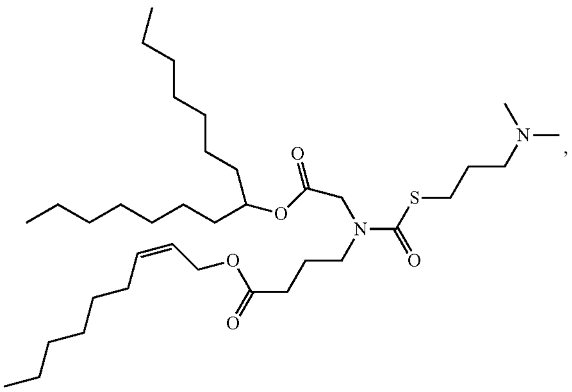
ATX-0116
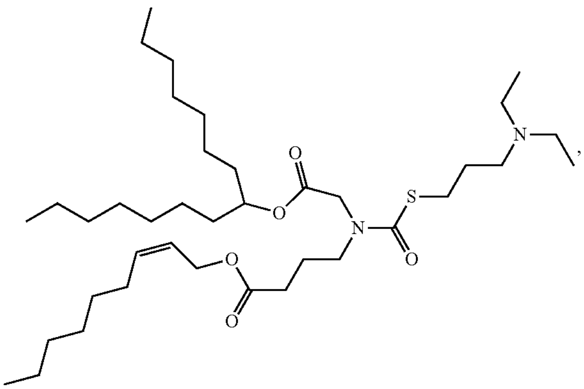

-continued

ATX-0123

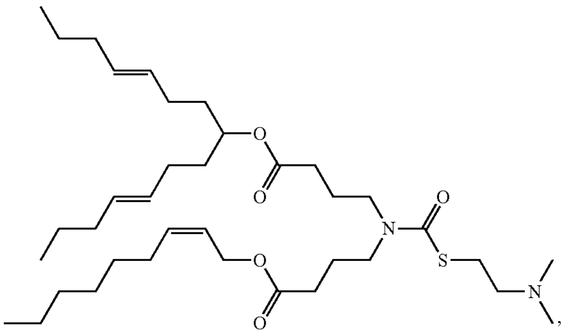

,

ATX-0122

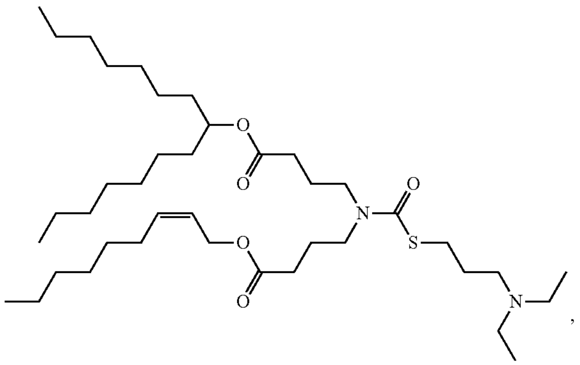

,

ATX-0124

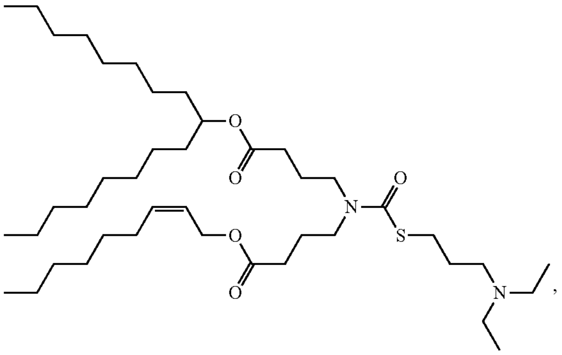

,

ATX-0126

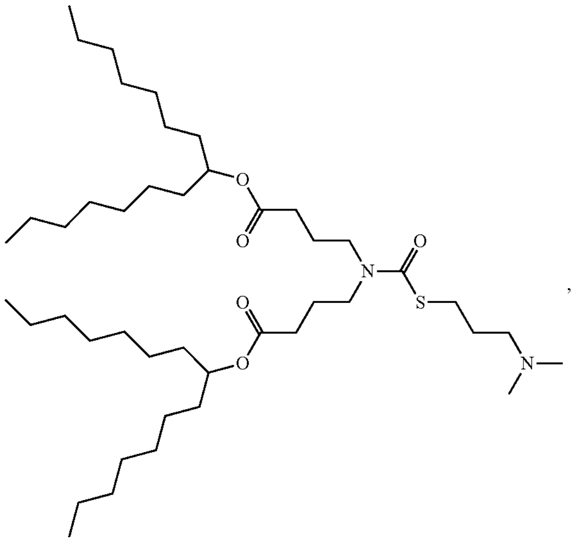

,

ATX-0129

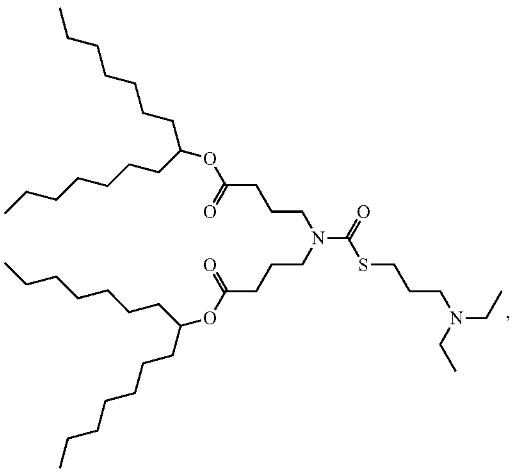

, and

ATX-0123

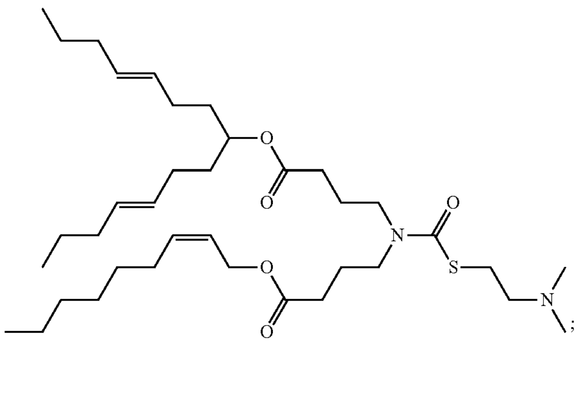

;

ii. cholesterol in an amount of 25 mol % to 45 mol % of the total lipid present in the lipid nanoparticle;

iii. a helper lipid in an amount of 2 mol % to 30 mol % of the total lipid present in the lipid nanoparticle, wherein the helper lipid is selected from lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, and dilinoleoylphosphatidylcholine; and iv. a polyethylene glycol lipid conjugate in an amount of 0.1 mol % to 2 mol % of the total lipids present in the lipid nanoparticle.

19. The pharmaceutical composition of claim 18, wherein the cationic lipid is

ATX-0095

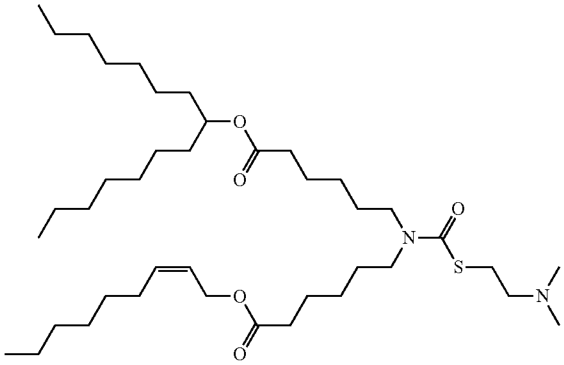

.

20. The pharmaceutical composition of claim 18, wherein the cationic lipid is

ATX-0126

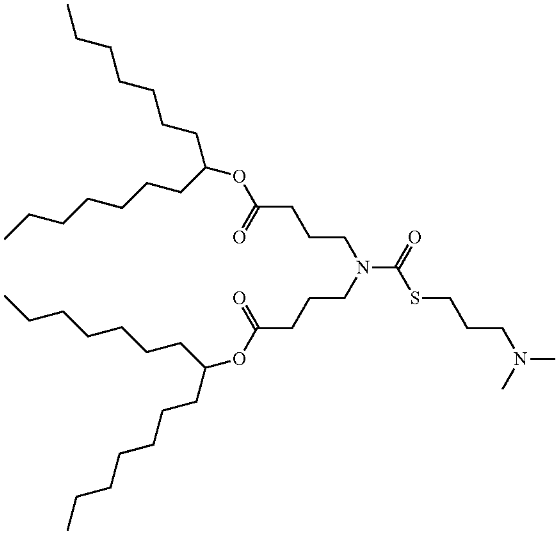

.

* * * * *